United States Patent
Li et al.

(10) Patent No.: US 11,605,784 B2
(45) Date of Patent: Mar. 14, 2023

(54) ORGANIC COMPOUND, ELECTRONIC ELEMENT, AND ELECTRONIC DEVICE

(71) Applicant: SHAANXI LIGHTE OPTOELECTRONICS MATERIAL CO., LTD., Xi'an (CN)

(72) Inventors: Jian Li, Xi'an (CN); Xunshan Sha, Xi'an (CN); Chao Yu, Xi'an (CN)

(73) Assignee: SHAANXI LIGHTE OPTOELECTRONICS MATERIAL CO., LTD., Xi'an (CN)

( * ) Notice: Subject to any disclaimer, the term of this patent is extended or adjusted under 35 U.S.C. 154(b) by 0 days.

(21) Appl. No.: 17/623,844

(22) PCT Filed: Oct. 22, 2020

(86) PCT No.: PCT/CN2020/122968
§ 371 (c)(1),
(2) Date: Dec. 29, 2021

(87) PCT Pub. No.: WO2021/120838
PCT Pub. Date: Jun. 24, 2021

(65) Prior Publication Data
US 2022/0336751 A1      Oct. 20, 2022

(30) Foreign Application Priority Data

Dec. 19, 2019   (CN) .......................... 201911320582.0
Apr. 3, 2020    (CN) .......................... 202010261391.8
Apr. 8, 2020    (CN) .......................... 202010270448.0

(51) Int. Cl.
C07D 319/14        (2006.01)
C07D 327/08        (2006.01)
(Continued)

(52) U.S. Cl.
CPC ........ *H01L 51/0061* (2013.01); *C07D 319/14* (2013.01); *C07D 327/06* (2013.01);
(Continued)

(58) Field of Classification Search
CPC .. C07D 319/14; C07D 327/08; C07D 339/08; C07F 7/0816; H01L 51/0061
See application file for complete search history.

(56) References Cited

U.S. PATENT DOCUMENTS 9,368,733 B2 * 6/2016 Ryu .................... H01L 51/0061

FOREIGN PATENT DOCUMENTS

CN    105121594 A   12/2015
CN    110494430 A   11/2019
(Continued)

OTHER PUBLICATIONS

The World Intellectual Property Organization (WIPO) International Search Report for PCT/CN2020/122968 dated Jan. 4, 2021 15 Pages (with translation).
(Continued)

*Primary Examiner* — Vu A Nguyen
(74) *Attorney, Agent, or Firm* — Anova Law Group, PLLC

(57) ABSTRACT

The application discloses an organic compound, an electronic element with the organic compound, and an electronic device including the electronic element. The organic compound of the present application has a fused heteroaromatic group containing fluorenyl or silylfluorenyl as its core structure, which presents a large planar structure in a three-dimensional (3D) space; and an electron-rich arylamine or heteroarylamine substituent is introduced at position 9 of the fluorenyl or silylfluorenyl to make the compound have excellent hole transport performance.

12 Claims, 2 Drawing Sheets

(51) Int. Cl.
- *C07D 339/08* (2006.01)
- *C07F 7/08* (2006.01)
- *C09K 11/06* (2006.01)
- *H01L 51/00* (2006.01)
- *H01L 51/50* (2006.01)
- *C07D 327/06* (2006.01)
- *C07D 405/12* (2006.01)
- *C07D 407/04* (2006.01)
- *C07D 407/12* (2006.01)
- *C07D 409/04* (2006.01)
- *C07D 471/04* (2006.01)

(52) U.S. Cl.
CPC ......... *C07D 339/08* (2013.01); *C07D 405/12* (2013.01); *C07D 407/04* (2013.01); *C07D 407/12* (2013.01); *C07D 409/04* (2013.01); *C07D 471/04* (2013.01); *C07F 7/0816* (2013.01); *C09K 11/06* (2013.01); *H01L 51/0094* (2013.01); *C09K 2211/1018* (2013.01); *H01L 51/0052* (2013.01); *H01L 51/0071* (2013.01); *H01L 51/0072* (2013.01); *H01L 51/0073* (2013.01); *H01L 51/0074* (2013.01); *H01L 51/5056* (2013.01)

(56) References Cited

FOREIGN PATENT DOCUMENTS

| | | |
|---|---|---|
| CN | 111004207 A | 4/2020 |
| CN | 106433614 A | 5/2020 |
| CN | 111303113 A | 6/2020 |
| WO | 2014051232 A1 | 4/2014 |
| WO | WO-2015084114 A1 * | 6/2015 ........... C07C 211/54 |
| WO | 2019078461 A1 | 4/2019 |

OTHER PUBLICATIONS

China National Intellectual Property Administration Notification of the first Office Action for CN 202010270448.0 dated Jul. 28, 2020 15 pages (with translation).

Korean Intellectual Property Office Notification of the first Office Action for KR20220008927 dated Mar. 25, 2022 12 pages (with translation).

* cited by examiner

ORGANIC COMPOUND, ELECTRONIC ELEMENT, AND ELECTRONIC DEVICE

CROSS REFERENCE TO RELATED APPLICATIONS

The application is a national phase entry under 35 U.S.C. § 371 of International Application No. PCT/CN2020/122968, filed on Oct. 22, 2020, which claims priority to Chinese Patent Application CN 201911320582.0 filed on Dec. 19, 2019 and entitled "ORGANIC COMPOUND, ELECTRONIC ELEMENT, AND ELECTRONIC DEVICE"; the application claims priority to Chinese Patent Application CN 202010261391.8 filed on Apr. 3, 2020 and entitled "ORGANIC COMPOUND, ELECTRONIC ELEMENT, AND ELECTRONIC DEVICE"; and the application claims priority to Chinese Patent Application CN 202010270448.0 filed on Apr. 8, 2020 and entitled "ORGANIC COMPOUND, ELECTRONIC ELEMENT, AND ELECTRONIC DEVICE". The full content of the Chinese patent applications is incorporated herein by reference in their entirety as part of the disclosure.

TECHNICAL FIELD

The application relates to the technical field of organic photoelectric material compounds, and in particular to an organic compound, an electronic element, and an electronic device.

BACKGROUND

Organic light emitting devices (OLEDs), which belong to electronic elements, are self-luminescent devices. OLED principle is that when an electric field is applied to a cathode and an anode, holes on the anode side and electrons on the cathode side move towards a light-emitting layer and are combined in the light-emitting layer to form excitons, and the excitons in an excited state release energy outwards to change from the excited state to a ground state, which results in light emission. Therefore, it is very important to improve the recombination of electrons and holes in OLEDs.

In order to improve the luminous intensity, efficiency, and life span of OLEDs, a multi-layer structure is usually used for OLEDs. The multi-layer structure includes a hole injection layer, a hole transport layer, an electron blocking layer, an emitting layer, an electron transport layer, and the like. These organic layers can improve the injection efficiency of carriers (holes and electrons) at an interface between the layers, and balance the ability to transport carriers between the layers, thereby improving the luminance and efficiency of OLED.

However, current commercial OLEDs still have many problems, such as high driving voltage, low luminous efficiency, poor thermal stability, and short life span, especially for blue light-emitting OLEDs. Therefore, the development of OLEDs with low driving voltage, high luminous efficiency, high thermal stability, and long life span and related materials has become a challenge that has to be overcome in the field of organic electroluminescence.

Chinese Patent CN201510472766.4 "Organic compound and use thereof and organic electroluminescent device" discloses a compound that can improve the luminous efficiency of OLEDs. However, it is still necessary to further develop new compounds for OLEDs to further improve the performance of electronic devices.

SUMMARY

The disclosure is intended to provide an organic compound with excellent carrier transport performance, an OLED with the organic compound, and an electronic device including the OLED; wherein the OLED has low driving voltage, high luminous efficiency, and long service life.

According to a first aspect of the disclosure, an organic compound is provided, with a structure shown in chemical formula I:

chemical formula I

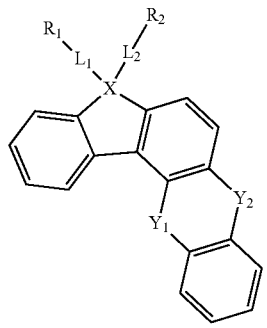

wherein X is selected from: C and Si;

$Y_1$ and $Y_2$ are the same or different, and are each independently selected from: O and S;

$R_1$ and $R_2$ are each independently selected from: hydrogen, deuterium, substituted or unsubstituted alkyl with 1 to 10 carbon atoms, substituted or unsubstituted cycloalkyl with 3 to 10 carbon atoms, substituted or unsubstituted aryl with 6 to 30 carbon atoms, substituted or unsubstituted heteroaryl with 1 to 30 carbon atoms, and

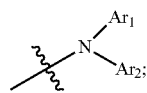

at least one of $R_1$ and $R_2$ is

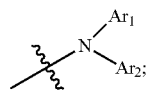

$Ar_1$ and $Ar_2$ are the same or different, and are each independently selected from: hydrogen, deuterium, substituted or unsubstituted aralkyl with 7 to 25 carbon atoms, substituted or unsubstituted heteroaralkyl with 2 to 20 carbon atoms, substituted or unsubstituted aryl with 6 to 30 carbon atoms, and substituted or unsubstituted heteroaryl with 1 to 30 carbon atoms;

$L_1$ and $L_2$ are the same or different, and are each independently selected from: a single bond, substituted or unsubstituted arylene with 6 to 30 carbon atoms, and substituted or unsubstituted heteroarylene with 1 to 30 carbon atoms; and when $R_1$ is

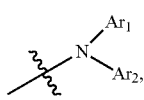

$L_1$ is not a single bond, and when $R_2$ is

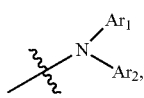

$L_2$ is not a single bond;

substituents of $Ar_1$, substituents of $Ar_2$, substituents of $L_1$, and substituents of $L_2$ are the same or different, and are each independently selected from: deuterium, halogen, cyano, alkyl with 1 to 12 carbon atoms, alkoxy with 1 to 12 carbon atoms, alkylthio with 1 to 12 carbon atoms, haloalkyl with 1 to 12 carbon atoms, trialkylsilyl with 3 to 12 carbon atoms, cycloalkyl with 3 to 12 carbon atoms, aryloxy with 6 to 18 carbon atoms, arylthio with 6 to 18 carbon atoms, aryl with 6 to 18 carbon atoms, and heteroaryl with 3 to 18 carbon atoms.

According to a second aspect of the disclosure, an electronic element is provided, including an anode and a cathode that are arranged oppositely, and a functional layer arranged between the anode and the cathode, wherein the functional layer includes the organic compound described above.

According to a third aspect of the disclosure, an electronic device is provided, including the electronic element described above.

The organic compound of the present application has a fused heteroaromatic group containing fluorenyl or silylfluorenyl as its core structure, which presents a large planar structure in a three-dimensional (3D) space; and an electron-rich arylamine or heteroarylamine substituent is introduced at position 9 of the fluorenyl or silylfluorenyl to make the compound have excellent hole transport performance. This is because a hyperconjugated system formed by the core structure enhances the ability of carriers to cross between different molecules. When the organic compound of the disclosure is used for a functional layer of an electronic element, the electronic element has the characteristics of high luminous efficiency, low voltage, and long life span.

The electronic device including the electronic element in the disclosure has the characteristics of high luminous efficiency, low voltage, and long life span.

BRIEF DESCRIPTION OF THE DRAWINGS

The objectives, technical solutions, and advantages of the disclosure will become more apparent by describing exemplary embodiments thereof with reference to the accompanying drawings.

Figure 1:
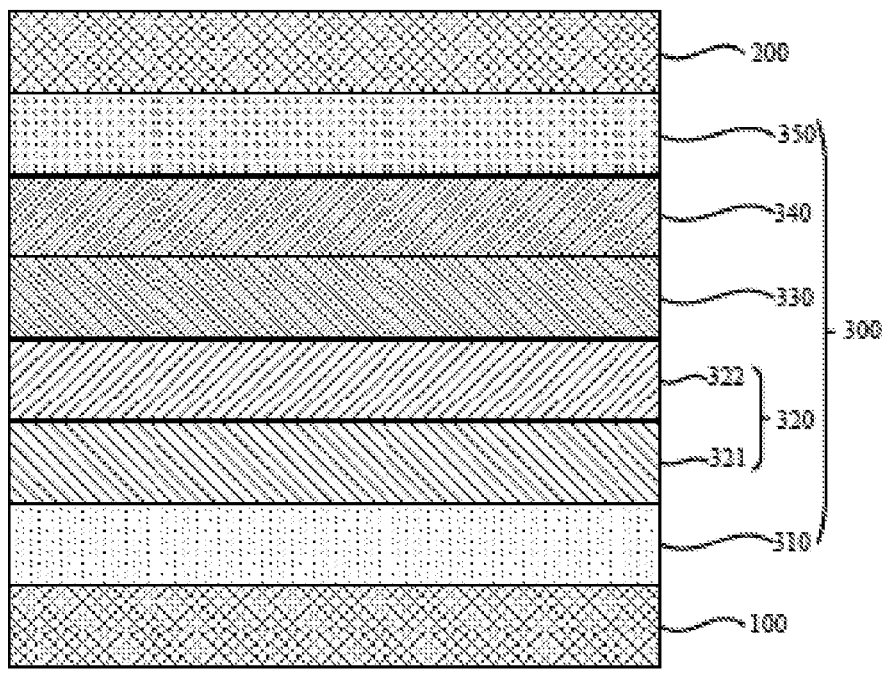
FIG. 1 is a schematic structure diagram of an OLED according to an embodiment of the disclosure.

Reference numerals in the figures:
100: anode; 200: cathode; 300: functional layer; 310: hole injection layer (HIL); 320: hole transport layer (HTL); 321: first hole transport layer (HTL); 322: second hole transport layer (HTL); 330: organic light-emitting layer (EML); 340: electron transport layer (ETL); 350: electron injection layer (EIL); 360: photoelectric conversion layer; 400: electronic device; and 500: electronic device.

DETAILED DESCRIPTION

Exemplary embodiments will be described below comprehensively with reference to the accompanying drawings. However, the exemplary embodiments can be implemented in various forms and should not be construed as being limited to examples described herein. On the contrary, these embodiments are provided such that the disclosure is comprehensive and complete and the concept of the exemplary embodiments is fully conveyed to persons skilled in the art. The described features, structures, or characteristics may be incorporated into one or more embodiments in any suitable manner. In the following description, many specific details are provided to give a full understanding of the embodiments of the disclosure.

The term "optional" or "optionally" means that the event or environment subsequently described may, but not necessarily, occur, and that the description includes situations wherein the event or environment occurs or does not occur. For example, "heterocyclyl optionally substituted by alkyl" means that alkyl may be, but not necessarily, present, and that the description includes situations wherein the heterocyclyl is or is not substituted by alkyl. The phrase "optionally, $R^e$ and $R^f$ attached to the same atom are linked together to form a saturated or unsaturated 5-10 membered aliphatic ring" means that $R^e$ and $R^f$ attached to the same atom may or may not form a ring, including the situation wherein $R^e$ and $R^f$ are linked together to form a saturated or unsaturated 5-10 membered aliphatic ring and the situation wherein $R^e$ and $R^f$ exist independently of each other.

In the disclosure,

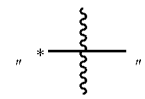

refers to a position attached to other substituents or other binding positions.

The description manners used in the disclosure such as " . . . is(are) each independently", "each of . . . is independently selected from" and " . . . each is(are) independently selected from the group consisting of" can be used interchangeably, and should be understood in a broad sense, which can mean that, in different groups, specific options expressed by the same symbols do not affect each other, or in the same group, specific options expressed by the same symbols do not affect each other. For example,

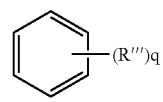

Formula Q-1

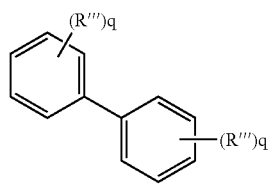

Formula Q-2 wherein q is independently 0, 1, 2, or 3, and substituents R" is each independently selected from: hydrogen, deuterium, fluorine, and chlorine" means that, in formula Q-1, there are q substituents R" on the benzene ring, the substituents R" can be the same or different, and options for each substituent R" do not affect each other; and in formula Q-2, there are q substituents R" on each benzene ring of the biphenyl, the numbers q of substituents R" on the two benzene rings can be the same or different, the substituents R" can be the same or different, and options for each substituent R" do not affect each other.

In the disclosure, the term "substituted or unsubstituted" means that there is no substituent or there is one or more substituents. The substituents include, but are not limited to, deuterium (D), halogen (F, Cl, or Br), cyano, alkyl, alkenyl, alkynyl, haloalkyl, aryl, heteroaryl, aryloxy, arylthio, silyl, alkylamino, arylamino, cycloalkyl, heterocyclyl, boranyl, and phosphino.

In the disclosure, the "aliphatic ring" includes saturated cycloalkyl and partially unsaturated cycloalkyl. For example, the saturated cycloalkyl may include cyclopentyl, cyclohexyl, adamantyl, and the like; and the partially unsaturated cycloalkyl may include cyclobutenyl and the like.

In the disclosure, the term "hetero" means that a functional group includes 1 to 3 heteroatoms selected from the group consisting of B, N, O, S, Se, Si, and P, and the rest atoms are carbon.

In the disclosure, the term "alkyl" refers to linear or branched saturated monovalent hydrocarbyl with 1 to 20 carbon atoms, wherein the alkyl may optionally be substituted by one or more substituents described in the disclosure. Unless otherwise specified, the alkyl includes 1 to 20 carbon atoms. In some embodiments, the alkyl may include 1 to 10 carbon atoms; in other embodiments, the alkyl may include 1 to 6 carbon atoms; and in still other embodiments, the alkyl may include 1 to 4 carbon atoms. Examples of the alkyl include, but are not limited to, methyl (Me, —CH$_3$), ethyl (Et, —CH$_2$CH$_3$), n-propyl (n-Pr, —CH$_2$CH$_2$CH$_3$), isopropyl (i-Pr, —CH(CH$_3$)$_2$), n-butyl (n-Bu, —CH$_2$CH$_2$CH$_2$CH$_3$), isobutyl (i-Bu, —CH$_2$CH(CH$_3$)$_2$), sec-butyl (s-Bu, —CH(CH$_3$)CH$_2$CH$_3$), and tert-butyl (t-Bu, —C(CH$_3$)$_3$).

In the disclosure, the aryl can be a monocyclic structure formed by multiple carbon atoms, or can be a bicyclic or polycyclic system formed by multiple carbon atoms, wherein there may be at least one aromatic ring system, and each ring system may include a ring formed by 3 to 7 atoms. That is, the aryl can be monocyclic aryl or polycyclic aryl. In other words, the aryl may refer to a monocyclic aryl group, a fused-ring aryl group, two or more monocyclic aryl groups conjugated through carbon-carbon bonds, a monocyclic aryl group and a fused-ring aryl group conjugated through carbon-carbon bonds, and two or more fused-ring aryl groups conjugated through carbon-carbon bonds. That is, two or more aromatic groups conjugated through carbon-carbon bonds can also be regarded as the aryl of the disclosure. For example, in the disclosure, biphenyl, terphenyl, and the like are aryl. The aryl in the disclosure may include 6 to 30 carbon atoms. In some embodiments, the aryl may include 6 to 25 carbon atoms; in other embodiments, the aryl may include 6 to 18 carbon atoms; and in still other embodiments, the aryl may include 6 to 13 carbon atoms. For example, the number of carbon atoms in an aryl can be 6, 12, 13, 18, 20, 25, or 30 carbon atoms. Of course, there can be any other number of carbon atoms, which will not be listed here.

In the disclosure, aryl with 6 to 20 ring-forming carbon atoms means that the number of carbon atoms in an aromatic ring of the aryl is 6 to 20, which excludes the number of carbon atoms in substituents on the aryl. The aryl can include 6 to 20, 6 to 18, 6 to 14, or 6 to 10 ring-forming carbon atoms, but is not limited thereto.

Examples of aryl may include phenyl, naphthyl, fluorenyl, anthracenyl, phenanthryl, biphenyl, terphenyl, tetraphenyl, pentaphenyl, benzo[9,10]phenanthryl, fluoranthenyl, pyrenyl, benzofluoranthenyl, chrysenyl, and perylenyl, but are not limited thereto.

In the disclosure, aryl to serve as a substituent includes, but is not limited to, phenyl, naphthyl, fluorenyl, anthracenyl, phenanthryl, biphenyl, and dimethylfluorenyl.

In the disclosure, a ring system formed by n atoms is an n-membered ring. For example, phenyl is 6-membered aryl. A 6- to 10-membered aromatic ring refers to a benzene ring or a naphthalene ring.

The "aryl" of the disclosure can be attached to the remaining part of the molecule through one or more attachment points. In the disclosure, the explanation of aryl can be applied to arylene.

In the disclosure, substituted aryl refers to aryl in which one or more hydrogen atoms are substituted by other groups. For example, at least one hydrogen atom is substituted by deuterium, F, Cl, Br, CN, amino, alkyl, haloalkyl, cycloalkyl, aryloxy, arylthio, silyl, alkylamino, arylamino, boranyl, phosphino, heteroaryl, or the like.

It should be explained that "substituted C$_6$-C$_{30}$ aryl" refers to substituted aryl with 6 to 30 carbon atoms, which means that the total number of carbon atoms in the aryl and substituents on the aryl is 6 to 30. Aryl with 6 to 18 ring-forming carbon atoms means that the number of carbon atoms in an aromatic ring of the aryl is 6 to 18, which excludes the number of carbon atoms in substituents on the aryl. The aryl can include 6 to 30, 6 to 18, or 6 to 13 ring-forming carbon atoms, but is not limited thereto. For example, fluorenyl is aryl with 13 ring-forming carbon atoms, and 9,9-dimethylfluorenyl is substituted aryl with 15 carbon atoms.

The term "heteroaryl" refers to a monocyclic, bicyclic, and polycyclic system, wherein at least one ring system is an aromatic ring system; at least one aromatic ring system includes one or more heteroatoms selected from the group consisting of B, O, N, P, Si, Se, and S; and each ring system includes a ring composed of 5 to 7 atoms and has one or more attachment points attached to the remaining part in the molecule. In the disclosure, the heteroaryl has 3 to 30, or 3 to 18, or 3 to 12 carbon atoms. The heteroaryl can be monocyclic heteroaryl or polycyclic heteroaryl. In other words, the heteroaryl may refer to a single aromatic ring system or multiple aromatic ring systems conjugated through carbon-carbon bonds, wherein each aromatic ring system is an aromatic monocyclic ring or an aromatic fused ring. For example, the heteroaryl may include thienyl, furyl, pyrrolyl, imidazolyl, thiazolyl, oxazolyl, pyridyl, bipyridyl, pyrimidinyl, triazinyl, acridinyl, pyridazinyl, pyrazinyl, quinolinyl, quinazolinyl, quinoxalinyl, phenoxazinyl, phthalazinyl, pyridopyrimidinyl, pyridopyrazinyl, pyrazinopyrazinyl, isoquinolinyl, indolyl, carbazolyl, benzoxazolyl, benzimidazolyl, benzothiazolyl, N-phenylcarbazolyl, benzothienyl, dibenzothienyl, thienothienyl, benzofuranyl, phenanthrolinyl, isoxazolyl, thiadiazolyl, benzothiazolyl, phenothiazinyl, dibenzosilyl, and dibenzofuranyl, but is not limited thereto. The thienyl, furyl, phenanthrolinyl, and the like are heteroaryl with a single aromatic ring system; and the N-phenylcarbazolyl, N-pyridylcarbazolyl, phenyl-substituted dibenzofuranyl, pyridyl-substituted pyridyl, and the like are heteroaryl with multiple aromatic ring systems conjugated through carbon-carbon bonds.

In the disclosure, heteroaryl to serve as a substituent includes, but is not limited to, thienyl, furyl, pyrrolyl, imidazolyl, pyridyl, bipyridyl, pyrimidinyl, triazinyl, phenanthrolinyl, indolyl, carbazolyl, benzoxazolyl, benzimidazolyl, benzothiazolyl, N-phenylcarbazolyl, benzothienyl, dibenzothienyl, dibenzosilyl, and dibenzofuranyl.

In the disclosure, substituted heteroaryl refers to heteroaryl in which one or more hydrogen atoms are substituted by other groups. For example, at least one hydrogen atom is substituted by deuterium, F, Cl, Br, CN, amino, alkyl, haloalkyl, cycloalkyl, aryloxy, arylthio, silyl, alkylamino, arylamino, boranyl, phosphino, aryl, or the like.

It should be explained that one bond, two bonds, or more bonds in the "heteroaryl" can be attached to the remaining part in the molecule.

It should be explained that "substituted $C_3$-$C_{30}$ heteroaryl" refers to substituted heteroaryl with 3 to 30 carbon atoms, which means that the total number of carbon atoms in the heteroaryl and substituents on the heteroaryl is 3 to 30.

Heteroaryl with 3 to 18 ring-forming carbon atoms means that the number of carbon atoms in a heteroaromatic ring of the heteroaryl is 3 to 18, which excludes the number of carbon atoms in substituents on the heteroaryl. The heteroaryl can include 3 to 18, 4 to 18, 12 to 18, 3 to 12, or 3 to 8 ring-forming carbon atoms, but is not limited thereto.

In the disclosure, trialkylsilyl with 3 to 12 carbon atoms refers to

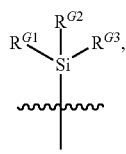

wherein $R^{G1}$, $R^{G2}$, and $R^{G3}$ each is independently alkyl. Specific examples of alkylsilyl include, but are not limited to, trimethylsilyl and triethylsilyl.

In the disclosure, triarylsilyl refers to

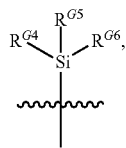

wherein $R^{G4}$, $R^{G5}$, and $R^{G6}$ each is independently aryl. Specific examples of arylsilyl include, but are not limited to triphenylsilyl. In the disclosure, a non-positional bond refers to a single bond

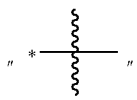

extending from a ring system, which means that one end of the bond can be attached to any position in the ring system through which the bond penetrates, and the other end is attached to the remaining part in the compound molecule. For example, as shown in the following formula (X), the naphthyl represented by the formula (X) is attached to the remaining part in the molecule through two non-positional bonds that penetrate through the bicyclic ring, which indicates any possible attachment modes shown in formula (X-1) to formula (X-10).

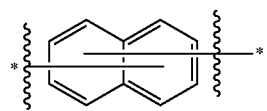 (X)

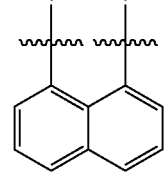 (X-1)

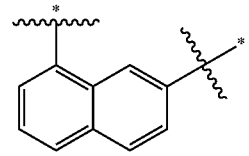 (X-2)

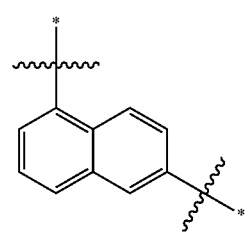 (X-3)

(X-4)

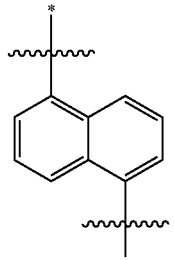 (X-5)

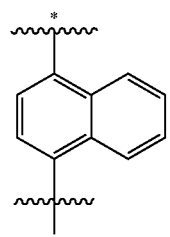 (X-6)

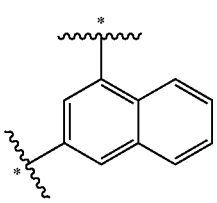 (X-7)

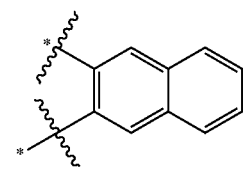

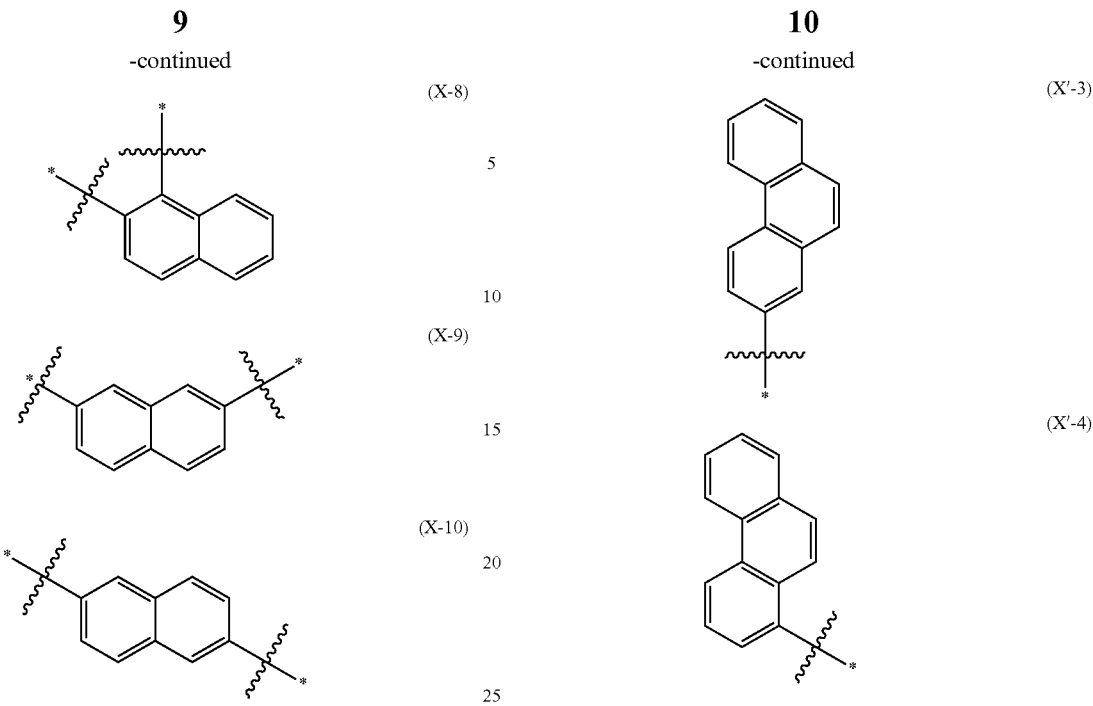

For example, as shown in the following formula (X'), the phenanthryl represented by the formula (X') is attached to the remaining part in the molecule through a non-positional bond extending from the middle of a benzene ring at a side, which indicates any possible attachment modes shown in formula (X'-1) to formula (X'-4).

In the disclosure, a non-positional substituent refers to a substituent linked through a single bond extending from the center of a ring system, which means that the substituent can be attached to any possible position in the ring system. For example, as shown in the following formula (Y), the substituent R represented by the formula (Y) is attached to a quinoline ring through a non-positional bond, which indicates any possible attachment modes shown in formula (Y-1) to formula (Y-7).

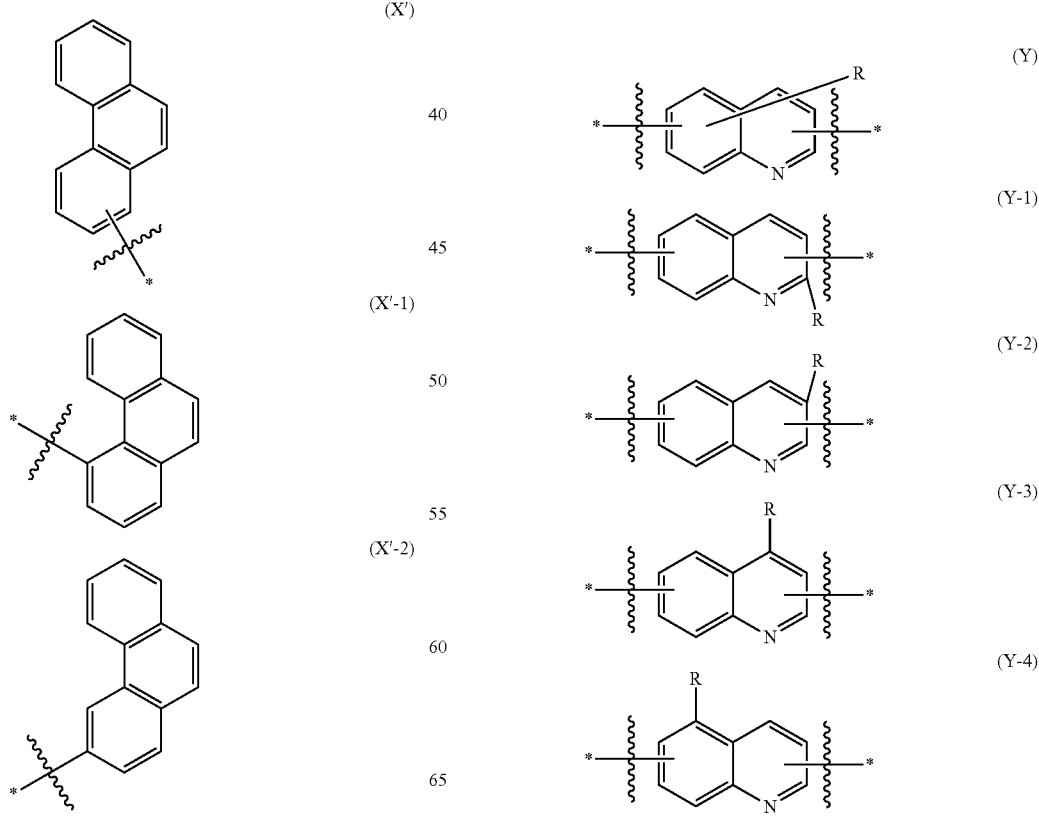

-continued

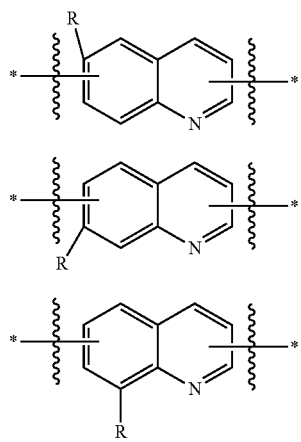

(Y-5)

(Y-6)

(Y-7)

In the disclosure, the explanation of aryl can be applied to arylene, and the explanation of heteroaryl can also be applied to heteroarylene.

The disclosure provides an organic compound, with a structure shown in chemical formula I:

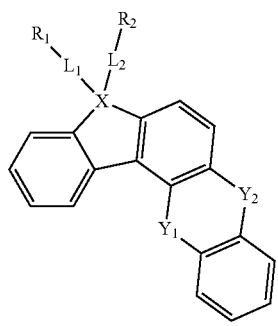

chemical formula I wherein X is selected from: C and Si;

$Y_1$ and $Y_2$ are the same or different, and are each independently selected from: O and S;

$R_1$ and $R_2$ are each independently selected from: hydrogen, deuterium, substituted or unsubstituted alkyl with 1 to 10 carbon atoms, substituted or unsubstituted cycloalkyl with 3 to 10 carbon atoms, substituted or unsubstituted aryl with 6 to 30 carbon atoms, substituted or unsubstituted heteroaryl with 1 to 30 carbon atoms, and

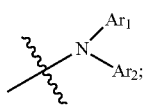

at least one of $R_1$ and $R_2$ is

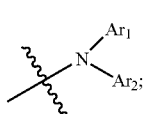

$Ar_1$ and $Ar_2$ are the same or different, and are each independently selected from: hydrogen, deuterium, substituted or unsubstituted aralkyl with 7 to 25 carbon atoms, substituted or unsubstituted heteroaralkyl with 2 to 20 carbon atoms, substituted or unsubstituted aryl with 6 to 30 carbon atoms, and substituted or unsubstituted heteroaryl with 1 to 30 carbon atoms;

$L_1$ and $L_2$ are the same or different, and are each independently selected from: a single bond, substituted or unsubstituted arylene with 6 to 30 carbon atoms, and substituted or unsubstituted heteroarylene with 1 to 30 carbon atoms;

and when $R_1$ is

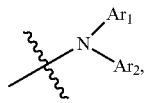

$L_1$ is not a single bond, and when $R_2$ is

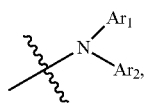

$L_2$ is not a single bond;

substituents of $Ar_1$, substituents of $Ar_2$, substituents of $L_1$, and substituents of $L_2$ are the same or different, and are each independently selected from: deuterium, halogen, cyano, alkyl with 1 to 12 carbon atoms, alkoxy with 1 to 12 carbon atoms, alkylthio with 1 to 12 carbon atoms, haloalkyl with 1 to 12 carbon atoms, trialkylsilyl with 3 to 12 carbon atoms, cycloalkyl with 3 to 12 carbon atoms, aryloxy with 6 to 18 carbon atoms, arylthio with 6 to 18 carbon atoms, aryl with 6 to 18 carbon atoms, and heteroaryl with 3 to 18 carbon atoms.

In some embodiments, the organic compound shown in chemical formula I according to the disclosure is selected from the following compounds:

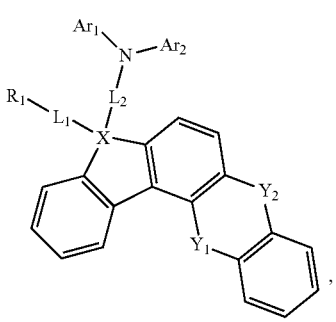

chemical formula 2

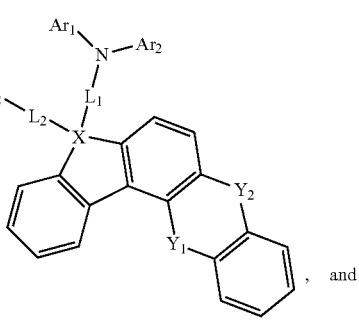

chemical formula 3

, and chemical formula 4

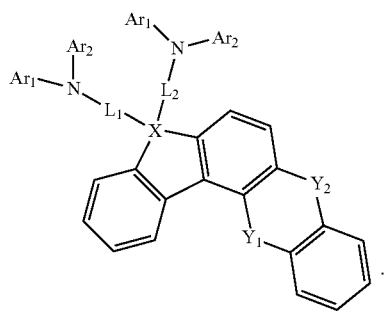

In some embodiments, in the compound shown in chemical formula I of the disclosure, $L_1$ and $L_2$ are the same or different, and are each independently selected from: a single bond, substituted or unsubstituted arylene with 6 to 25 carbon atoms, and substituted or unsubstituted heteroarylene with 4 to 18 carbon atoms.

In some embodiments, in the compound shown in chemical formula I of the disclosure, $L_1$ and $L_2$ are the same or different, and are each independently selected from: a single bond and substituted or unsubstituted the following groups:

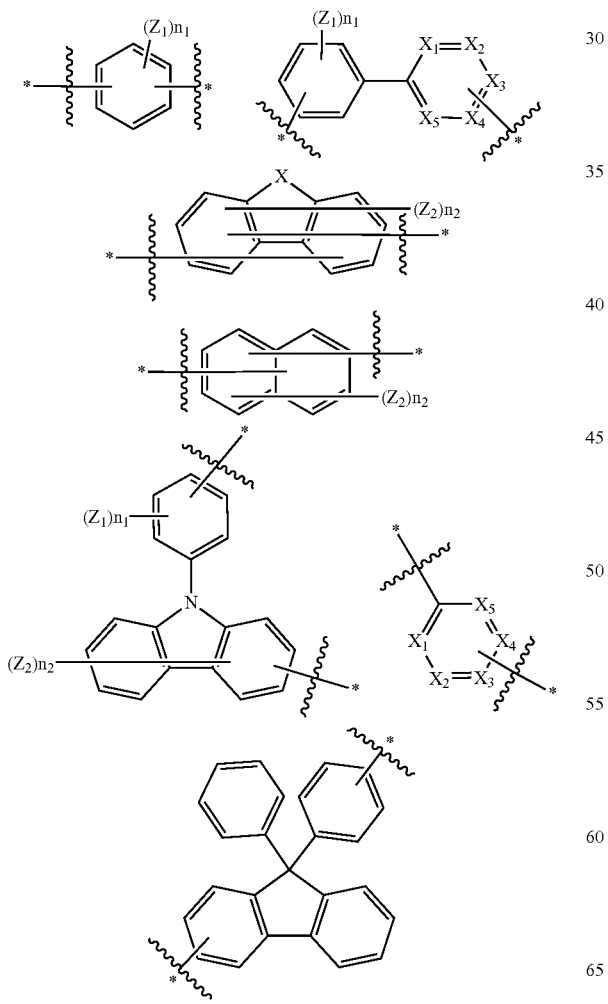

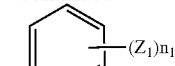

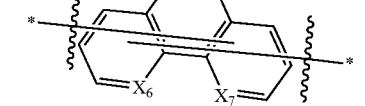
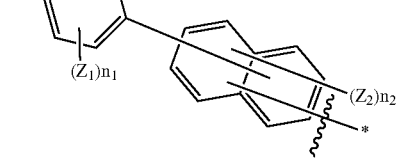
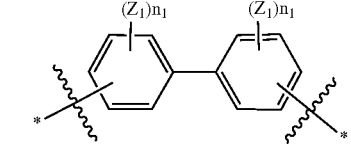
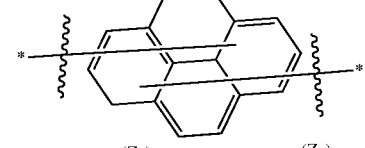
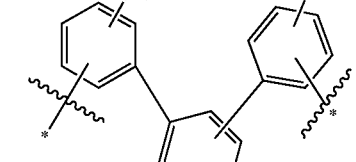
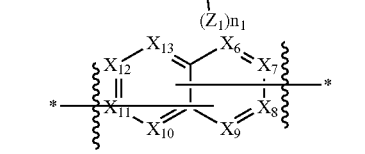
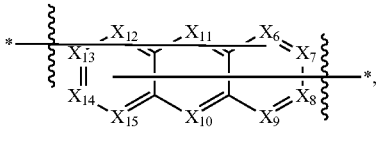

wherein X is selected from: O, S, Se, $C(R_3R_4)$, $N(R_5)$, and $Si(R_3R_4)$;

$X_1$, $X_2$, $X_3$, $X_4$, and $X_5$ are each independently selected from: $CR_6$ and N, and at least one of $X_1$ to $X_5$ is N;

$X_6$ to $X_{15}$ are each independently selected from: $CR_6$ and N, and when a group includes two or more $R_6$ groups, any two of the $R_6$ groups are the same or different;

$Z_1$, $Z_2$, $R_3$, $R_4$, and $R_6$ are each independently selected from: hydrogen, deuterium, fluorine, chlorine, bromine, cyano, alkyl with 1 to 6 carbon atoms, haloalkyl with 1 to 6 carbon atoms, alkoxy with 1 to 6 carbon atoms, aryloxy with 6 to 18 carbon atoms, arylthio with 6 to 18 carbon atoms, aryl with 6 to 12 carbon atoms, heteroaryl with 3 to 12 carbon atoms, alkylsilyl with 3 to 12 carbon atoms, and cycloalkyl with 3 to 10 carbon atoms; or, optionally, $R_3$ and $R_4$, which are attached to the same atom, are linked together to form a saturated or unsaturated 5- to 10-membered aliphatic ring (that is, in the disclosure, $R_3$ and $R_4$, together with the atom attached to $R_3$ and $R_4$, can form an aliphatic ring, or $R_3$ and $R_4$ can exist independently of each other);

$R_5$ is selected from: hydrogen, alkyl with 1 to 6 carbon atoms, haloalkyl with 1 to 6 carbon atoms, aryl with 6 to 12 carbon atoms, heteroaryl with 3 to 12 carbon atoms, and cycloalkyl with 3 to 10 carbon atoms;

$n_1$ each is independently selected from: 0, 1, 2, 3, 4, and 5, and $n_2$ each is independently selected from: 0, 1, 2, 3, 4, 5, 6, and 7.

In some embodiments, in the compound shown in chemical formula I of the disclosure, $L_1$ and $L_2$ are the same or different, and are each independently selected from: a single bond, substituted or unsubstituted arylene with 6 to 12 carbon atoms, and substituted or unsubstituted heteroarylene with 9 to 12 carbon atoms. Further, substituents of $L_1$ and substituents of $L_2$ are each independently selected from: deuterium, fluorine, chlorine, cyano, methyl, ethyl, isopropyl, tert-butyl, methoxy, ethoxy, isopropoxy, propoxy, cyclopentyl, cyclohexyl, trifluoromethyl, phenyl, naphthyl, trimethylsilyl, and triphenylsilyl.

In some more specific embodiments, in the compound shown in chemical formula I of the disclosure, $L_1$ and $L_2$ are the same or different, and are each independently selected from: a single bond, substituted or unsubstituted phenylene, substituted or unsubstituted naphthylene, substituted or unsubstituted anthracenylene, substituted or unsubstituted phenanthrylene, substituted or unsubstituted biphenylene, substituted or unsubstituted terphenylene, substituted or unsubstituted fluorenylene, substituted or unsubstituted dibenzofuranylene, substituted or unsubstituted dibenzothienylene, substituted or unsubstituted pyridylene, substituted or unsubstituted quinolinylene, substituted or unsubstituted carbazolylene, and substituted or unsubstituted N-phenylcarbazolylene, and a subunit formed by linking two or three thereof through single bonds; and $L_1$ or $L_2$ is optionally substituted by 0, 1, 2, 3, 4 or 5 substituents, and the substituents are each independently selected from: deuterium, fluorine, chlorine, cyano, methyl, ethyl, isopropyl, tert-butyl, methoxy, ethoxy, isopropoxy, propoxy, cyclopentyl, cyclohexyl, trifluoromethyl, phenyl, naphthyl, trimethylsilyl, and triphenylsilyl.

In some more specific embodiments, in the compound shown in chemical formula I of the disclosure, $L_1$ and $L_2$ are the same or different, and are each independently selected from: a single bond and substituted or unsubstituted the following groups:

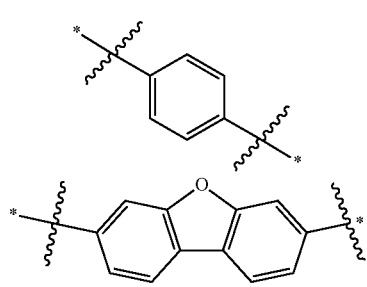

-continued

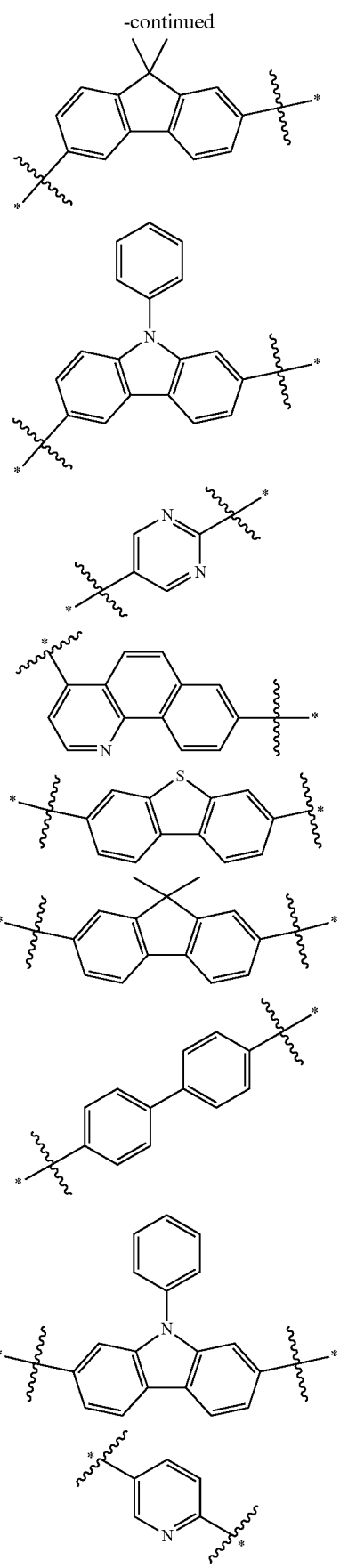

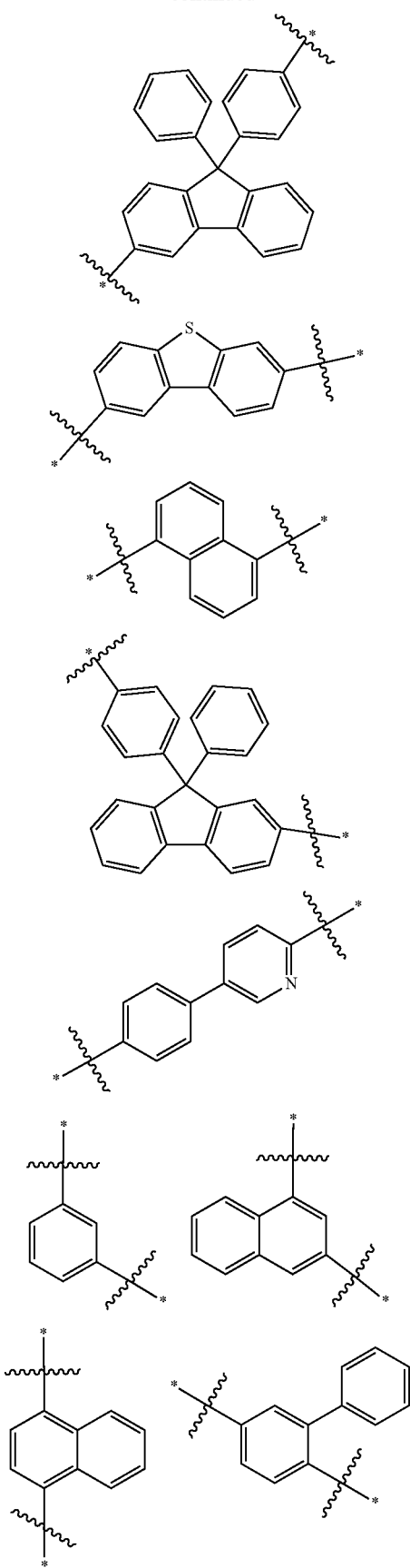
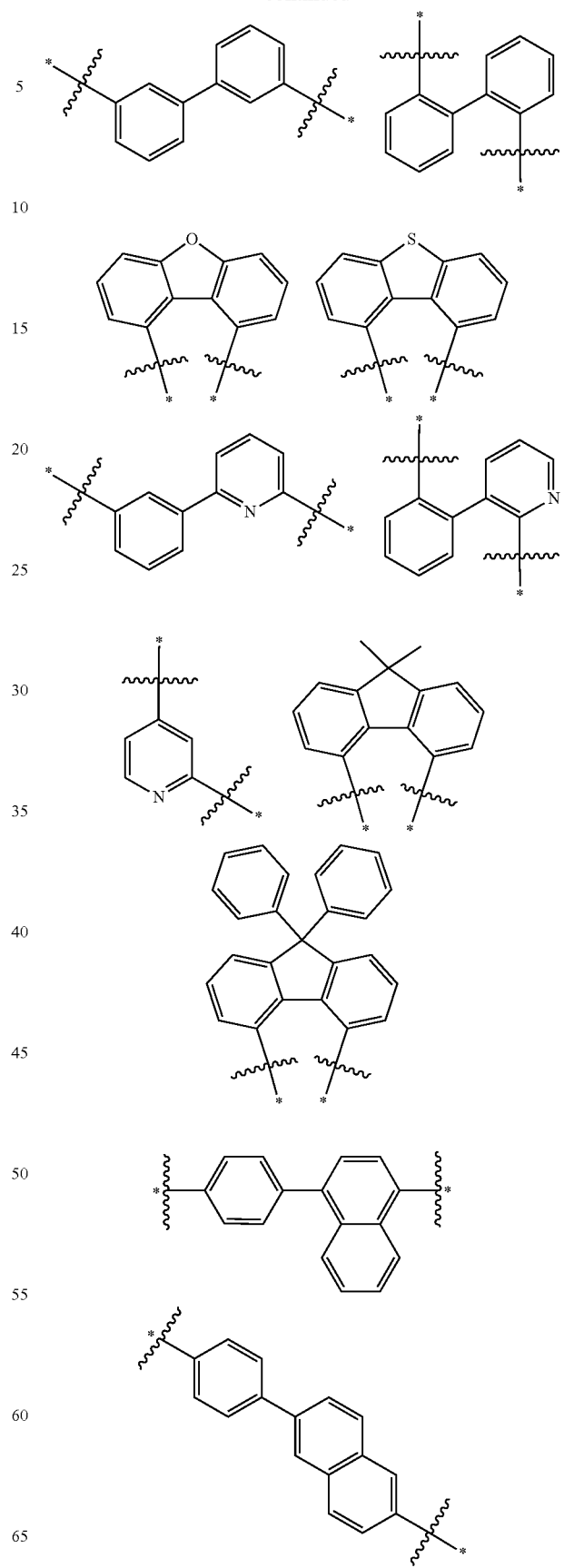

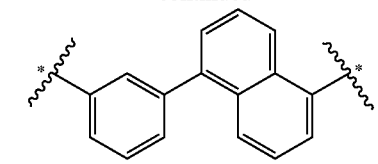

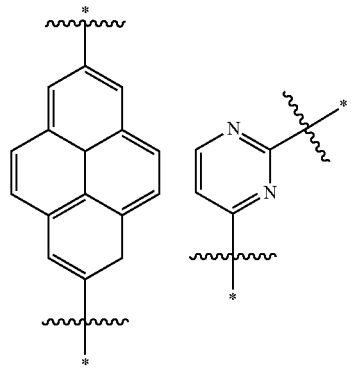

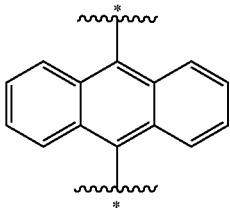

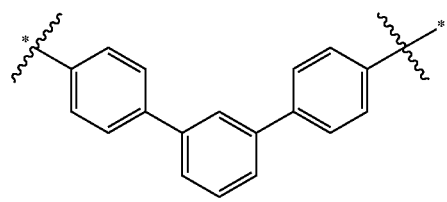

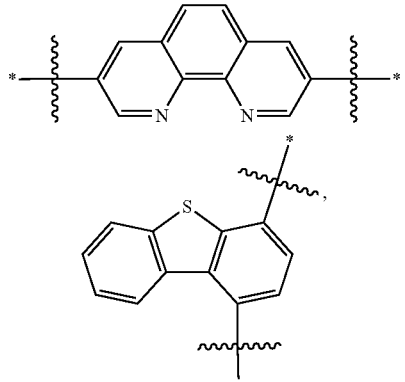

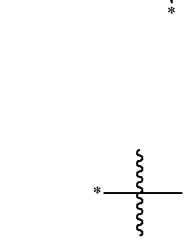

wherein

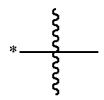

means that a position where the above group is intended to link to

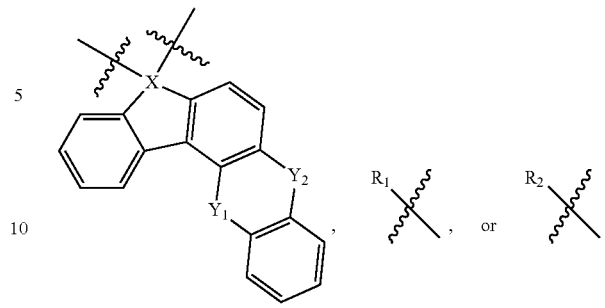

in the chemical formula I; and the above groups are each optionally substituted by 0, 1, 2, 3, 4, or 5 substituents, and the substituents are each independently selected from: deuterium, fluorine, chlorine, cyano, methyl, ethyl, isopropyl, tert-butyl, methoxy, ethoxy, isopropoxy, propoxy, cyclopentyl, cyclohexyl, trifluoromethyl, and alkylsilyl with 3 to 9 carbon atoms.

In some more specific embodiments, in the compound shown in chemical formula I of the disclosure, $L_1$ and $L_2$ are the same or different, and are each independently selected from: a single bond and substituted or unsubstituted the following groups:

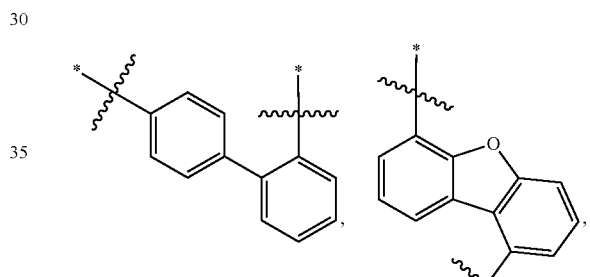

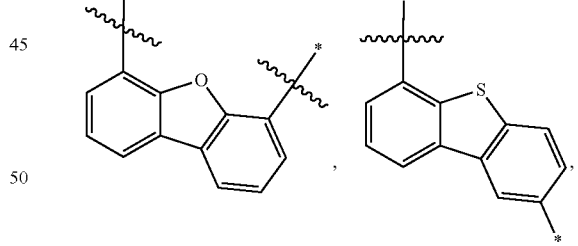

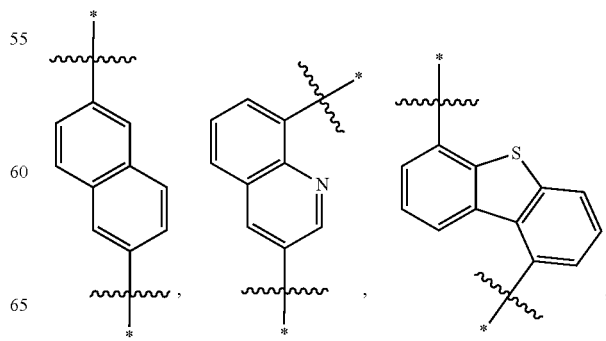

-continued

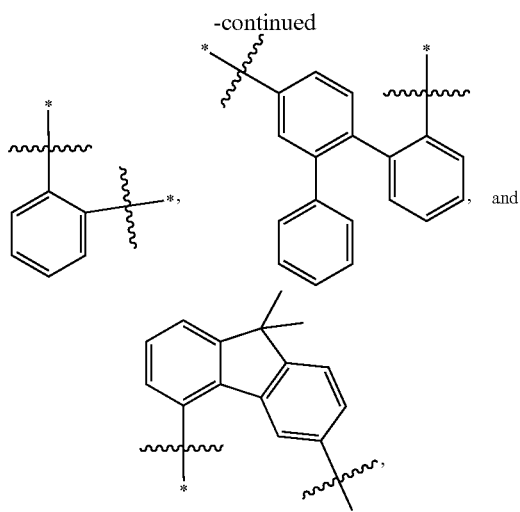
and wherein

means that a position where the above group is intended to link to

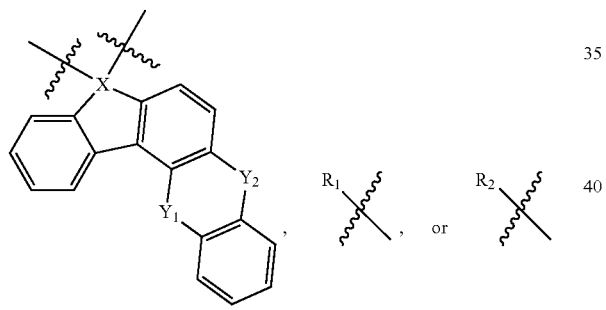

in the chemical formula I; and the above groups are each optionally substituted by 0, 1, 2, 3, 4, or 5 substituents, and the substituents are each independently selected from: deuterium, fluorine, chlorine, cyano, methyl, ethyl, isopropyl, tert-butyl, methoxy, ethoxy, isopropoxy, propoxy, cyclopentyl, cyclohexyl, trifluoromethyl, phenyl, naphthyl, trimethylsilyl, and triphenylsilyl.

However, in the disclosure, $L_1$ and $L_2$ in the compound shown in chemical formula I are not limited to the above structures.

In some embodiments, in the compound shown in chemical formula I of the disclosure, $Ar_1$, $Ar_2$, $R_1$, and $R_2$ are the same or different, and are each independently selected from: substituted or unsubstituted aryl with 6 to 25 carbon atoms, and substituted or unsubstituted heteroaryl with 4 to 18 carbon atoms.

In some embodiments, in the compound shown in chemical formula I of the disclosure, $Ar_1$, $Ar_2$, $R_1$, and $R_2$ are the same or different, and are each independently selected from: substituted or unsubstituted aryl with 6 to 18 carbon atoms, and substituted or unsubstituted heteroaryl with 5 to 12 carbon atoms.

In some embodiments, substituents of $Ar_1$, substituents of $Ar_2$, substituents of $R_1$, and substituents of $R_2$ are the same or different, are each independently selected from: deuterium, fluorine, chlorine, cyano, methyl, ethyl, isopropyl, tert-butyl, methoxy, ethoxy, isopropoxy, propoxy, cyclopentyl, cyclohexyl, trifluoromethyl, phenyl, naphthyl, dibenzofuranyl, dibenzothienyl, carbazolyl, and trimethylsilyl.

In some embodiments, the substituents of $Ar_1$, substituents of $Ar_2$, substituents of $R_1$, and substituents of $R_2$ are the same or different, and are each independently selected from: deuterium, halogen, cyano, alkyl with 1 to 4 carbon atoms, alkoxy with 1 to 4 carbon atoms, alkylthio with 1 to 4 carbon atoms, haloalkyl with 1 to 4 carbon atoms, trimethylsilyl, triphenylsilyl, cycloalkyl with 5 to 10 carbon atoms, aryloxy with 6 to 18 carbon atoms, arylthio with 6 to 18 carbon atoms, aryl with 6 to 18 carbon atoms, and heteroaryl with 3 to 18 carbon atoms.

In some embodiments, in the compound shown in chemical formula I of the disclosure, $Ar_1$, $Ar_2$, $R_1$, and $R_2$ are the same or different, and are each independently selected from: hydrogen, deuterium, and substituted or unsubstituted the following groups:

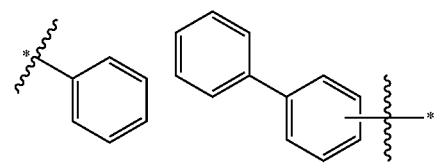

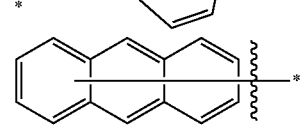

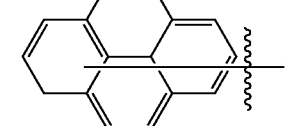

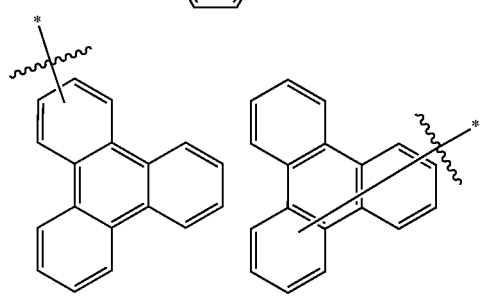

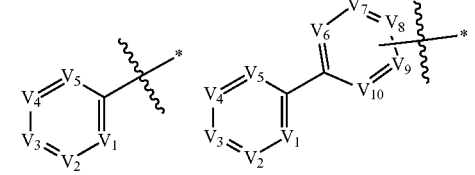

-continued

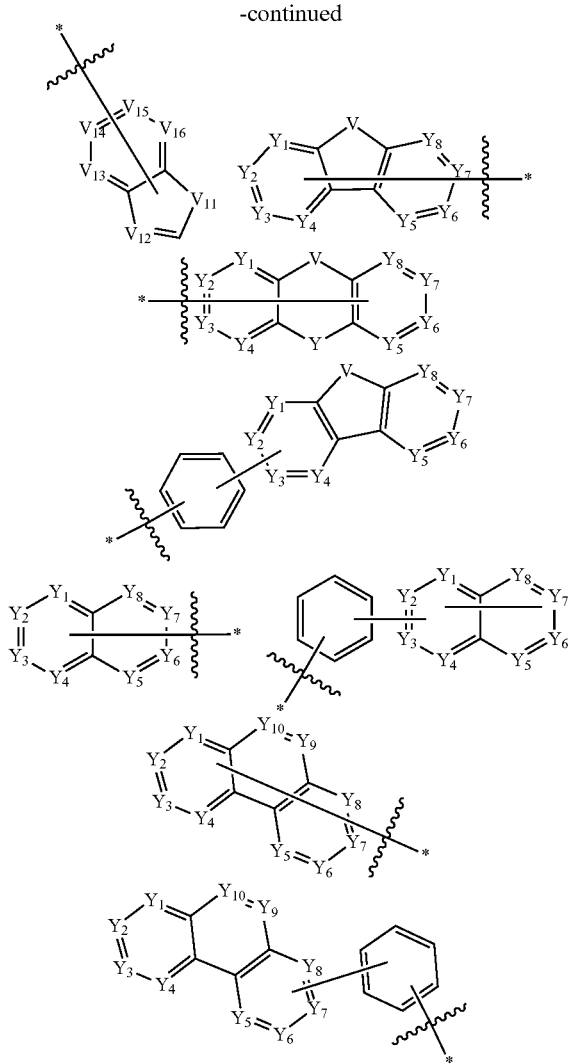

wherein $V_1$ to $V_{10}$, and $V_{12}$ to $V_{16}$ are each independently selected from: $CR_8$ and N, and at least one of $V_1$ to $V_5$ is N;

each of V is independently selected from: O, S, Se, $N(R_7)$, $C(R_9R_{10})$, and $Si(R_9R_{10})$;

Y and $V_{11}$ are each independently selected from: O, S, and $N(R_7)$;

$Y_1$ to $Y_{10}$ are each independently selected from: $C(R_8)$ and N, and when a group includes two or more $R_8$ groups, any two of the $R_8$ groups are the same or different;

$R_9$, $R_{10}$, and $R_8$ are each independently selected from: hydrogen, deuterium, fluorine, chlorine, bromine, cyano, alkyl with 1 to 6 carbon atoms, haloalkyl with 1 to 6 carbon atoms, aryl with 6 to 12 carbon atoms, heteroaryl with 3 to 12 carbon atoms, aryloxy with 6 to 18 carbon atoms, arylthio with 6 to 18 carbon atoms, alkylsilyl with 3 to 12 carbon atoms, alkylamino with 1 to 10 carbon atoms, arylamino with 6 to 18 carbon atoms, and cycloalkyl with 3 to 10 carbon atoms;

$R_7$ is selected from: hydrogen, alkyl with 1 to 6 carbon atoms, haloalkyl with 1 to 6 carbon atoms, aryl with 6 to 12 carbon atoms, heteroaryl with 3 to 12 carbon atoms, and cycloalkyl with 3 to 10 carbon atoms; or optionally, two adjacent $R_8$ groups, and carbon atoms being linked to the two adjacent $R_8$ groups, form an aromatic ring with 6 to 10 ring-forming atoms or a heteroaromatic ring with 5 to 12 ring-forming atoms (that is, in the disclosure, two adjacent $R_8$ groups, and carbon atoms being linked to the two adjacent $R_8$ groups, can form an aromatic ring or a heteroaromatic ring, or the $R_8$ groups can exist independently);

optionally, $R_9$ and $R_{10}$, which are attached to the same atom, are linked together to form a saturated or unsaturated 5- to 10-membered aliphatic ring (that is, in the disclosure, $R_9$ and $R_{10}$, together with the atom attached to $R_9$ and $R_{10}$, can form an aliphatic ring, or $R_9$ and $R_{10}$ can exist independently of each other);

$Ar_1$ and $Ar_2$ are each optionally substituted by 0, 1, 2, 3, 4, or 5 substituents, and each of the substituents is independently selected from: deuterium, fluorine, chlorine, cyano, alkyl with 1 to 6 carbon atoms, cycloalkyl with 3 to 10 carbon atoms, aryl with 6 to 18 carbon atoms, heteroaryl with 3 to 18 carbon atoms, alkoxy with 1 to 4 carbon atoms, haloalkyl with 1 to 4 carbon atoms, and alkylsilyl with 3 to 9 carbon atoms.

In some embodiments, in the compound shown in chemical formula I of the disclosure, $Ar_1$, $Ar_2$, $R_1$, and $R_2$ are the same or different, and are each independently selected from: hydrogen, deuterium, and substituted or unsubstituted the following groups:

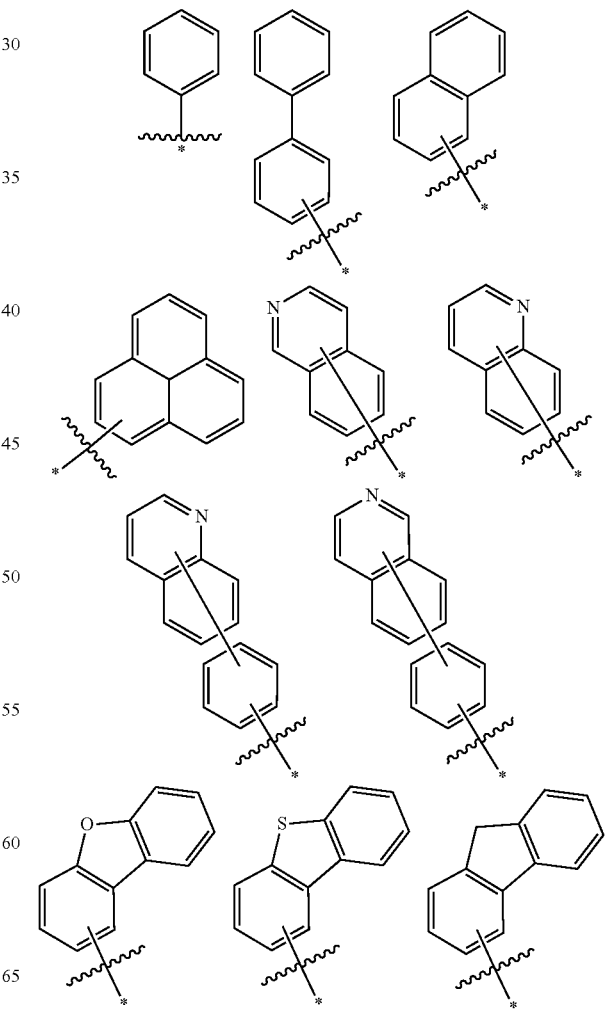

-continued
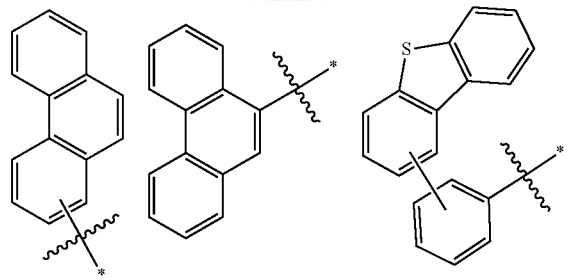
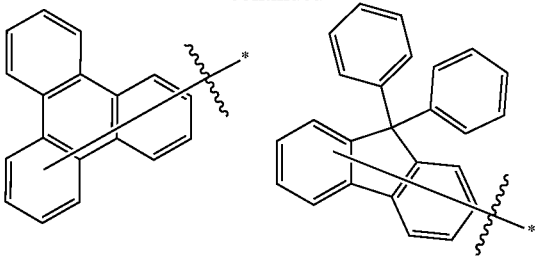
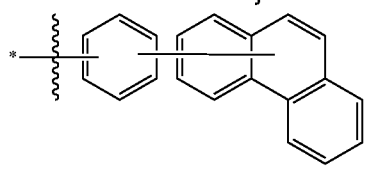
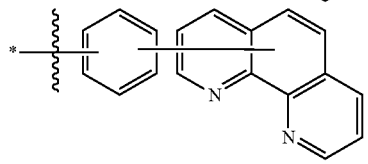
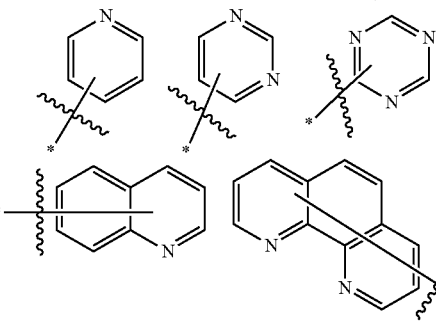
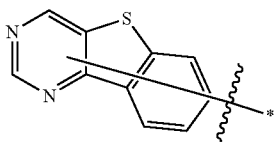
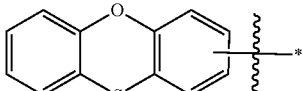
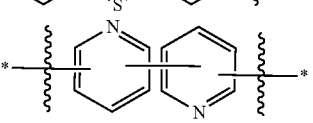
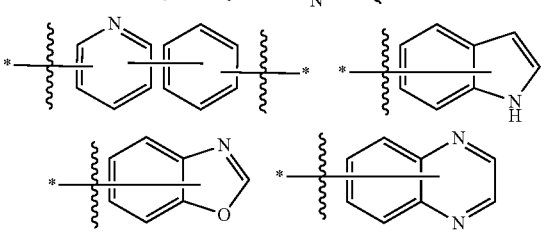

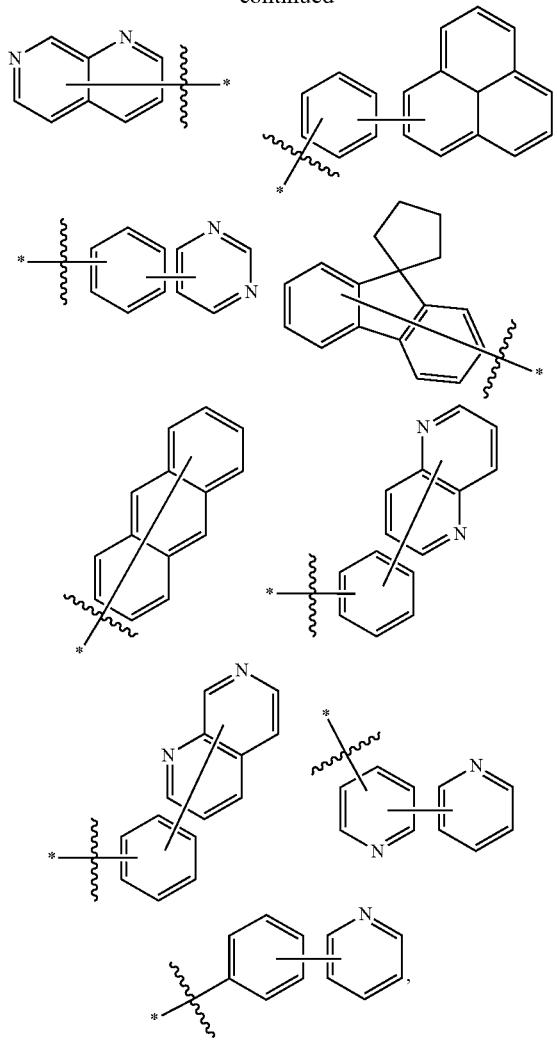

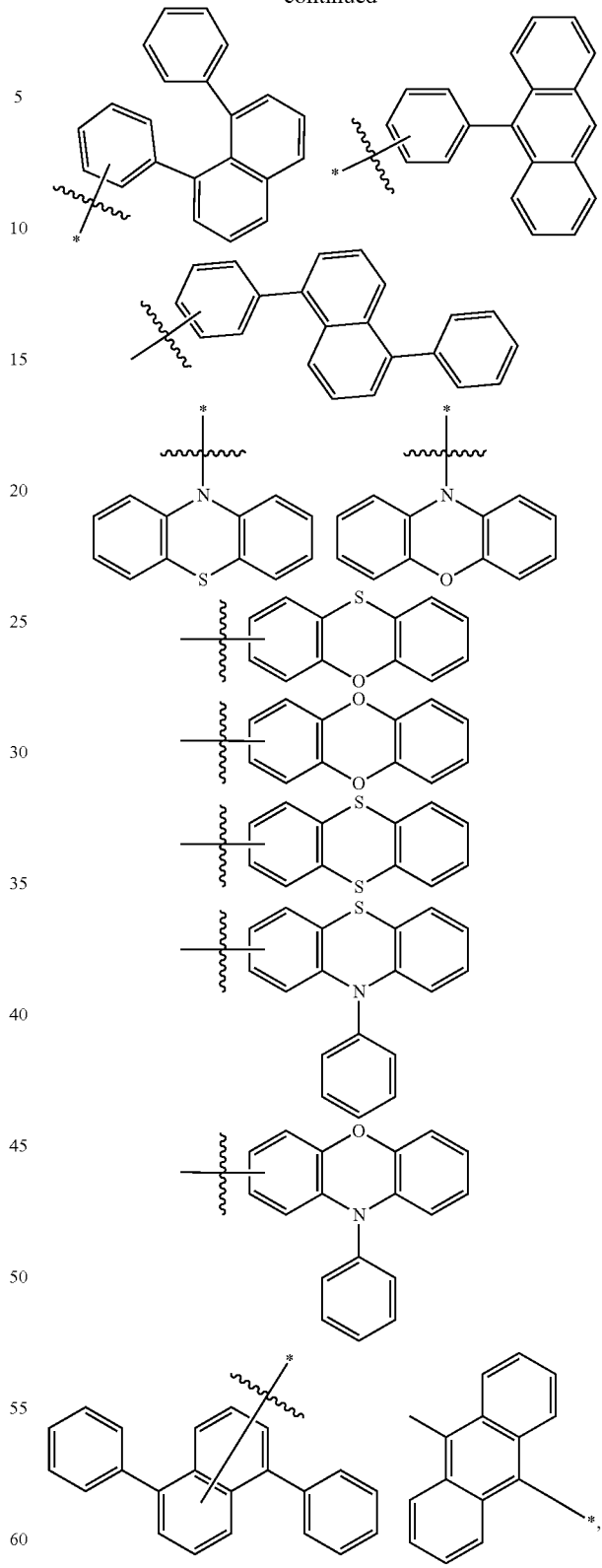

wherein the above groups are each optionally substituted by 0, 1, 2, 3, 4, or 5 substituents, and each of the substituents is independently selected from: deuterium, fluorine, chlorine, cyano, alkyl with 1 to 6 carbon atoms, alkoxy with 1 to 4 carbon atoms, haloalkyl with 1 to 4 carbon atoms, alkylsilyl with 3 to 9 carbon atoms, cycloalkyl with 3 to 10 carbon atoms, aryl with 6 to 18 carbon atoms, and heteroaryl with 3 to 18 carbon atoms.

In some embodiments, in the compound shown in chemical formula I of the disclosure, $Ar_1$, $Ar_2$, $R_1$, and $R_2$ are the same or different, and are each independently selected from: hydrogen, deuterium, and substituted or unsubstituted the following groups:

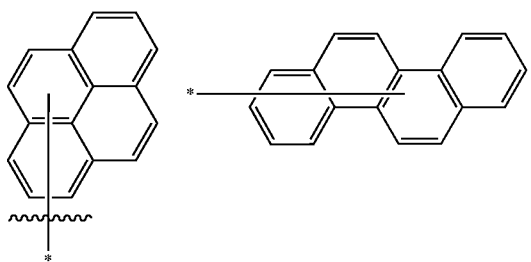

wherein the above groups are each optionally substituted by 0, 1, 2, 3, 4, or 5 substituents, and each of the substituents is independently selected from: deuterium, fluorine, chlorine, cyano, alkyl with 1 to 6 carbon atoms, alkoxy with 1 to 4 carbon atoms, haloalkyl with 1 to 4 carbon atoms, trimethylsilyl, cycloalkyl with 3 to 10 carbon atoms, aryl with 6 to 13 carbon atoms, and heteroaryl with 3 to 12 carbon atoms.

In some more specific embodiments, in the compound shown in chemical formula I of the disclosure, $Ar_1$ and $Ar_2$ are the same or different, and are each e independently selected from: hydrogen, deuterium, and substituted or unsubstituted the following groups:

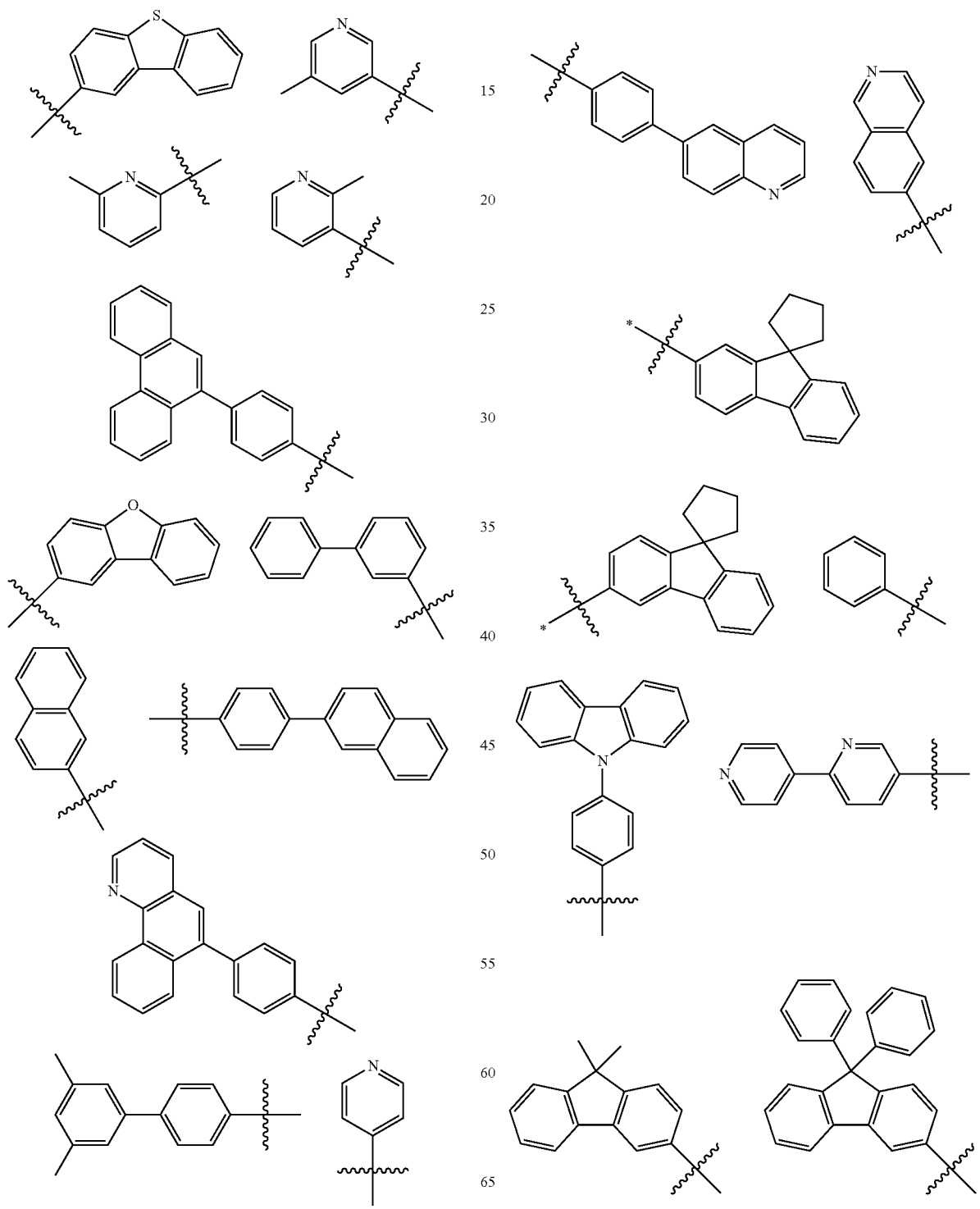

-continued
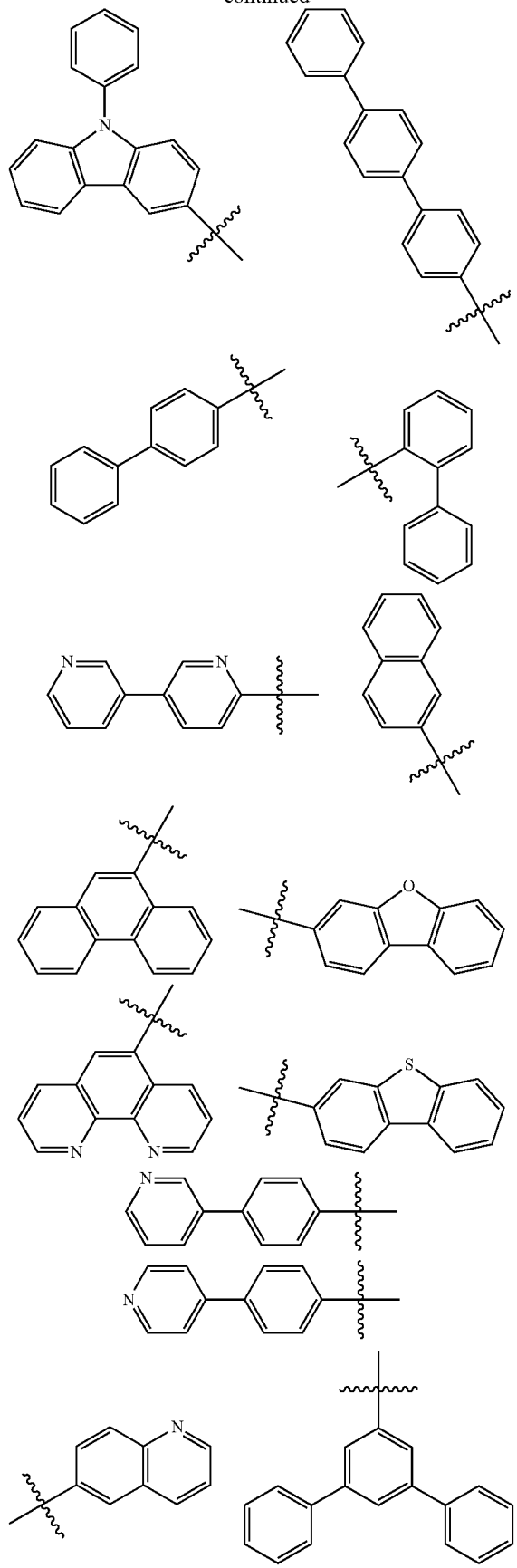
-continued
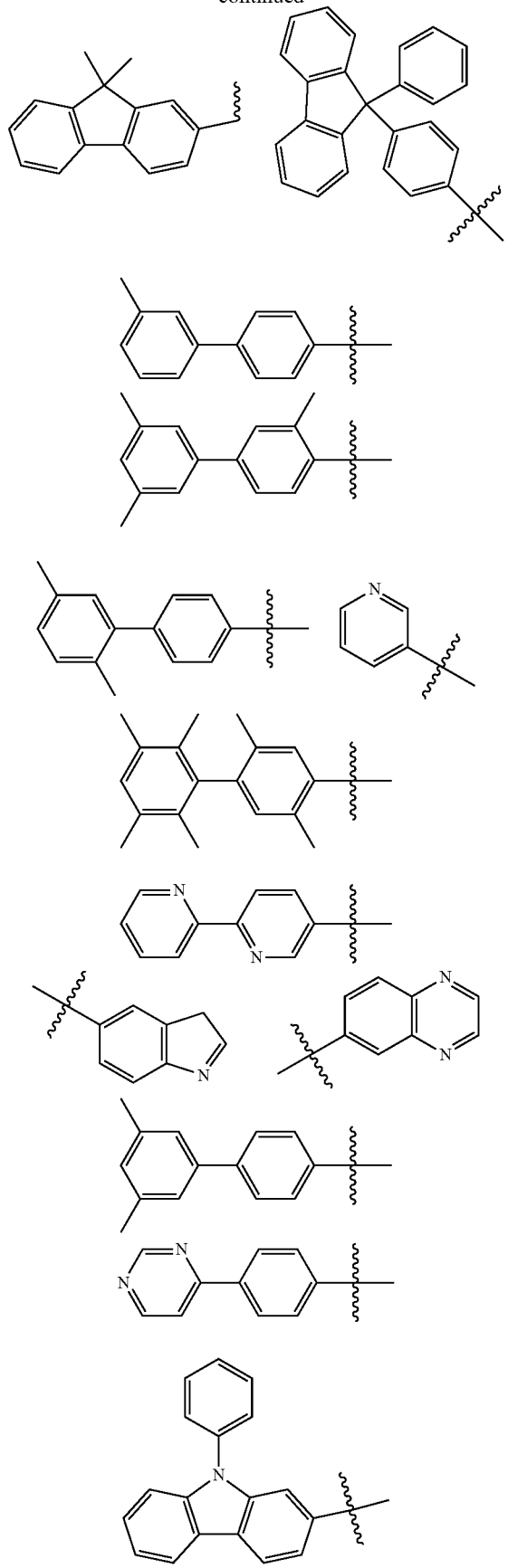

-continued

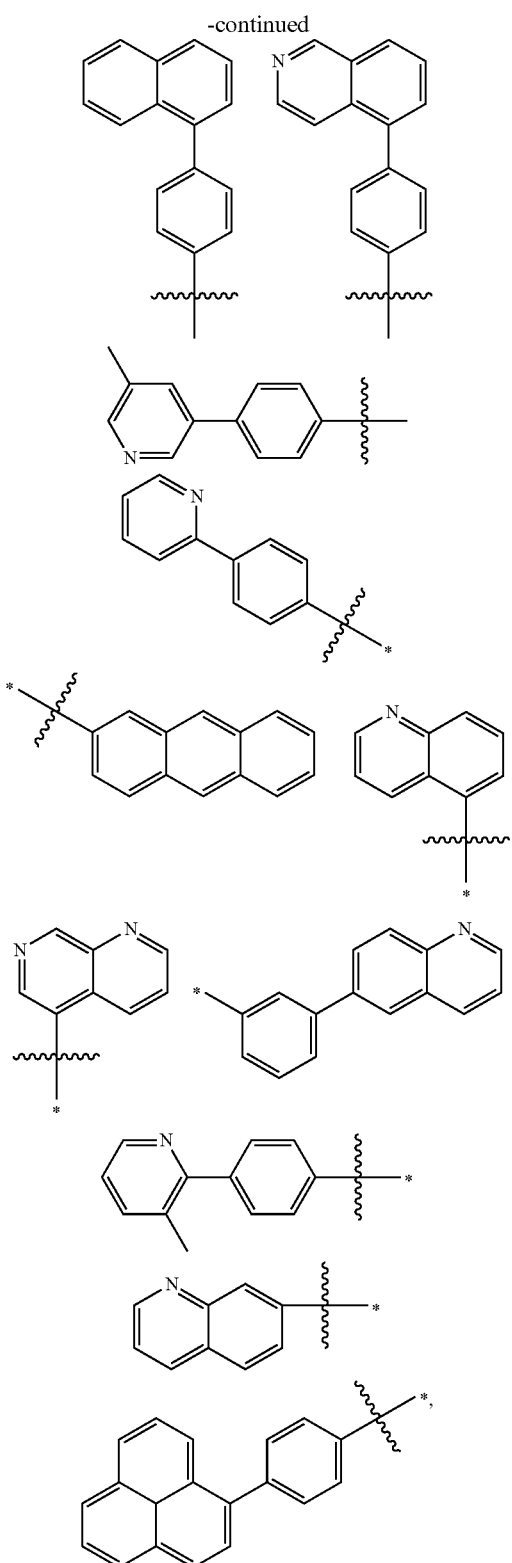

wherein the above groups are each optionally substituted by 0, 1, 2, 3, 4, or 5 substituents, and the substituents are each independently selected from: deuterium, fluorine, chlorine, cyano, methyl, ethyl, isopropyl, tert-butyl, methoxy, ethoxy, isopropoxy, propoxy, cyclopentyl, cyclohexyl, trifluoromethyl, and alkylsilyl with 3 to 9 carbon atoms.

In some more specific embodiments, in the compound shown in chemical formula I of the disclosure, $Ar_1$ and $Ar_2$ are the same or different, and are each independently selected from: hydrogen, deuterium, and substituted or unsubstituted the following groups:

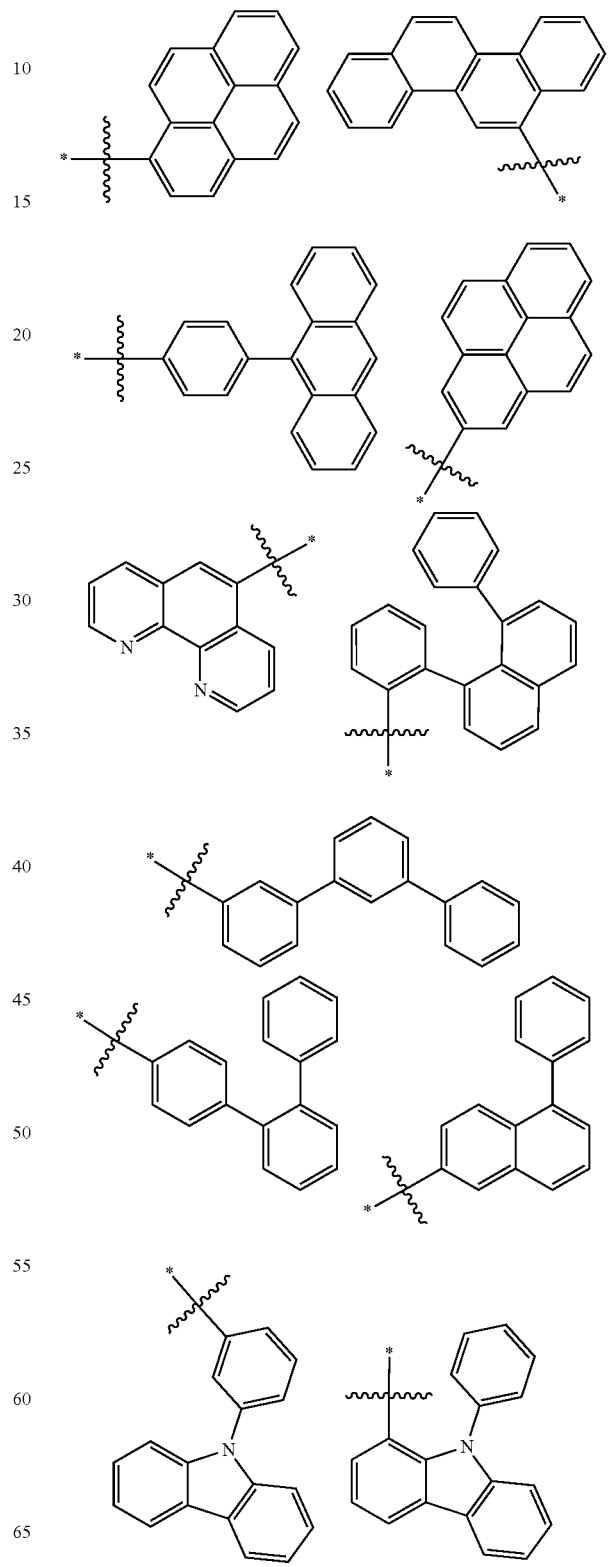

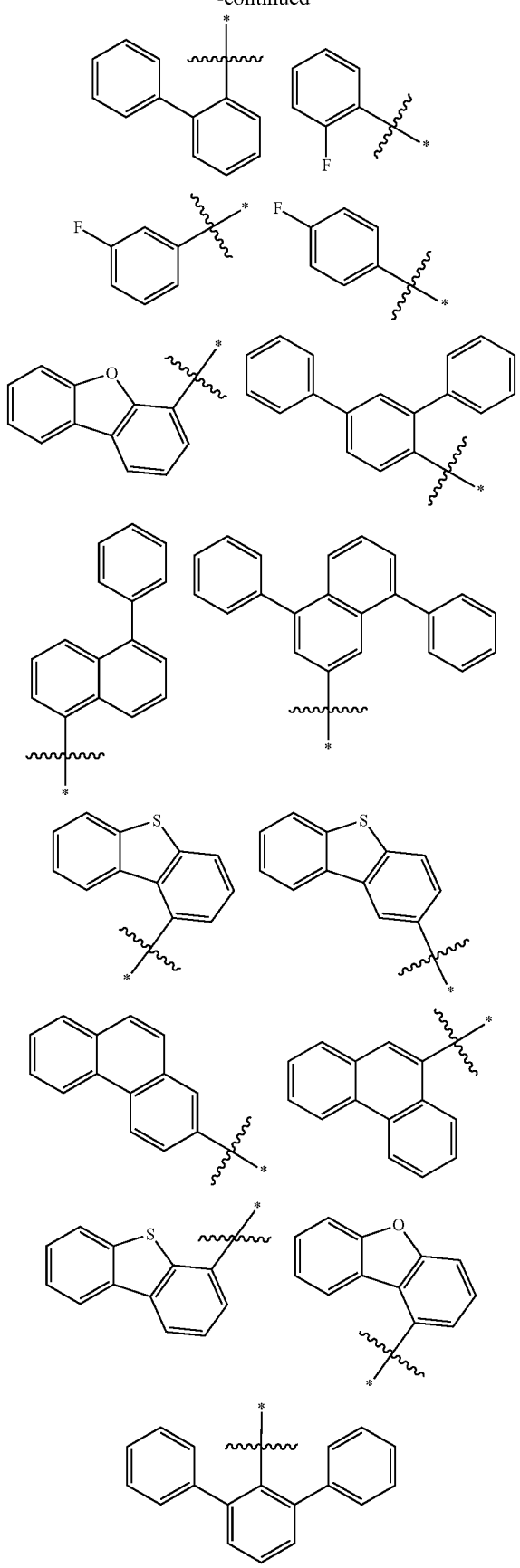
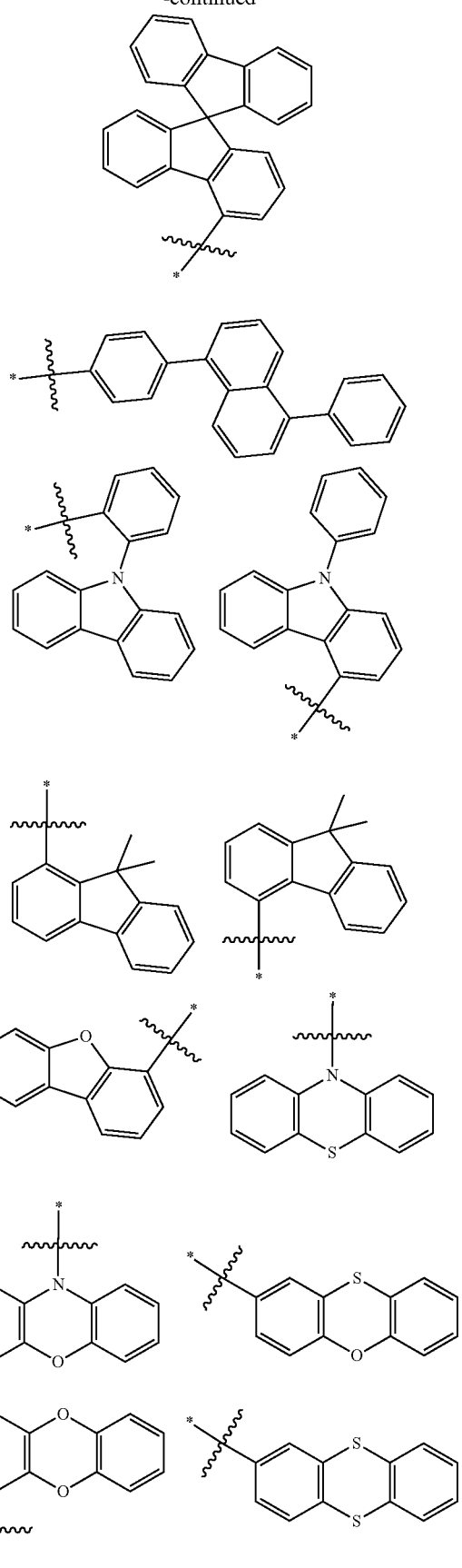

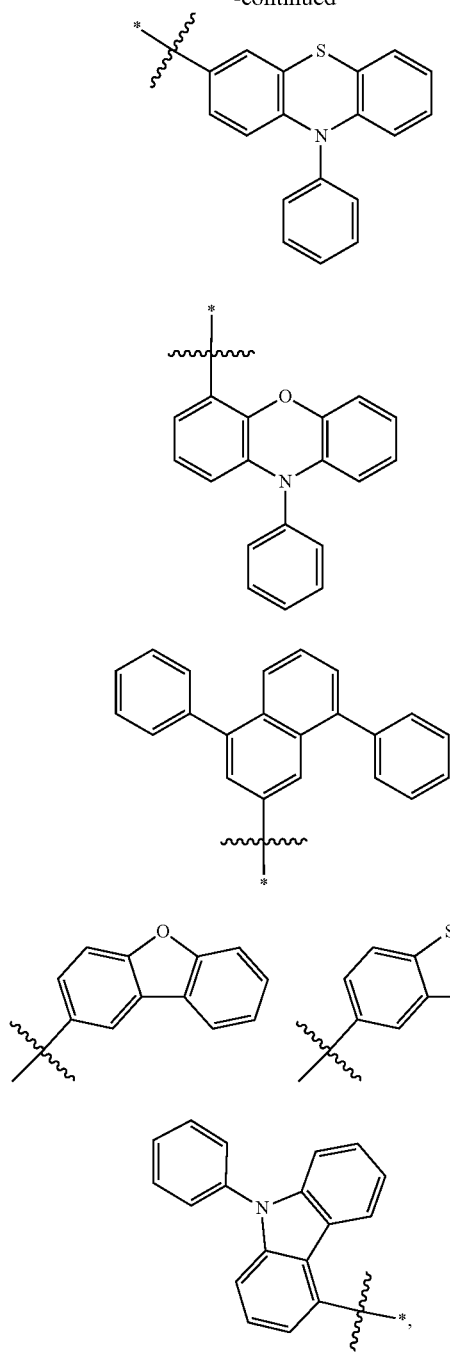

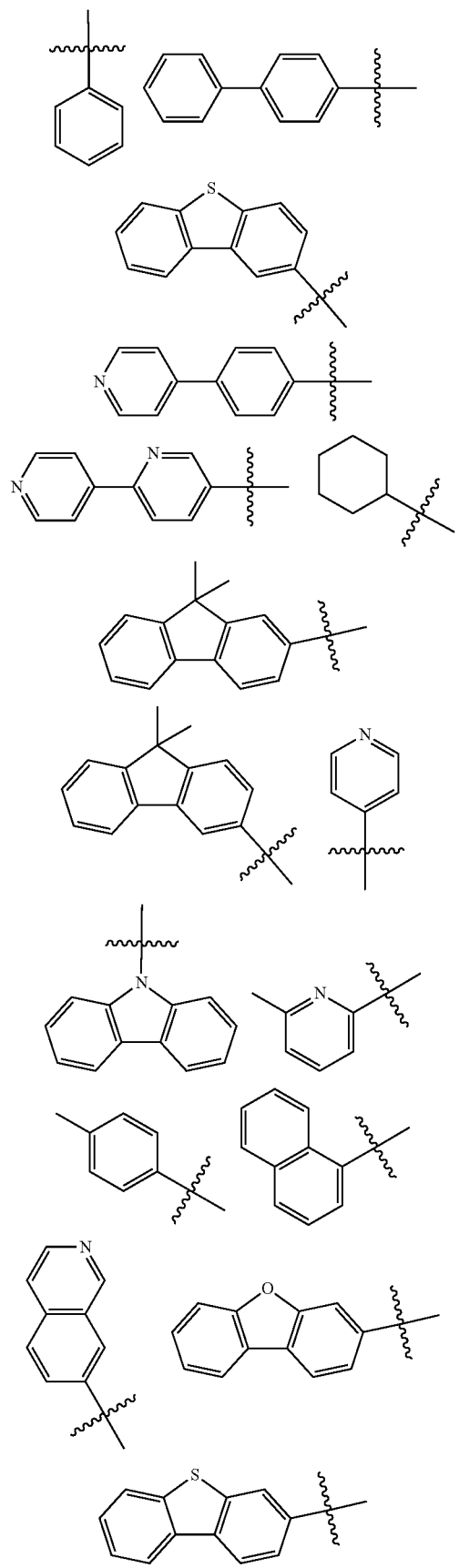

wherein the above groups are each optionally substituted by 0, 1, 2, 3, 4, or 5 substituents, and each of the substituents is independently selected from: deuterium, fluorine, chlorine, cyano, methyl, ethyl, isopropyl, tert-butyl, methoxy, ethoxy, isopropoxy, propoxy, cyclopentyl, cyclohexyl, trifluoromethyl, trimethylsilyl, phenyl, and naphthyl.

In some other embodiments, $Ar_1$ and $Ar_2$ in the compound shown in chemical formula I of the disclosure are not limited to the above groups.

Further, in the compound shown in chemical formula I of the disclosure, $R_1$ and $R_2$ are the same or different, and are each independently selected from: hydrogen, deuterium, and substituted or unsubstituted the following groups:

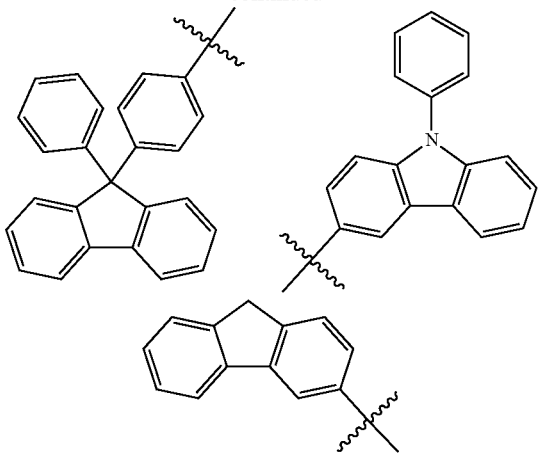

wherein the above groups are each optionally substituted by 0, 1, 2, 3, 4, or 5 substituents, and each of the substituents is independently selected from: deuterium, fluorine, chlorine, cyano, methyl, ethyl, isopropyl, tert-butyl, methoxy, ethoxy, isopropoxy, propoxy, cyclopentyl, cyclohexyl, trifluoromethyl, and alkylsilyl with 3 to 9 carbon atoms.

Further, in the compound shown in chemical formula I of the disclosure, $R_1$ and $R_2$ are the same or different, and are each independently selected from: hydrogen, deuterium, and substituted or unsubstituted the following groups:

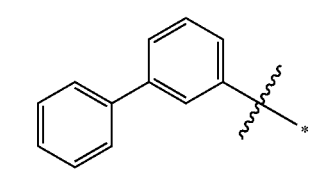

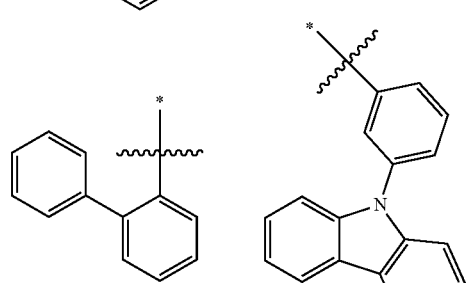

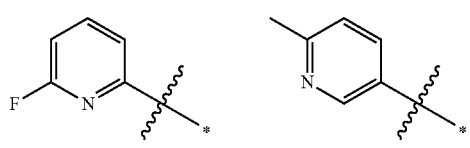

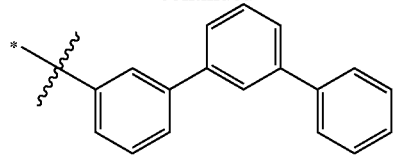

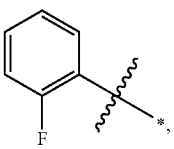

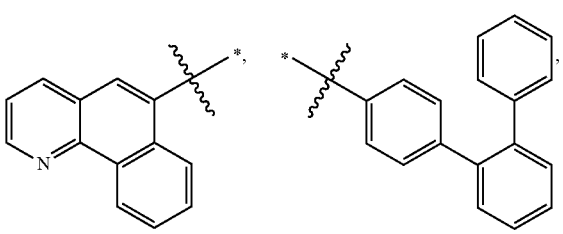

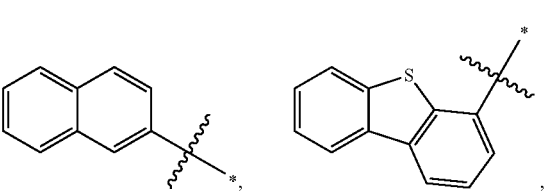

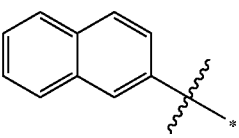

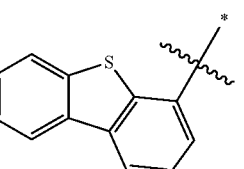

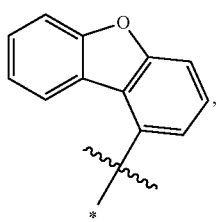

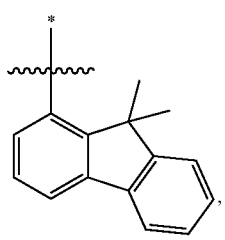

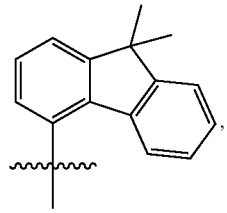

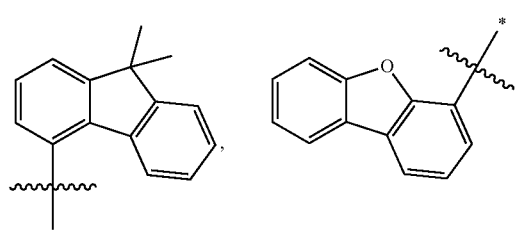

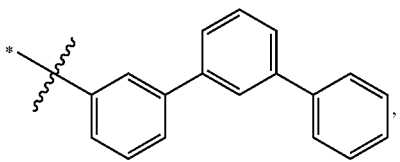

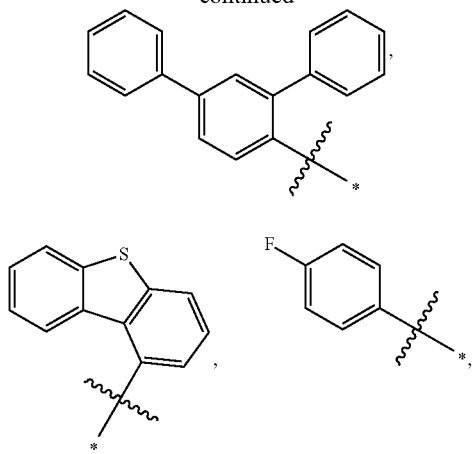

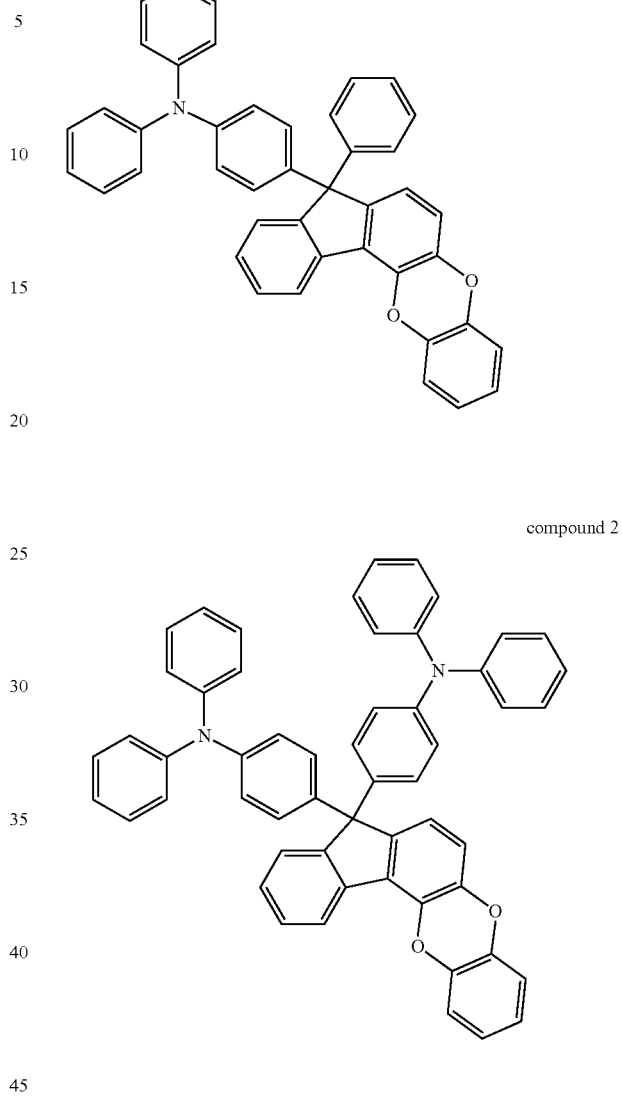

compound 1 compound 2

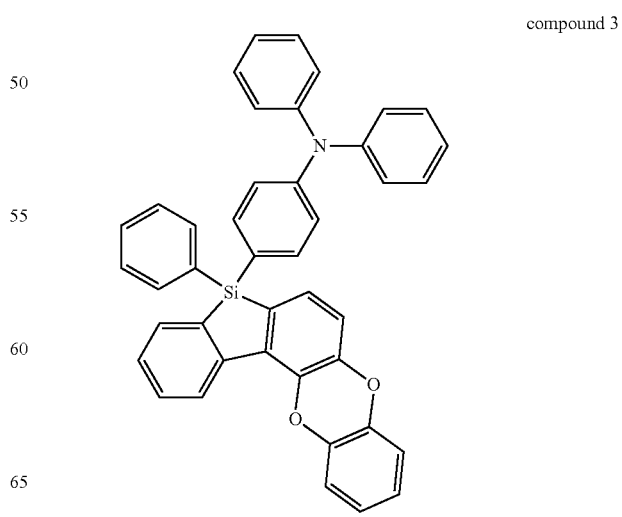

compound 3 wherein the above groups are each optionally substituted by 0, 1, 2, 3, 4, or 5 substituents, and each of the substituents is independently selected from: deuterium, fluorine, chlorine, cyano, methyl, ethyl, isopropyl, tert-butyl, methoxy, ethoxy, isopropoxy, propoxy, cyclopentyl, cyclohexyl, trifluoromethyl, phenyl, naphthyl, and alkylsilyl with 3 to 9 carbon atoms.

In some other embodiments, $R_1$ and $R_2$ in the compound shown in chemical formula I of the disclosure are not limited to the above groups.

Further, a specific compound of the chemical formula I is selected from the following compounds, but is not limited thereto:

compound 4
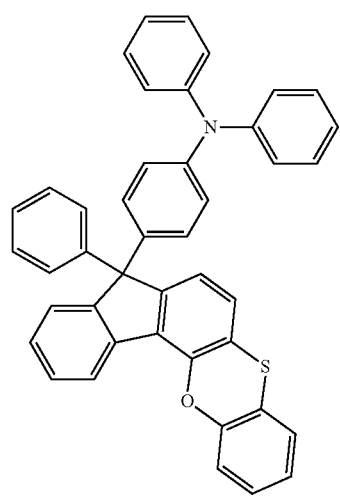
compound 5
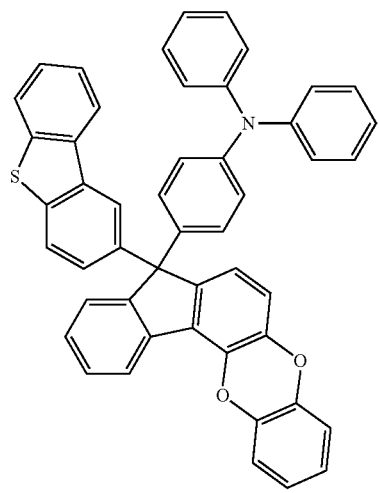
compound 6
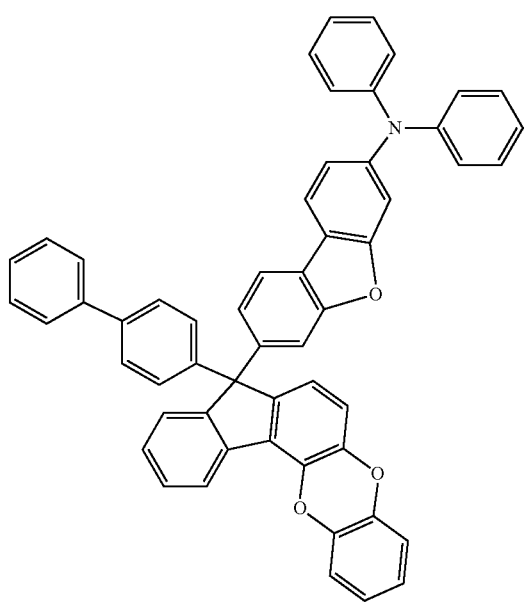
compound 7
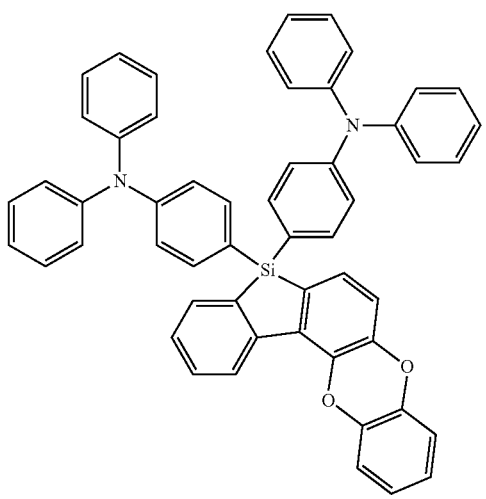
compound 8
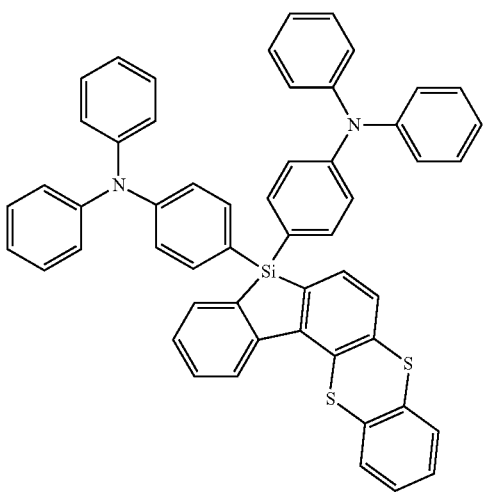
compound 9
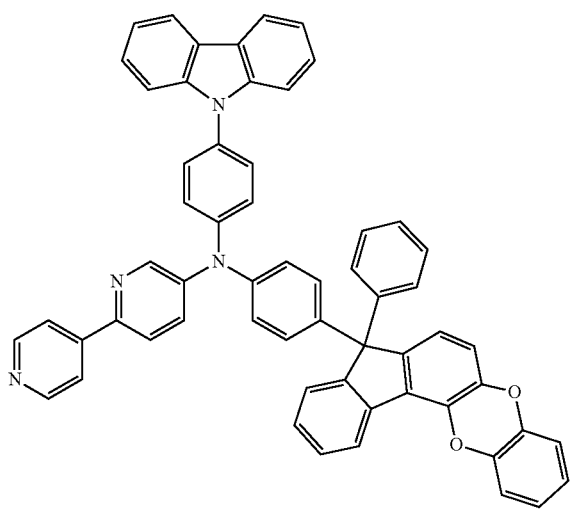

compound 10
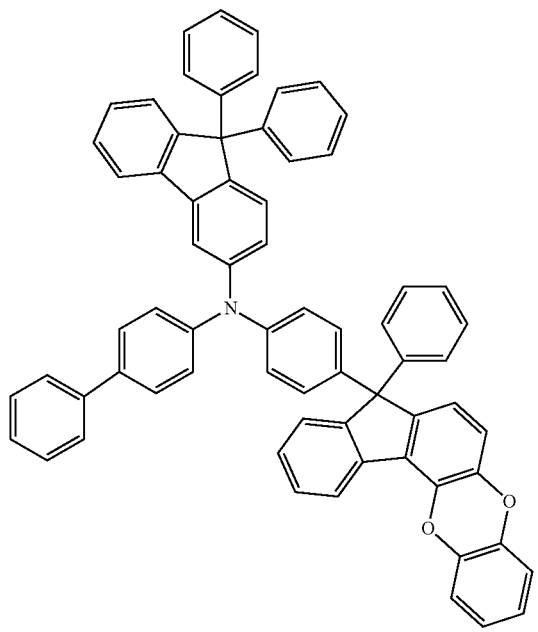
compound 11
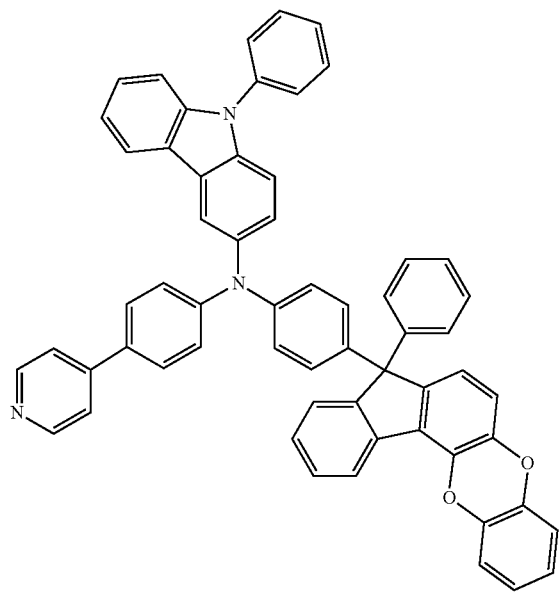
compound 12
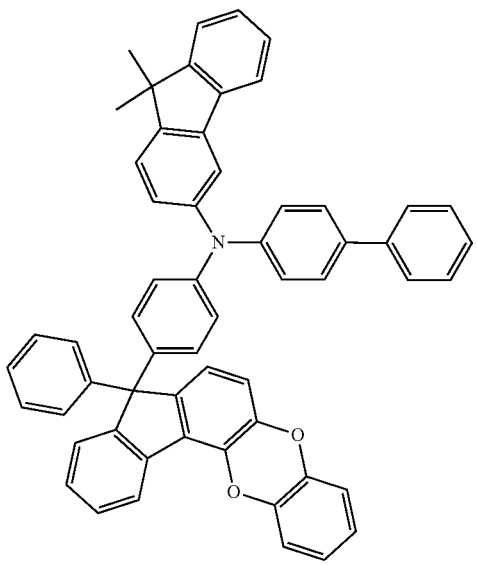
compound 13
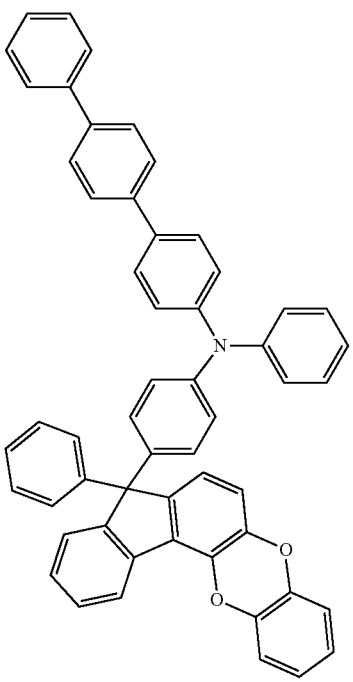

compound 14
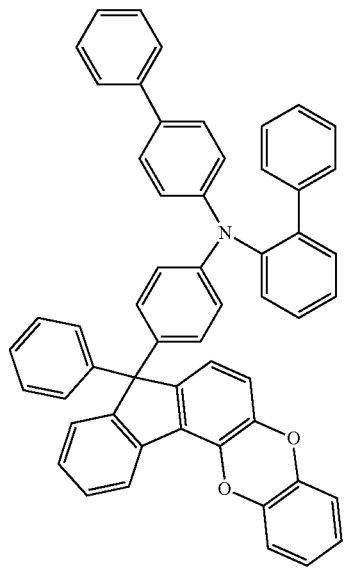
compound 16
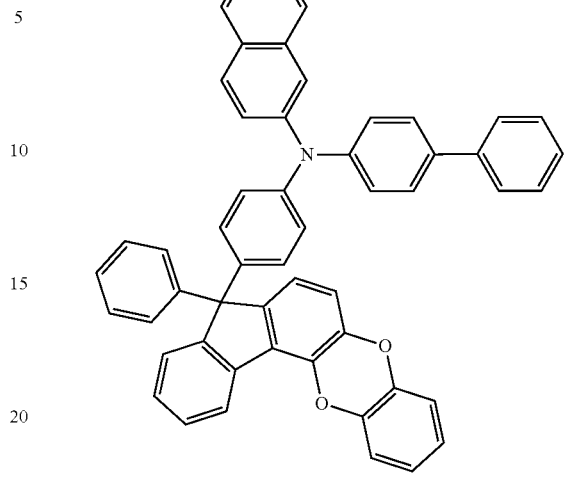
compound 17
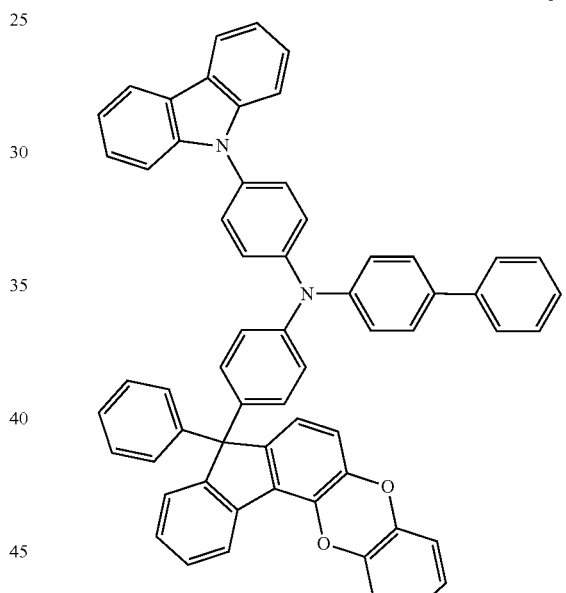
compound 15
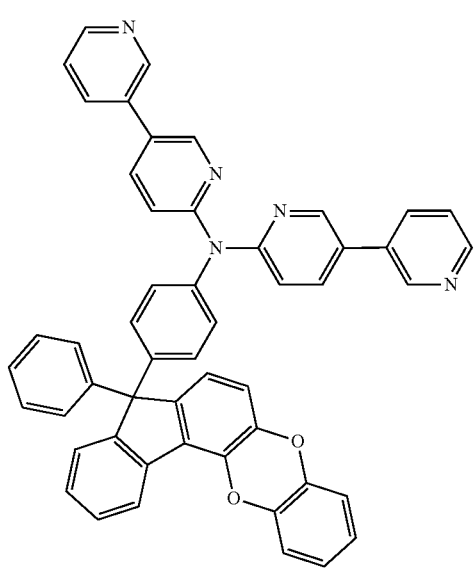
compound 18
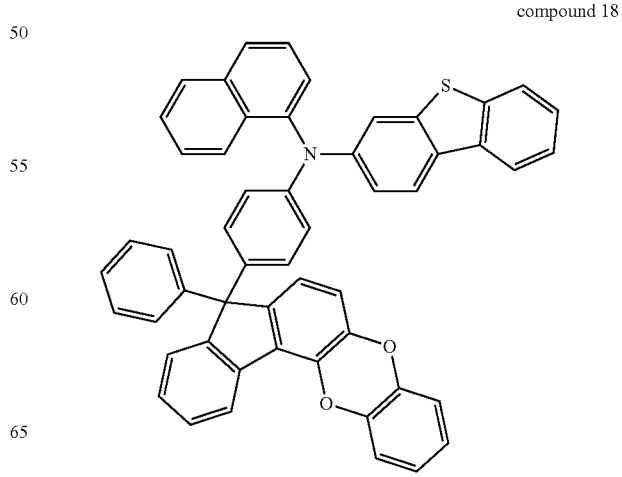

compound 19
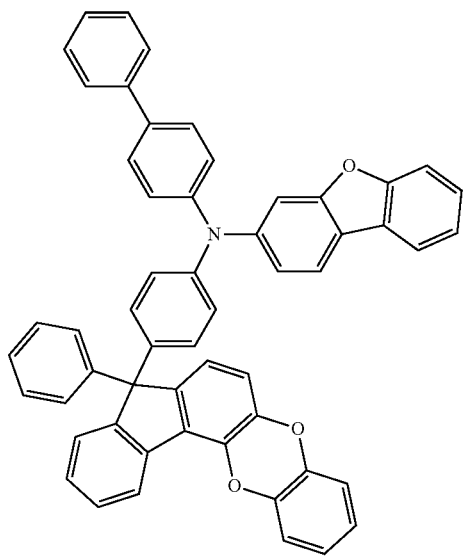
compound 21
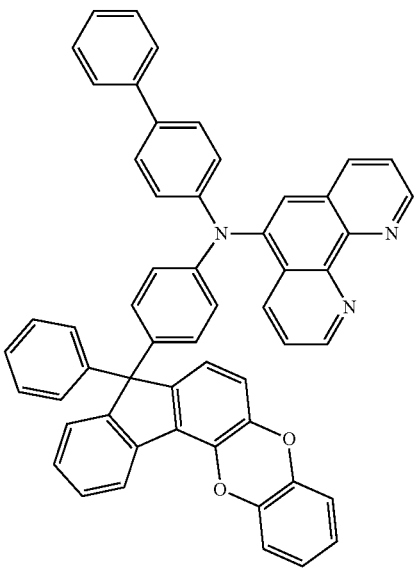
compound 20
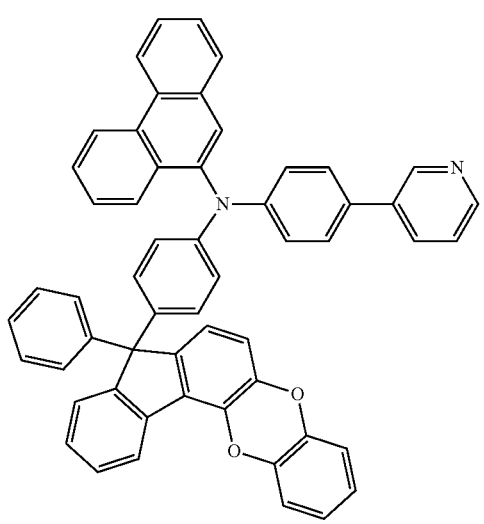
compound 22
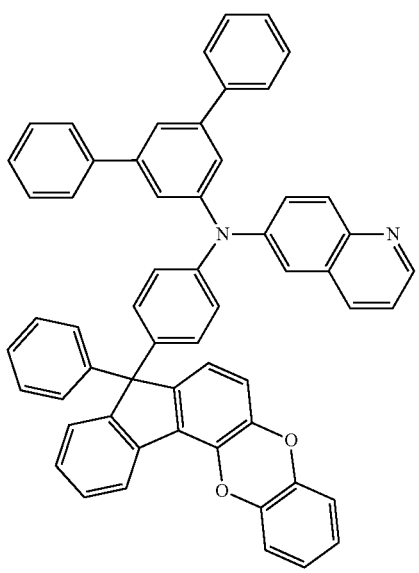

compound 23
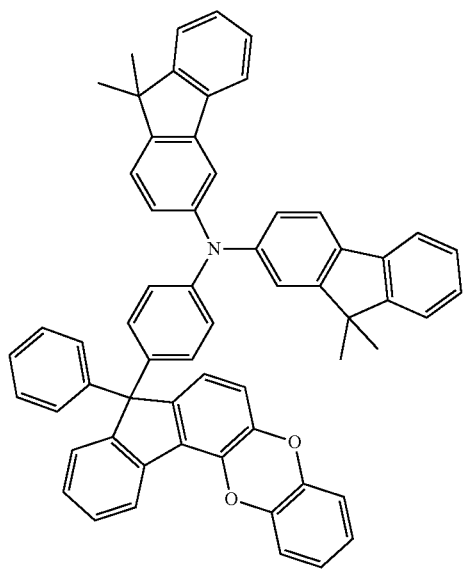
compound 24
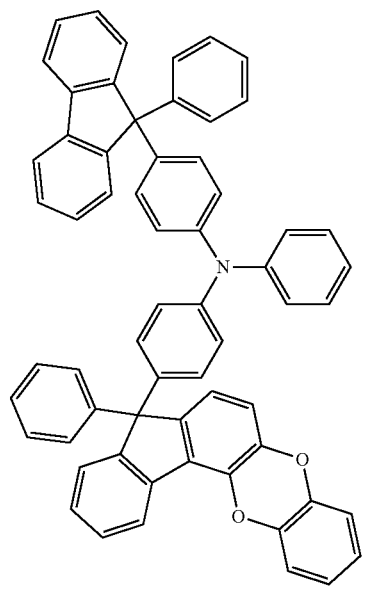
compound 25
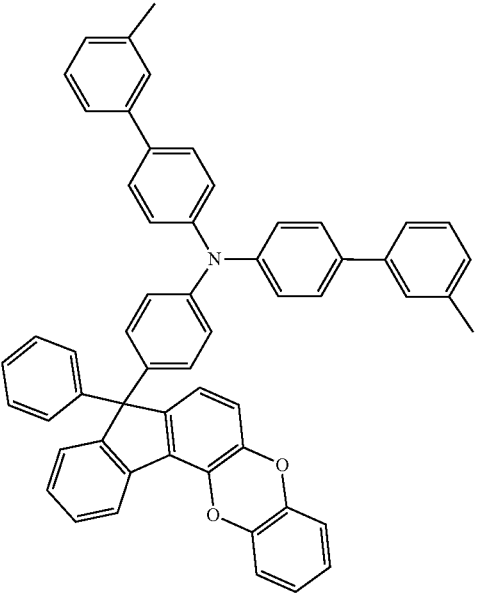
compound 26
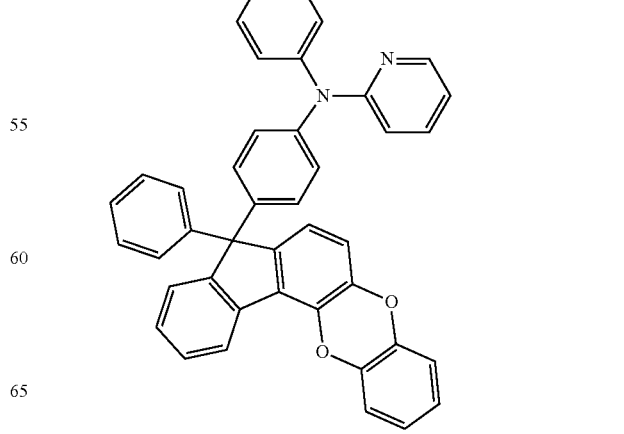

compound 27
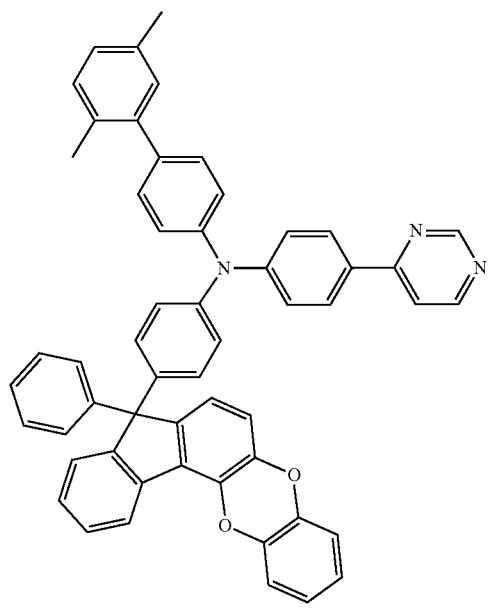
compound 29
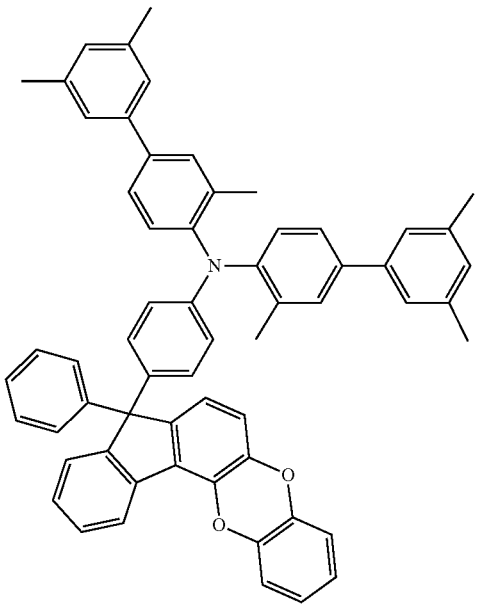
compound 28
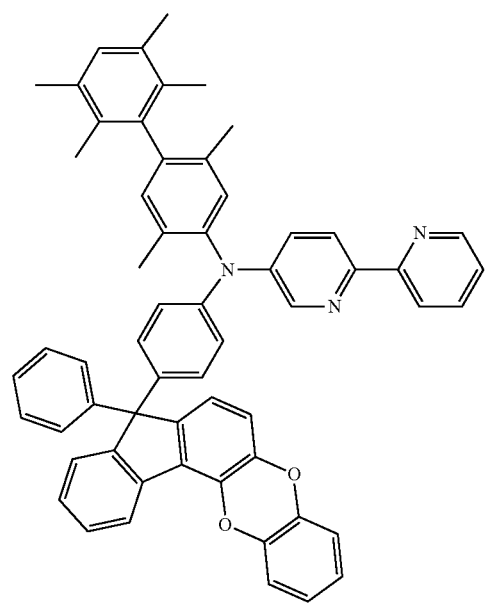
compound 30
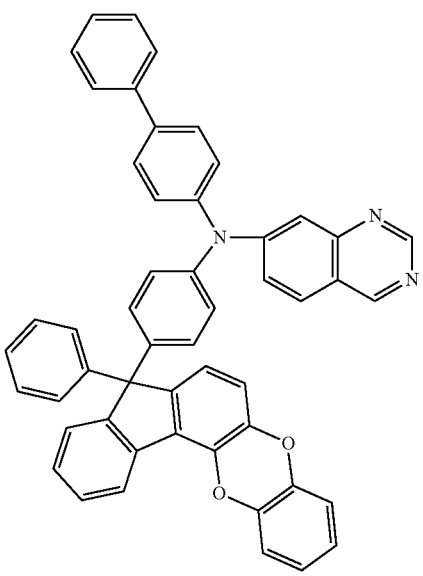

compound 31
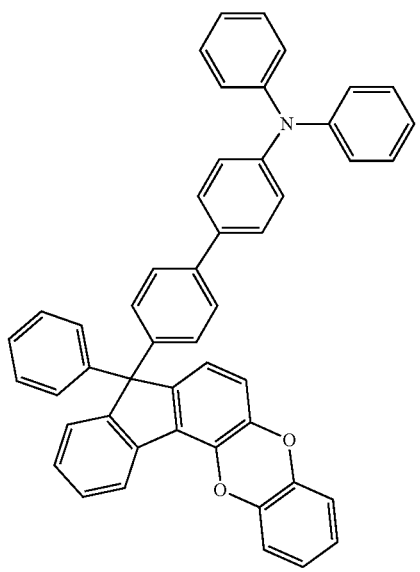
compound 33
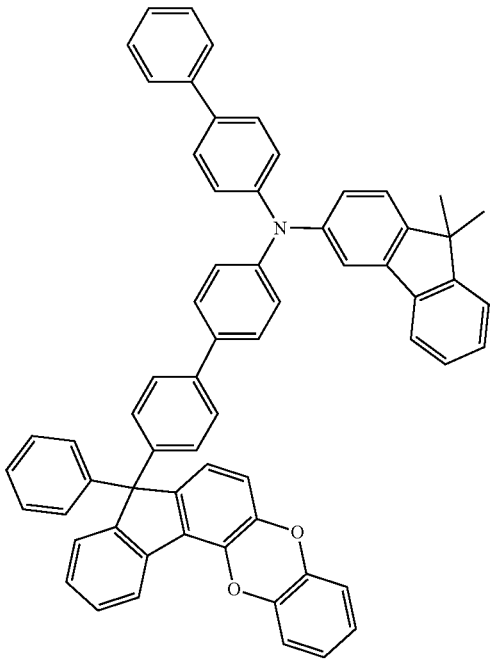
compound 32
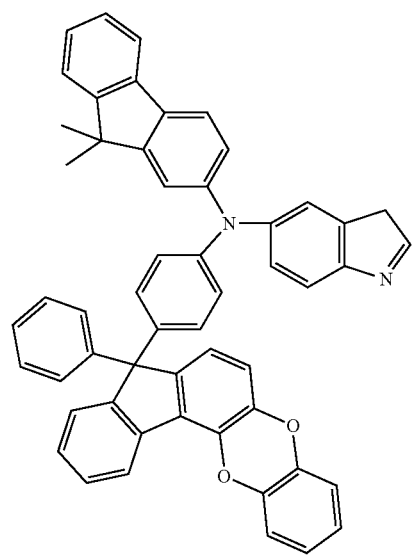
compound 34
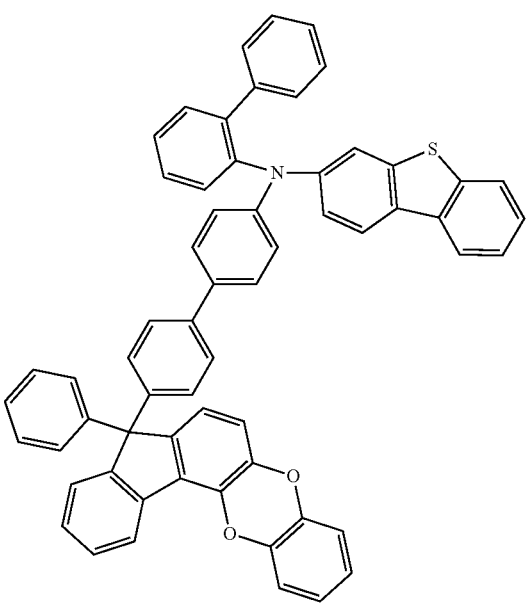

compound 35
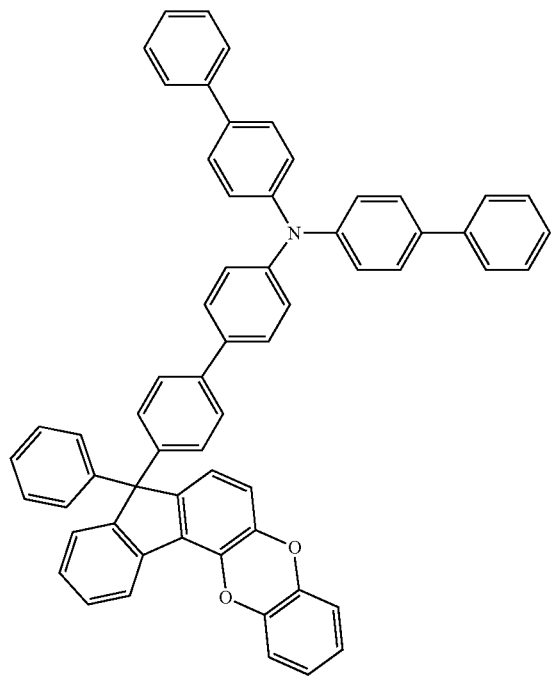
compound 37
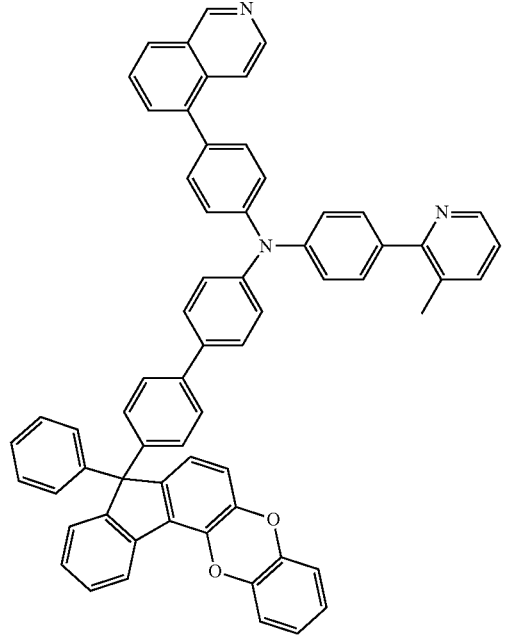
compound 36
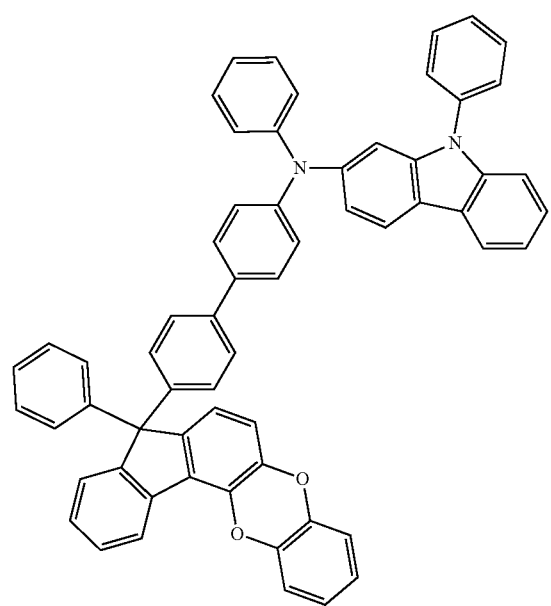
compound 38
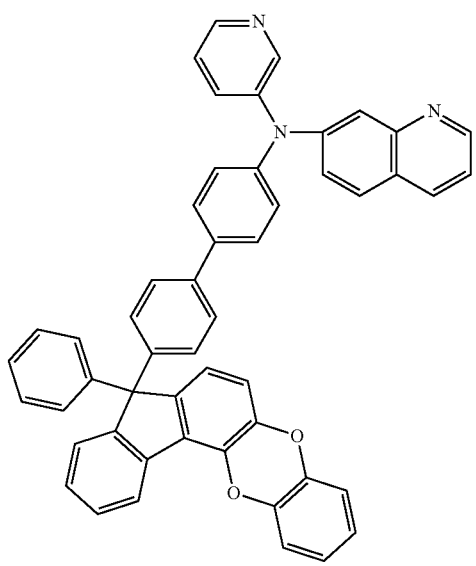

compound 39
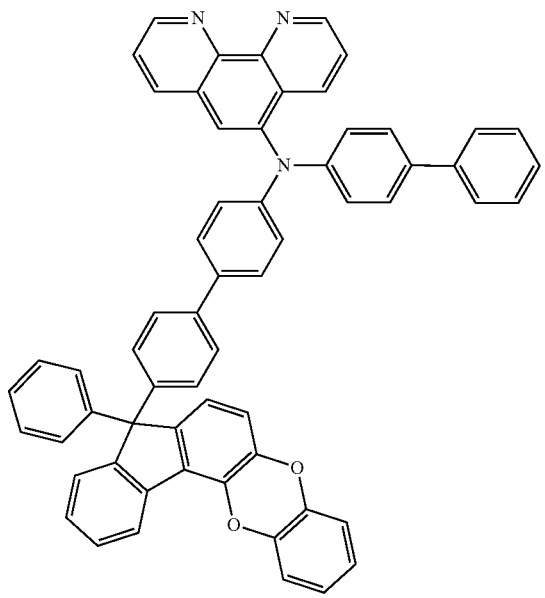
compound 41
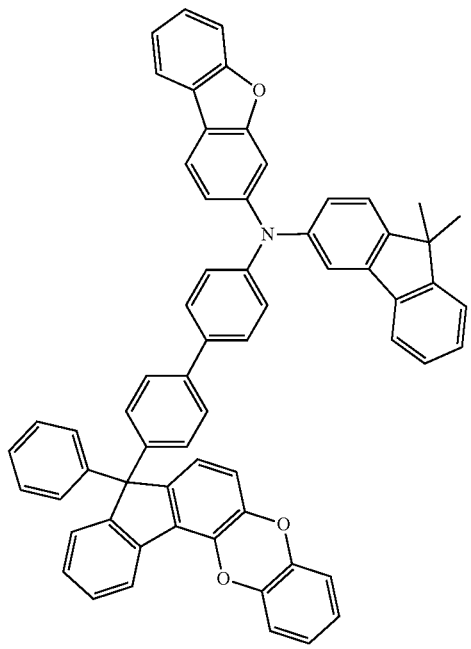
compound 40
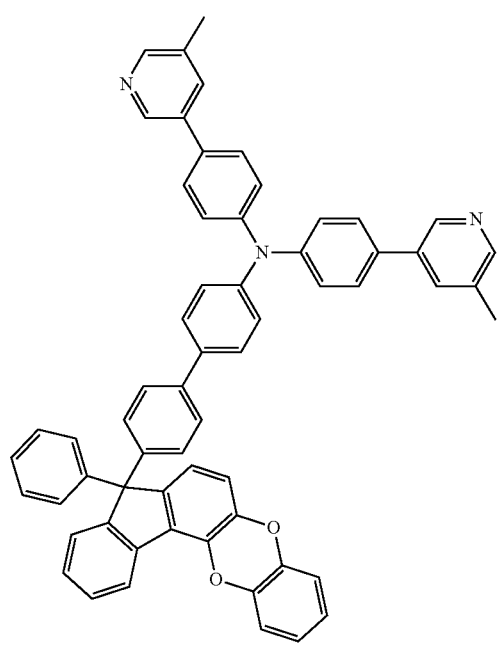
compound 42
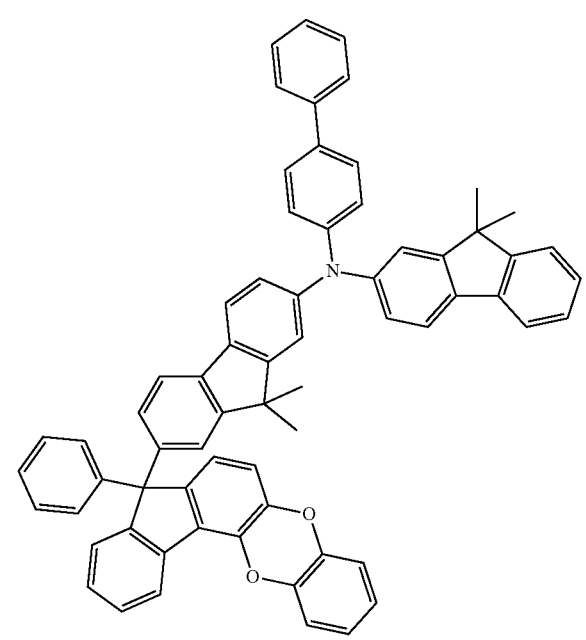

compound 43
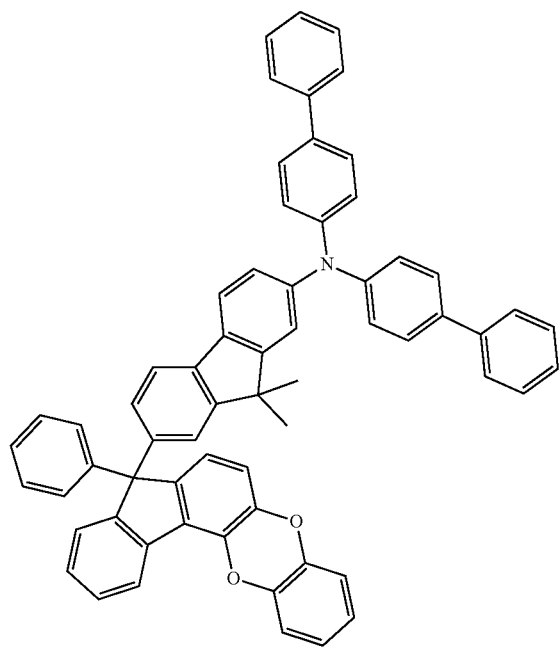
compound 44
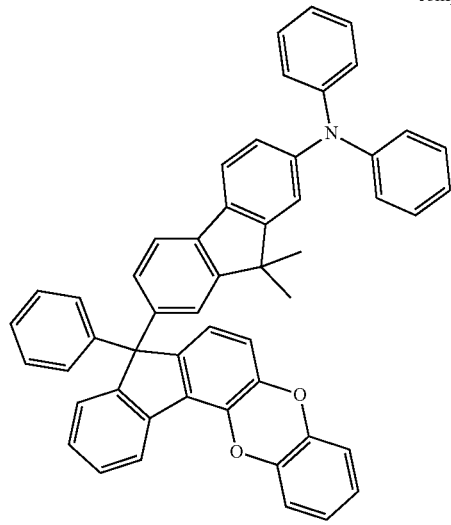
compound 45
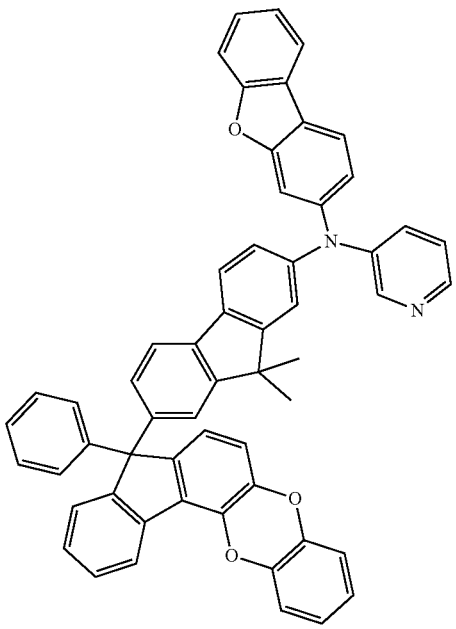
compound 46
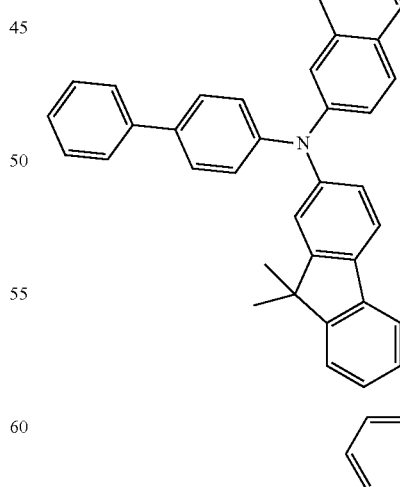

compound 47
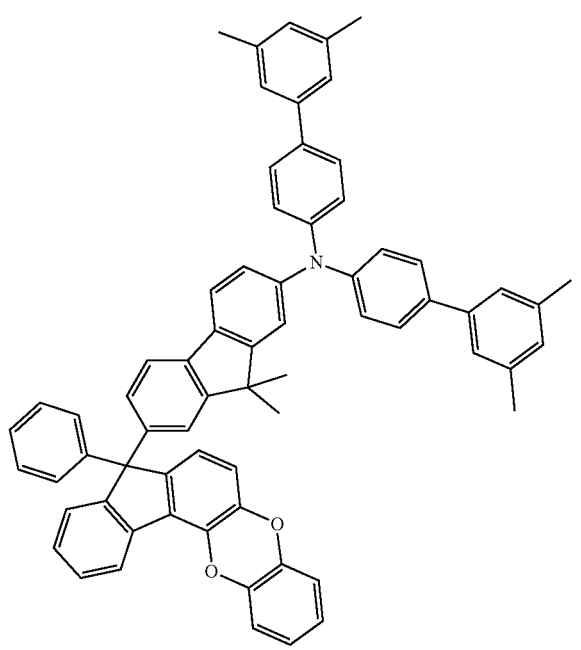
compound 49
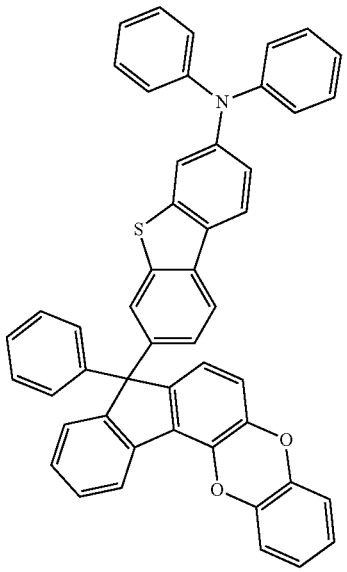
compound 48
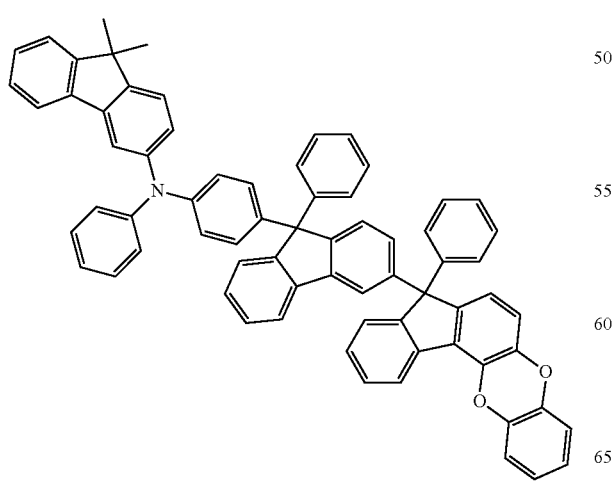
compound 50
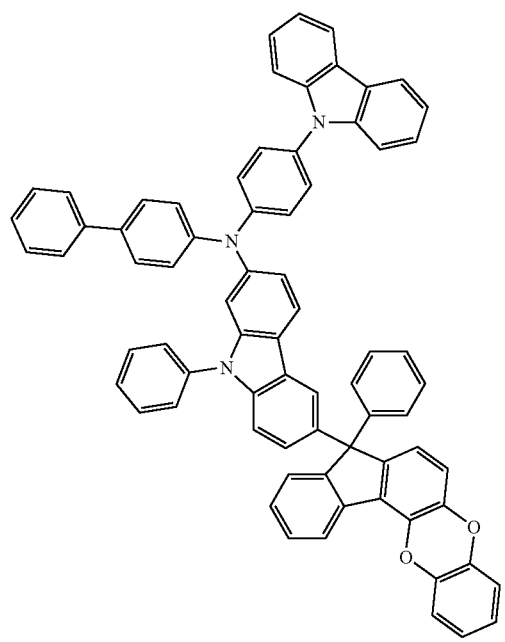

compound 51
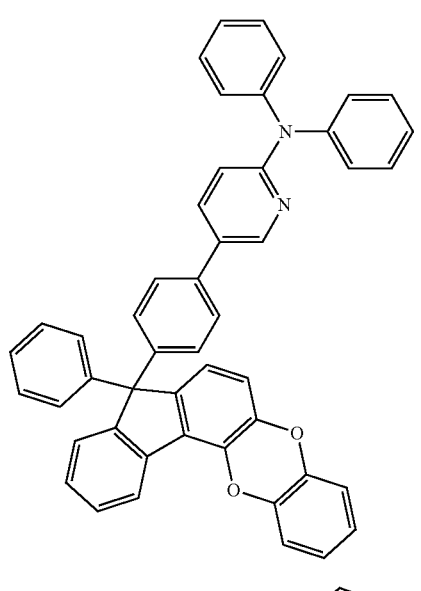
compound 52
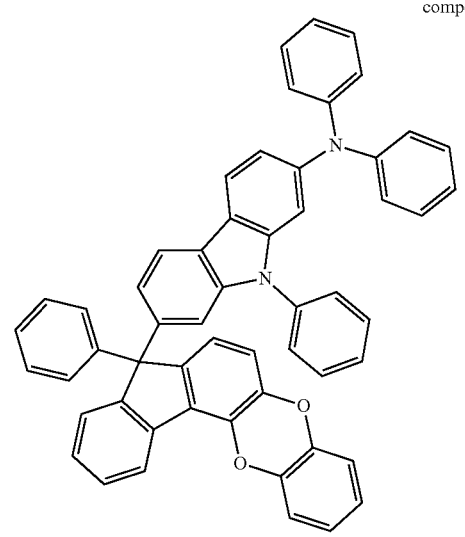
compound 53
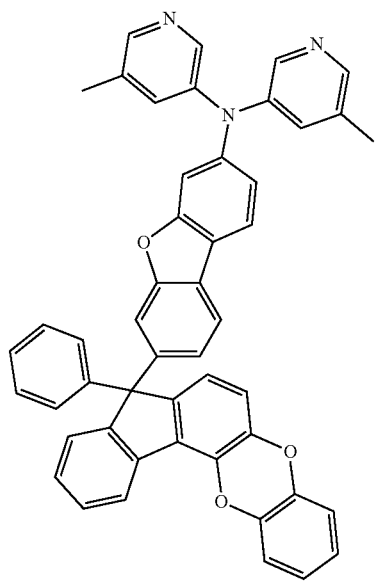
compound 54
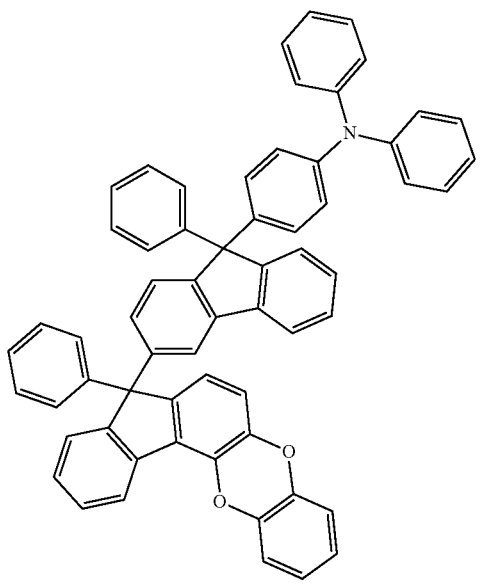
compound 55
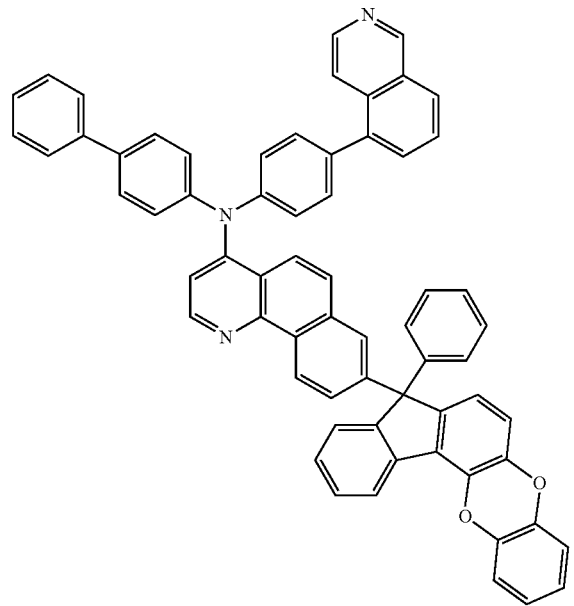

compound 56
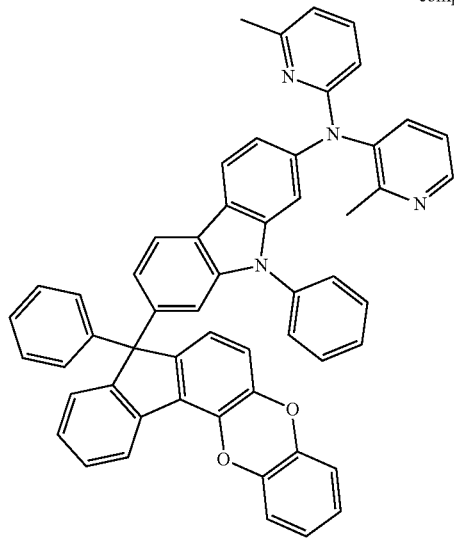
compound 57
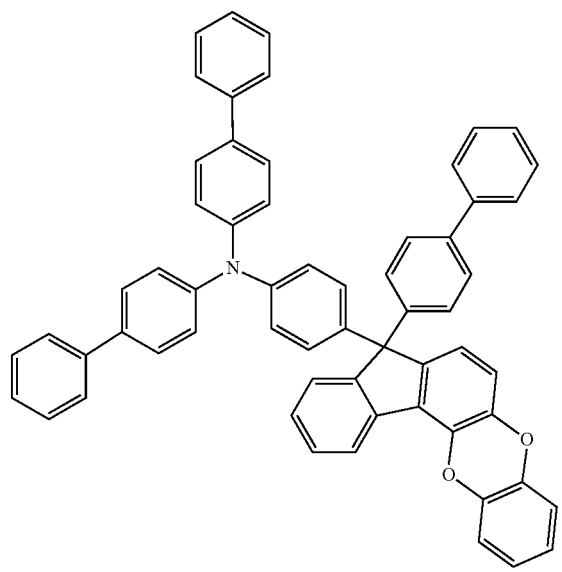
compound 58
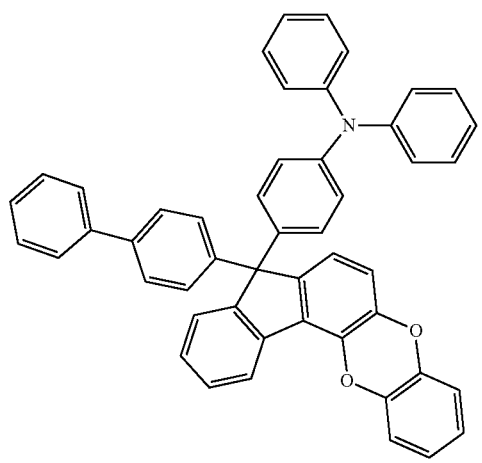
compound 59
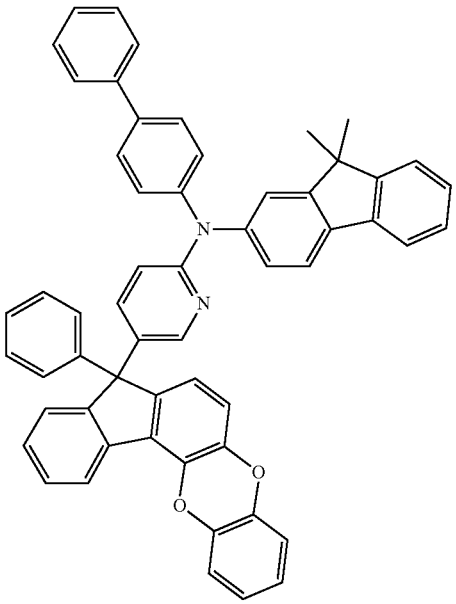
compound 60
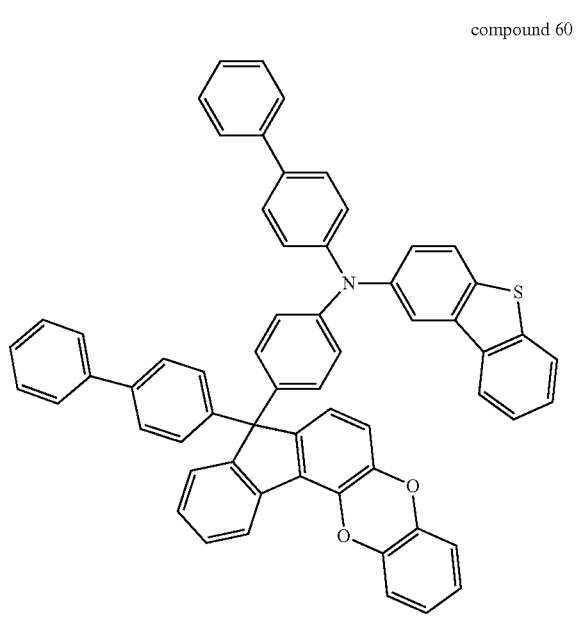

compound 61
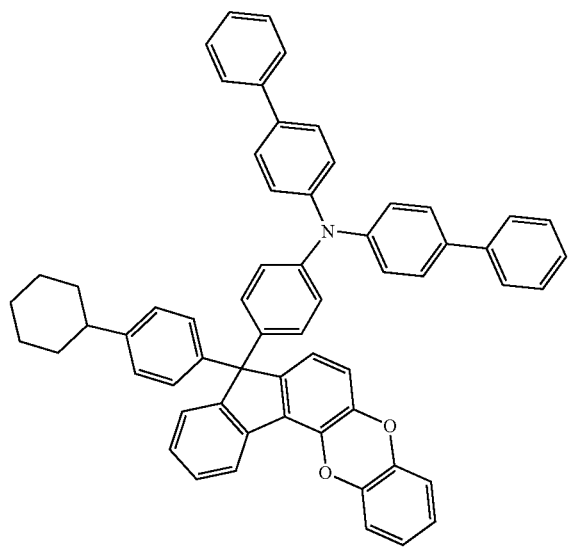
compound 62
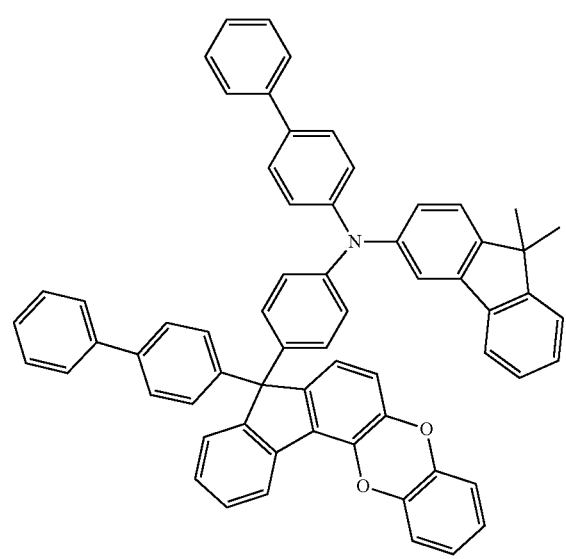
compound 63
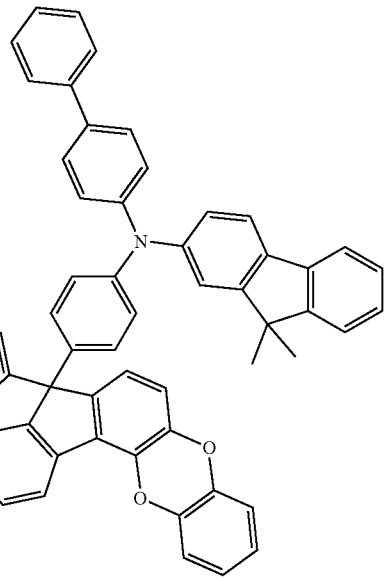
compound 64
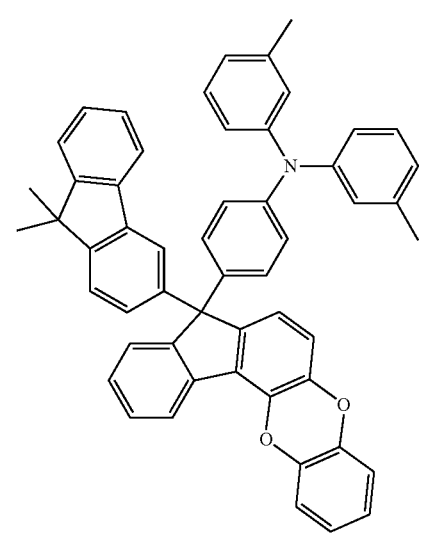
compound 65
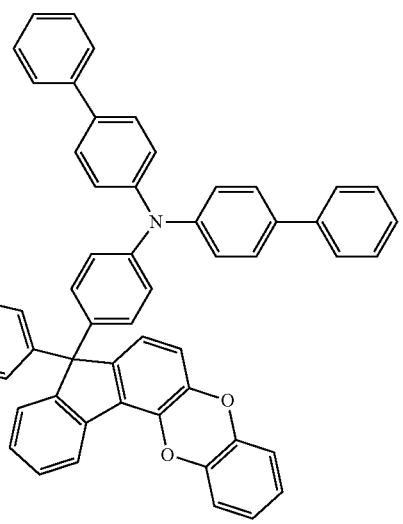

-continued
compound 66
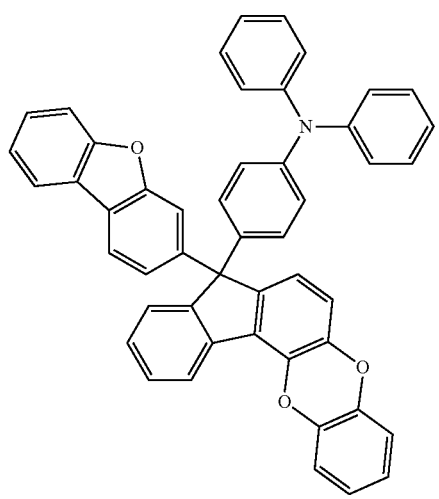
compound 68
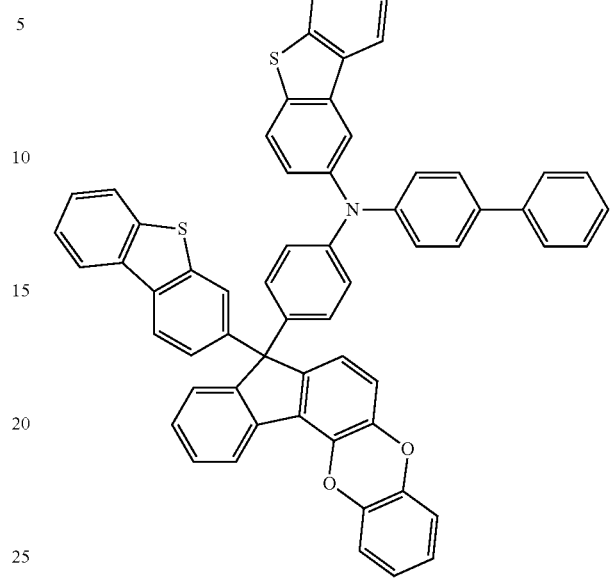
compound 67
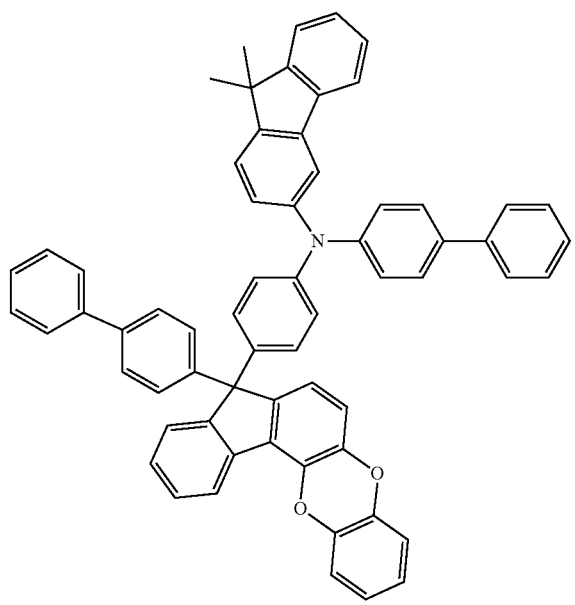
compound 69
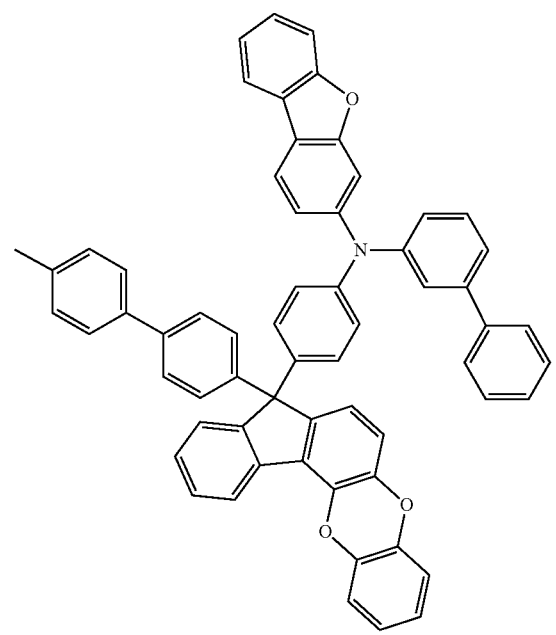

compound 70
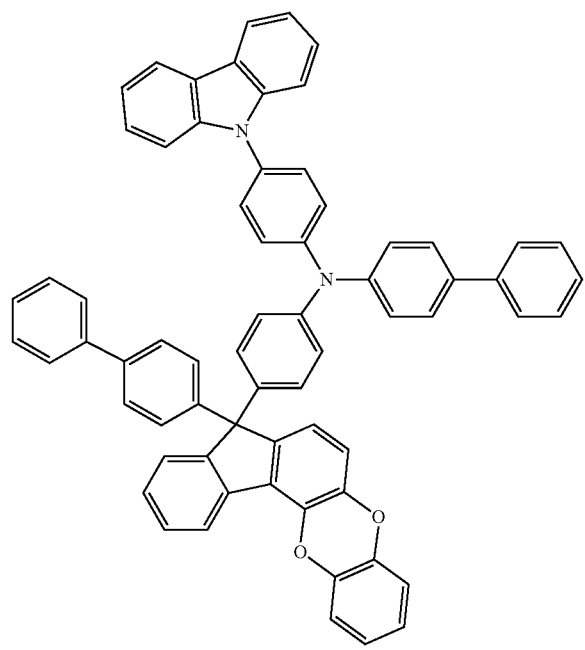
compound 72
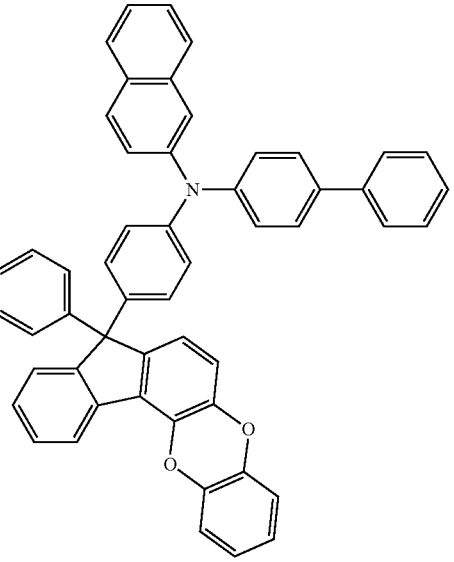
compound 71
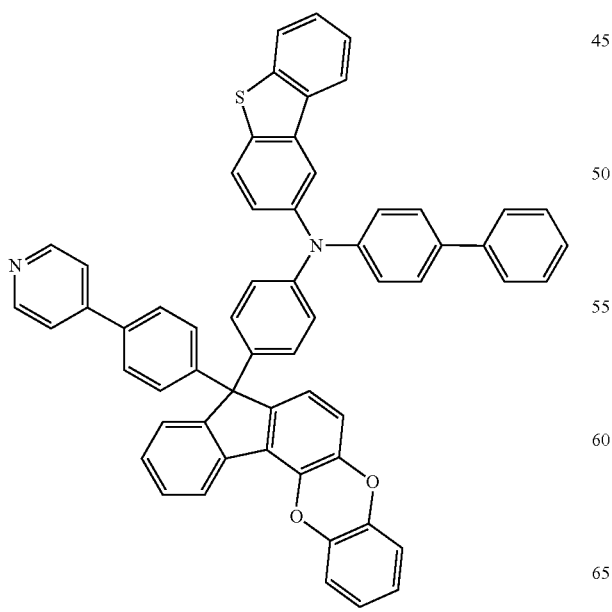
compound 73
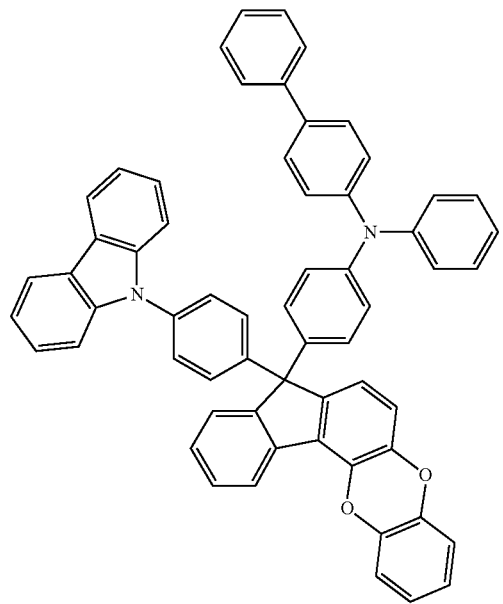

compound 74
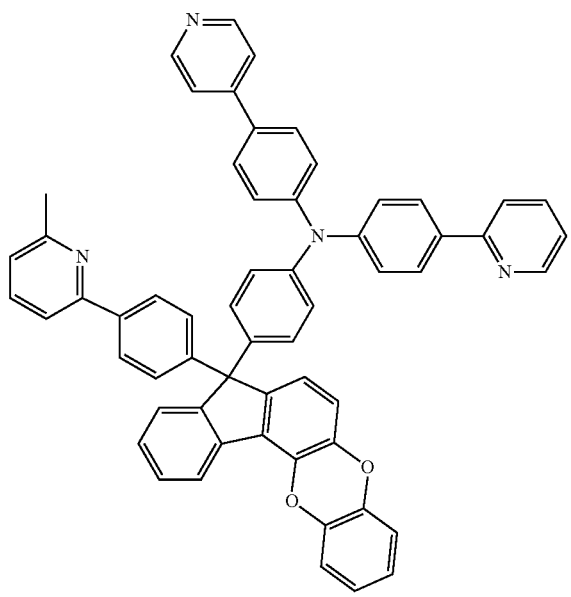
compound 76
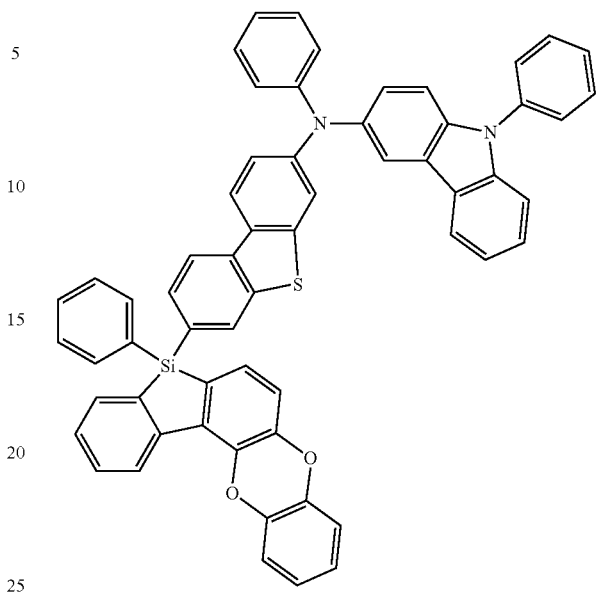
compound 75
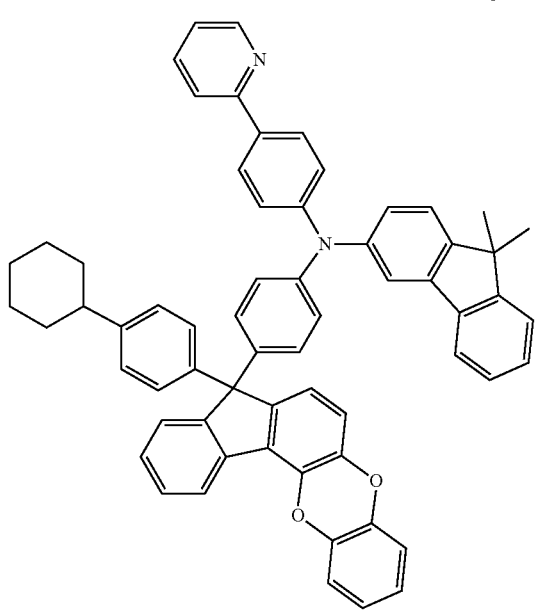
compound 77
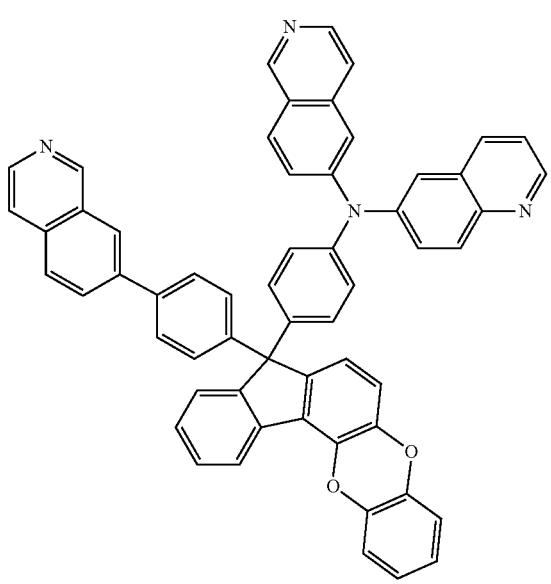

compound 78
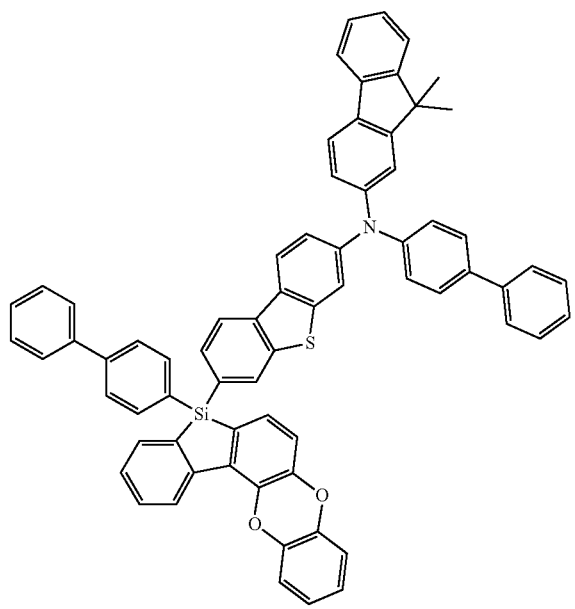
compound 79
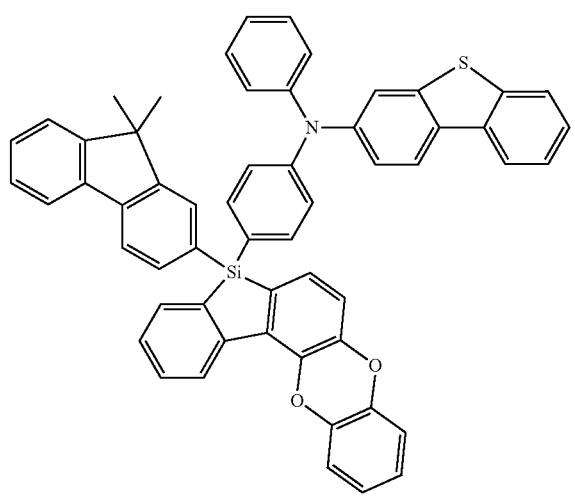
compound 80
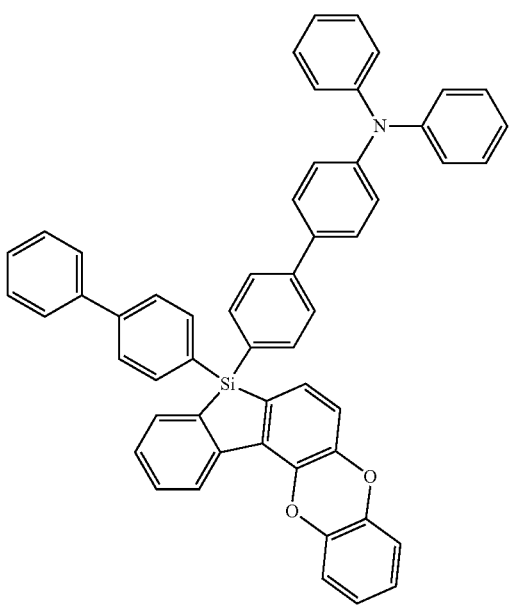
compound 81
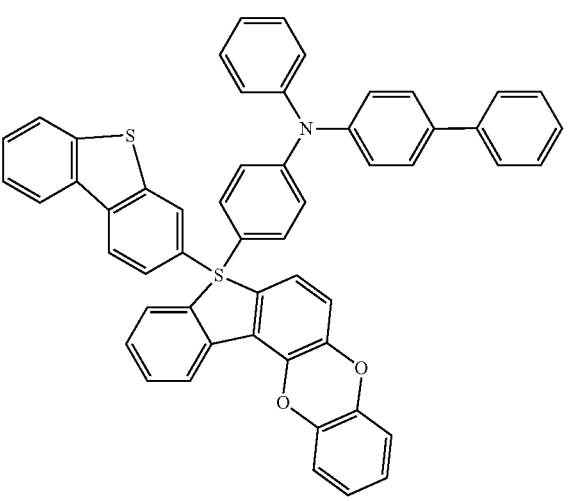

compound 82
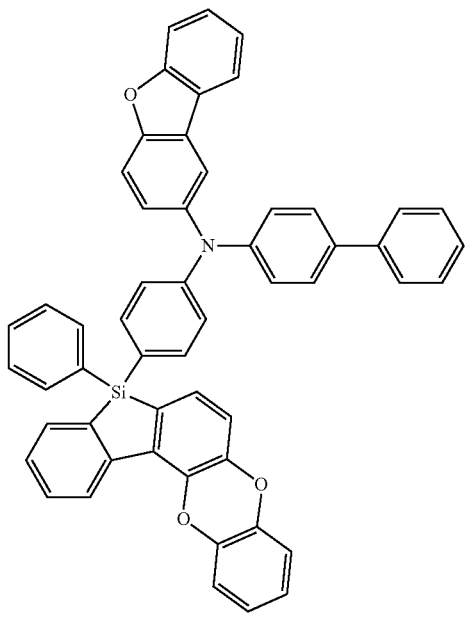
compound 83
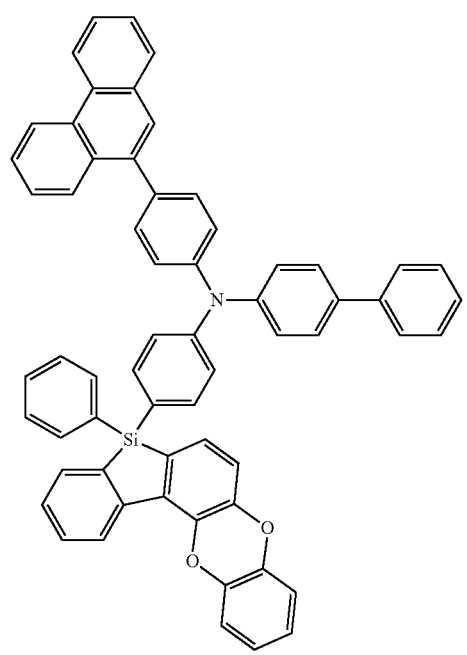
compound 84
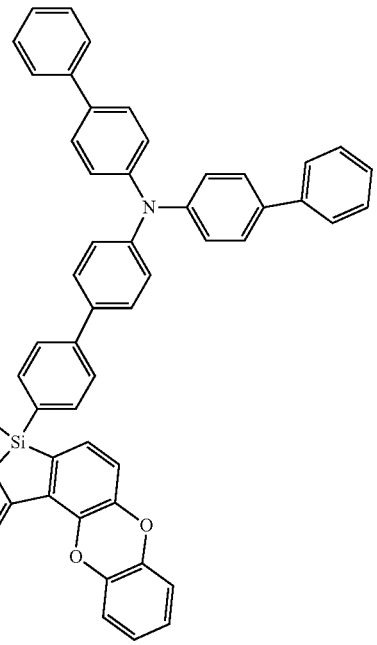
compound 85
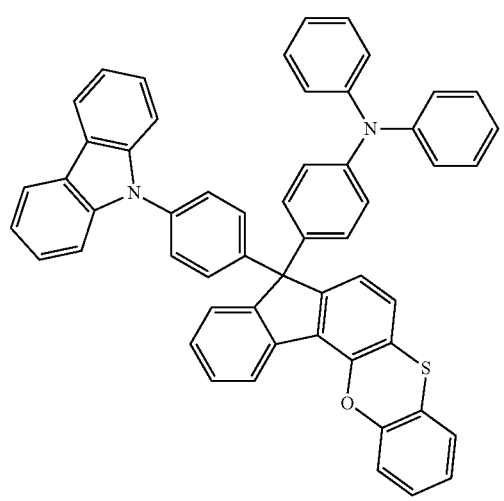

compound 86
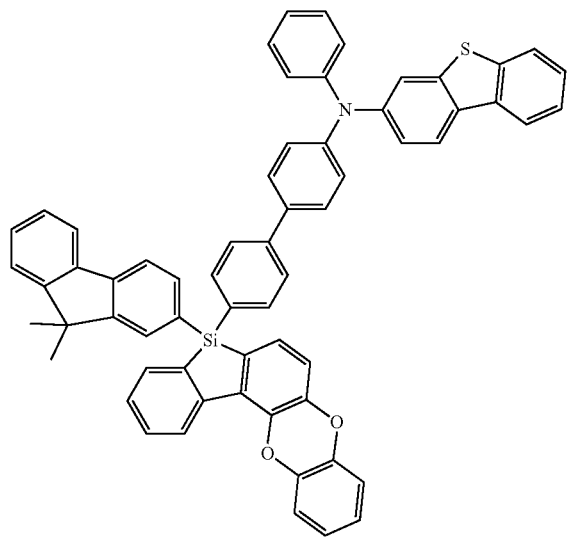
compound 87
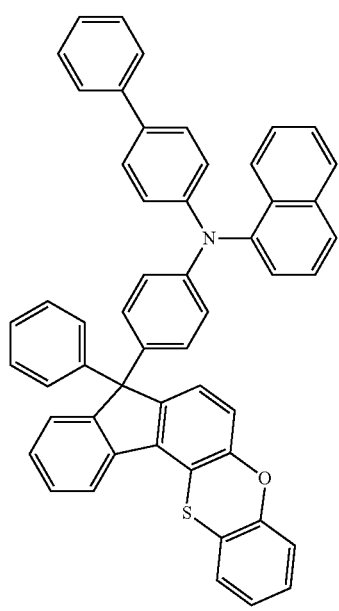
compound 88
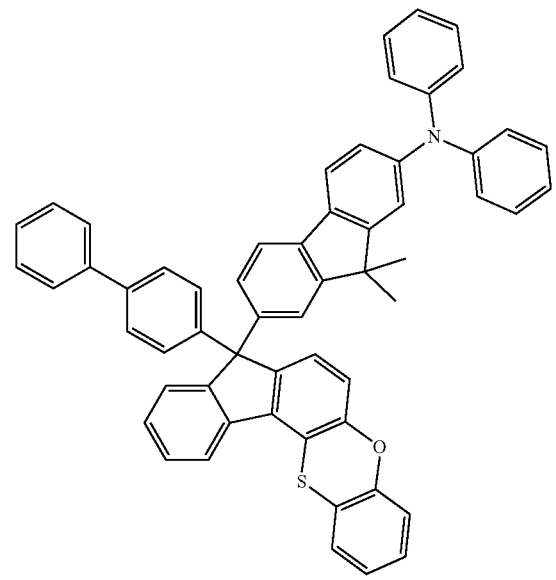
compound 89
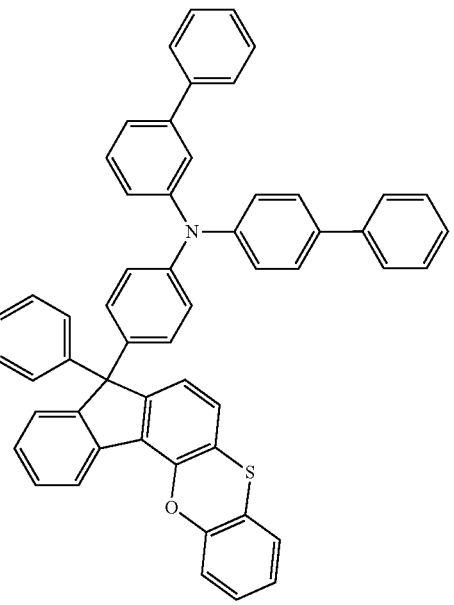

compound 90
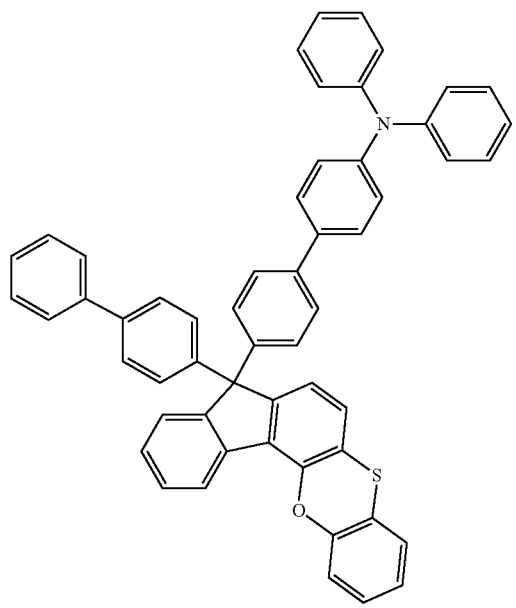
compound 92
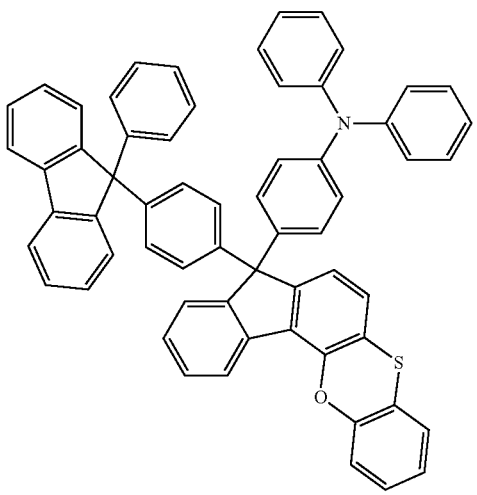
compound 91
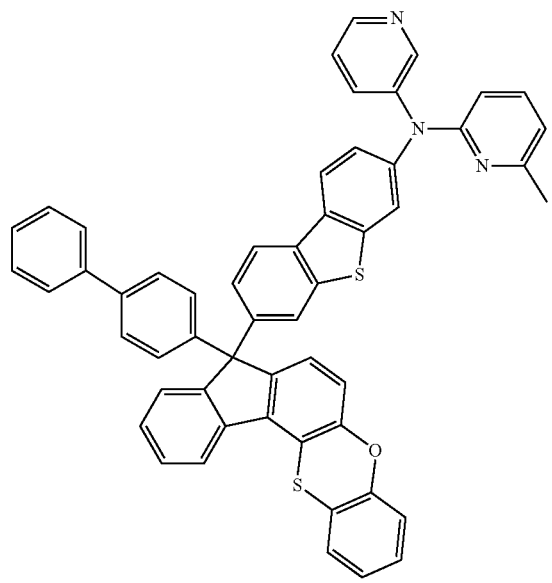
compound 93
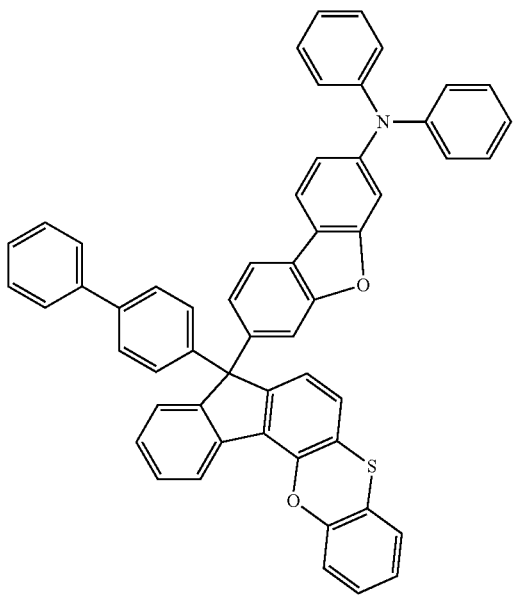

compound 94
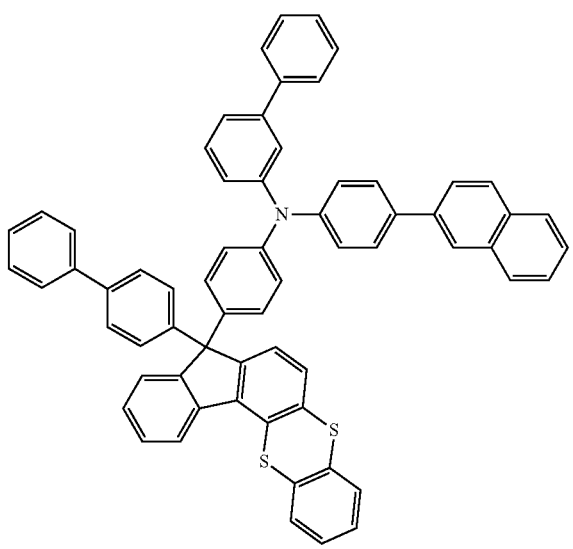
compound 96
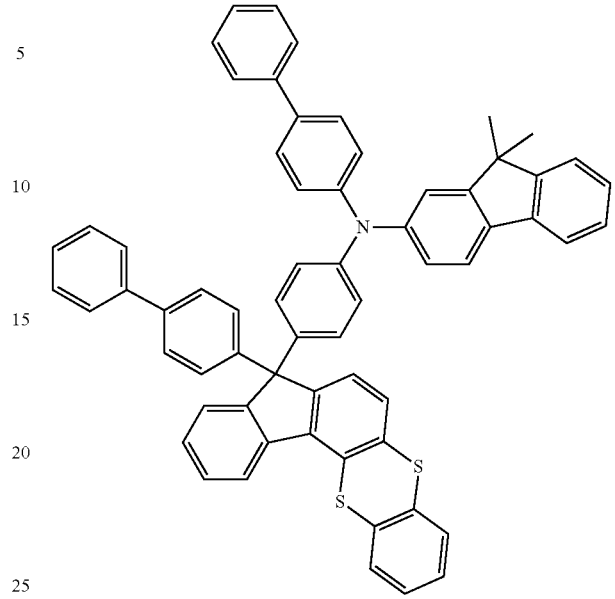
compound 95
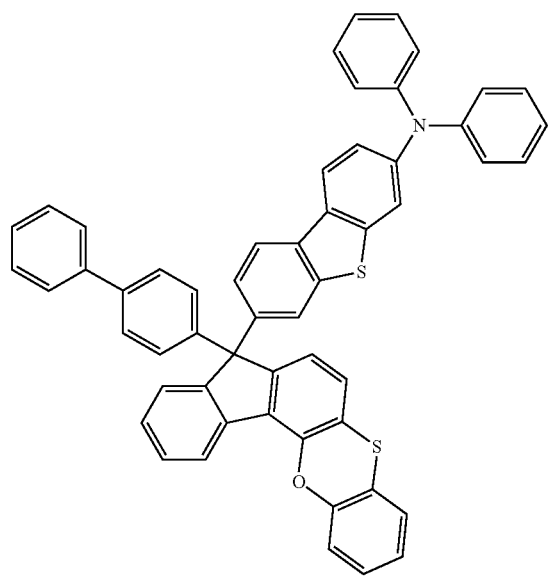
compound 97
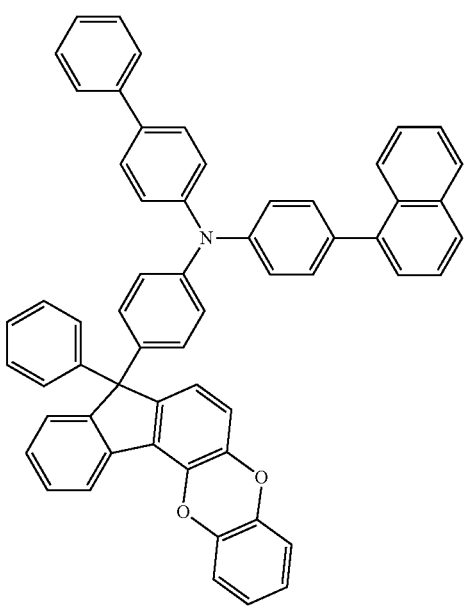

compound 98
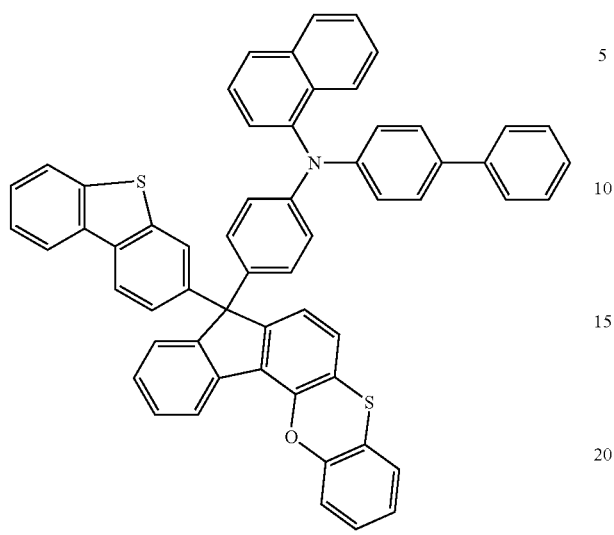
compound 99
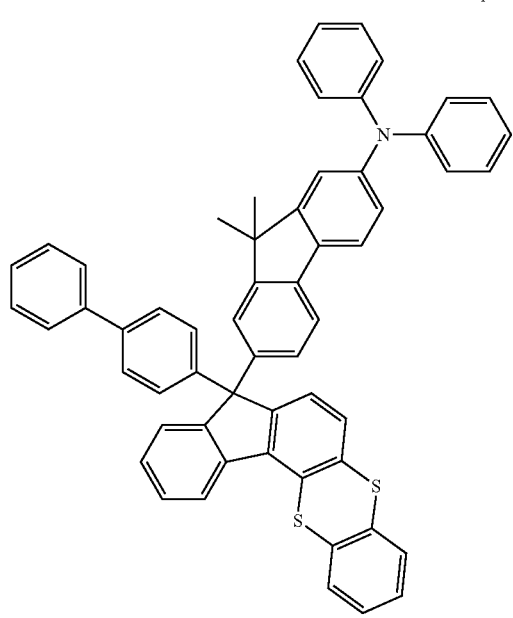
compound 100
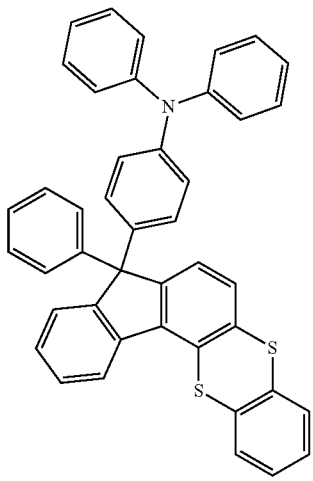
compound 101
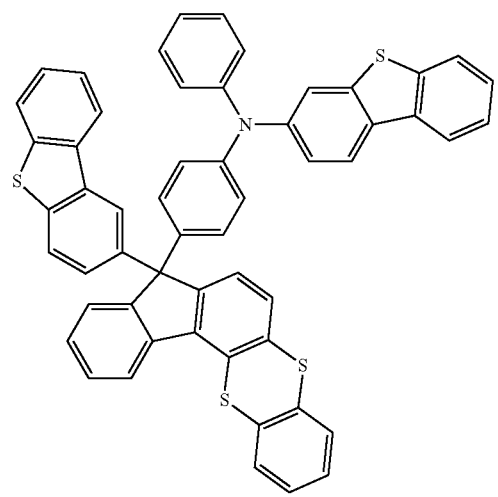
compound 102
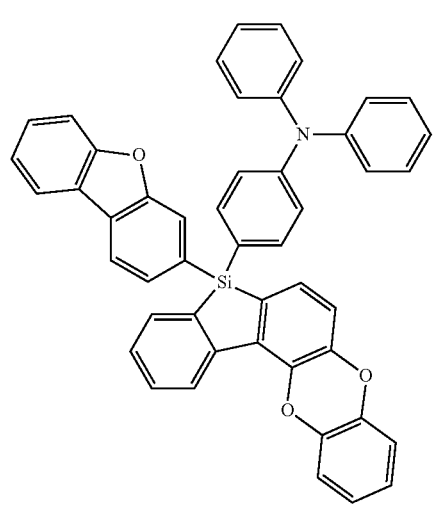
compound 103
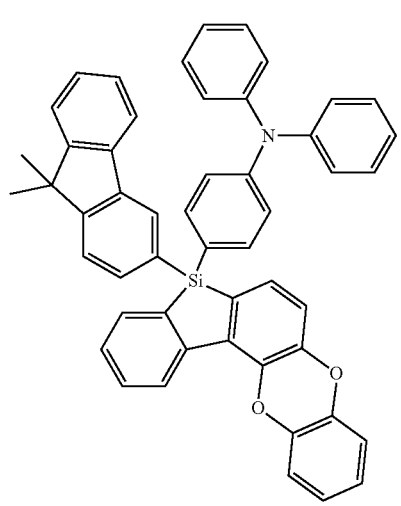

compound 104
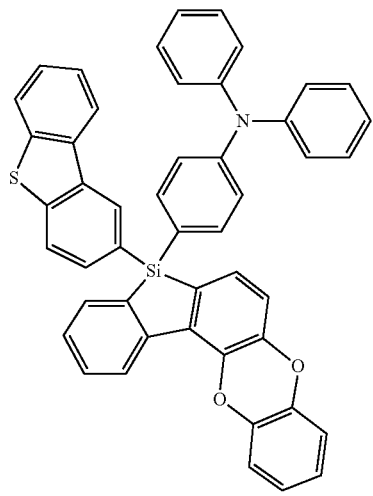
compound 106
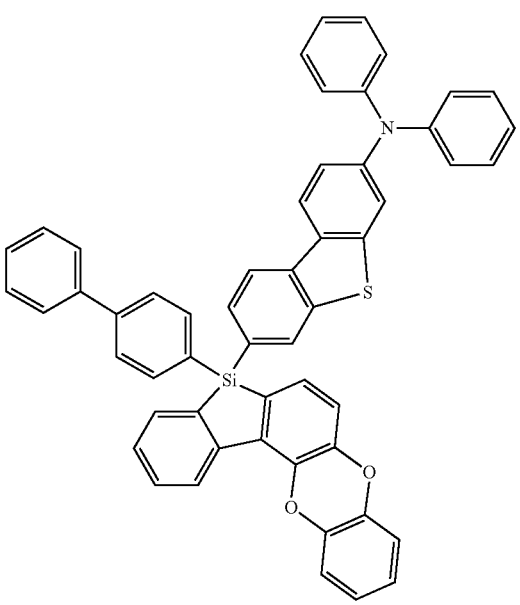
compound 105
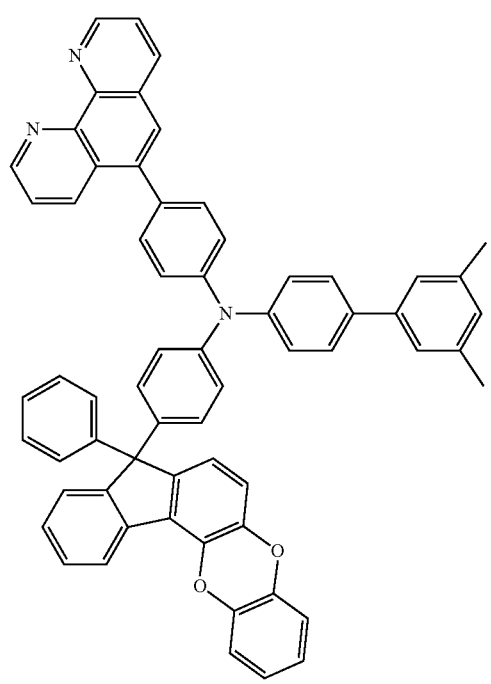
compound 107
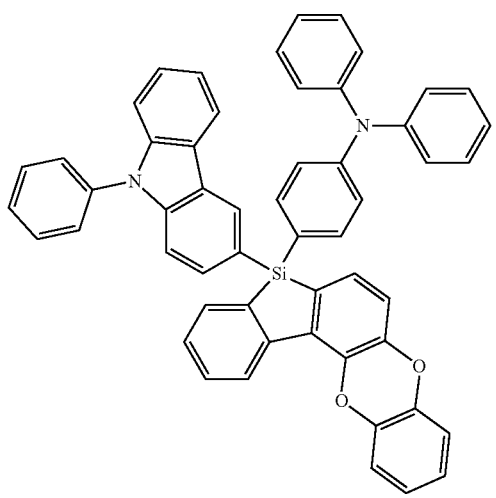

compound 108
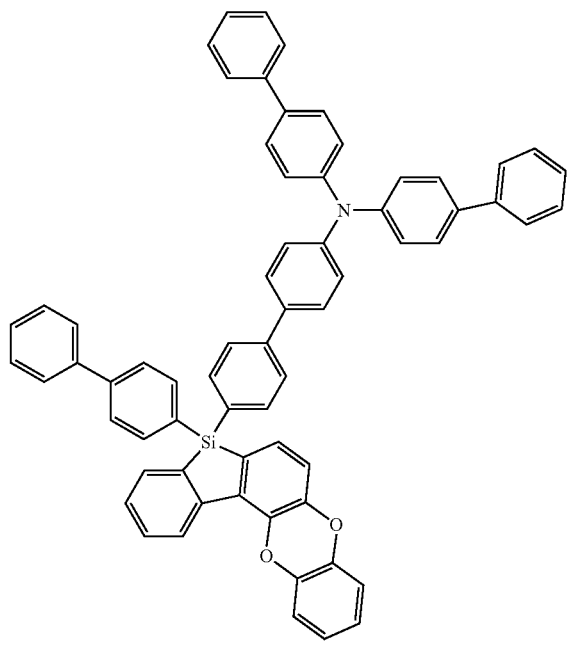
compound 110
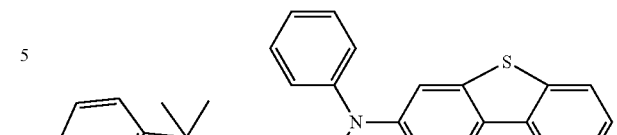
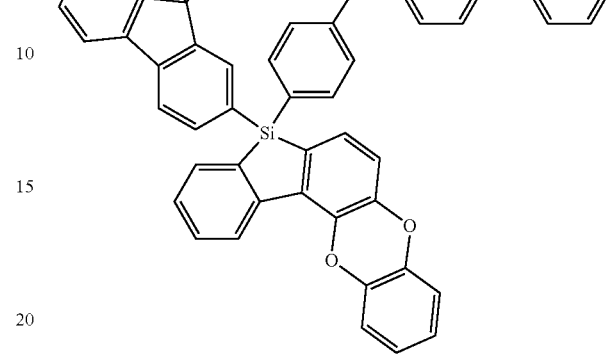
compound 111
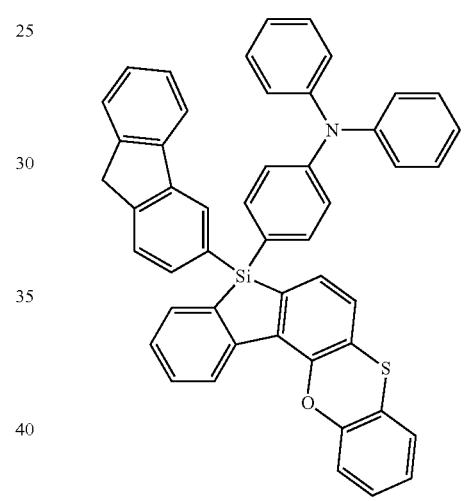
compound 109
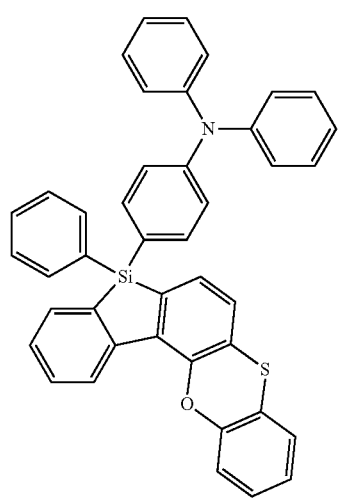
compound 112

-continued
compound 113
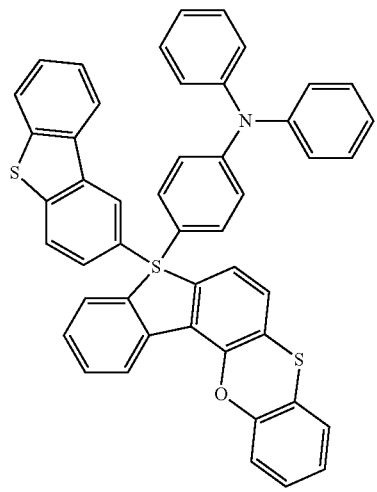
compound 114
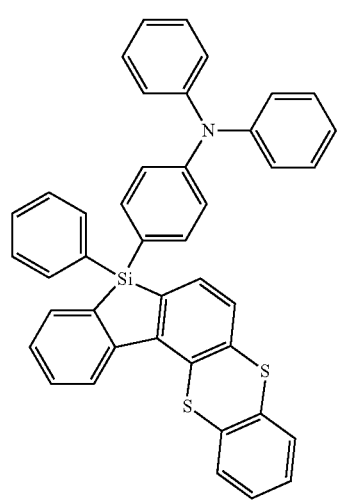
compound 115
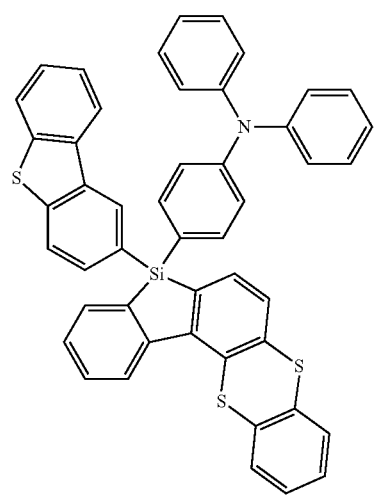
-continued
compound 116
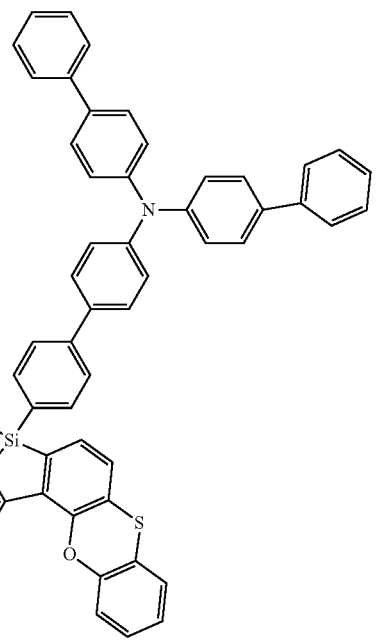
compound 117
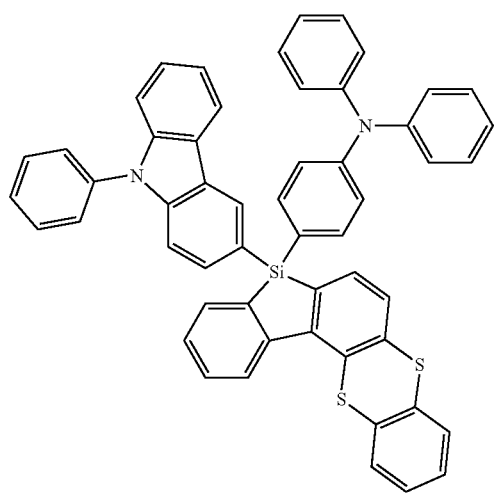

compound 118
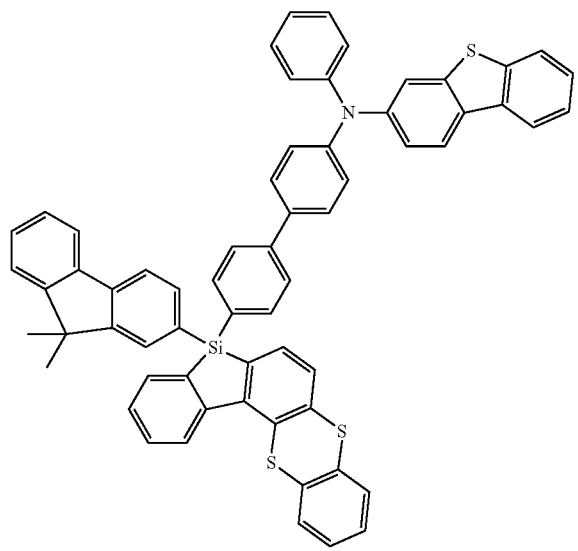
compound 119
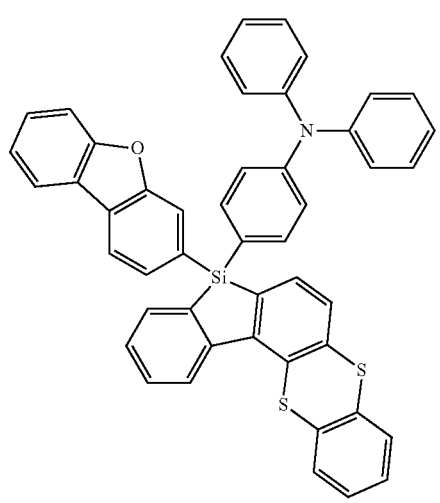
compound 120
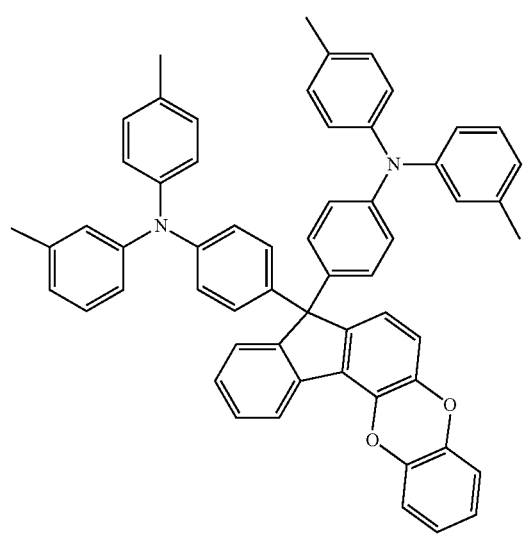
compound 121
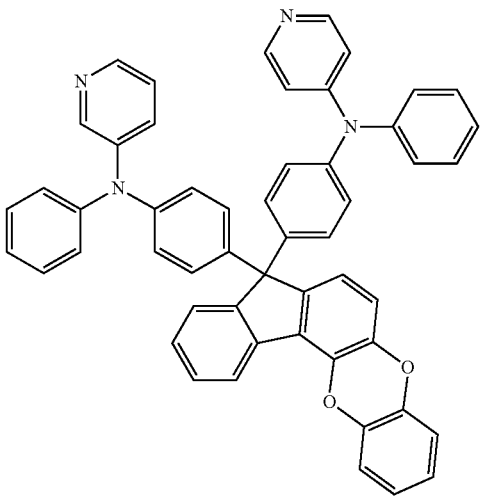
compound 122
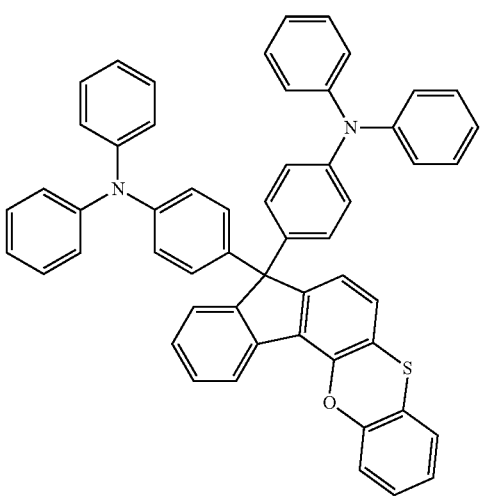
compound 123
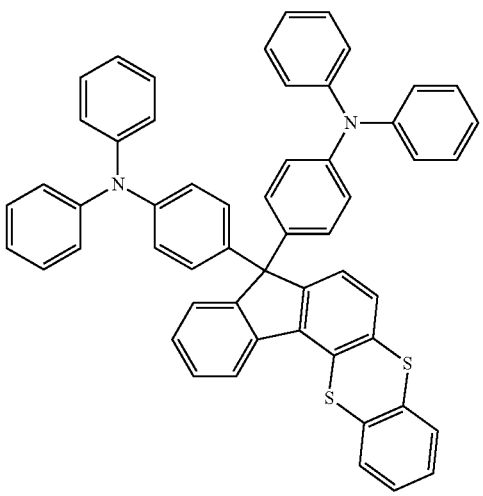

compound 124
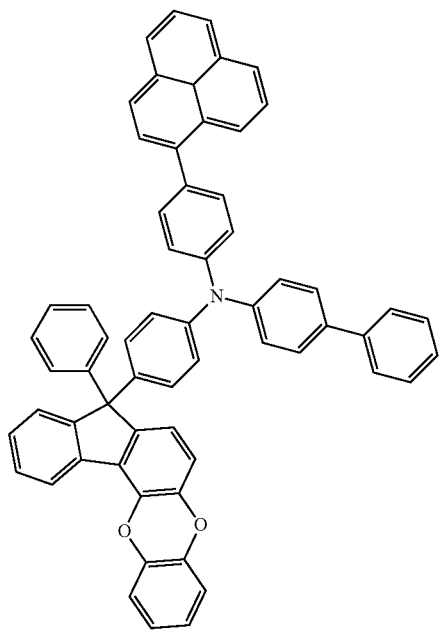
compound 125
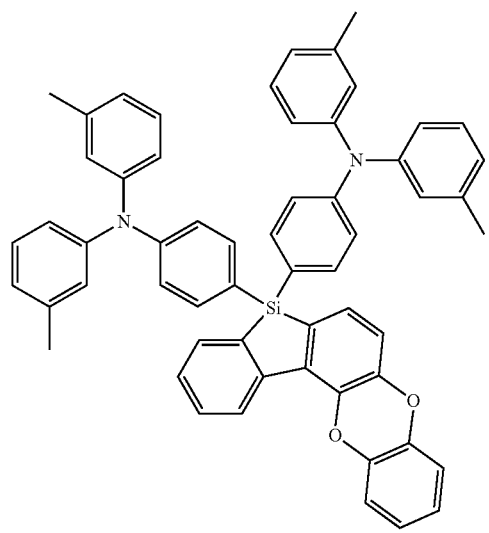
compound 126
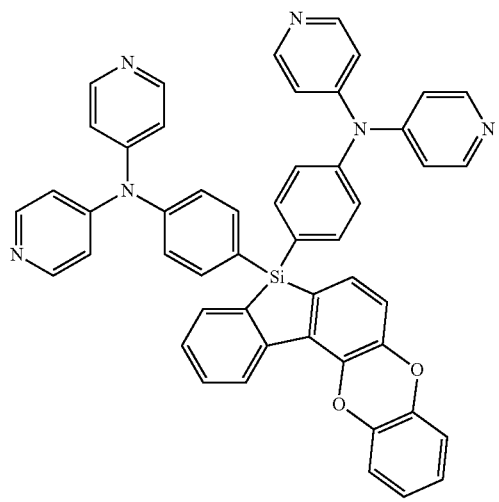
compound 127
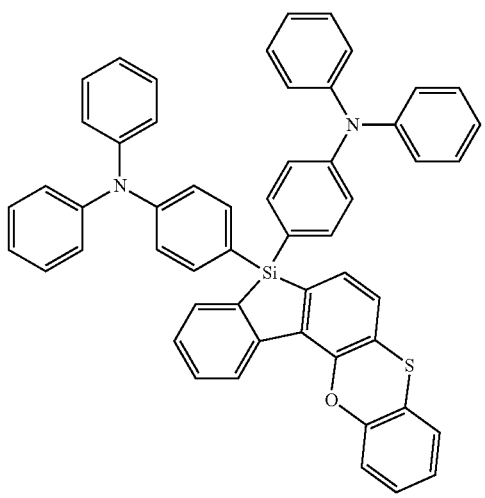

compound 128
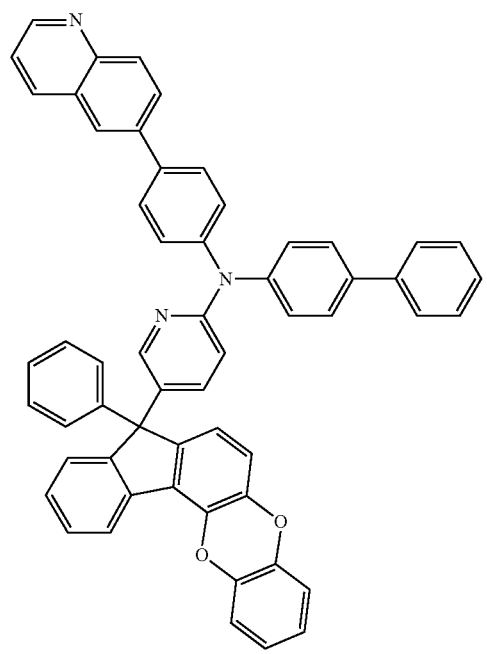
compound 130
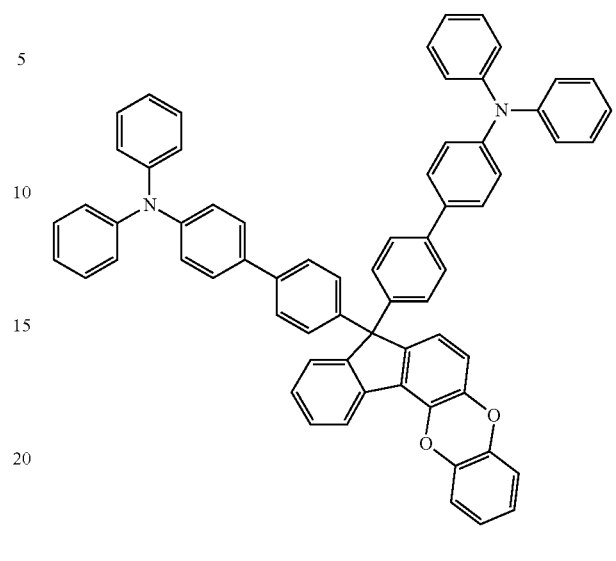
compound 131
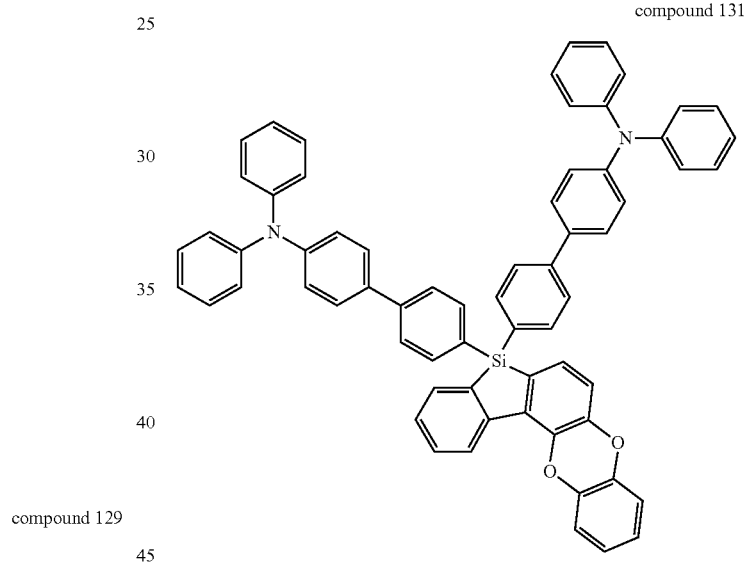
compound 129
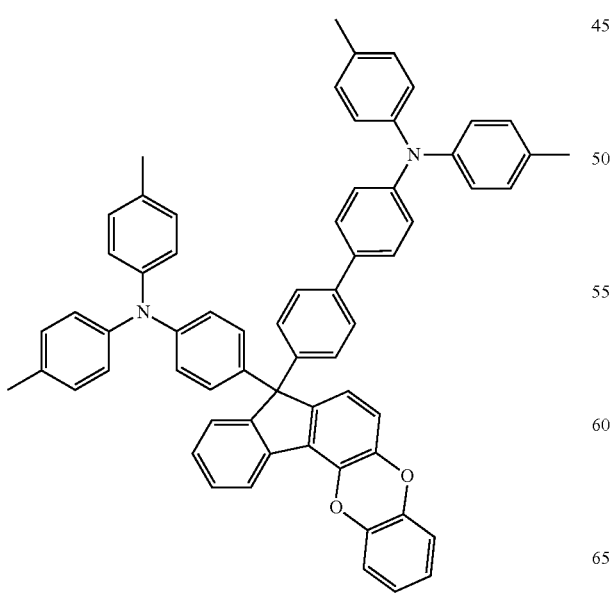
compound 132

compound 133
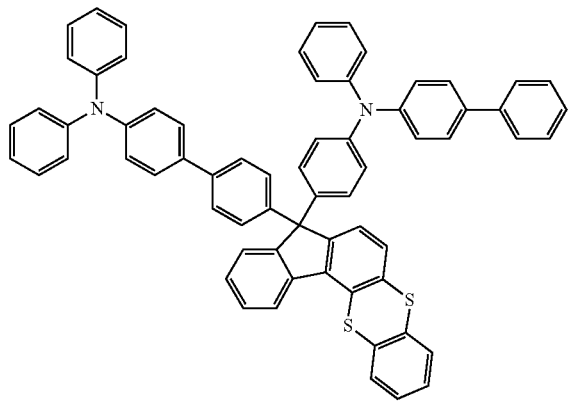
compound 134
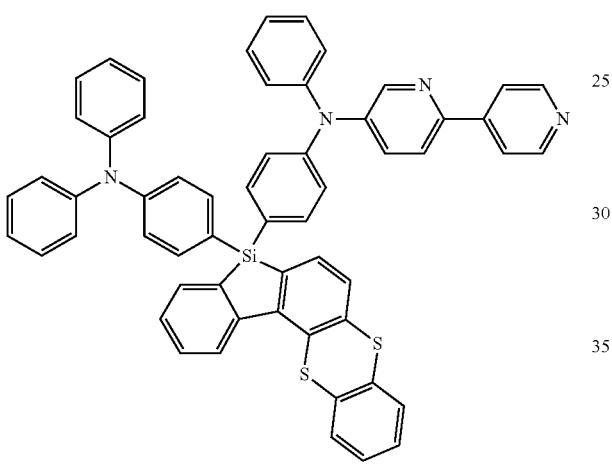
compound 135
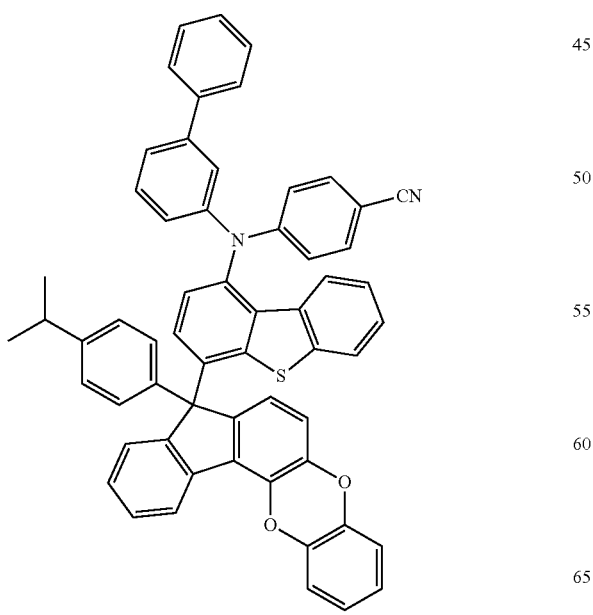
compound 136
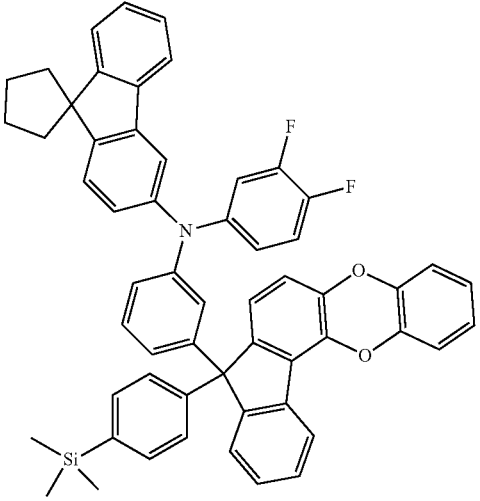
compound 137
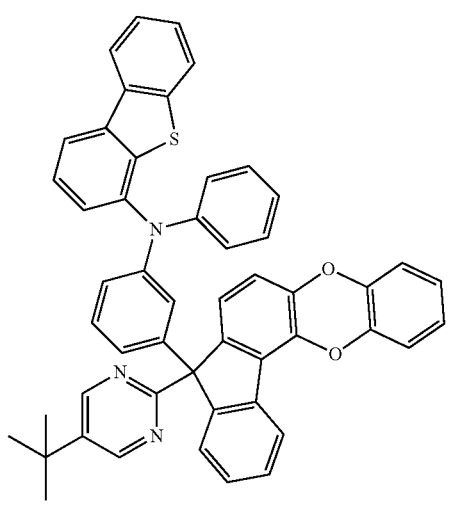
compound 138
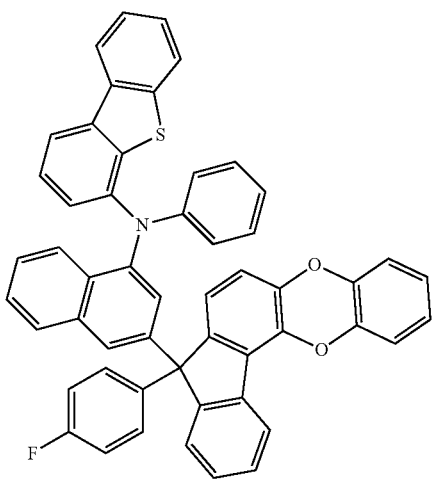

compound 139
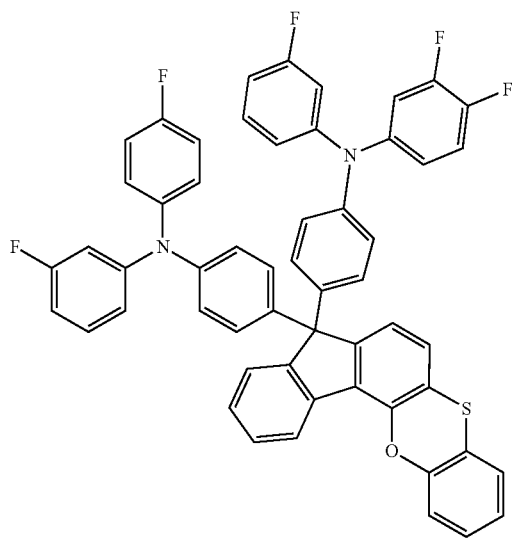
compound 140
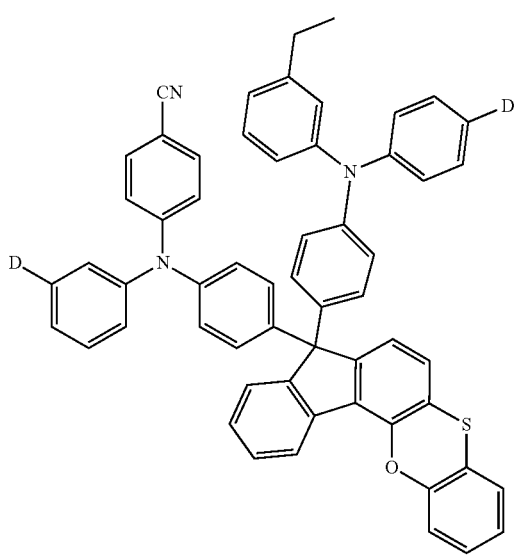
compound 141
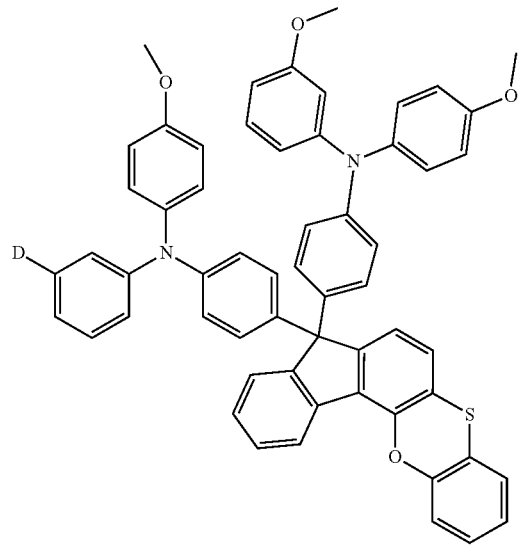
compound 142
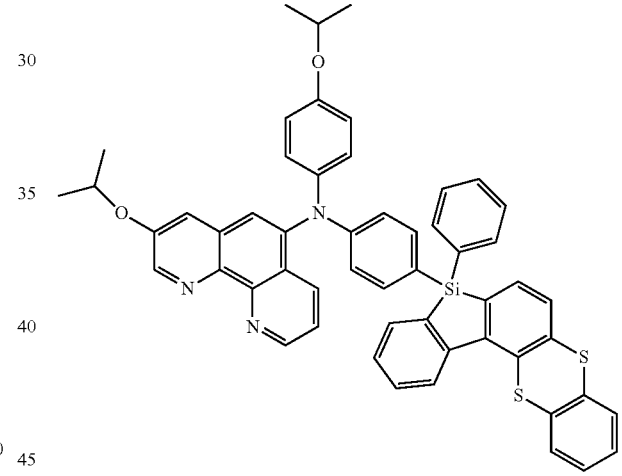
compound 143
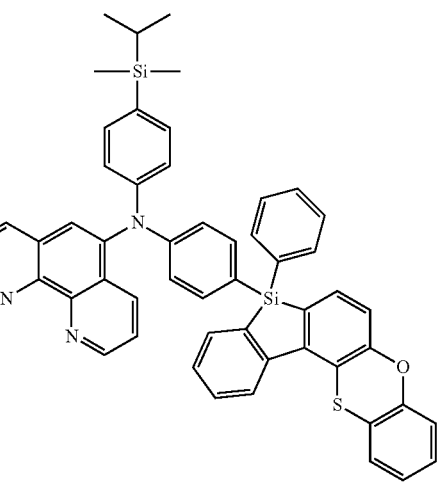

compound 144
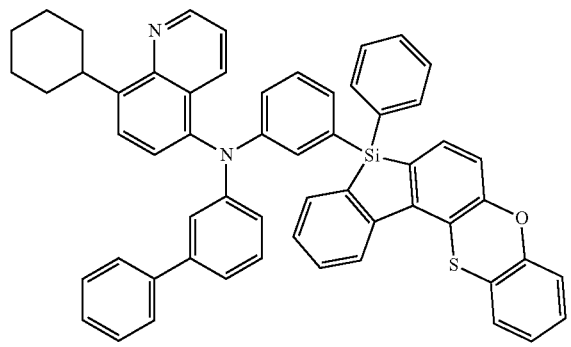
compound 147
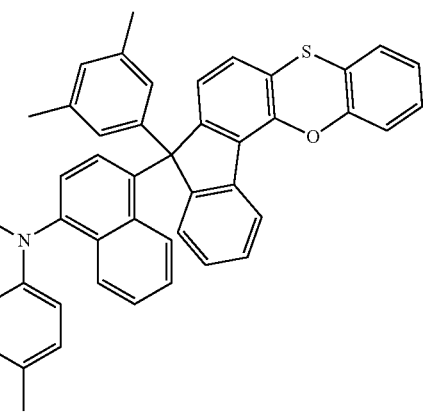
compound 145
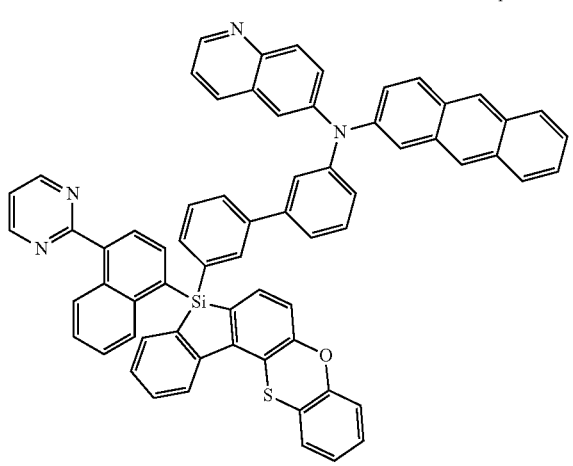
compound 148
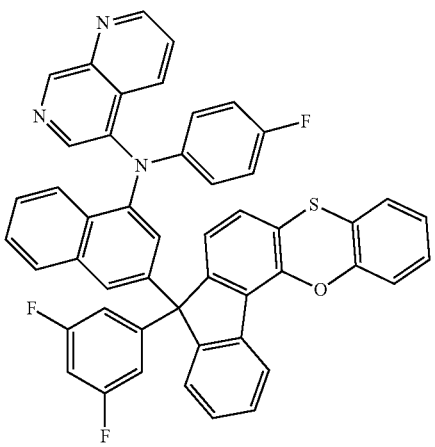
compound 146
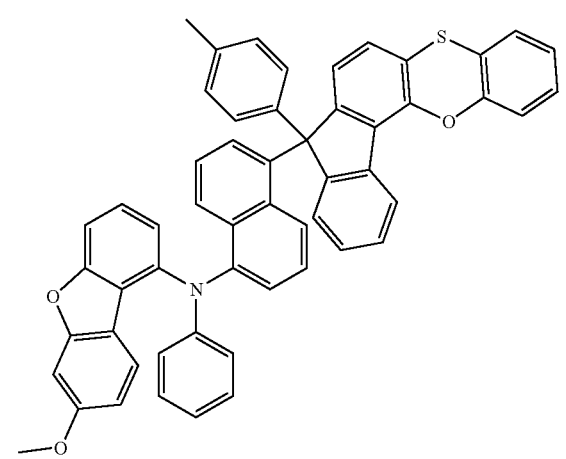
compound 149
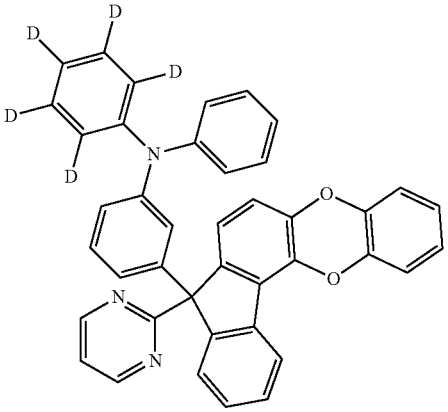

compound 150
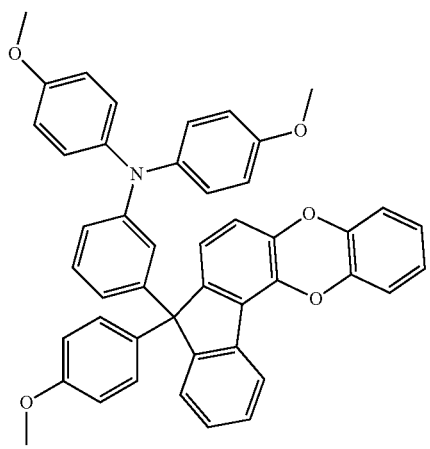
compound 153
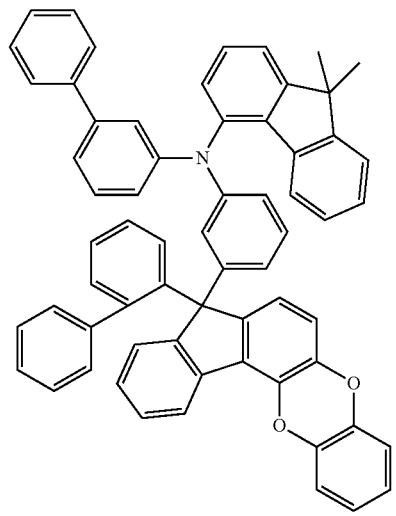
compound 151
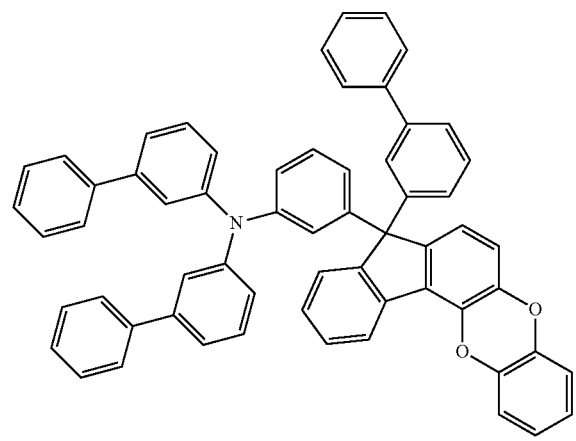
compound 154
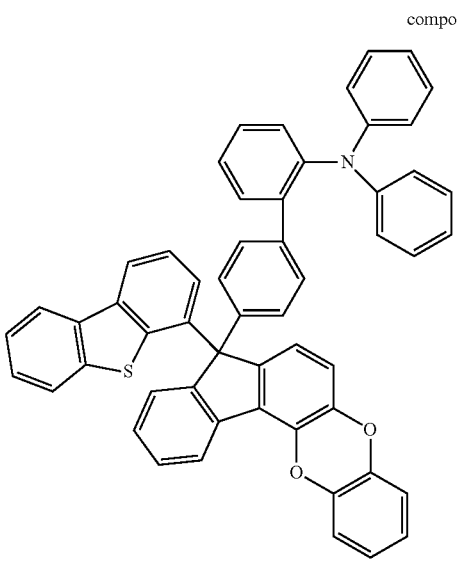
compound 152
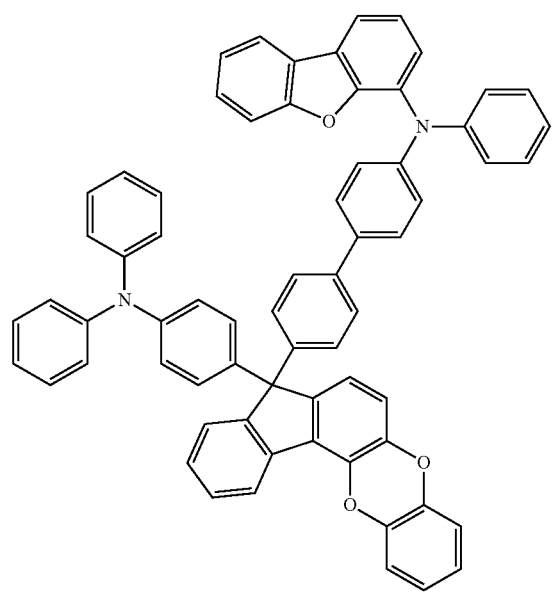
compound 155
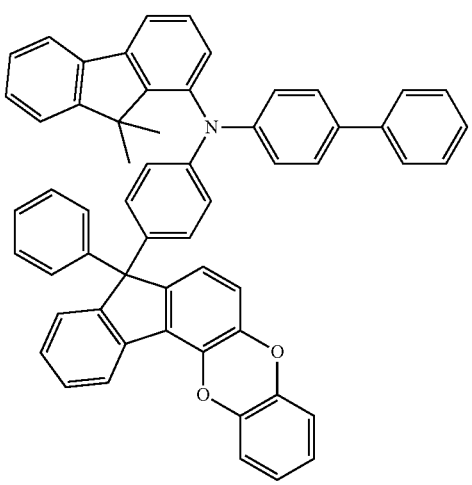

compound 156
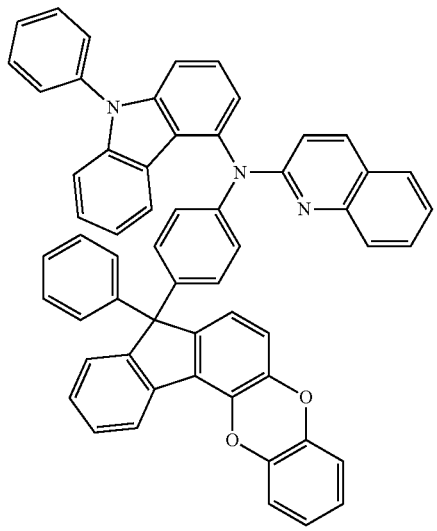
compound 157
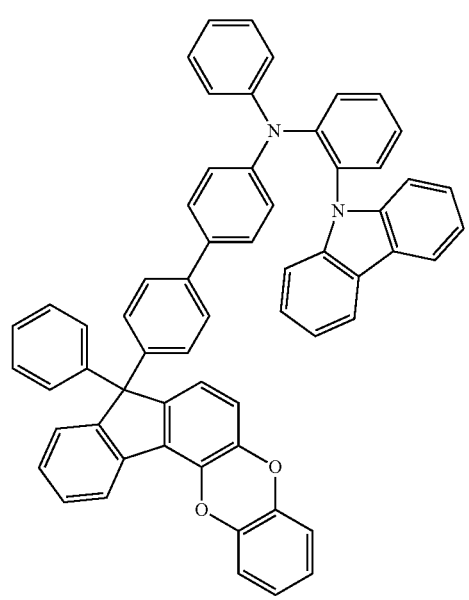
compound 158
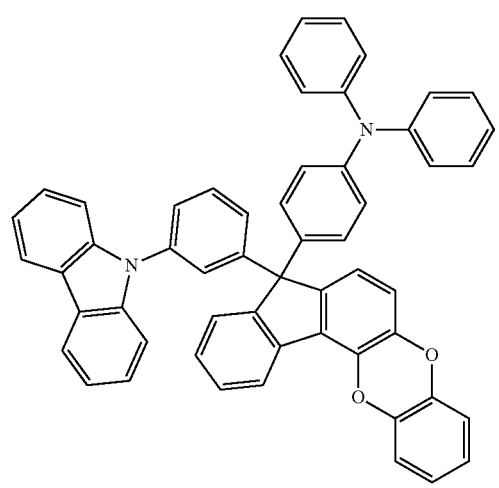
compound 159
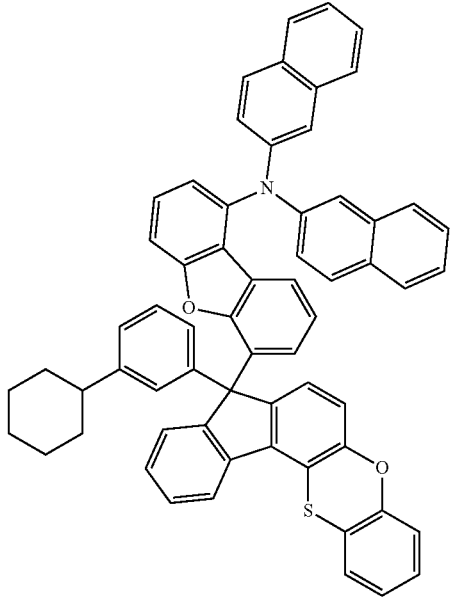
compound 160
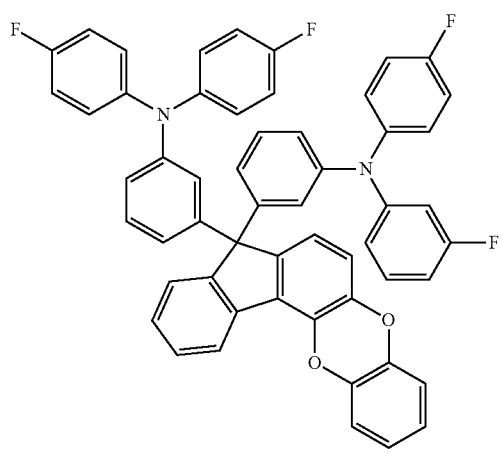
compound 161
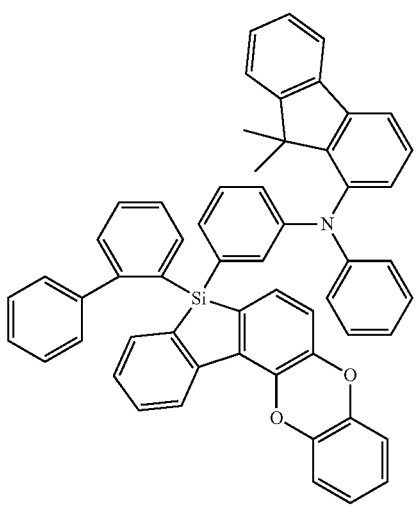

compound 162
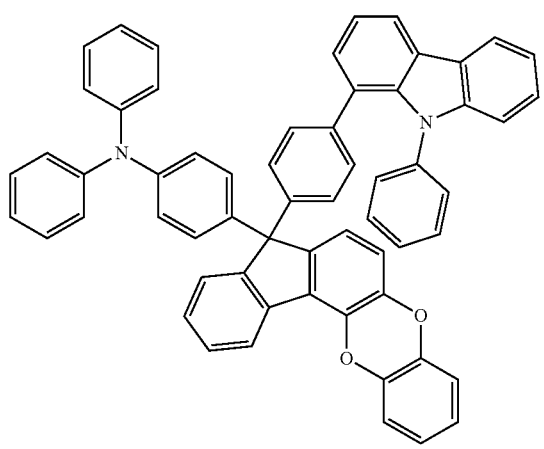
compound 163
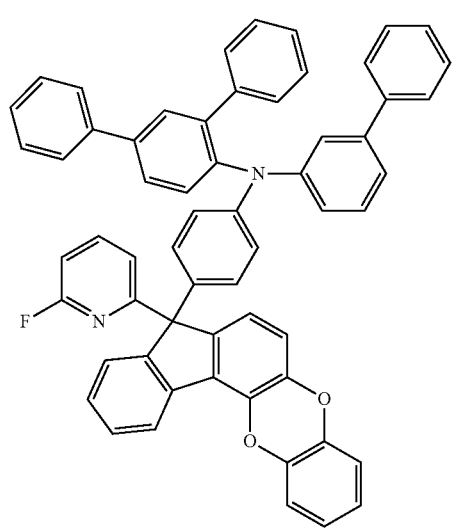
compound 164
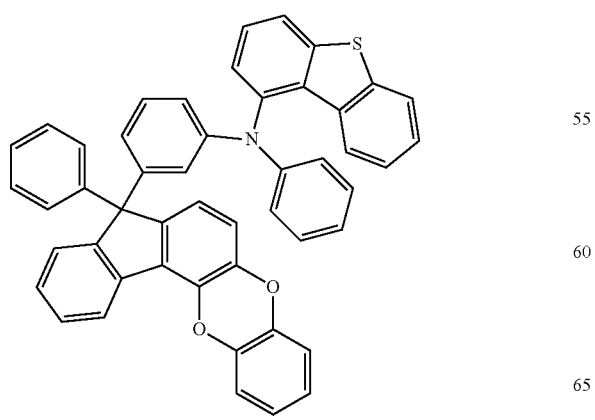
compound 165
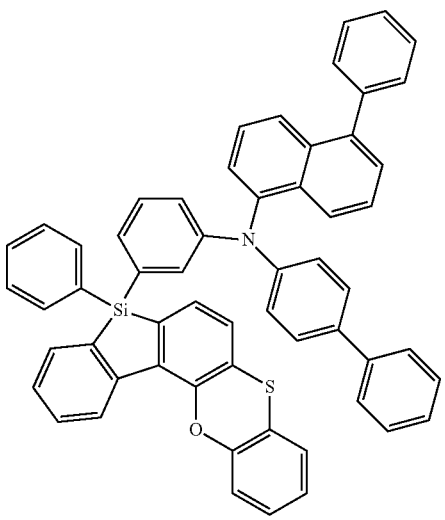
compound 166
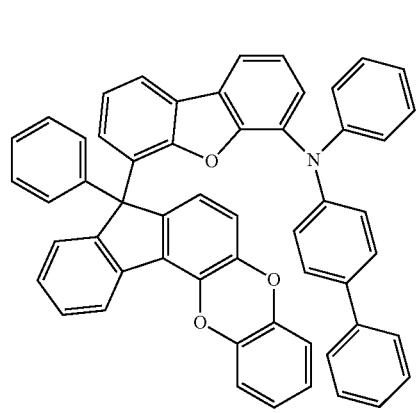
compound 167
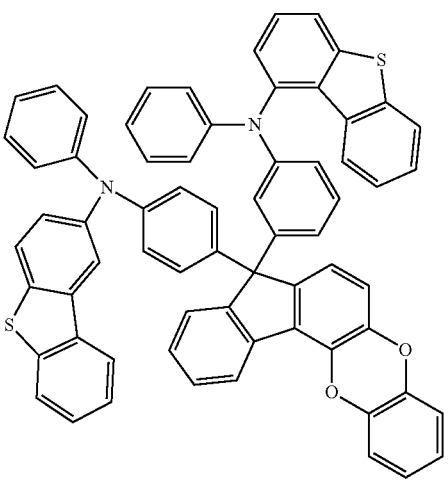

compound 168
compound 169
compound 170
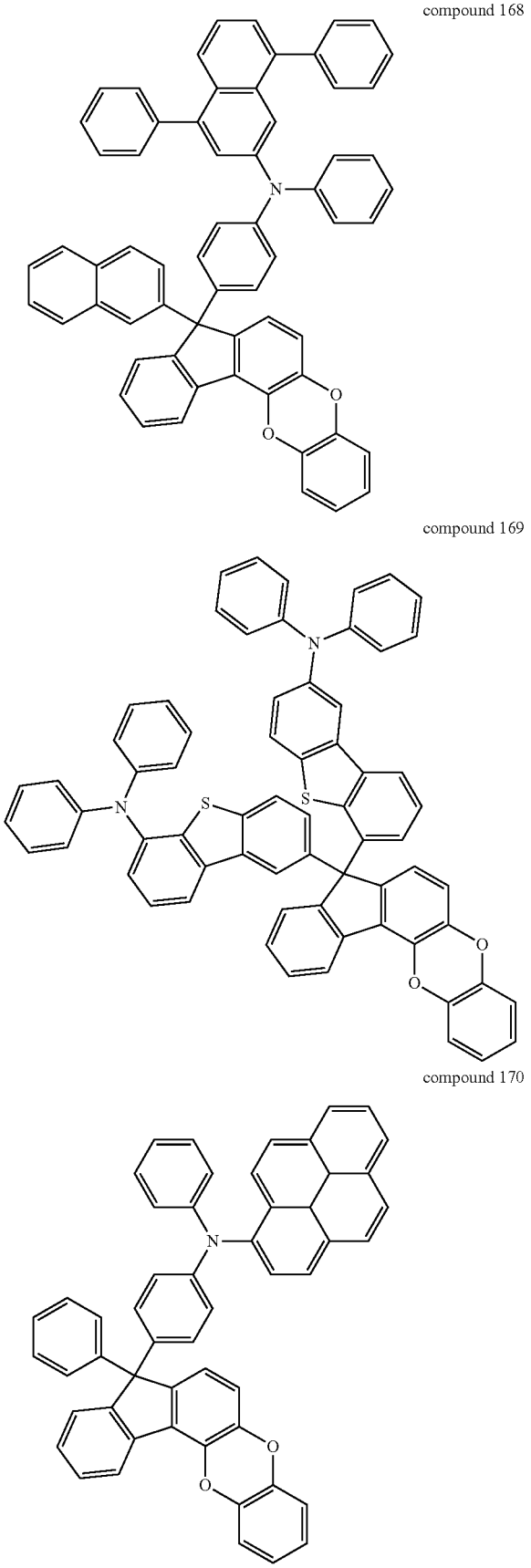
compound 171
compound 172
compound 173
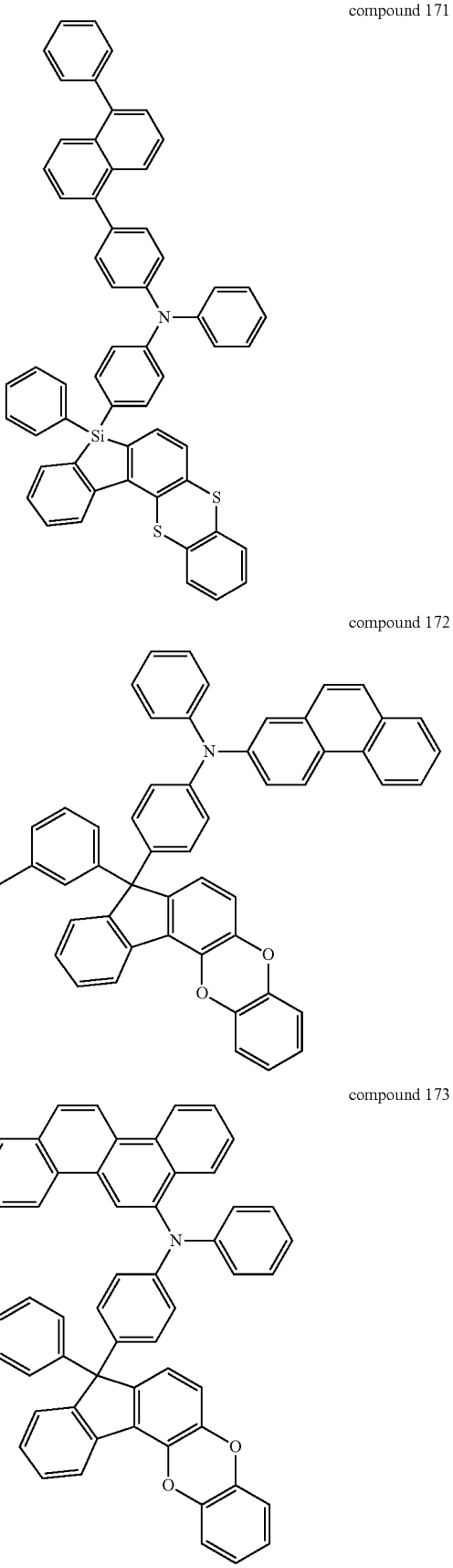

compound 174
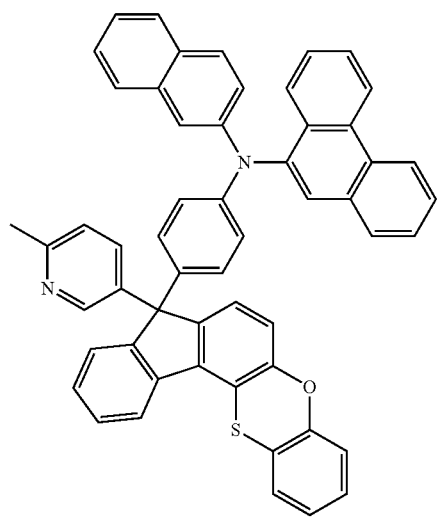
compound 175
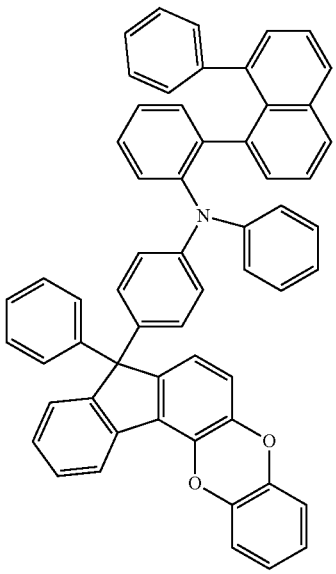
compound 176
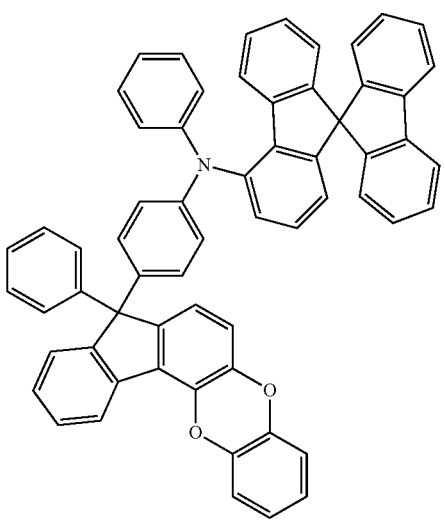
compound 177
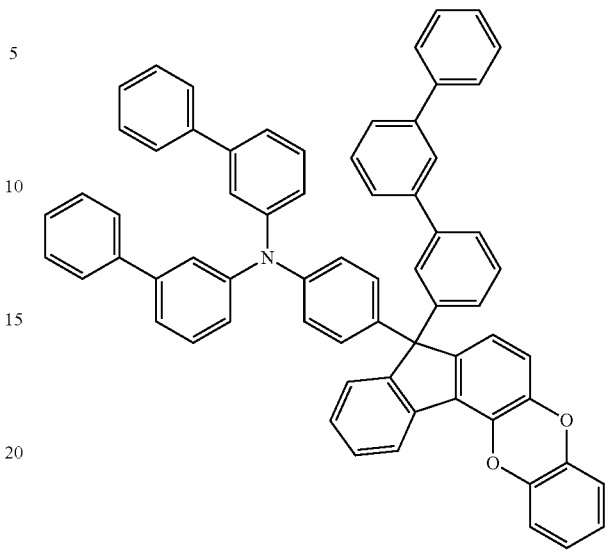
compound 178
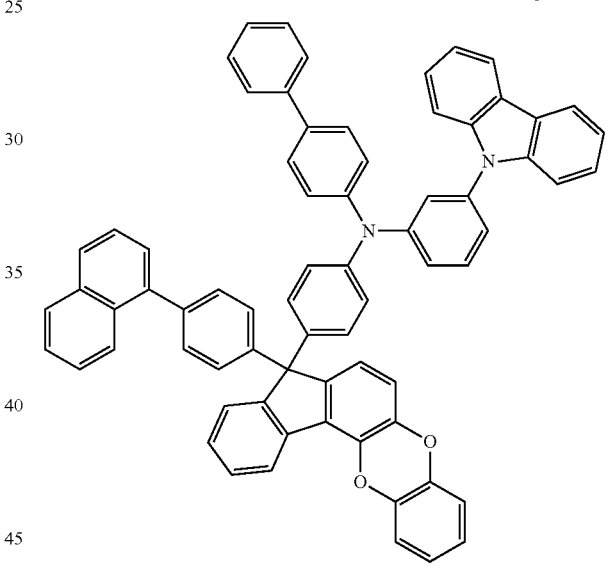
compound 179
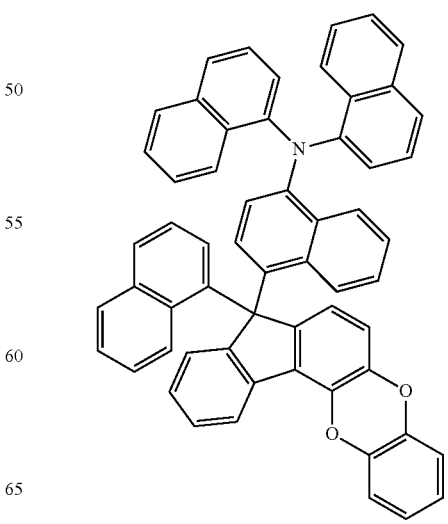

compound 180
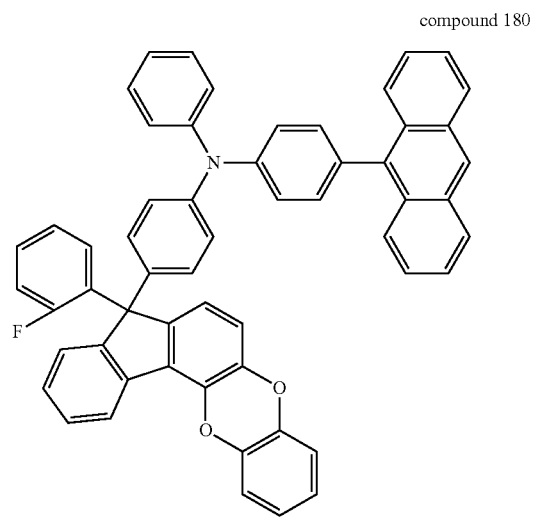
compound 181
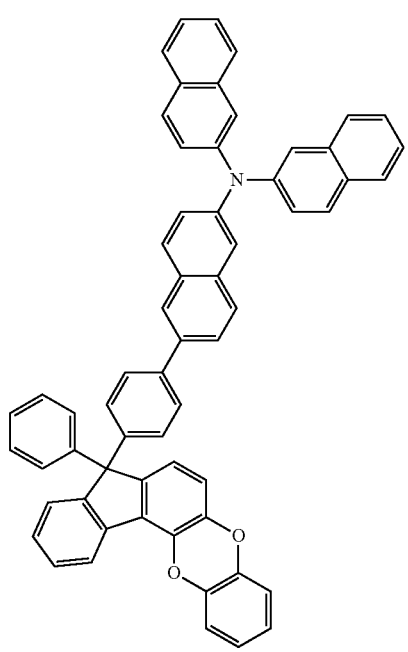
compound 182
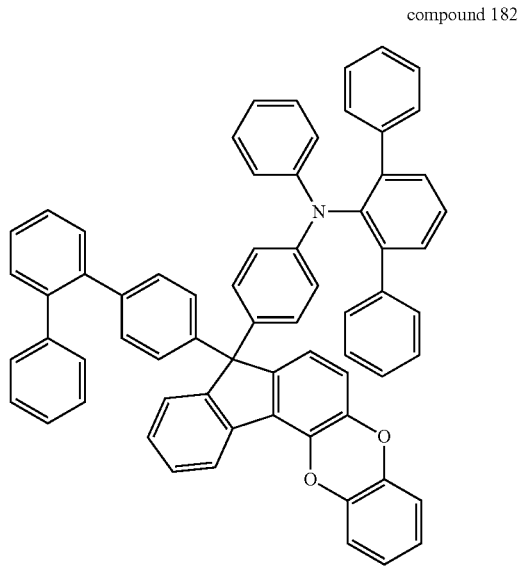
compound 183
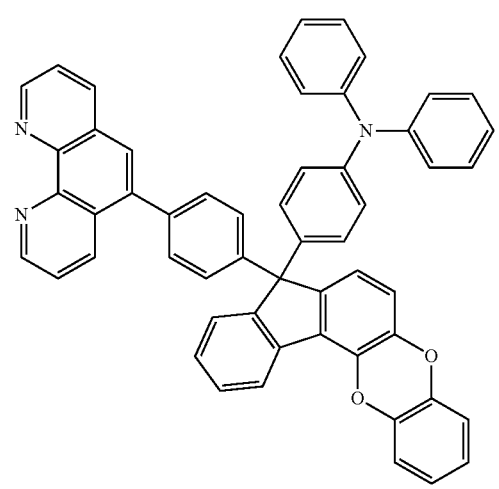
compound 184
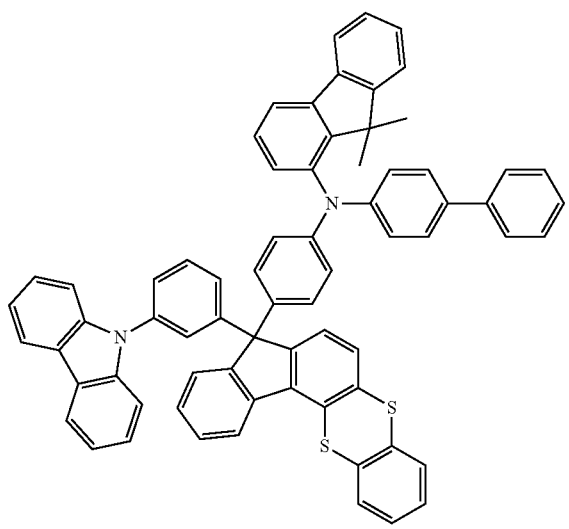

compound 185
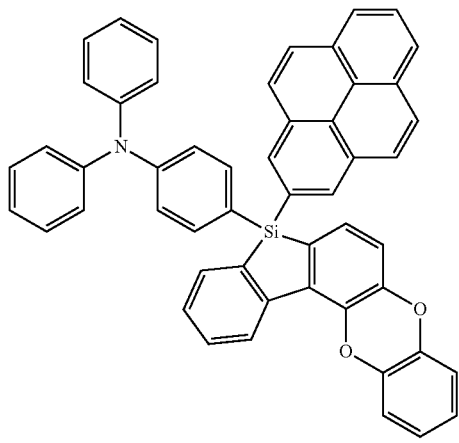
compound 188
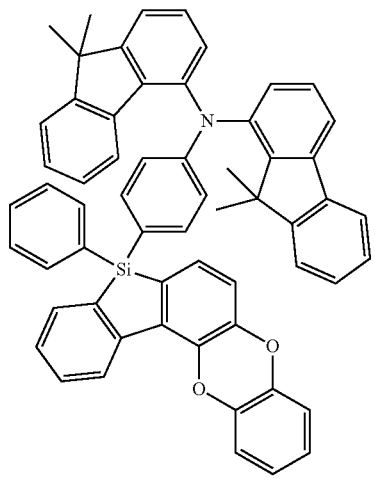
compound 186
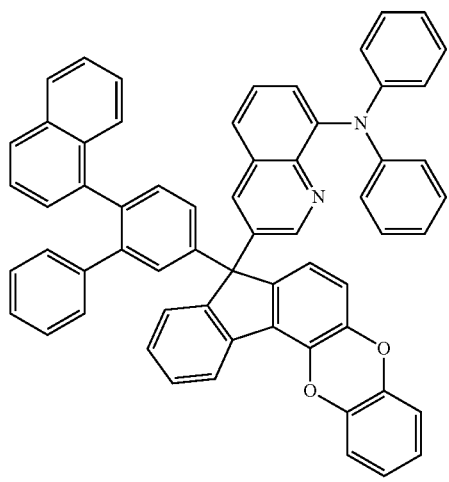
compound 189
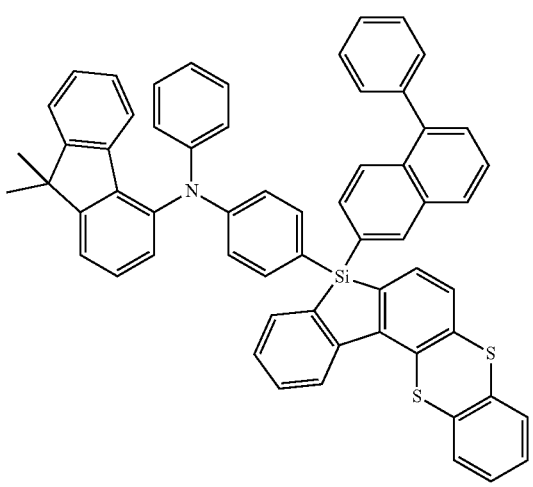
compound 187
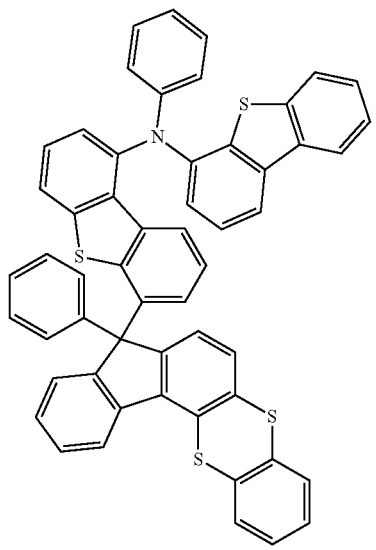
compound 190
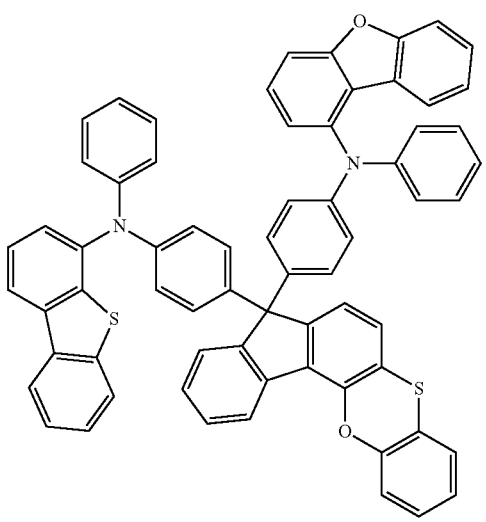

-continued compound 191

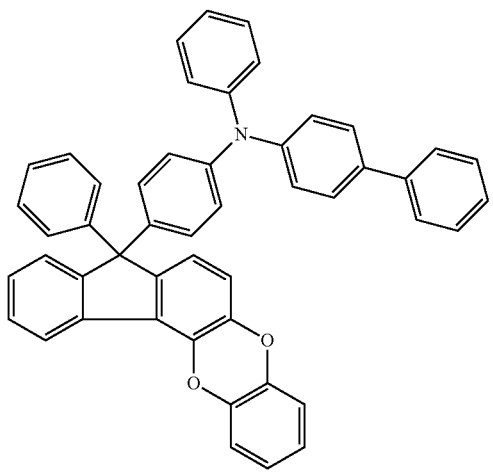

compound 192

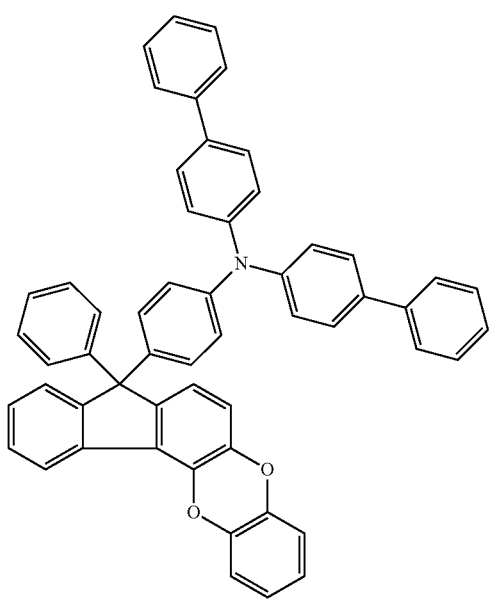

-continued compound 193

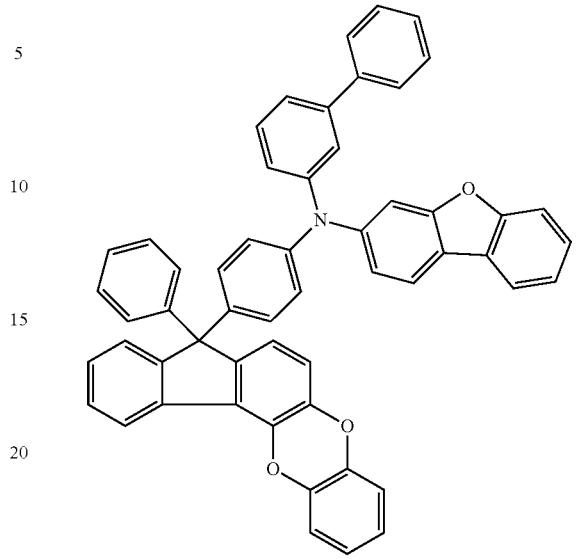

compound 194

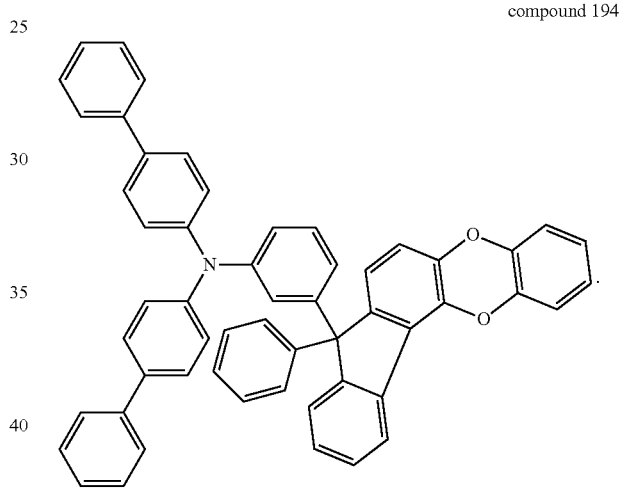

The disclosure also provides an electronic element, including an anode and a cathode that are arranged oppositely, and a functional layer arranged between the anode and the cathode, wherein the functional layer includes the organic compound described above.

The organic compound provided in the disclosure can be used to form at least one organic film layer in the functional layer to improve the voltage, efficiency, and life span characteristics of the electronic element. Optionally, the organic film layer with the organic compound of the disclosure may be located between the anode and an energy conversion layer of the electronic element, such as to improve the electron transport between the anode and the energy conversion layer. Further, the functional layer may include a hole transport layer (HTL), and the HTL may include the organic compound described above.

For example, the electronic element may be an OLED, which belongs to one kind of electronic elements. As shown in FIG. 1, the OLED includes an anode 100 and a cathode 200 that are arranged oppositely, and a functional layer 300 arranged between the anode 100 and the cathode 200, wherein the functional layer 300 includes the organic compound provided in the disclosure.

Optionally, the organic compound provided in the disclosure can be used to form at least one organic film layer in the functional layer 300 to improve the life span and efficiency characteristics of the OLED and reduce the driving voltage. In some embodiments, the organic compound can also improve the electrochemical stability and thermal stability of the OLED and improve the performance uniformity of mass-produced OLEDs.

Optionally, the functional layer 300 may include an HTL 320, and the HTL 320 may include the organic compound provided in the disclosure. The HTL 320 may be composed of the organic compound provided in the disclosure, or may be composed of the organic compound provided in the disclosure and other materials.

Optionally, the HTL 320 may include a first HTL 321 and a second HTL 322, wherein the first HTL 321 is provided on a surface of the second HTL 322 close to the anode 100, and the first HTL 321 or the second HTL 322 includes the organic compound provided in the disclosure. Either the first HTL 321 or the second HTL 322 includes the organic compound provided in the disclosure; or both the first HTL 321 and the second HTL 322 include the organic compound provided in the disclosure. It should be explained that the first HTL 321 or the second HTL 322 may include other materials, or may not include other materials. It should be explained that, in another embodiment of the disclosure, the second HTL 322 may serve as an electron blocking layer (EBL) of the OLED.

In an embodiment of the disclosure, as shown in FIG. 1, the OLED may include an anode 100, a first HTL 321, a second HTL 322, an organic light-emitting layer (EML) 330, an electron transport layer (ETL) 340, and a cathode 200 that are successively stacked. The organic compound provided in the disclosure can be used for a first HTL 321 or a second HTL 322 of an OLED to effectively improve the hole characteristics of the OLED. The hole characteristics are improved such that holes formed in the anode 100 are easily injected into the EML 330 and then transported in the EML 330 according to conduction characteristics at the HOMO level.

Optionally, the anode 100 may include a material with a large work function that facilitates the injection of holes into the functional layer. Specific examples of the anode material may include: metals such as nickel, platinum, vanadium, chromium, copper, zinc, and gold or alloys thereof; metal oxides such as zinc oxide, indium oxide, indium tin oxide (ITO), and indium zinc oxide (IZO); a combination of a metal and an oxide such as ZnO:Al or $SnO_2$:Sb; or conductive polymers such as poly(3-methylthiophene), poly[3,4-(ethylene-1,2-dioxy)thiophene] (PEDT), polypyrrole, and polyaniline; but are not limited thereto. Preferably, a transparent electrode with ITO may be adopted as the anode.

Optionally, the EML 330 may be composed of a single light-emitting material, or may include a host material and a guest material. Optionally, the EML 330 may be composed of a host material and a guest material, wherein holes injected into the EML 330 and electrons injected into the EML 330 can recombine in the EML 330 to form excitons, the excitons transfer energy to the host material, and then the host material transfers energy to the guest material, such that the guest material can emit light.

The host material of the EML 330 may be a metal chelate compound, a bisstyryl derivative, an aromatic amine derivative, a dibenzofuran derivative, or the like, which is not particularly limited in the disclosure. In an embodiment of the disclosure, the host material of the EML 330 may be 4,4'-N,N'-dicarbazole-biphenyl (CBP). In another embodiment of the disclosure, the host material of the EML 330 may be 9-(1-naphthyl)-10-(2-naphthyl)anthracene (α, β-ADN).

The guest material of the EML 330 may be a compound with a condensed aryl ring or a derivative thereof, a compound with a heteroaryl ring or a derivative thereof, an aromatic amine derivative, or the like, which is not particularly limited in the disclosure. In an embodiment of the disclosure, the guest material of the EML 330 may be $Ir(piq)_2$ (acac). In another embodiment of the disclosure, the guest material of the EML 330 may be BD-1.

The ETL 340 may have a single-layer structure or a multi-layer structure, which may include one or more electron transport materials. The electron transport materials may be benzimidazole derivatives, oxadiazole derivatives, quinoxaline derivatives, or other electron transport materials, which is not particularly limited in the disclosure. For example, in an embodiment of the disclosure, the ETL 340 may be composed of 4,7-diphenyl-2,9-bis(4-(1-phenyl-1H-benzo[d]imidazol-2-yl)phenyl)-1,10-phenanthroline (DBimiBphen) and 8-hydroxyquinolinolato-lithium (LiQ).

Optionally, the cathode 200 may include a material with a small work function that facilitates the injection of electrons into the functional layer. Specific examples of the cathode material may include: metals such as magnesium, calcium, sodium, potassium, titanium, indium, yttrium, lithium, gadolinium, aluminum, silver, tin, and lead or alloys thereof; or multi-layer materials such as LiF/Al, Liq/Al, $LiO_2$/Al, LiF/Ca, LiF/Al, and $BaF_2$/Ca; but are not limited thereto. Preferably, a metal electrode with aluminum may be adopted as the cathode.

Optionally, as shown in FIG. 1, a hole injection layer (HIL) 310 may be further provided between the anode 100 and the first HTL 321 to enhance the ability to inject holes into the first HTL 321. The HIL 310 can be made of a benzidine derivative, a starburst arylamine compound, a phthalocyanine derivative, or another material, which is not particularly limited in the disclosure. In an embodiment of the disclosure, the HIL 310 may be composed of 4,4',4''-tris(N-3-methylphenyl-N-phenylamino)triphenylamine (m-MTDATA).

Optionally, the HTL 320 may include the first HTL 321 and the second HTL 322, wherein the first HTL 321 is provided on a surface of the second HTL 322 close to the anode 100, and the first HTL 321 or the second HTL 322 includes the organic compound provided in the disclosure. Either the first HTL 321 or the second HTL 322 includes the organic compound provided in the disclosure; or both the first HTL 321 and the second HTL 322 include the organic compound provided in the disclosure. It should be explained that the first HTL 321 or the second HTL 322 may include other materials, or may not include other materials.

Optionally, the HTL 320 may further include an inorganic doped material to improve the hole transport performance of the HTL 320.

Optionally, as shown in FIG. 1, an electron injection layer (EIL) 350 may be further provided between the cathode 200 and the ETL 340 to enhance the ability to inject electrons into the ETL 340. The EIL 350 may include an inorganic material such as an alkali metal sulfide and an alkali metal halide, or may include a complex of an alkali metal and an organic substance. In an embodiment of the disclosure, the EIL 350 may include Yb.

Figure 3:
FIG. 3 is a schematic structure diagram of a photoelectric conversion device according an embodiment of the disclosure.

For example, the electronic element can be a photoelectric conversion device. As shown in FIG. 3, the photoelectric conversion device can include an anode 100 and a cathode 200 that are arranged oppositely, and a functional layer 300 arranged between the anode 100 and the cathode 200, wherein the functional layer 300 includes the organic compound provided in the disclosure.

Optionally, the organic compound provided in the disclosure can be used to form at least one organic film layer in the functional layer 300 to improve the performance of the photoelectric conversion device, especially to increase the life span and open-circuit voltage of the photoelectric conversion device or improve the performance uniformity and stability of mass-produced photoelectric conversion devices.

Optionally, the functional layer 300 may include an HTL 320, and the HTL 320 may include the organic compound of the disclosure. The HTL 320 may be composed of the organic compound provided in the disclosure, or may be composed of the organic compound provided in the disclosure and other materials. It should be explained that the HTL 320 may include other materials, or may not include other materials.

Optionally, the HTL 320 may further include an inorganic doped material to improve the hole transport performance of the HTL 320.

In an embodiment of the disclosure, as shown in FIG. 3, the photoelectric conversion device may include an anode 100, an HTL 320, a photoelectric conversion layer 360 (energy conversion layer), an ETL 340, and a cathode 200 that are successively stacked.

Optionally, the photoelectric conversion device may be a solar cell, especially an organic thin-film solar cell. For example, in an embodiment of the disclosure, the solar cell may include an anode 100, an HTL 320, a photoelectric conversion layer 360, an ETL 340, and a cathode 200 that are successively stacked, wherein the HTL 320 includes the organic compound of the disclosure.

An embodiment of the disclosure also provides an electronic device, including the electronic element described in any one of the above-mentioned electronic element embodiments. Since the electronic device has the electronic element described in any one of the above-mentioned electronic element embodiments, the electronic device has the same beneficial effects as the electronic element, which will not be repeated in the disclosure.

Figure 2:
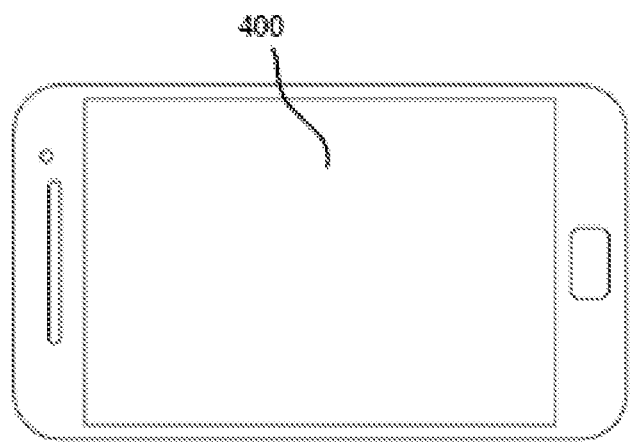
FIG. 2 is a schematic structure diagram of an electronic device according an embodiment of the disclosure.

For example, as shown in FIG. 2, the disclosure provides an electronic device 400, the electronic device 400 includes the OLED described in any one of the above-mentioned OLED embodiments. The electronic device 400 may be a display device, a lighting device, an optical communication device, or another electronic device, including but not limited to computer screen, mobile phone screen, television set, electronic paper, emergency light, and optical module. Since the electronic device 400 has the OLED described in any one of the above-mentioned OLED embodiments, the electronic device has the same beneficial effects as the OLED, which will not be repeated in the disclosure.

Figure 4:
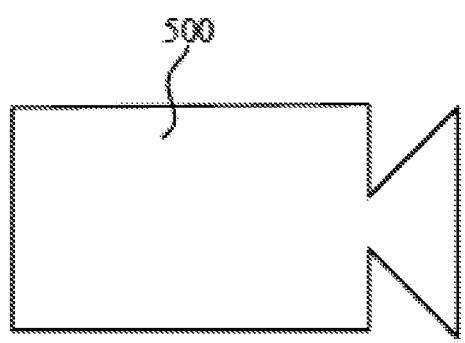
FIG. 4 is a schematic structure diagram of an electronic device according an embodiment of the disclosure.

For example, as shown in FIG. 4, the disclosure provides an electronic device 500 including the OLED described in any one of the above-mentioned OLED embodiments. The electronic device 500 may be a solar power generation device, a light detector, a fingerprint identification device, an optical module, a charged-coupled device (CCD) camera, or another electronic device. Since the electronic device 500 has the photoelectric conversion device described in any one of the above-mentioned photoelectric conversion device embodiments, the electronic device has the same beneficial effects as the photoelectric conversion device, which will not be repeated in the disclosure.

EXAMPLES

The disclosure will be described in detail below with reference to examples. However, the examples according to the specification may be modified into various other forms, and the scope of the specification should not be construed as being limited to the examples described below. The examples of the specification are provided to completely describe the specification to those skilled in the art.

Those skilled in the art will recognize that the chemical reactions described in the disclosure can be used to appropriately prepare many other compounds of the disclosure, and other methods for preparing the compounds of the disclosure are considered to be within the scope of the disclosure. For example, the synthesis of non-illustrative compounds according to the disclosure can be successfully completed by those skilled in the art through modified methods, such as appropriately protecting interfering groups, using other known reagents in addition to those described in the disclosure, or conventionally modifying reaction conditions. In addition, reactions applied by the disclosure or known reaction conditions are also recognized to be applicable to the preparation of other compounds of the disclosure.

In the examples described below, all temperatures are expressed in ° C. unless otherwise indicated. The reagents are purchased from commodity suppliers such as Aldrich Chemical Company, Arco Chemical Company, and Alfa ChemicalCompany, which are used without further purification unless otherwise stated. Common reagents are purchased from Shantou Xilong Chemical Co., Ltd., Guangdong Guanghua Chemical Reagent Factory Co., Ltd., Guangzhou Chemical Reagent Factory, Tianjin Haoyuyu Chemical Co., Ltd., Tianjin Fuchen Chemical Reagent Factory, Wuhan Xinhuayuan Technology Development Co., Ltd., Qingdao Tenglong Chemical Reagent Co., Ltd., and Qingdao Haiyang Chemical Co., Ltd. Raw materials are purchased from suppliers such as Henan Chuangan Optoelectronics Technology Co., Ltd.

The following reactions are generally conducted under a positive pressure of nitrogen or argon, wherein an anhydrous solvent is provided with a drying tube (unless otherwise stated), a reaction flask is plugged with a suitable rubber plug, a substrate is injected through a syringe, and glass wares are all dry.

A chromatographic column is a silica gel column. Silica gel (300 to 400 mesh) is purchased from Qingdao Haiyang Chemical Co., Ltd.

Low-resolution mass spectrometry (MS) data are obtained under the following condidtions: Agilent 6120 quadrupole HPLC-M (column model: Zorbax SB-C18, 2.1× 30 mm, 3.5 μm, 6 min, flow rate: 0.6 mL/min; and mobile phase: a proportion of ($CH_3CN$ with 0.1% formic acid) in ($H_2O$ with 0.1% formic acid): 5% to 95%), electrospray ionization (ESI), and ultraviolet (UV) detection at 210 nm/254 nm.

$^1$H nuclear magnetic resonance spectroscopy (HNMR): Through a Bruker 400 MHz NMR spectrometer, the HNMR is conducted at room temperature with $CDCl_3$ (in ppm) as a solvent and tetramethylsilane (TMS) (0 ppm) as a reference standard. When multiplets appear, the following abbreviations will be adopted: s: singlet, d: doublet, t: triplet, and m: multiplet.

Synthesis Examples

Synthesis of Compound 1

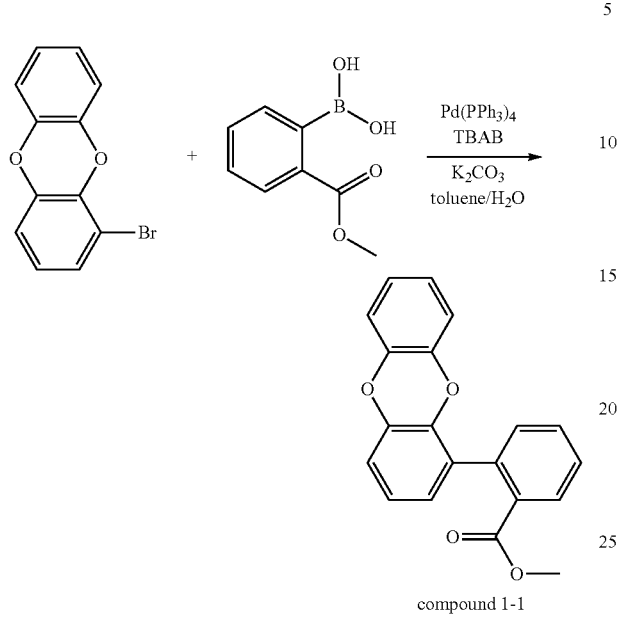

Step 1: A mixture of 3.95 g (15 mmol) of 1-bromodibenzodioxin, 2.71 g (15 mmol) of 2-(methoxycarbonyl)phenylboronic acid, 4.14 g (30 mmol) of potassium carbonate, 0.1733 g (0.15 mmol) of tetrakis(triphenylphosphine)palladium, and 0.0483 g (0.15 mmol) of tetrabutylammonium bromide (TBAB) was added to a 100 mL three-necked flask, and then a mixed solvent of toluene/water (32 mL/8 mL) was added to the flask; air in the flask was completely replaced with nitrogen, and then the reaction system was heated to 80° C. and stirred for 10 h. The resulting reaction solution was washed with water and then the separated organic phase was dried over anhydrous magnesium sulfate, and then concentrated in a vacuuo to obtain an oily solid; and the oily solid was heated to reflex and stirred with ethanol, and then subjected to recrystallization with a mixed solvent of dichloromethane (DCM) and n-heptane (1:5) to obtain a compound 1-1 (3.63 g, yield: 76%).

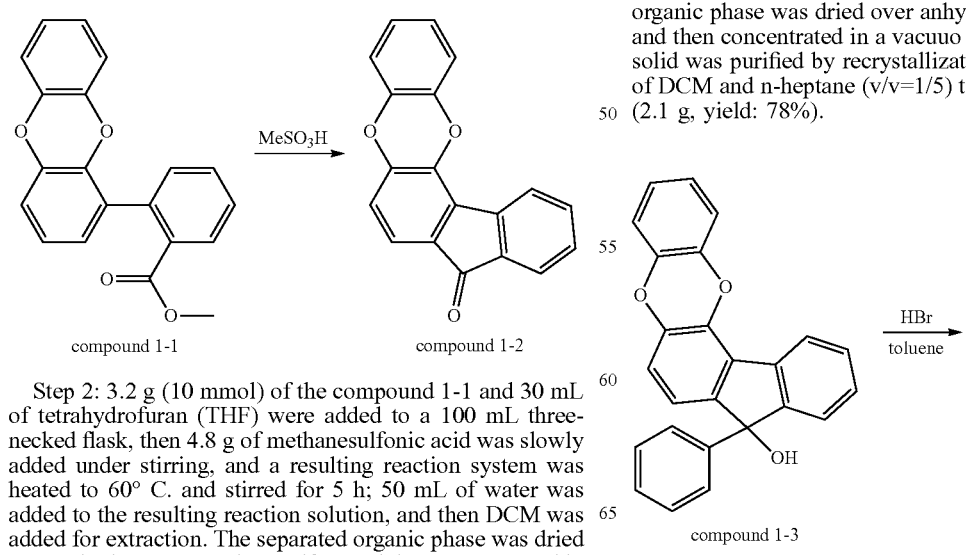

Step 2: 3.2 g (10 mmol) of the compound 1-1 and 30 mL of tetrahydrofuran (THF) were added to a 100 mL three-necked flask, then 4.8 g of methanesulfonic acid was slowly added under stirring, and a resulting reaction system was heated to 60° C. and stirred for 5 h; 50 mL of water was added to the resulting reaction solution, and then DCM was added for extraction. The separated organic phase was dried over anhydrous magnesium sulfate and then concentrated in a vacuuo to obtain a solid; and the solid was heated to reflux and stirred with n-heptane to obtain a compound 1-2 (2.2 g, yield: 77%).

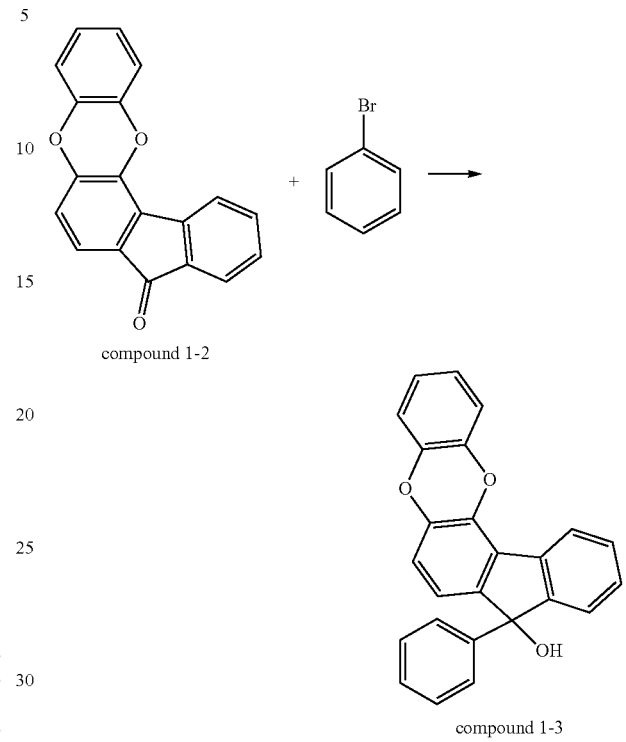

Step 3: 1.15 g (7.3 mmol) of bromobenzene and 10 mL of anhydrous THF were added to a 100 mL three-necked flask, and a resulting mixture was cooled to −30° C. under stirring; 3.85 mL (7.7 mmol) of a solution of 2 mol/L n-butyl lithium in n-hexane was added dropwise slowly under nitrogen atmosphere, and the resulting mixture was thermally insulated and stirred for 30 min; then a mixed solution of 2.2 g (7.7 mmol) of the compound 1-2 and 10 mL of THF was added dropwise slowly. The resulting mixture was thermally insulated and stirred for another 30 min, then naturally warmed to room temperature, and further stirred for 2 h. Water was added dropwise to quench the reaction, and then ethyl acetate was added for extraction. The separated organic phase was dried over anhydrous magnesium sulfate and then concentrated in a vacuuo to obtain a solid; and the solid was purified by recrystallization with a mixed solvent of DCM and n-heptane (v/v=1/5) to obtain a compound 1-3 (2.1 g, yield: 78%).

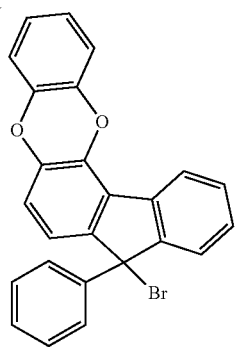

compound 1-4

Step 4: 2.1 g (5.8 mmol) of the compound 1-3, 20 mL of toluene, and 5 mL of hydrobromic acid (47%) were added to a 100 mL three-necked flask, the reaction mixture was stirred under nitrogen atmosphere for 24 h at room temperature; toluene was added to a resulting reaction solution for extraction, and the separated organic phase was dried with anhydrous magnesium sulfate and then concentrated in a vacuuo to obtain a solid; and the solid was purified by recrystallization with DCM and n-heptane (v/v=1/3) to obtain a compound 1-4 (2.07 g, yield: 84%).

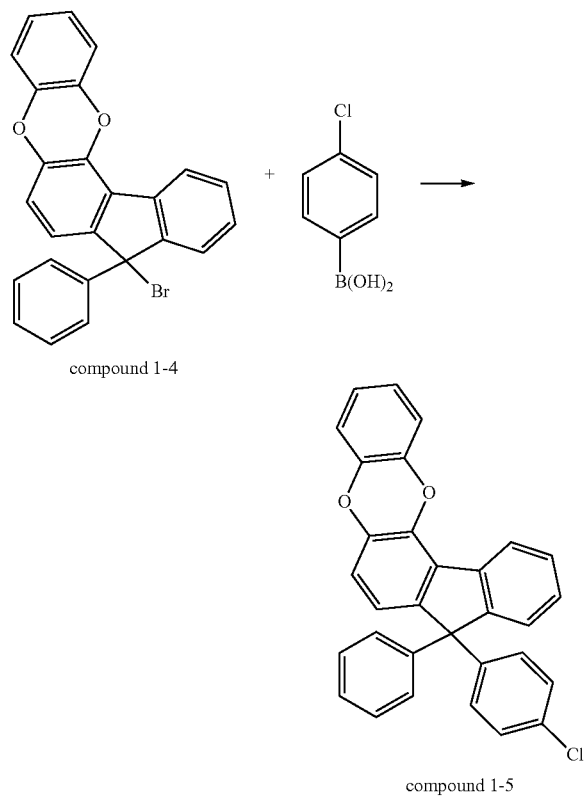

compound 1-4 compound 1-5

Step 5: Under a nitrogen atmosphere, a mixture of 2.07 g (4.8 mmol) of the compound 1-4, 0.76 g (4.8 mmol) of p-chlorophenylboronic acid, 0.028 g (0.024 mmol) of tetrakis(triphenylphosphine)palladium, 0.008 g (0.024 mmol) of TBAB, and 1.34 g (9.7 mmol) of potassium carbonate was added to a 100 mL three-necked flask, then a mixed solvent of toluene/water (16 mL/4 mL) was added to the flask, and a reaction system was heated to 80° C. and stirred for 15 h. The resulting reaction solution was washed with water, and then extracted with toluene. The separated organic phase was dried with anhydrous magnesium sulfate, and then concentrated in a vacuuo to obtain a solid; and the solid was heated to reflux and stirred with ethanol, and then purified by recrystallization with DCM to obtain a compound 1-5 (1.76 g, yield: 79%).

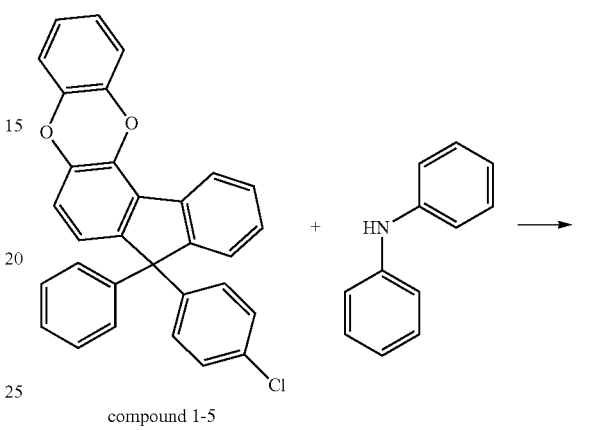

compound 1-5 compound 1

Step 6: Under a nitrogen atmosphere, a mixture of 1.76 g (3.8 mmol) of the compound 1-5, 0.65 g (3.8 mmol) of diphenylamine, 0.018 g (0.019 mmol) of tris(dibenzylideneacetone)dipalladium, 0.016 g (0.038 mmol) of 2-dicyclohexylphosphino-2',6'-dimethoxybiphenyl, and 0.55 g (5.7 mmol) of sodium tert-butoxide was added to a 100 mL three-necked flask, then 20 mL of toluene was added to the flask, and a reaction system was heated to reflux and stirred for 5 h; water was added to quench the reaction, and toluene was added for extraction. The separated organic phase was dried with anhydrous magnesium sulfate, and concentrated in a vacuuo to obtain a solid; and the solid was purified by silica gel column chromatography and eluted with a mixed solvent of DCM and n-heptane (v/v=1/4) to obtain a compound 1 (1.99 g, yield: 88%).

LC-MS: m/z=592.2[M+H]$^+$ $^1$H NMR (400 MHz, CDCl$_3$) δ: 8.05 (d, 1H), 7.63-7.42 (m, 15H), 7.36-7.30 (m, 4H), 7.27-7.02 (m, 7H), 6.89-6.85 (m, 2H) ppm.

Synthesis of Compound 2

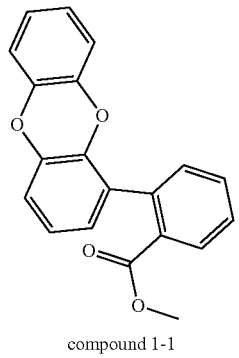

compound 1-1

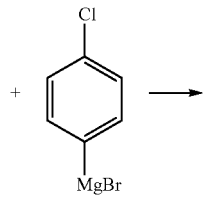

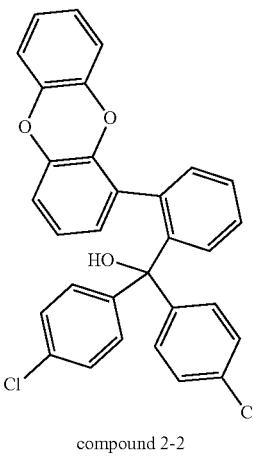

compound 2-2

Step 1: 3.19 g (10 mmol) of the compound 1-1 was added to a 100 mL three-necked flask, air in the flask was completely replaced with nitrogen, 20 mL of anhydrous THF was added, and a resulting mixture was cooled to −40° C. under stirring; 10 mL of a Grignard reagent (p-chlorophenylmagnesium bromide in n-hexane, with a concentration of 2 mol/L) was added dropwise slowly at −40° C., and then the reaction system was naturally warmed to room temperature and stirred for another 2 h. An aqueous ammonium chloride solution was added to quench the reaction, and ethyl acetate was added for extraction. The separated organic phase was dried with anhydrous magnesium sulfate, and then then concentrated in a vacuuo to obtain a solid compound 2-2 (4.4 g, purity: 83%), which would be directly used in the next reaction without purification.

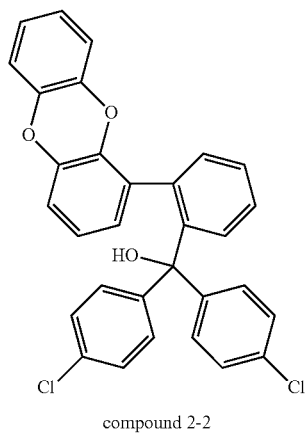

compound 2-2

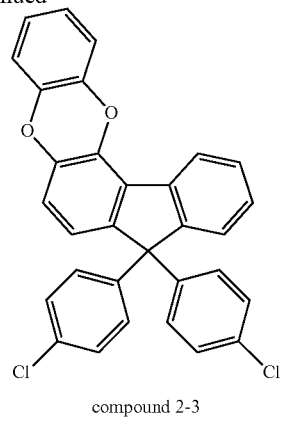

compound 2-3

Step 2: 3.13 g of the compound 2-2 (purity: 83%) and 30 mL of acetic acid were added to a 100 mL three-necked flask, 3 mL of concentrated sulfuric acid was slowly added dropwise under stirring, and a reaction system was heated to 80° C. and stirred for 8 h. Water was added to quench the reaction, then ethyl acetate was added for extraction. The separated organic phase was dried with anhydrous magnesium sulfate and then concentrated in a vacuuo to obtain a solid, and the solid was subjected to recrystallization with DCM to obtain a compound 2-3 (1.63 g, yield: 65%).

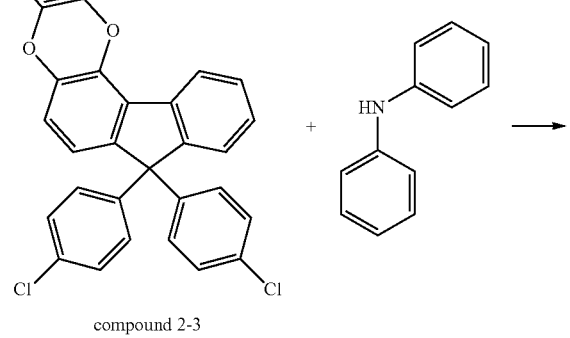

compound 2-3

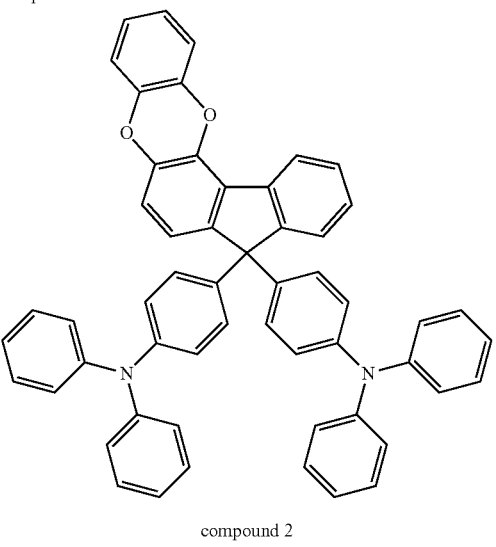

compound 2

Step 3: A mixture of 1.63 g (3.3 mmol) of the compound 2-3, 1.12 g (6.6 mmol) of diphenylamine, 0.476 g (4.96 mmol) of sodium tert-butoxide, 0.0151 g (0.016 mmol) of tris(dibenzylideneacetone)dipalladium, and 0.0136 g (0.033 mmol) of 2-dicyclohexylphosphino-2',6'-dimethoxybiphenyl was added to a 100 mL three-necked flask, then 20 mL of toluene was added to the flask, air in the flask was completely replaced with nitrogen, and a reaction system was heated to 110° C. and stirred for 7 h; water was added to the resulting reaction solution for quenching and washing, and a resulting solution was allowed to be separated into layers. The separated organic phase was dried with anhydrous magnesium sulfate and then concentrated in a vacuuo to obtain a solid; and the solid was purified by silica gel column chromatography and eluted with a mixture of DCM and n-heptane (v/v=1/3) to obtain a compound 2 (2.01 g, yield: 80%).

LC-MS: m/z=759.3[M+H]$^+$ $^1$H NMR (400 MHz, CDCl$_3$) δ: 8.03 (d, 1H), 7.60-7.44 (m, 14H), 7.37-7.32 (m, 8H), 7.24-7.06 (m, 13H), 6.91-6.87 (m, 2H) ppm.

Synthesis of Compound 3

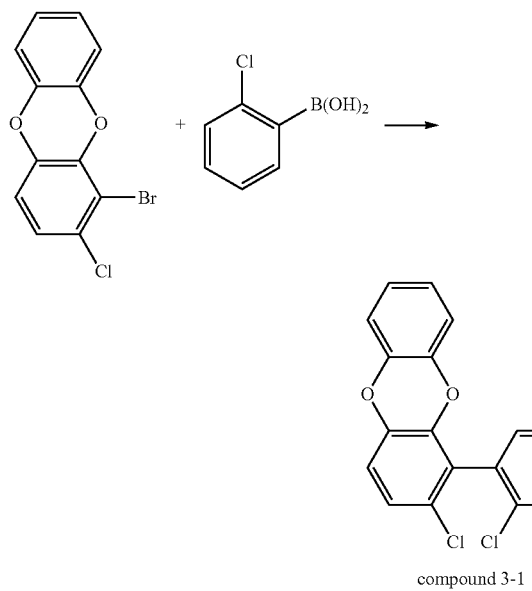

Step 1: A mixture of 3 g (10 mmol) of 1-bromo-2-chlorodibenzodioxin, 1.58 g (10 mmol) of 2-chlorophenylboronic acid, 0.12 g (0.1 mmol) of tetrakis(triphenylphosphine)palladium, 0.033 g (0.1 mmol) of TBAB, and 2.8 g (20 mmol) of potassium carbonate was added to a 100 mL three-necked flask, then a mixed solvent of toluene/ethanol/water (20 mL/5 mL/5 mL) was added to the flask, and a reaction system was heated to 80° C. and stirred for 12 h under nitrogen atmosphere. Toluene was added to the resulting reaction solution for extraction, and the separated organic phase was dried with anhydrous magnesium sulfate and then concentrated in a vacuuo to obtain a solid; and the solid was heated to reflux and stirred with n-heptane, a resulting mixture was filtered, and a filter cake was rinsed with a small amount of ethanol to obtain a compound 3-1 (2.6 g, yield: 78%).

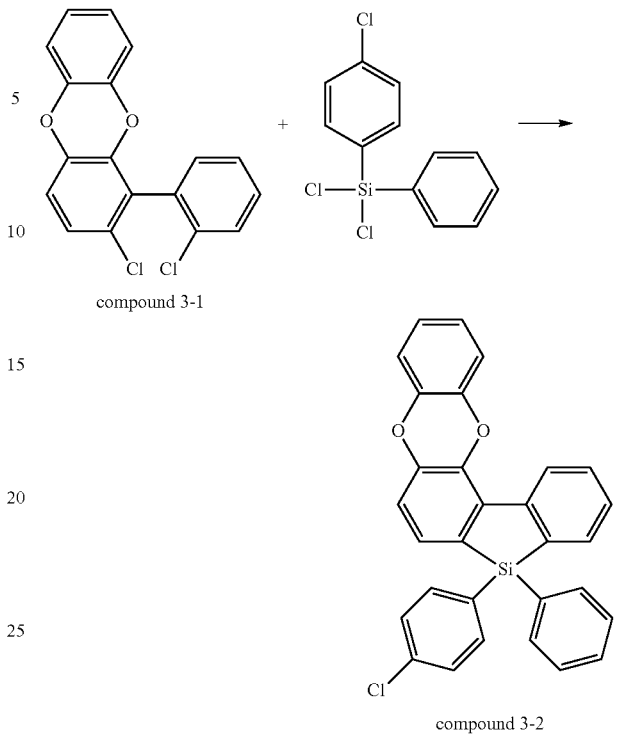

Step 2: Under a nitrogen atmosphere, 2.54 g (7.7 mmol) of the compound 3-1 was dissolved in 20 mL of anhydrous THF, and the solution was cooled to −5° C. under stirring; then 5 mL (10 mmol) of a solution of n-butyl lithium in n-hexane (2M) was slowly added dropwise, and a resulting mixture was thermally insulated and stirred for 4 h. A solution of 4-chlorophenyl-phenyldichlorosilane (7.7 mmol) and 10 mL THF were slowly added dropwise, and the resulting reaction mixture was thermally insulated and stirred for 1 h, and then naturally warmed to room temperature, and then stirred for 16 h. After the reaction was completed, a resulting reaction solution was poured into a dilute hydrochloric acid solution; and then a solid was precipitated. The resulting mixture was filtered to obtain a filter cake, and the filter cake was dried to obtain a compound 3-2 (2.87 g, purity: 77%), which would be directly used in the next reaction.

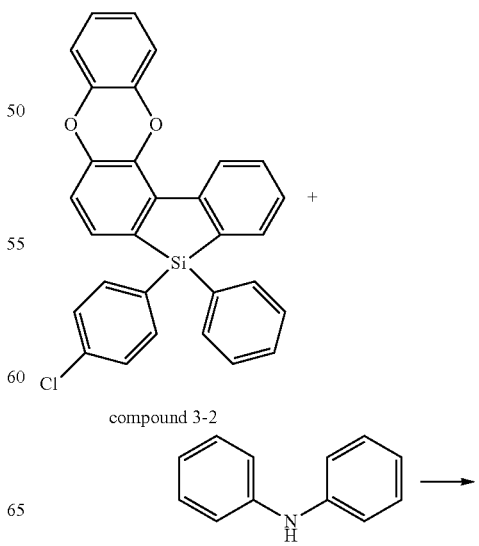

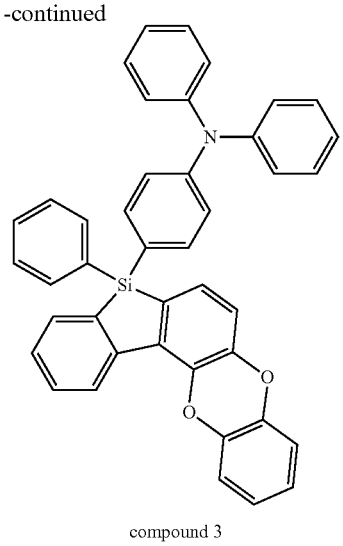

compound 3

Step 3: A mixture of 2.87 g (purity: 77%) of the compound 3-2, 0.78 g (4.6 mmol) of diphenylamine, 0.042 g (0.05 mmol) of tris(dibenzylideneacetone)dipalladium, 0.038 g (0.1 mmol) of 2-dicyclohexylphosphino-2',6'-dimethoxybiphenyl, and 0.67 g (6.9 mmol) of sodium tert-butoxide was added to a 100 mL three-necked flask, air in the flask was completely replaced with nitrogen, then 30 mL of toluene was added to the flask, and the reaction mixture was heated to reflux and stirred for 8 h under. Some water was added to the resulting reaction solution, and a resulting mixture was stirred for 30 min and then filtered to obtain a filter cake; and the filter cake was rinsed with ethanol and then purified by recrystallization with toluene to obtain a compound 3 (2.34 g, yield: 83%).

LC-MS: m/z=608.2[M+H]$^+$ $^1$H NMR (400 MHz, CDCl$_3$) δ: 7.97 (d, 1H), 7.86-7.80 (m, 2H), 7.74-7.51 (m, 5H), 7.42-7.14 (m, 11H), 7.09-6.90 (m, 8H), 6.89-6.85 (m, 2H) ppm.

Synthesis of Compound 4

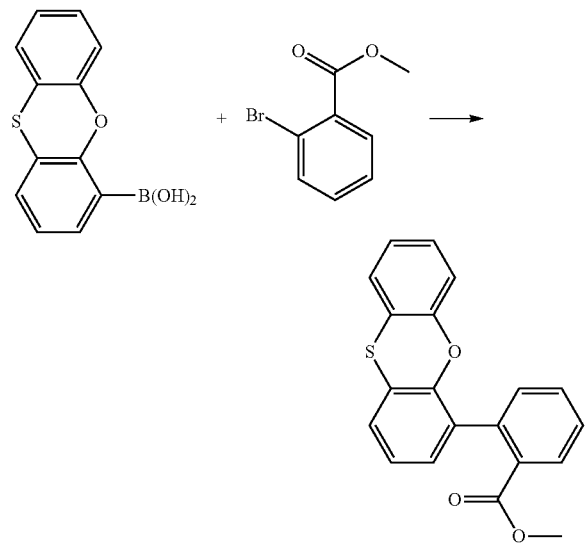

compound 4-1

Step 1: A mixture of 2.7 g (11 mmol) of phenoxathiin-4-boronic acid, 2.38 g (11 mmol) of methyl 2-bromobenzoate, 3.06 g (22 mmol) of potassium carbonate, 0.1278 g (0.1 mmol) of tetrakis(triphenylphosphine)palladium, and 0.0357 g (0.1 mmol) of TBAB was added to a 100 mL three-necked flask, and then a mixed solvent of toluene/water (20 mL/10 mL) was added to the flask; air in the flask was completely replaced with nitrogen, and then the reaction mixture was heated to 80° C. and stirred for 6 h. A resulting reaction solution was washed with water and then dried with anhydrous magnesium sulfate, and then concentrated in a vacuuo to obtain a solid; and the solid was purified by recrystallization with ethyl acetate to obtain a compound 4-1 (2.91 g, yield: 83%).

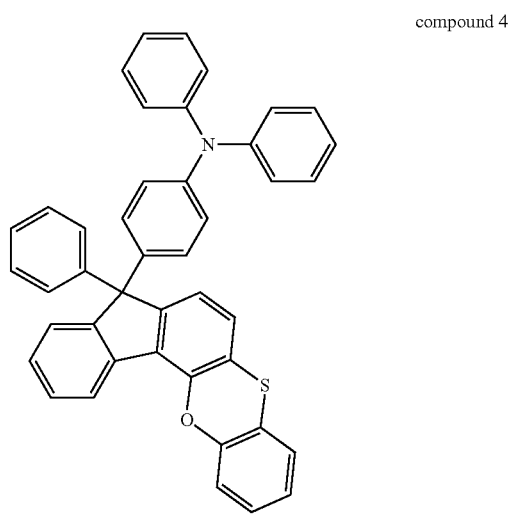 [SMILES: c1ccc(N(c2ccccc2)c2ccc(C3(c4ccccc4)c4ccccc4-c4c3ccc3c4Oc4ccccc4S3)cc2)cc1]

compound 4

Step 2: A compound 4 (2.17 g, yield: 63%) was synthesized by the same process as in steps 2 to 5 for synthesizing the compound 1, except that the compound 4-1 was used instead of the compound 1-1 in step 2 for synthesizing the compound 1.

LC-MS: m/z=608.2[M+H]$^+$ $^1$H NMR (400 MHz, CDCl$_3$): 8.11 (d, 1H), 7.60-7.39 (m, 15H), 7.32-7.21 (m, 5H), 7.16-6.93 (m, 8H).

Synthesis of Compound 5

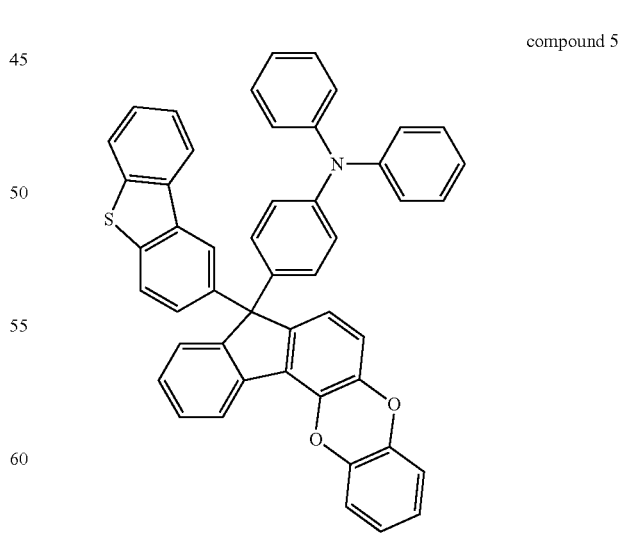

compound 5

A compound 5 (1.96 g, yield: 71%) was synthesized by the same method as the compound 1, except that 2-bromodibenzothiophene was used instead of bromobenzene in step 3 for synthesizing the compound 1.

LC-MS: m/z=698.2[M+H]⁺

¹H NMR (400 MHz, CDCl₃) δ: 8.3 (d, 1H), 8.0~7.8 (m, 2H), 7.75~7.32 (m, 10H), 7.29~7.12 (m, 11H), 7.09~6.95 (m. 6H), 6.87 (m, 1H) ppm.

Synthesis of Compound 6 compound 6

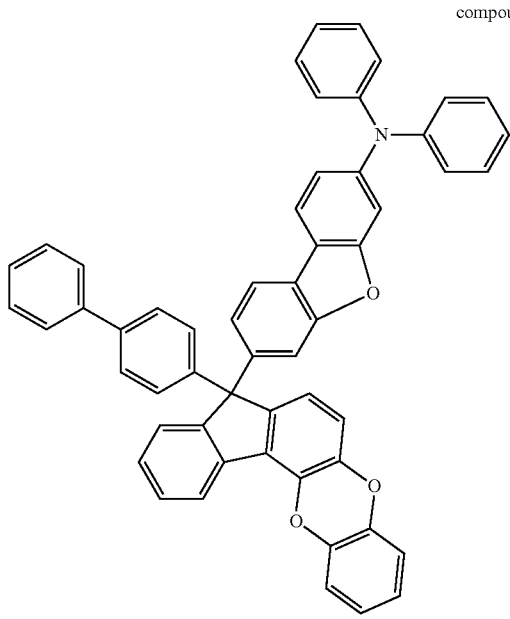

A compound 6 (2.33 g, yield: 58%) was synthesized by the same method as the compound 1, except that 4-bromobiphenyl was used instead of bromobenzene in step 3 and 7-chlorodibenzofuran-3-boronic acid was used instead of p-chlorophenylboronic acid in step 5 for synthesizing the compound 1. A structure of the obtained compound was confirmed by LC-MS. LC-MS: m/z=758.3[M+H]⁺.

Synthesis of Compound 7 compound 7

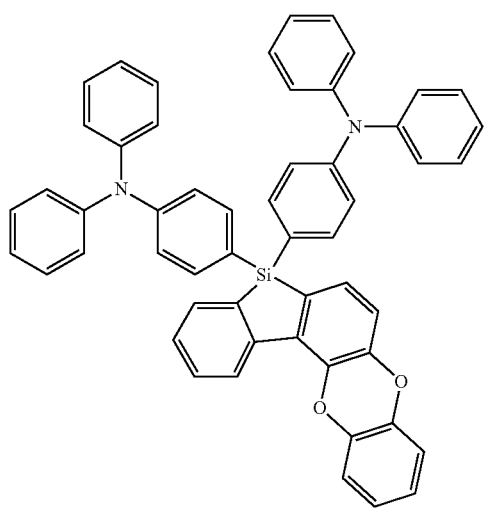

A compound 7 (1.95 g, yield: 46%) was synthesized by the same method as the compound 3, except that bis(4-chlorophenyl)-dichlorosilane was used instead of 4-chlorophenyl-phenyldichlorosilane in step 2 for synthesizing the compound 3. A structure of the obtained compound was confirmed by LC-MS. LC-MS: m/z=775.3[M+H]⁺.

Synthesis of Compound 17

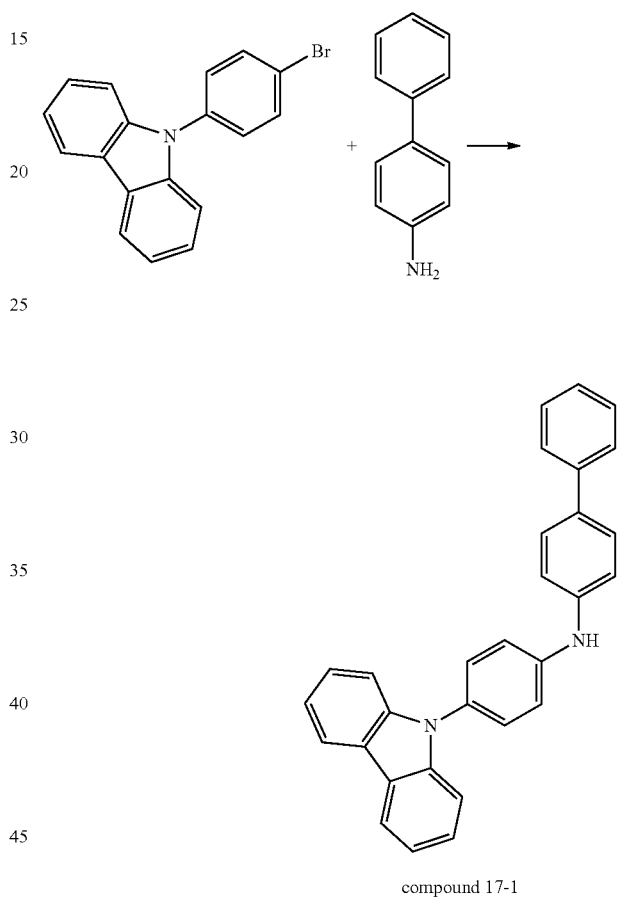

compound 17-1

Step 1: Under a nitrogen atmosphere, a mixture of 3.22 g (10 mmol) of N-(4-bromophenyl)carbazole, 1.69 g (10 mmol) of 4-aminobiphenyl, 0.09 g (0.1 mmol) of tris(dibenzylideneacetone)dipalladium, 0.082 g (0.2 mmol) of 2-dicyclohexylphosphino-2',6'-dimethoxybiphenyl, and 1.44 g (15 mmol) of sodium tert-butoxide was added to a 100 mL three-necked flask, then 30 mL of toluene was added to the flask, and a reaction system was heated to reflux and stirred for 2 h. Water was added to quench the reaction, and toluene was added for extraction. The separated organic phase was dried with anhydrous magnesium sulfate, and then filtered. The filtrate was purified by flash silica gel column chromatography, and a resulting liquid was concentrated in a vacuuo to obtain a solid; and the solid was purified by recrystallization with dichloroethane (DCE) to obtain a compound 17-1 (3.2 g, yield: 78%).

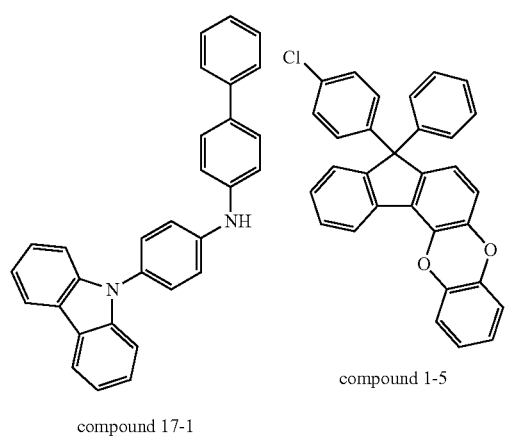

compound 17-1 compound 1-5

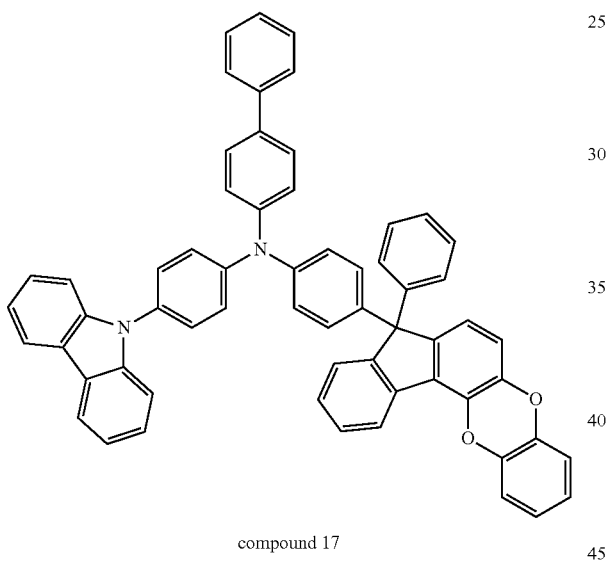

compound 17

Step 2: 3.2 g (7.8 mmol) of the compound 17-1, 3.58 g (7.8 mmol) of the compound 1-5, 0.07 g (0.078 mmol) of tris(dibenzylideneacetone)dipalladium, 0.06 g (0.16 mmol) of 2-dicyclohexylphosphino-2',6'-dimethoxybiphenyl, and 1.12 g (11.7 mmol) of sodium tert-butoxide were added to a 100 mL three-necked flask, nitrogen was introduced for protection, then 30 mL of toluene was added to the flask, and a reaction system was heated to reflux and stirred for 17 h. The resulting organic phase was washed with water for three times, and the combined aqueous phases were extracted with toluene. The combined organic phases were concentrated in a vacuuo to obtain a solid; and the solid was purified by recrystallization with a mixed solvent of DCM and n-heptane (1:1) to obtain a compound 17 (3.63 g, yield: 56%). A structure of the obtained compound was confirmed by LC-MS. LC-MS: m/z=833.3[M+H]$^+$ Synthesis of Compound 21

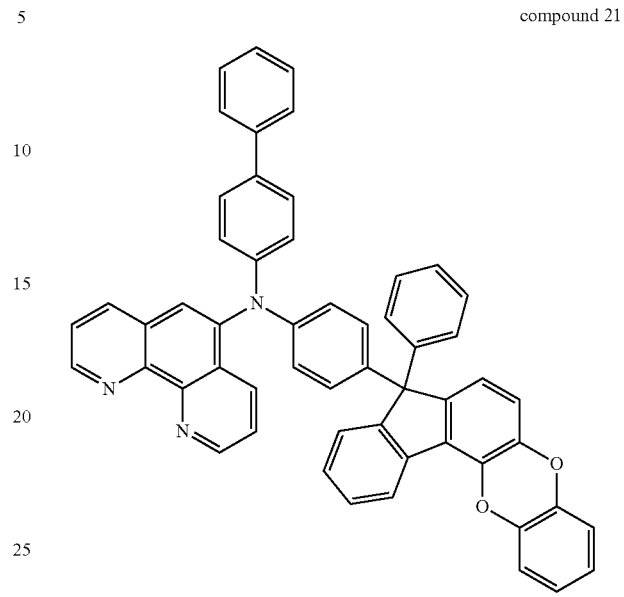

compound 21

A compound 21 (2.77 g, yield: 66%) was synthesized by the same method as the compound 17, except that 5-bromo-1,10-phenanthroline was used instead of N-(4-bromophenyl)carbazole in step 1 for synthesizing the compound 17. A structure of the obtained compound was confirmed by LC-MS. LC-MS: m/z=770.3[M+H]$^+$.

Synthesis of Compound 41

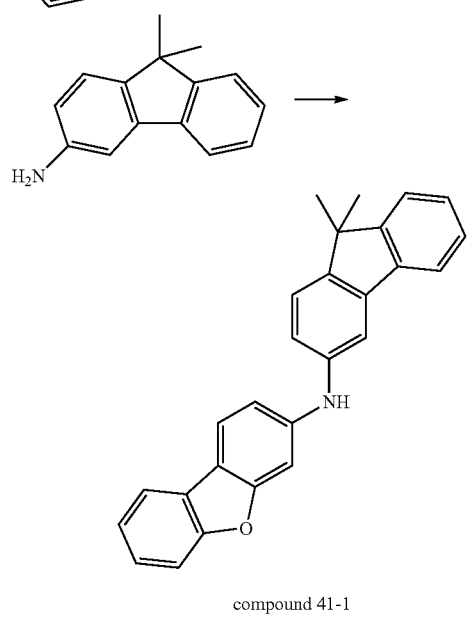

compound 41-1

Step 1: Under a nitrogen atmosphere, a mixture of 3.71 g (15 mmol) of 3-bromodibenzofuran, 3.14 g (15 mmol) of 3-amino-9,9'-dimethylfluorene, 0.14 g (0.15 mmol) of tris(dibenzylideneacetone)dipalladium, 0.12 g (0.3 mmol) of 2-dicyclohexylphosphino-2',6'-dimethoxybiphenyl, and 2.16 g (22.5 mmol) of sodium tert-butoxide was added to a 100 mL three-necked flask, then 30 mL of toluene was added to the flask, and the reaction system was heated to reflux and stirred for 4 h. The resulting reaction solution was washed with water, and the separated organic phase was dried with anhydrous magnesium sulfate and then concentrated in a vacuuo to obtain a solid; and the solid was subjected to recrystallization with a mixed solvent of DCM and n-heptane (1:5) to obtain a compound 41-1 (5 g, yield: 89%).

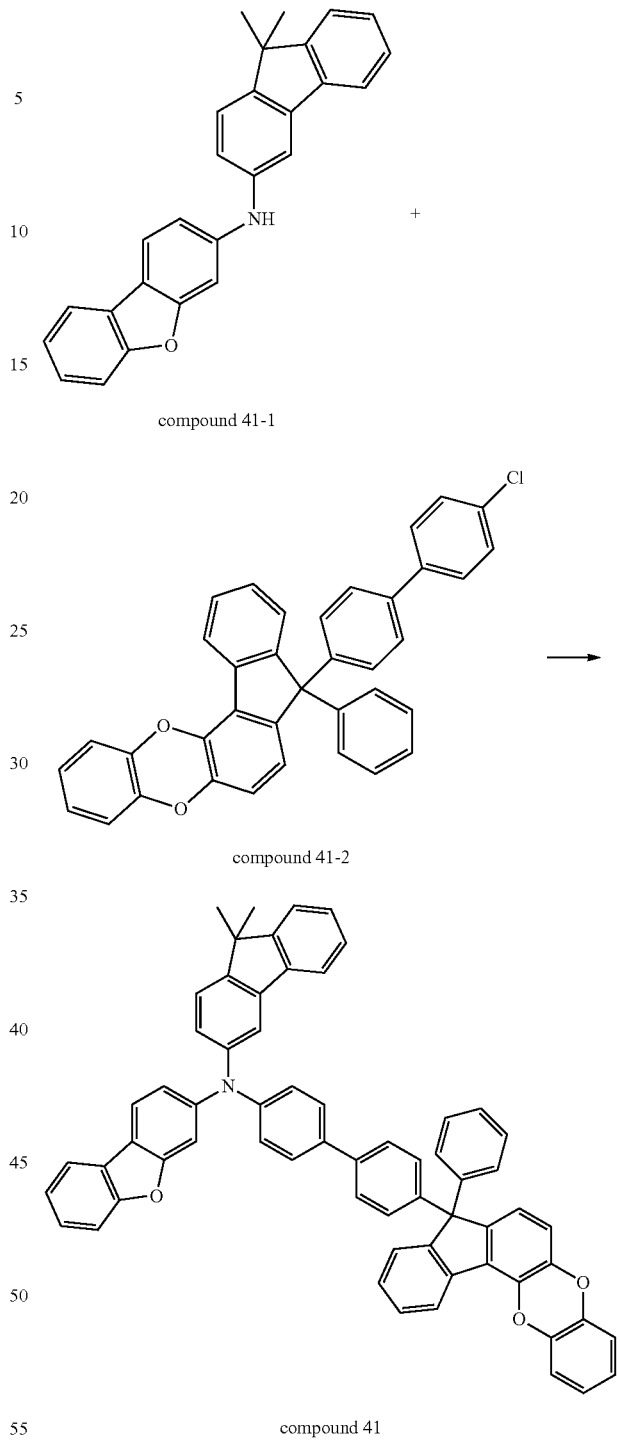

compound 41-1 compound 1-4 compound 41-2 compound 41-2 compound 41

Step 2: Under a nitrogen atmosphere, a mixture of 4.28 g (10 mmol) of the compound 1-4, 2.33 g (10 mmol) of 4'-chloro-4-biphenylboronic acid, 0.12 g (0.1 mmol) of tetrakis(triphenylphosphine)palladium, 0.03 g (0.1 mmol) of TBAB, and 2.8 g (20 mmol) of potassium carbonate was added to a 100 mL three-necked flask, then a mixed solvent of toluene/ethanol/water (24 mL/8 mL/4 mL) was added to the flask, and a reaction system was heated to 80° C. and stirred for 24 h. The resulting reaction solution was washed with water, and then toluene was added for extraction. The separated organic phase was dried with anhydrous magnesium sulfate, and then concentrated in a vacuuo to obtain a solid; and the solid was subjected to recrystallization with ethyl acetate to obtain a compound 41-2 (3.9 g, yield: 73%).

Step 3: Under a nitrogen atmosphere, a mixture of 2.73 g (7.3 mmol) of the compound 41-1, 3.9 g (7.3 mmol) of the compound 41-2, 0.07 g (0.07 mmol) of tris(dibenzylideneacetone)dipalladium, 0.03 g (0.07 mmol) of 2-dicyclohexylphosphino-2',6'-dimethoxybiphenyl, and 1.4 g (14.5 mmol) of sodium tert-butoxide was added to a 100 mL three-necked flask, then 30 mL of toluene was added to the flask, and a reaction system was heated to reflux and stirred for 16 h; the resulting reaction solution was washed with water, and the separated aqueous phase was subjected to extraction with toluene. The combined organic phases were dried with anhydrous magnesium sulfate, filtered. The filtrate was concentrated in a vacuuo to obtain a solid; and the solid was dissolved in a mixture of DCM and n-heptane (v/v=1/4) and then purified by silica gel column chromatography to obtain a compound 41 (3.4 g, yield: 54%). A structure of the obtained compound was confirmed by LC-MS. LC-MS: m/z=874.3[M+H]$^+$.

Synthesis of Compound 49

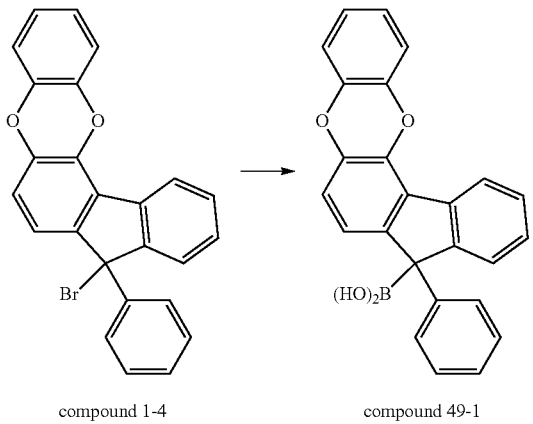 [SMILES: BrC1(c2ccccc2)c2ccccc2-c2c1ccc1c2Oc2ccccc2O1 ; OB(O)C1(c2ccccc2)c2ccccc2-c2c1ccc1c2Oc2ccccc2O1]

compound 1-4    compound 49-1

Step 1: 5 g (11.7 mmol) of the compound 1-4 and 40 mL of anhydrous THF were added to a 100 mL three-necked flask, and a resulting mixture was cooled to −85° C. under stirring; 1 g (15.2 mmol) of a solution of 2 mol/L n-butyl lithium in n-hexane was added in batches under nitrogen atmosphere, and the resulting mixture was thermally insulated and stirred for 30 min; then 1.8 g (17.6 mmol) of trimethyl borate was slowly added dropwise, and the resulting mixture was thermally insulated and stirred for 60 min, then naturally warmed to room temperature, and then further stirred for 10 h. Dilute hydrochloric acid was added dropwise to quench the reaction, and then ethyl acetate was added for extraction. The separated organic phase was dried with anhydrous magnesium sulfate and then concentrated in a vacuuo to obtain a solid; and the solid was subjected to recrystallization with DCM to obtain a compound 49-1 (2.16 g, yield: 47%).

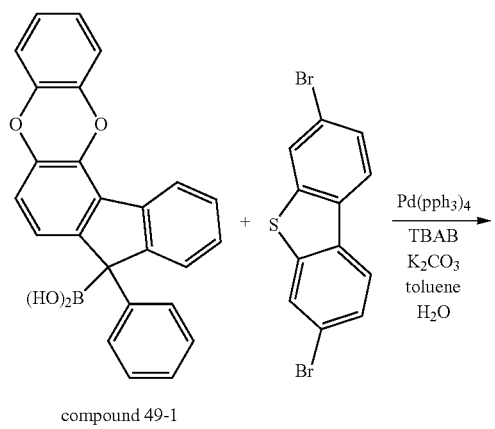

compound 49-1

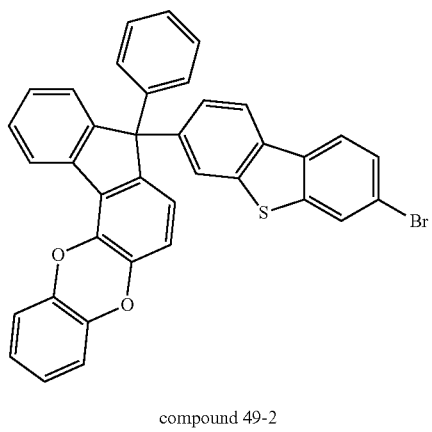

compound 49-2

Step 2: Under a nitrogen atmosphere, a mixture of 2.16 g (5.5 mmol) of the compound 49-1, 1.88 g (5.5 mmol) of 3,7-dibromodibenzothiophene, 0.06 g (0.06 mmol) of tetrakis(triphenylphosphine)palladium, 0.018 g (0.06 mmol) of TBAB, and 1.52 g (11 mmol) of potassium carbonate was added to a 100 mL three-necked flask, then a mixed solvent of toluene/water (18 mL/6 mL) was added to the flask, and a reaction system was heated to 80° C. and stirred for 12 h. After the reaction was completed, the reaction solution was washed with water for three times; and the separated organic phase was dried with anhydrous magnesium sulfate, and then concentrated in a vacuuo to obtain a solid; and the solid was dissolved in n-heptane under heating, and then purified by silica gel column chromatography to obtain a compound 49-2 (2.48 g, yield: 74%).

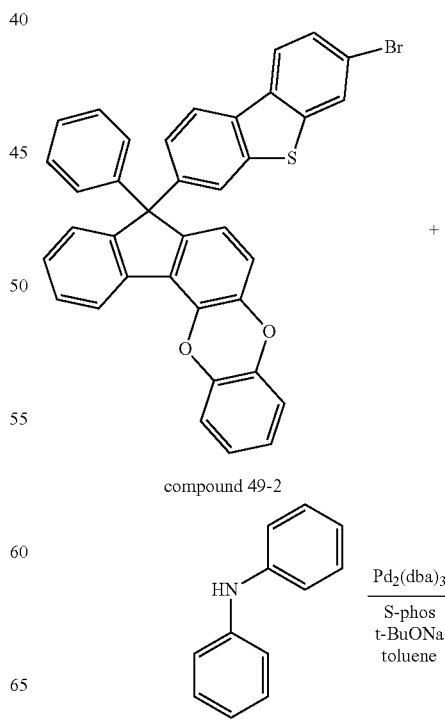

compound 49-2

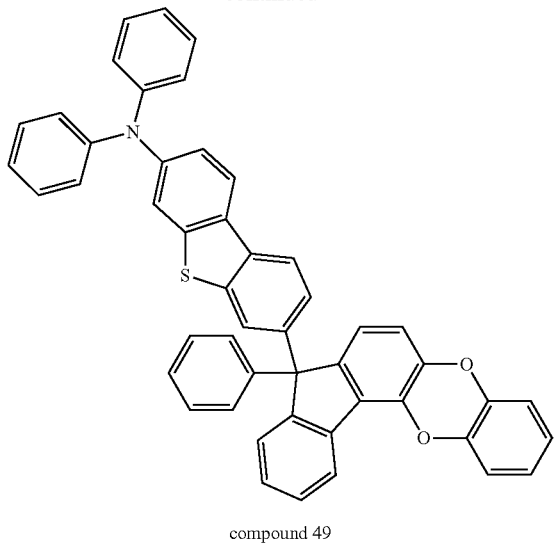

compound 49

Step 3: A compound 49 (1.99 g, yield: 70%) was synthesized by the same process as in step 6 for synthesizing the compound 1. A structure of the obtained compound was confirmed by LC-MS. LCMS: m/z=698.2[M+H]$^+$.

Synthesis of Compound 61

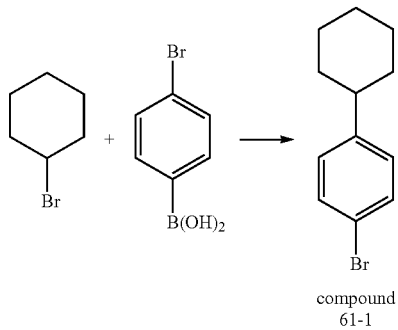

compound 61-1

Step 1: Under a nitrogen atmosphere, a mixture of 2.45 g (15 mmol) of 1-bromocyclohexane, 3.02 g (15 mmol) of p-bromophenylboronic acid, 0.17 g (0.15 mmol) of tetrakis(triphenylphosphine)palladium, 0.05 g (0.15 mmol) of TBAB, and 4.15 g (30 mmol) of potassium carbonate was added to a 100 mL three-necked flask, then a mixed solvent of toluene/water (20 mL/5 mL) was added to the flask, and a reaction system was heated to 80° C. and stirred for 4 h. After the reaction was completed, the resulting reaction solution was subjected to extraction with ethyl acetate; the separated organic phase was dried with anhydrous magnesium sulfate, and then concentrated in a vacuuo to obtain a solid; and the solid was subjected to recrystallization with n-heptane to obtain a compound 61-1 (3.13 g, yield: 87%).

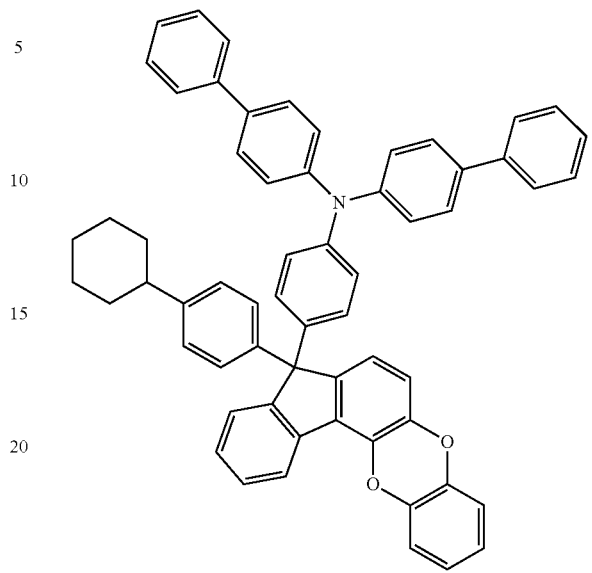

compound 61

Step 2: A compound 61 (3.54 g, yield: 33%) was synthesized by the same process as in steps 3 to 6 for synthesizing the compound 1, except that the compound 61-1 was used instead of bromobenzene in step 3 for synthesizing the compound 1, and bis(4-biphenyl)amine was used instead of diphenylamine in step 6 for synthesizing the compound 1. A structure of the obtained compound was confirmed by LC-MS. LC-MS: m/z=826.4 [M+H]$^+$.

Synthesis of Compound 87

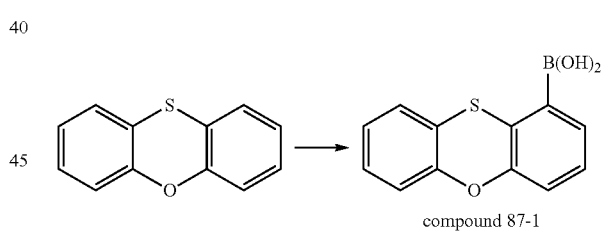

compound 87-1

Step 1: 4 g (20 mmol) of phenoxanthine and 40 mL of dry THF were added to a 100 mL three-necked flask, and a resulting mixture was cooled to −78° C. under stirring; 13 mL (26 mmol) of a solution of 2 mol/L n-butyl lithium in n-hexane was added dropwise under nitrogen atmosphere, and a resulting mixture was thermally insulated and stirred for 60 min; then 5.64 g (30 mmol) of triisopropyl borate was slowly added dropwise, and the resulting mixture was thermally insulated and stirred for 60 min, then naturally warmed to room temperature, and further stirred for 12 h. A dilute hydrochloric acid was added dropwise to quench the reaction, and then ethyl acetate was added for extraction; the separated organic phase was dried with anhydrous magnesium sulfate and then concentrated in a vacuuo to obtain a solid; and the solid was heated to reflux and stirred with n-heptane, then filtered to obtain a compound 87-1 (3.7 g, yield: 76%).

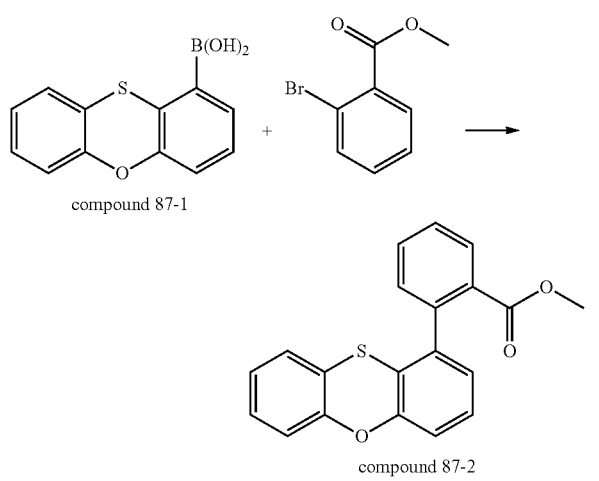

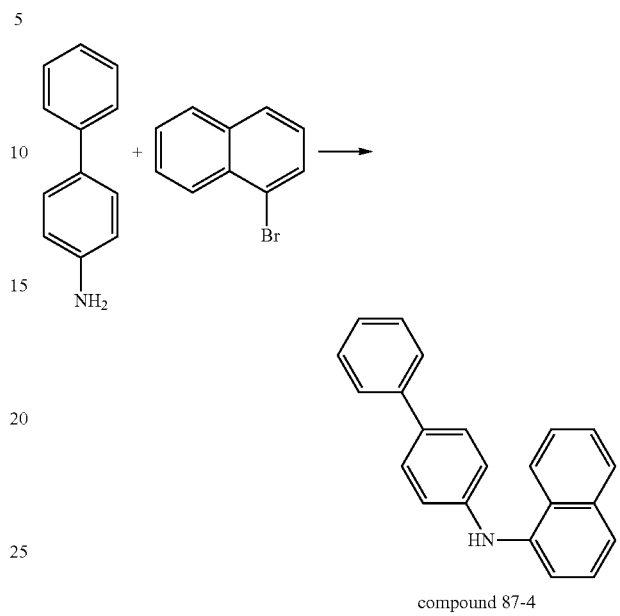

Step 2: A mixture of 3.7 g (15.2 mmol) of the compound 87-1, 3.26 g (15.2 mmol) of methyl 2-bromobenzoate, 4.2 g (30.3 mmol) of potassium carbonate, 0.18 g (0.15 mmol) of tetrakis(triphenylphosphine)palladium, and 0.05 g (0.15 mmol) of TBAB was added to a 100 mL three-necked flask, and then a mixed solvent of toluene/ethanol/water (30 mL/10 mL/5 mL) was added to the flask; air in the flask was completely replaced with nitrogen, and then a reaction system was heated to 80° C. and stirred for 8 h; a resulting reaction solution was washed with water. The separated organic phase was dried with anhydrous magnesium sulfate, and concentrated in a vacuuo to obtain a solid; and the solid was subjected to recrystallization with a mixed solvent of DCM and ethyl acetate (1:2) to obtain a compound 87-2 (4.1 g, yield: 81%).

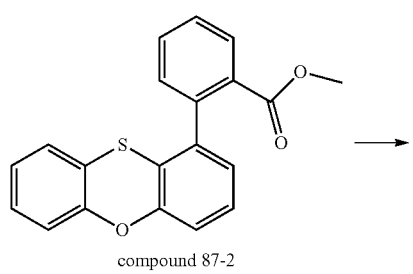

Step 3: A compound 87-3 (3.3 g, yield: 46%) was synthesized by the same process as in steps 2 to 5 for synthesizing the compound 1, except that the compound 87-2 was used instead of the compound 1-1 in step 2 for synthesizing the compound 1.

Step 4: Under a nitrogen atmosphere, a mixture of 5 g (29.5 mmol) of 4-aminobiphenyl, 6.1 g (29.5 mmol) of 1-bromonaphthalene, 0.27 g (0.3 mmol) of tris(dibenzylideneacetone)dipalladium, 0.24 g (0.6 mmol) of 2-dicyclohexylphosphino-2',6'-dimethoxybiphenyl, and 4.3 g (44.3 mmol) of sodium tert-butoxide was added to a 100 mL three-necked flask, then 50 mL of toluene was added to the flask, and the reaction mixture was heated to reflux and stirred for 2 h. The resulting reaction solution was washed with water, and extracted with toluene; and the separated organic phase was dried with anhydrous magnesium sulfate, and filtered; and the organic phase was purified by silica gel column chromatography, and the eluent was concentrated in a vacuuo to obtain a solid; and the solid was purified by recrystallization with a mixed solvent of DCM and n-heptane (v/v=1/1) to obtain a compound 87-4 (7 g, yield: 80%).

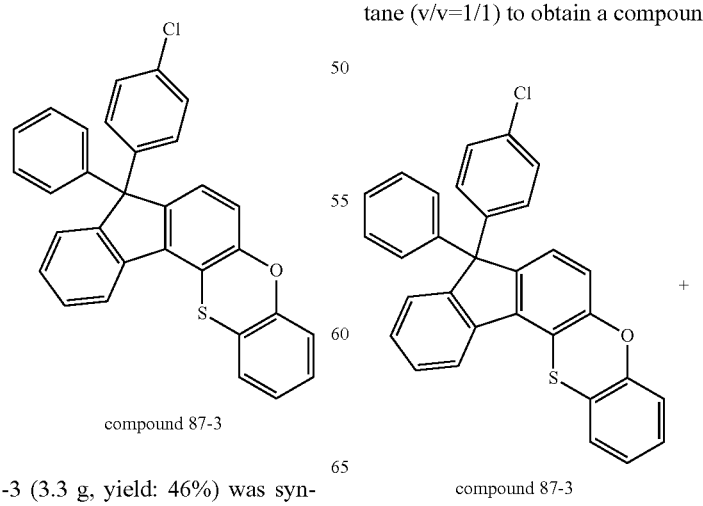

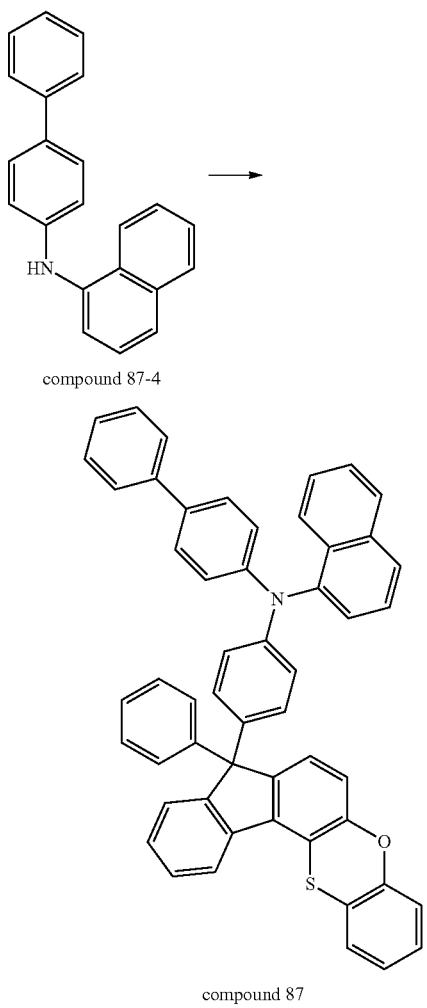

compound 87-4

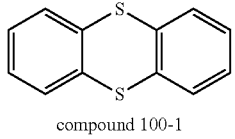

compound 100-1

Step 1: Under nitrogen protection, 8.3 g (25.2 mmol) of o-diiodobenzene, 1.6 g (50 mmol) of a sulfur powder, 10.4 g (75 mmol) of potassium carbonate, 0.36 g (2.5 mmol) of cuprous bromide, and 2.5 g (12.5 mmol) of 1,10-phenanthroline were added to a 100 mL three-necked flask, then 40 mL of dimethyl sulfoxide (DMSO) was added to the flask, and a reaction system was heated to 90° C. and stirred for 24 h. After the resulting reaction solution was cooled to room temperature, a sodium thiosulfate solution was added to quench the reaction, and then extraction was conducted multiple times with ethyl acetate. The combined organic phases were dried with anhydrous magnesium sulfate and then concentrated in a vacuuo to obtain a solid; and the solid was purified by silica gel column chromatography using a mixture of DCM and n-heptane (v/v=1/10) to obtain a compound 100-1 (3.7 g, yield: 68%).

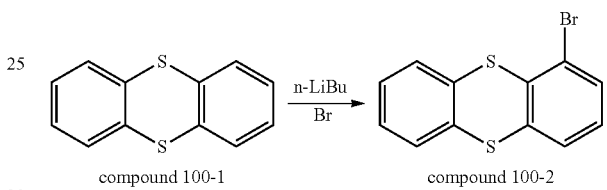

compound 100-1          compound 100-2

Step 2: Under nitrogen protection, 3.7 g (17.1 mmol) of the compound 100-1 and 30 mL of anhydrous THF were added to a 100 mL three-necked flask, and a resulting mixture was cooled to −78° C.; 11 mL (22.2 mmol) of a solution of 2 mol/L n-butyl lithium in n-hexane was slowly added dropwise at the temperature, and the resulting mixture was thermally insulated and stirred for 60 min; then 1.5 g (9.4 mmol) of bromine was slowly added dropwise, and then the resulting mixture was thermally insulated and stirred for another 2 h, then naturally warmed to room temperature, and further stirred for 24 h. A dilute sodium bicarbonate solution was added to quench the reaction, and then ethyl acetate was added for extraction; a separated organic phase was dried with magnesium sulfate and then concentrated in a vacuuo to obtain a solid; and the solid was subjected to recrystallization with n-heptane to obtain a compound 100-2 (2.8 g, yield: 55%).

compound 87

Step 5: Under a nitrogen atmosphere, a mixture of 3.3 g (6.9 mmol) of the compound 87-3, 2.1 g (6.9 mmol) of the compound 87-4, 0.06 g (0.07 mmol) of tris(dibenzylideneacetone)dipalladium, 0.06 g (0.14 mmol) of 2-dicyclohexylphosphino-2',6'-dimethoxybiphenyl, and 1 g (10.4 mmol) of sodium tert-butoxide was added to a 100 mL three-necked flask, then 30 mL of toluene was added to the flask, and the reaction mixture was heated to reflux and stirred for 16 h. Some water was added to quench the reaction, then the resulting reaction solution was washed with water, and the separated aqueous phase was subjected to extraction with toluene; the combined organic phases were dried with anhydrous magnesium sulfate, and concentrated in a vacuuo to obtain a solid; and the solid was subjected to recrystallization with toluene to obtain a compound 87 (3.36 g, yield: 66%). A structure of the obtained compound was confirmed by LC-MS. LC-MS: m/z=734.2 [M+H]$^+$.

Synthesis of Compound 100

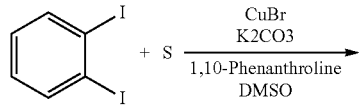

compound 100

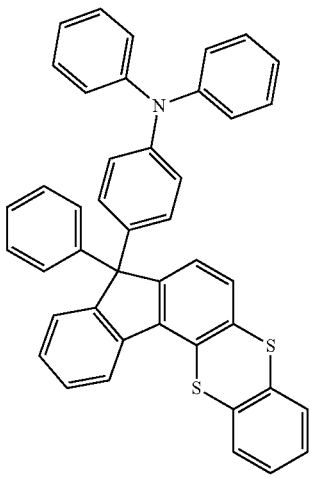

Step 3: A compound 100 (2.13 g, yield: 36%) was synthesized by the same method as the compound 1, except that the compound 100-2 was used instead of 1-bromodibenzodioxin in step 1 for synthesizing the compound 1. A structure of the obtained compound was confirmed by LC-MS. LC-MS: m/z=624.2[M+H]$^+$.

Synthesis of Compound 122

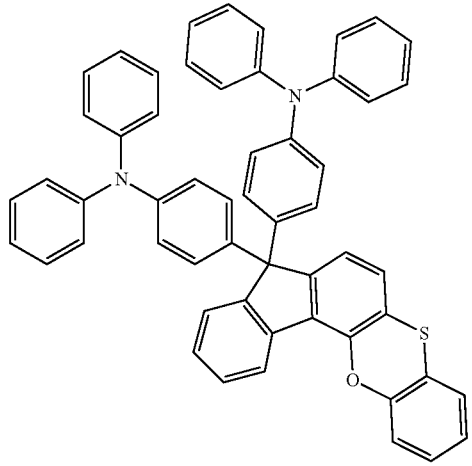

compound 122

A compound 122 (3.26 g, yield: 33%) was synthesized by the same method as the compound 2, except that the compound 4-1 was used instead of the compound 1-1 in step 1 for synthesizing the compound 2. A structure of the obtained compound was confirmed by LC-MS. LC-MS: m/z=775.3[M+H]$^+$.

Synthesis of Compound 155

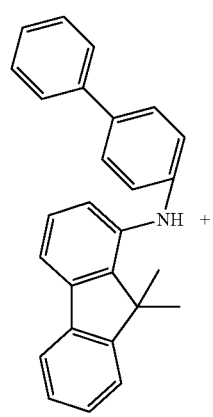

compound 155-1

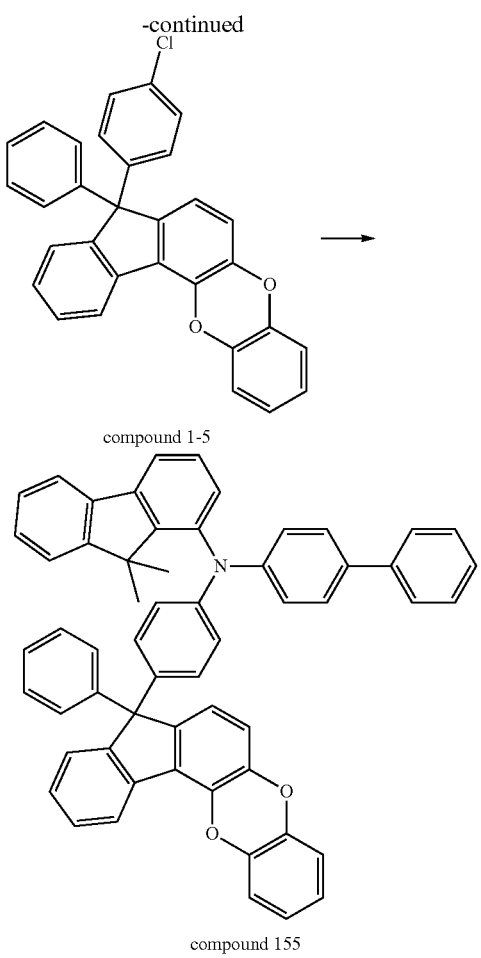

compound 1-5 compound 155

A compound 155-1 was synthesized by the same process as in step 1 for synthesizing the compound 17, except that 1-bromo-9,9'-dimethylfluorene was used instead of N-(4-bromophenyl)carbazole in step 1 for synthesizing the compound 17; and then a compound 155 (2.23 g, yield: 28%) was synthesized by the same process as in step 6 for synthesizing the compound 1, except that the compound 155-1 was used instead of diphenylamine in step 6 for synthesizing the compound 1. A structure of the obtained compound was confirmed by LC-MS. LC-MS: m/z=784.3 [M+H]$^+$.

Production and Performance Evaluation of OLEDs

Example 1

OLED with compound 1 as an HTL material

The OLED was produced through the following process:
An ITO substrate (manufactured by Corning) with a thickness of 1,500 Å was cut into a size of 40 mm (length)× 40 mm (width)×0.7 mm (thickness), then the substrate was processed through photolithography into an experimental substrate (light-emitting pixel size: 3 mm×3 mm) with an anode, a cathode overlap region, and an insulating layer, and the experimental substrate was subjected to a surface treatment with ultraviolet (UV)-ozone and $O_2:N_2$ plasma to increase a work function of the anode (experimental substrate) and remove scums.

Hexaazatriphenylene hexacarbonitrile (HAT-CN) (CAS No.: 105598-27-4) was vapor-deposited on the anode to form an HIL with a thickness of 10 nm.

Then the compound 1 of the disclosure was vapor-deposited to form an HTL with a thickness of 100 nm.

4,4',4''-tris(carbazol-9-yl)-triphenylamine (TCTA) (CAS No.: 139092-78-7) was vacuum-deposited on the HTL to form an EBL with a thickness of 15 nm.

9,10-bis(2-naphthyl)anthracene (ADN) (CAS No.: 122648-99-1, as a host material) and bis(2,4-difluorophenylpyridinato)(5-(pyridin-2-yl)-1H-tetrazolate)iridium (FIrN4) (CAS No.: 1219078-44-0, dopant) each were deposited in a film thickness ratio of 30:3 to form an organic electroluminescent layer with a thickness of 22 nm.

1,3,5-Tris(N-phenylbenzimidazol-2-yl)benzene (TPBI) (CAS No.: 192198-85-9) and LiQ (CAS No.: 850918-68-2) were vacuum-deposited on the EML in a ratio of 1:1 to form an organic film layer with a thickness of 30 nm, which served as an ETL.

Yb (CAS No.: 7440-64-4) was vapor-deposited on the ETL to form an EIL with a thickness of 1 nm.

Then, magnesium (Mg) and silver (Ag) were vapor-deposited in a ratio of 1:9 to form a cathode with a thickness of 12 nm. Finally, N4,N4'-bis[4-[bis(3-methylphenyl)amino]phenyl]-N4,N4'-dimethyl-[1,1'-dimethyl]-4,4'-diurea (DNTPD) (CAS No.: 199121-98-7) was vapor-deposited on the cathode to form a capping layer with a thickness of 70 nm.

An OLED obtained after the vapor deposition was completed was encapsulated with UV curing resin in a nitrogen glove box (with strictly-controlled water and oxygen contents).

Examples 2 to 16

OLEDs in Examples 2 to 16 were produced by the same method as in Example 1, except that compounds 2, 3, 4, 5, 6, 7, 17, 21, 41, 49, 61, 87, 100, 122, and 155 each was used instead of the compound 1 of HTL.

Comparative Example 1

An OLED in this comparative example was produced by the same method as in Example 1, except that the compound N,N'-di-1-naphthalenyl-N,N'-diphenyl-[1,1'-biphenyl]-4,4'-diamine (NPB) (CAS No.: 123847-85-8) was used instead of the compound 1 of HTL.

Comparative Example 2

An OLED in this comparative example was produced by the same method as in Example 1, except that 1,3,5-Tri(9-carbazolyl)benzene (TCP) (CAS No.: 148044-07-9) was used instead of the compound 1 of HTL.

Comparative Example 3

An OLED in this comparative example was produced by the same method as in Example 1, except that the compound 4,4'4''-Tris(N,N-diphenylamino)triphenylamine (TDATA) (CAS No.: 105389-36-4) was used instead of the compound 1 of HTL.

Comparative Example 4

An OLED in this comparative example was produced by the same method as in Example 1, except that the compound A was used instead of the compound 1 of HTL.

Comparative Example 5

An OLED in this comparative example was produced by the same method as in Example 1, except that the compound B was used instead of the compound 1 of HTL.

Comparative Example 6

An OLED in this comparative example was produced by the same method as in Example 1, except that the compound C was used instead of the compound 1 of HTL.

Structures of HAT-CN, TCTA, ADN, FIrN4, TPBI, LiQ, DNTPD, NPB, TCP, TDATA, and compounds A, B, and C were as follows:

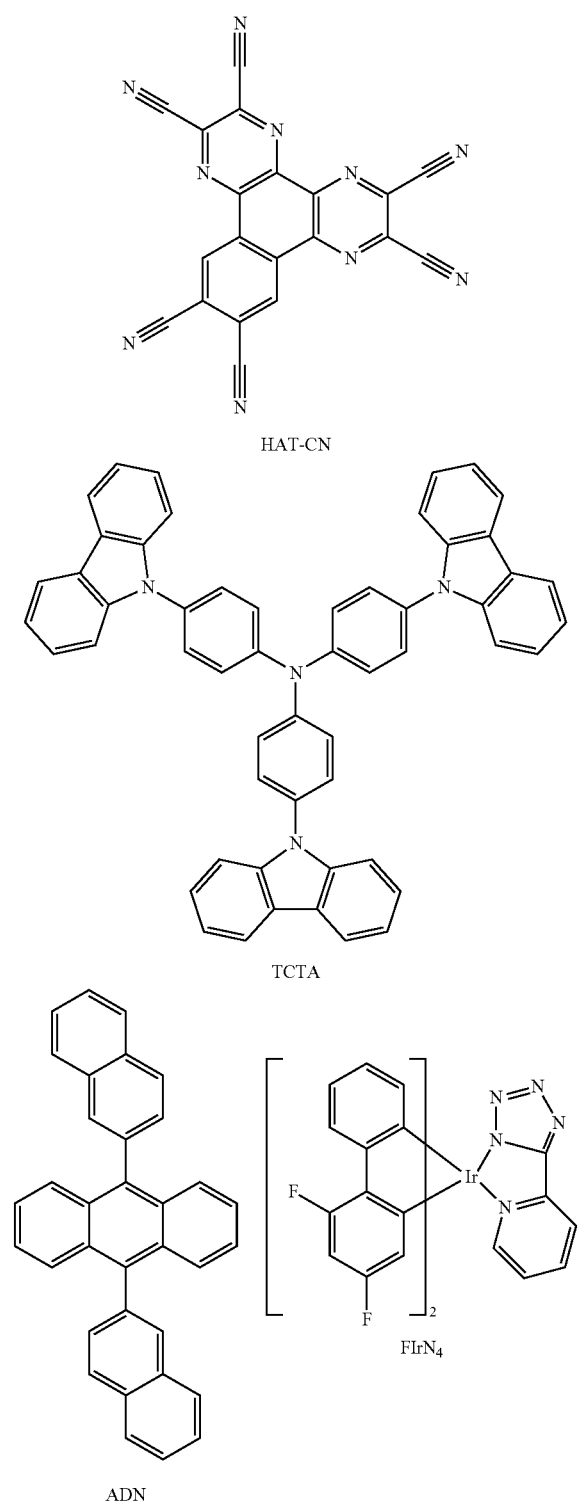

155
-continued
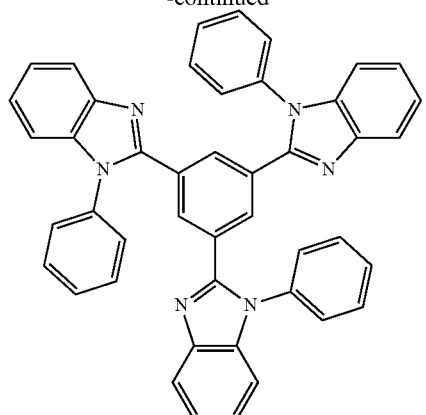
TPBi
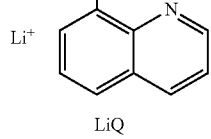
LiQ
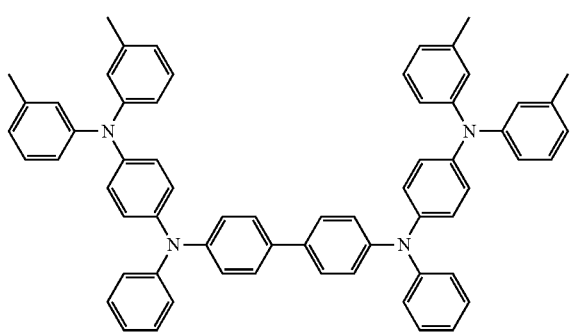
DNTPD
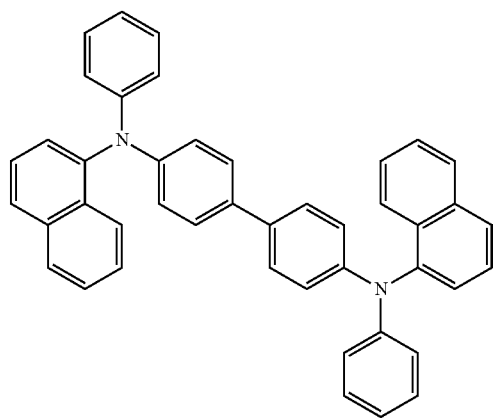
NPB
156
-continued
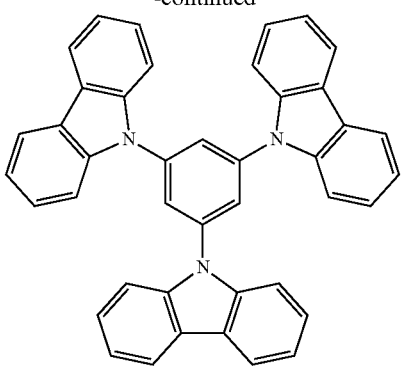
TCP
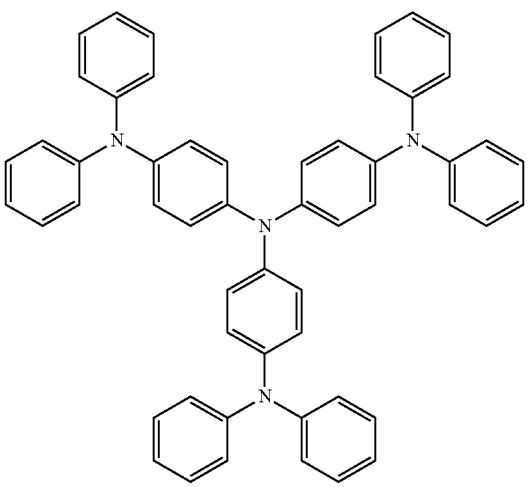
TDATA
compound A
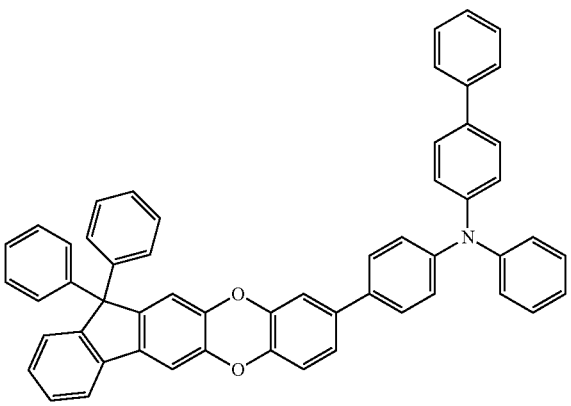

compound B

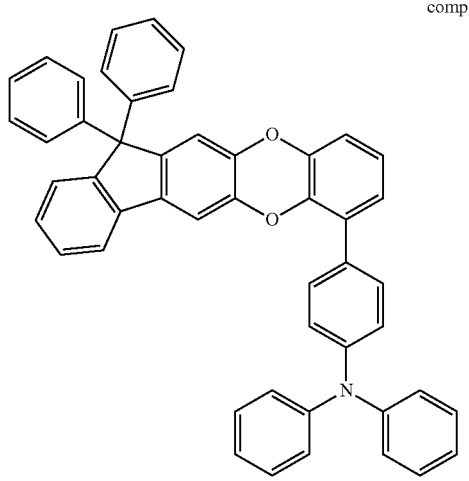

compound C

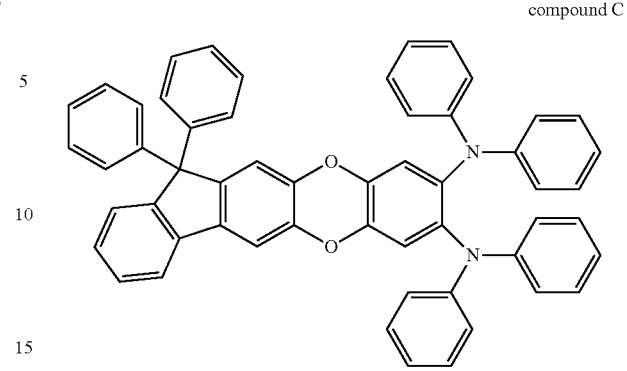

The performance was tested for the OLEDs produced in Examples 1 to 16 and Comparative Examples 1 to 6, and test results were shown in Table 1.

TABLE 1

Performance of the OLEDs produced in the examples and comparative examples

| Example | HTL | Driving voltage (V) | Current efficiency cd/A | Chromaticity coordinate (CIEx, CIEy) | T95 (hr) @ 15 mA/cm$^2$ |
| --- | --- | --- | --- | --- | --- |
| Example 1 | Compound 1 | 3.97 | 6.1 | (0.139, 0.050) | 172 |
| Example 2 | Compound 2 | 4.04 | 6.2 | (0.138, 0.051) | 181 |
| Example 3 | Compound 3 | 4.04 | 6.2 | (0.141, 0.051) | 184 |
| Example 4 | Compound 4 | 4.07 | 6.0 | (0.140, 0.049) | 183 |
| Example 5 | Compound 5 | 3.97 | 6.2 | (0.139, 0.050) | 174 |
| Example 6 | Compound 6 | 4.03 | 6.3 | (0.139, 0.051) | 172 |
| Example 7 | Compound 7 | 4.00 | 6.1 | (0.138, 0.051) | 174 |
| Example 8 | Compound 17 | 4.07 | 6.1 | (0.138, 0.050) | 180 |
| Example 9 | Compound 21 | 4.01 | 6.0 | (0.140, 0.050) | 181 |
| Example 10 | Compound 41 | 4.02 | 6.2 | (0.139, 0.051) | 180 |
| Example 11 | Compound 49 | 4.06 | 6.0 | (0.138, 0.049) | 170 |
| Example 12 | Compound 61 | 3.99 | 6.2 | (0.140, 0.051) | 175 |
| Example 13 | Compound 87 | 4.03 | 6.1 | (0.139, 0.050) | 175 |
| Example 14 | Compound 100 | 4.05 | 6.3 | (0.141, 0.051) | 171 |
| Example 15 | Compound 122 | 4.03 | 6.3 | (0.139, 0.050) | 176 |
| Example 16 | Compound 155 | 4.05 | 6.1 | (0.138, 0.050) | 178 |
| Comparative Example 1 | NPB | 4.29 | 5.4 | (0.139, 0.050) | 142 |
| Comparative Example 2 | TCP | 4.47 | 4.9 | (0.139, 0.051) | 157 |
| Comparative Example 3 | TDATA | 4.42 | 5.0 | (0.140, 0.051) | 139 |
| Comparative Example 4 | Compound A | 4.12 | 5.9 | (0.140, 0.050) | 155 |
| Comparative Example 5 | Compound B | 4.09 | 6.1 | (0.139, 0.051) | 147 |
| Comparative Example 6 | Compound C | 4.15 | 6.2 | (0.140, 0.050) | 144 |

The driving voltage, current efficiency, and chromaticity coordinates in Table 1 were test results at a constant current density of 10 mA/cm², and the T95 life span was a test result at a constant current density of 15 mA/cm².

It can be seen from the data in Table 1 that, with comparable CIE values, compared with the OLEDs of Comparative Examples 1, 2, and 3, the OLEDs of Examples 1 to 16 show a voltage reduced by at least 0.22 V, an luminous efficiency increased by at least 11.1%, and a life span increased by at least 8.3%; and in blue light-emitting OLEDs, the luminous efficiency is significantly improved. Therefore, compared with the OLEDs of Comparative Examples 1 to 3, the OLEDs of Examples 1 to 16 generally have the characteristics of high efficiency, low voltage, and long life. However, the OLEDs of Examples 1 to 16 show basically the same voltage and efficiency as the OLEDs of Comparative Examples 4 to 6, but show a life span increased by at least 9.7%. Therefore, the OLEDs of Examples 1 to 16 generally have a longer life span than the OLEDs of Comparative Examples 4 to 6.

Therefore, the compound of the disclosure, when used for an HTL of an OLED, can significantly reduce the operating voltage of the OLED, improve the luminous efficiency of the OLED, and extend the life span of the OLED.

This is because a fused heteroaromatic group with fluorenyl or silylfluorenyl is a core structure in the compounds listed in the examples of the disclosure, which presents a large planar structure in a 3D space; and an electron-rich arylamine or heteroarylamine substituent is introduced at position 9 of the fluorenyl or silylfluorenyl to make the compound have excellent hole transport performance.

In summary, the organic compound of the disclosure has a specific structure, such that when used in an HTL of an OLED, the compound shows excellent carrier transport performance compared with previous materials, which facilitates the voltage reduction, efficiency improvement, and life span extension of the OLED.

The above examples are only used for describing the technical solutions of the disclosure, and are not intended to limit the disclosure. Although the disclosure is described in detail with reference to the above examples, those of ordinary skill in the art should understand that they can still make modifications to the technical solutions described in the above examples, or make equivalent substitutions for some technical features therein.

These modifications or substitutions do not make the essence of the corresponding technical solutions deviate from the spirit and scope of the technical solutions of the examples of the disclosure.

What is claimed is:

1. An organic compound, with a structure shown in chemical formula I:

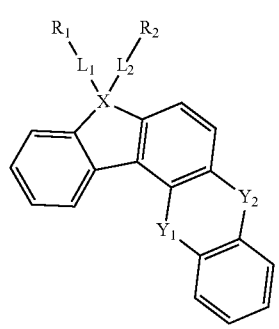

chemical formula I wherein X is selected from: C and Si;

$Y_1$ and $Y_2$ are the same or different, and are each independently selected from: O and S;

$R_1$ and $R_2$ are each independently selected from:

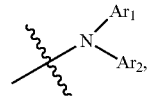

and substituted or unsubstituted following groups:

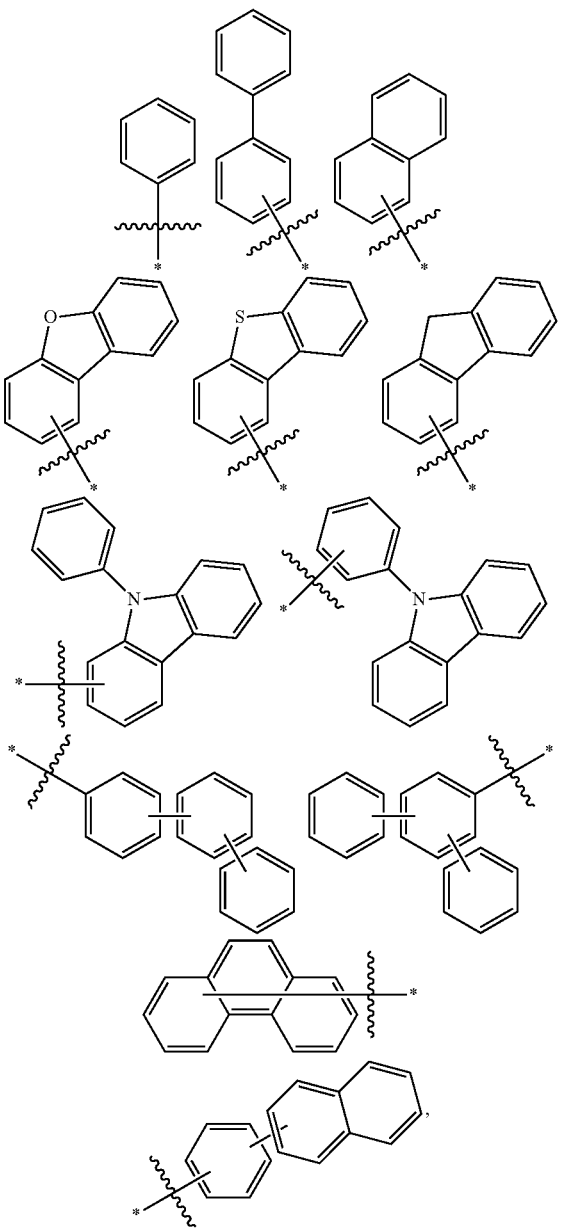

the above groups are each optionally substituted by 0, 1, 2, 3, 4, or 5 substituents, and each of the substituents is independently selected from: deuterium, fluorine, chlorine, cyano, alkyl with 1 to 6 carbon atoms, alkoxy with 1 to 4 carbon atoms, trimethylsilyl, cycloalkyl with 3 to 10 carbon atoms; and at least one of $R_1$ and $R_2$ is
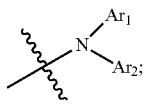
$Ar_1$ and $Ar_2$ are the same or different, and are each independently selected from substituted or unsubstituted following groups:
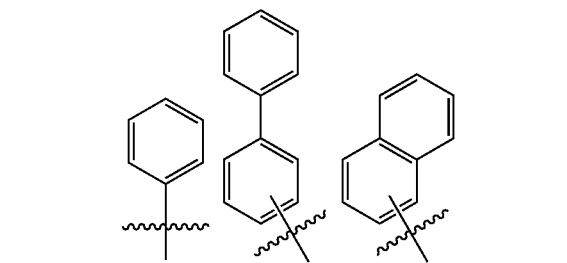
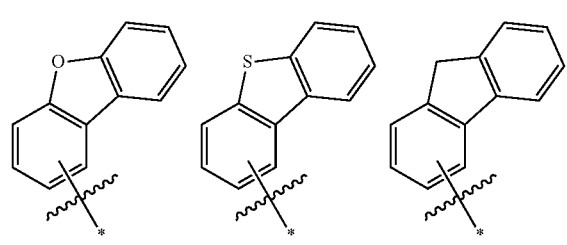
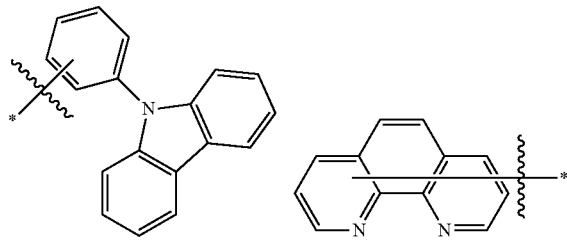
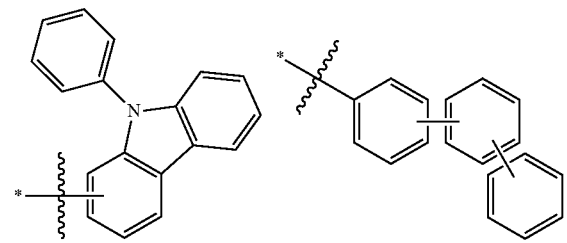
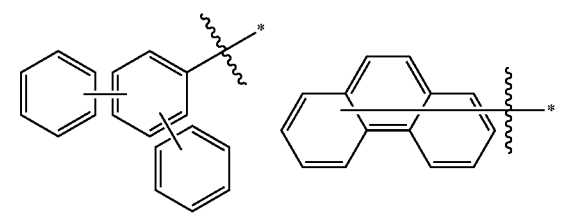
-continued
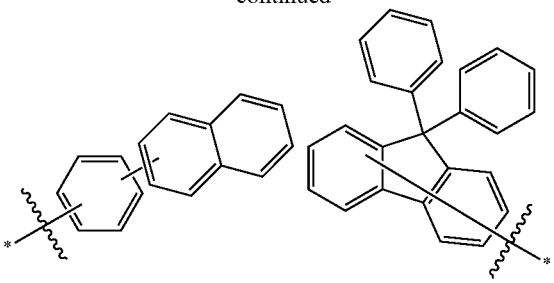
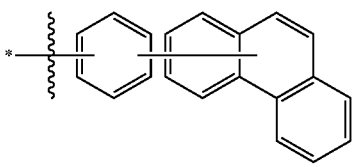
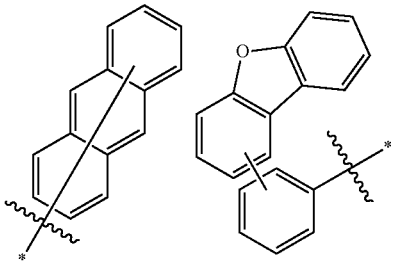
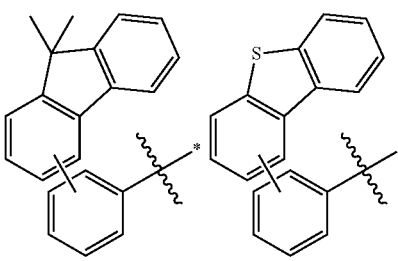
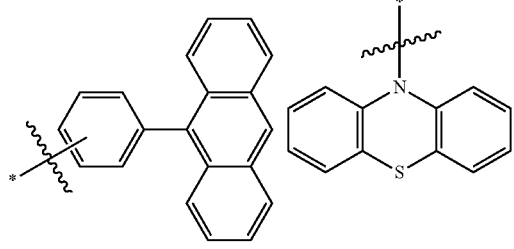
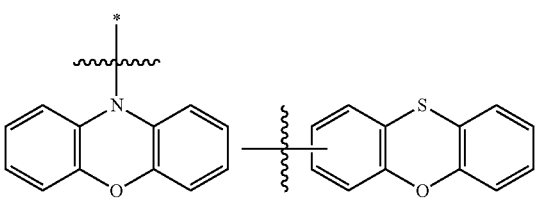
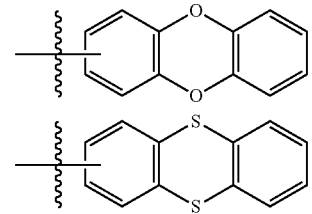

-continued

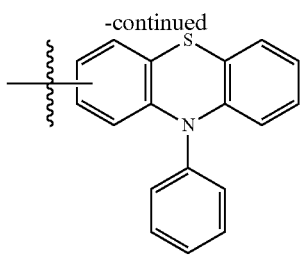

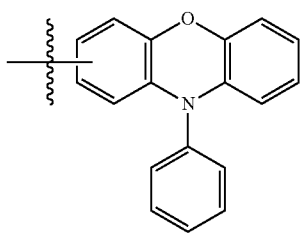

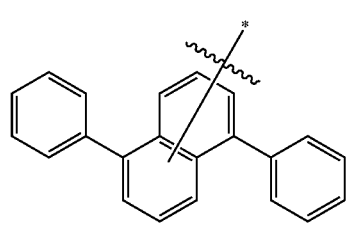

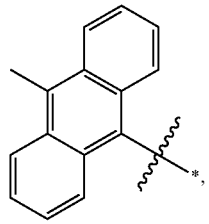

the above groups are each optionally substituted by 0, 1, 2, 3, 4, or 5 substituents, and each of the substituents is independently selected from: deuterium, fluorine, chlorine, cyano, alkyl with 1 to 6 carbon atoms, alkoxy with 1 to 4 carbon atoms, haloalkyl with 1 to 4 carbon atoms, trimethylsilyl, cycloalkyl with 3 to 10 carbon atoms, aryl with 6 to 13 carbon atoms, and heteroaryl with 3 to 12 carbon atoms;

$L_1$ and $L_2$ are the same or different, and are each independently selected from: a single bond, substituted or unsubstituted phenylene, substituted or unsubstituted naphthylene, substituted or unsubstituted anthracenylene, substituted or unsubstituted phenanthrylene, substituted or unsubstituted biphenylene, substituted or unsubstituted terphenylene, substituted or unsubstituted fluorenylene, substituted or unsubstituted dibenzofuranylene, substituted or unsubstituted dibenzothienylene, and a subunit formed by linking two or three thereof through single bonds; and $L_1$ or $L_2$ is optionally substituted by 0, 1, 2, 3, 4 or 5 substituents, and the substituents are each independently selected from: deuterium, fluorine, chlorine, cyano, methyl, ethyl, isopropyl, tert-butyl, methoxy, ethoxy, isopropoxy, propoxy, cyclopentyl, cyclohexyl, trifluoromethyl, phenyl, naphthyl, trimethylsilyl;

and when $R_1$ is

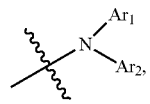

$L_1$ is not a single bond; and when $R_2$ is

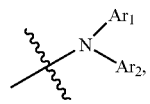

$L_2$ is not a single bond.

2. The organic compound according to claim 1, wherein the organic compound shown in chemical formula I is selected from following compounds:

chemical formula 2

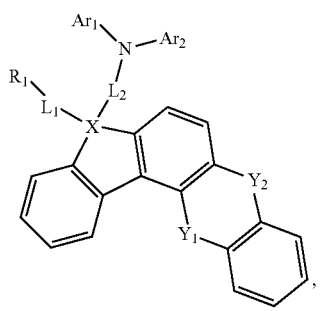

chemical formula 3

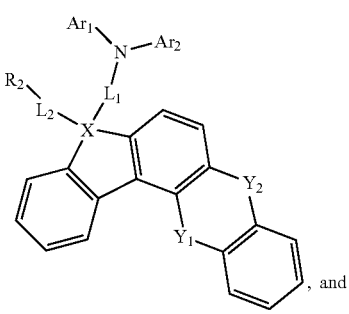

, and chemical formula 4

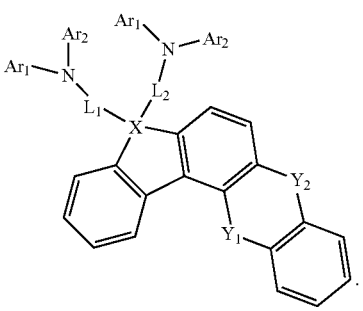

.

3. The organic compound according to claim 1, wherein $L_1$ and $L_2$ are the same or different, and are each independently selected from: a single bond and substituted or unsubstituted following groups:

165
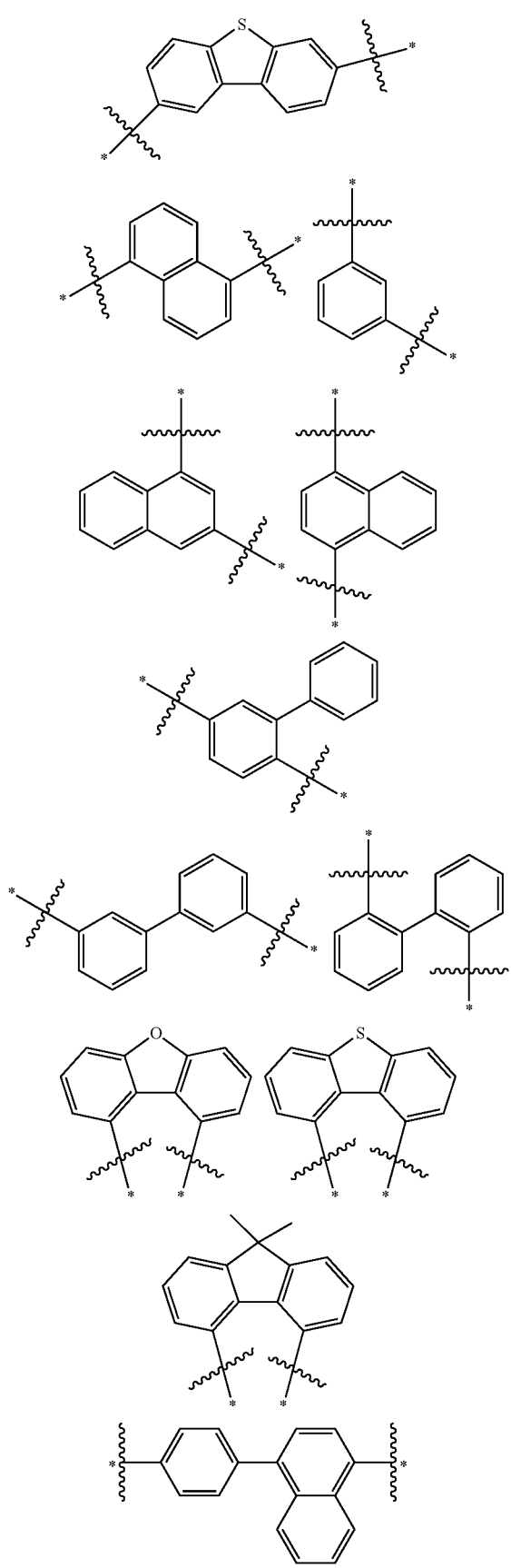
166
-continued
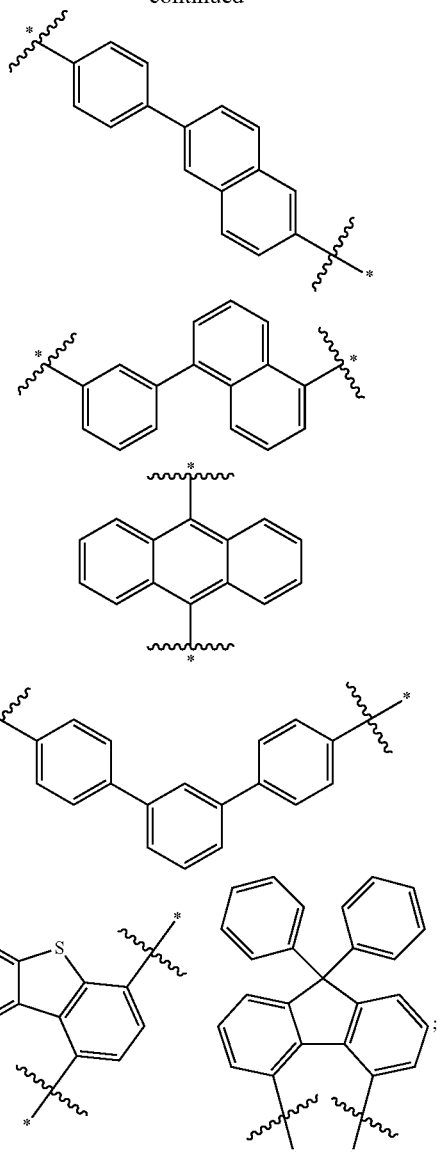
wherein
means that a position where the above group is intended to link to
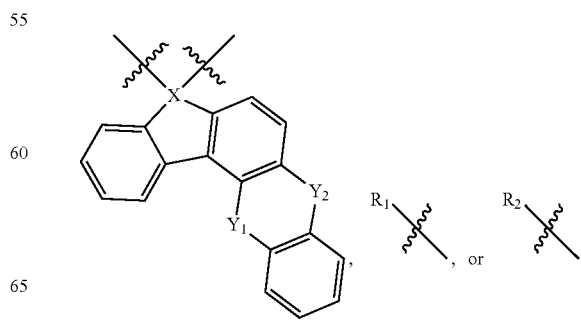

in the chemical formula I;

the above groups are each optionally substituted by 0, 1, 2, 3, 4, or 5 substituents, and each of the substituents is independently selected from: deuterium, fluorine, chlorine, cyano, methyl, ethyl, isopropyl, tert-butyl, methoxy, ethoxy, isopropoxy, propoxy, cyclopentyl, cyclohexyl, trifluoromethyl, and alkylsilyl with 3 carbon atoms.

4. The organic compound according to claim 1, wherein $L_1$ and $L_2$ are the same or different, and are each independently selected from: a single bond and substituted or unsubstituted following groups:

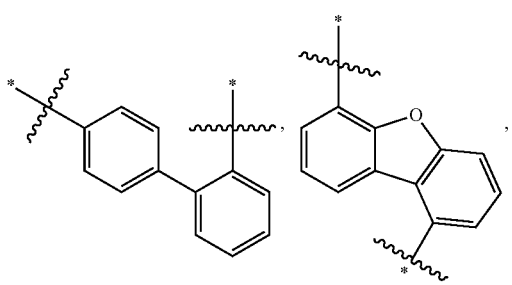

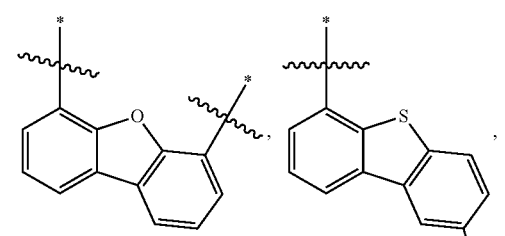

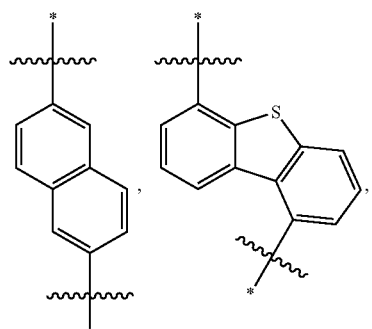

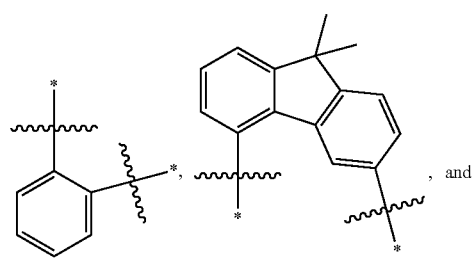, and

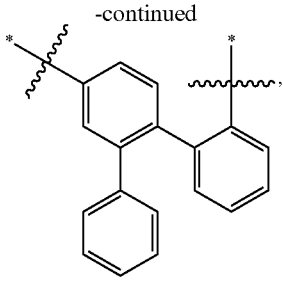

wherein

means that a position where the above group is intended to link to

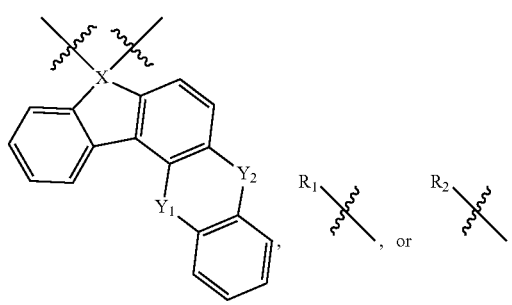

in the chemical formula I;

the above groups are each optionally substituted by 0, 1, 2, 3, 4, or 5 substituents, and each of the substituents is independently selected from: deuterium, fluorine, chlorine, cyano, methyl, ethyl, isopropyl, tert-butyl, methoxy, ethoxy, isopropoxy, propoxy, cyclopentyl, cyclohexyl, trifluoromethyl, phenyl, naphthyl, trimethylsilyl, and triphenylsilyl.

5. The organic compound according to claim 1, wherein $Ar_1$ and $Ar_2$ are the same or different, and are each independently selected from substituted or unsubstituted following groups:

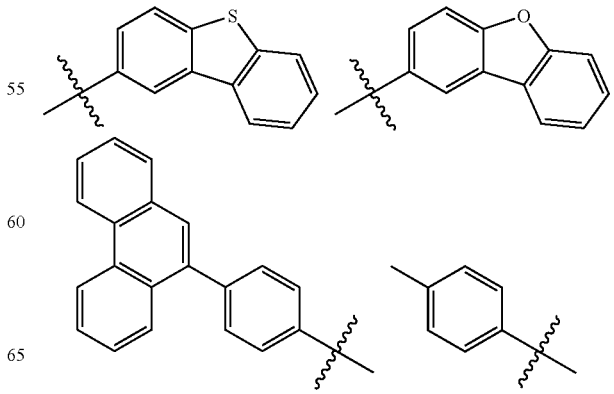

-continued
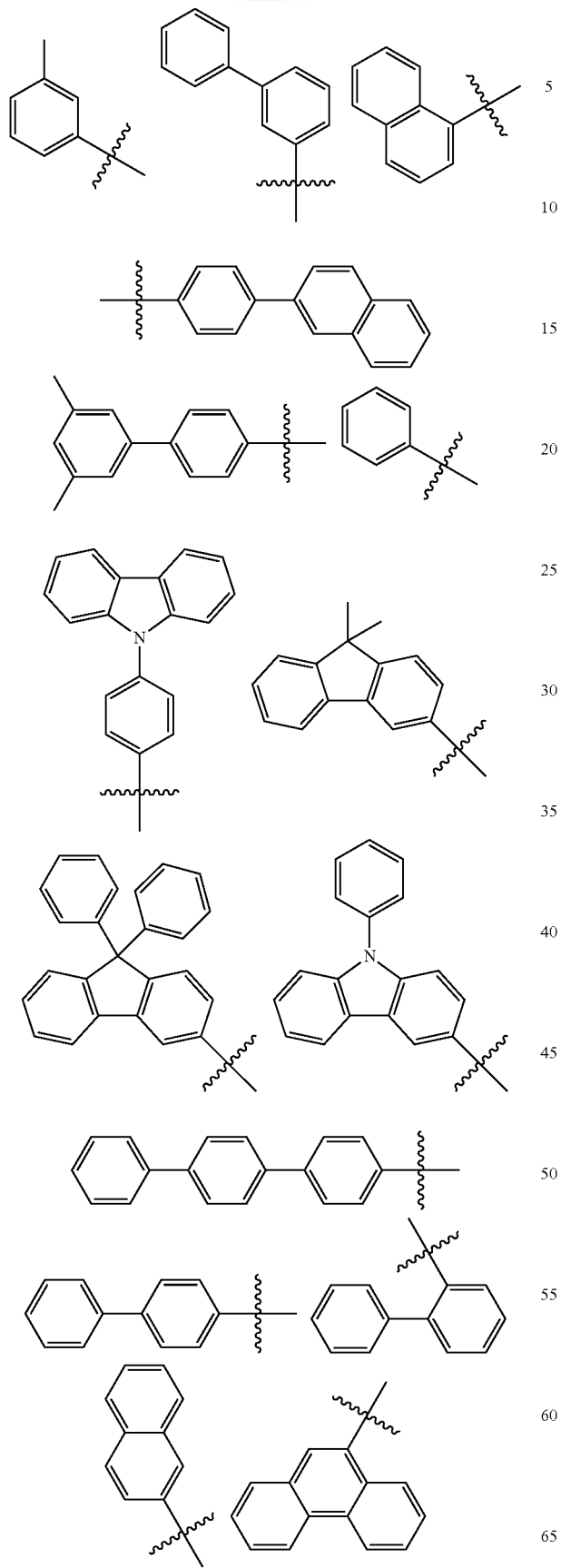
-continued
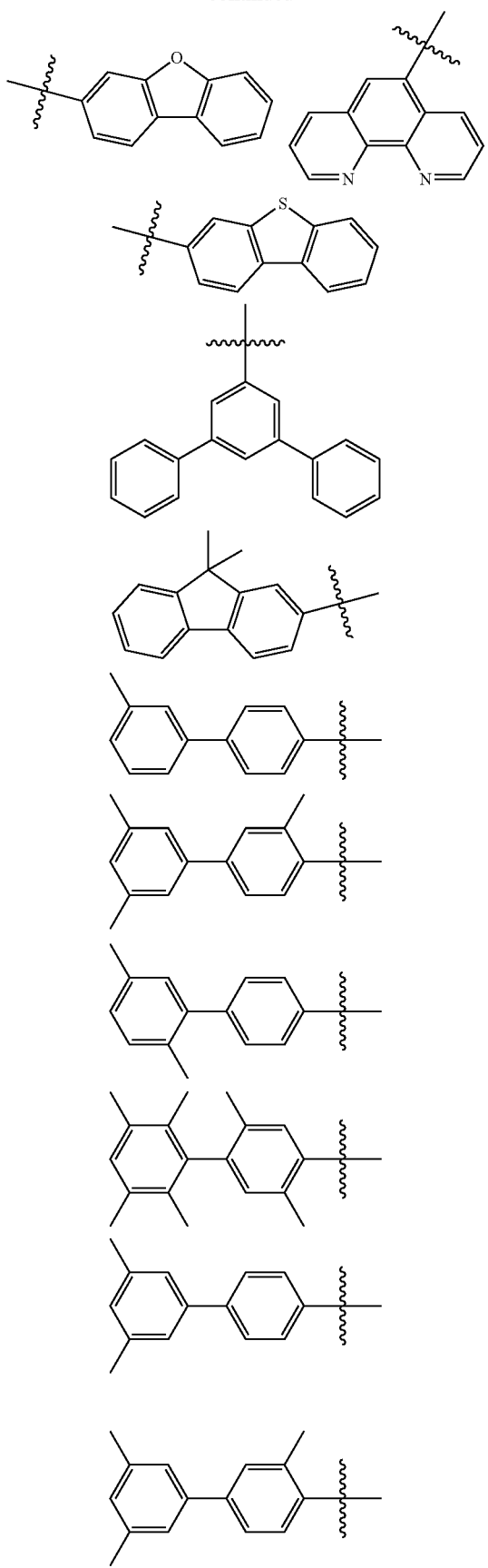

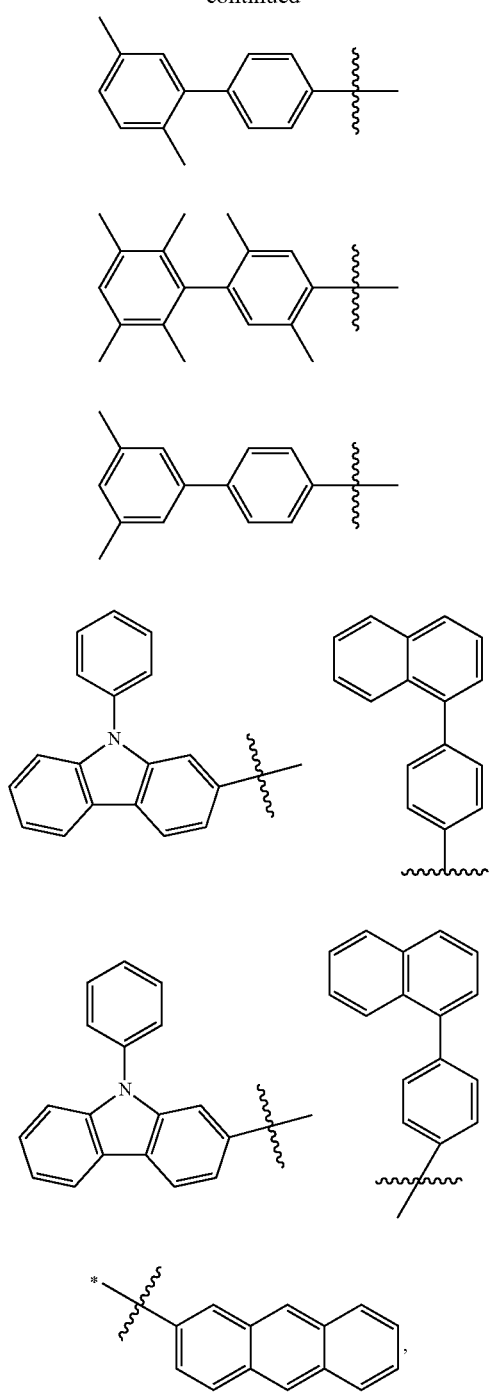

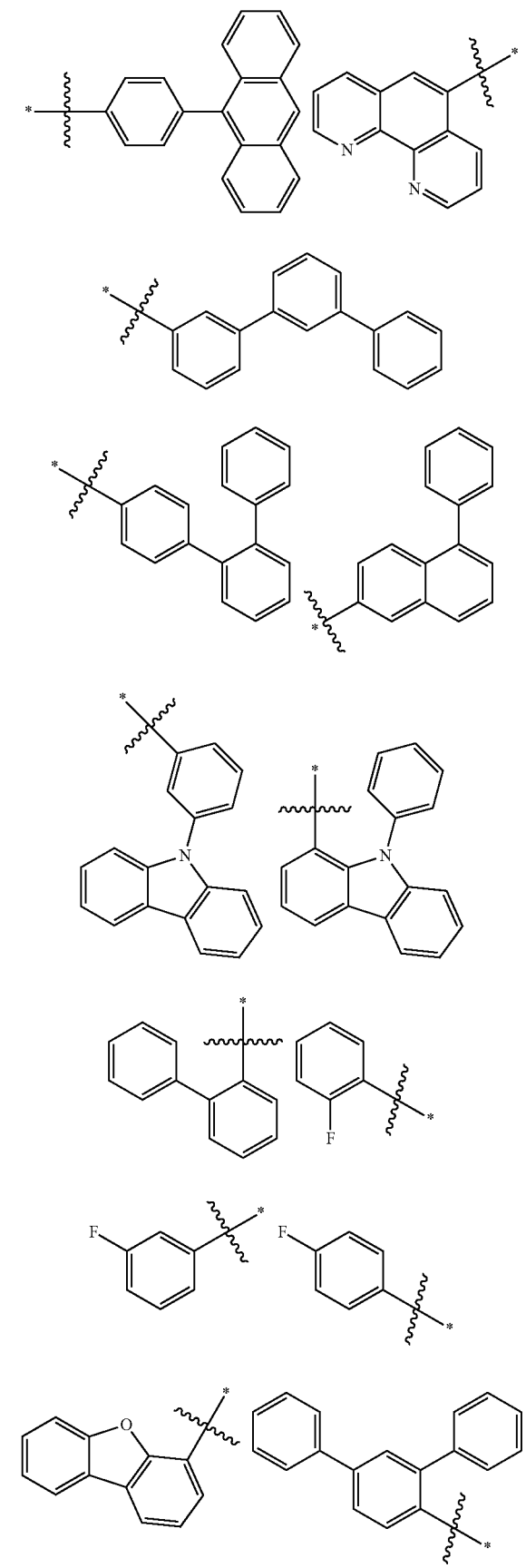

wherein the above groups are each optionally substituted by 0, 1, 2, 3, 4, or 5 substituents, and each of the substituents is independently selected from: deuterium, fluorine, chlorine, cyano, methyl, ethyl, isopropyl, tert-butyl, methoxy, ethoxy, isopropoxy, propoxy, cyclopentyl, cyclohexyl, trifluoromethyl, and trimethylsilyl.

6. The organic compound according to claim 1, wherein $Ar_1$ and $Ar_2$ are the same or different, and are each independently selected from substituted or unsubstituted following groups:

173
-continued

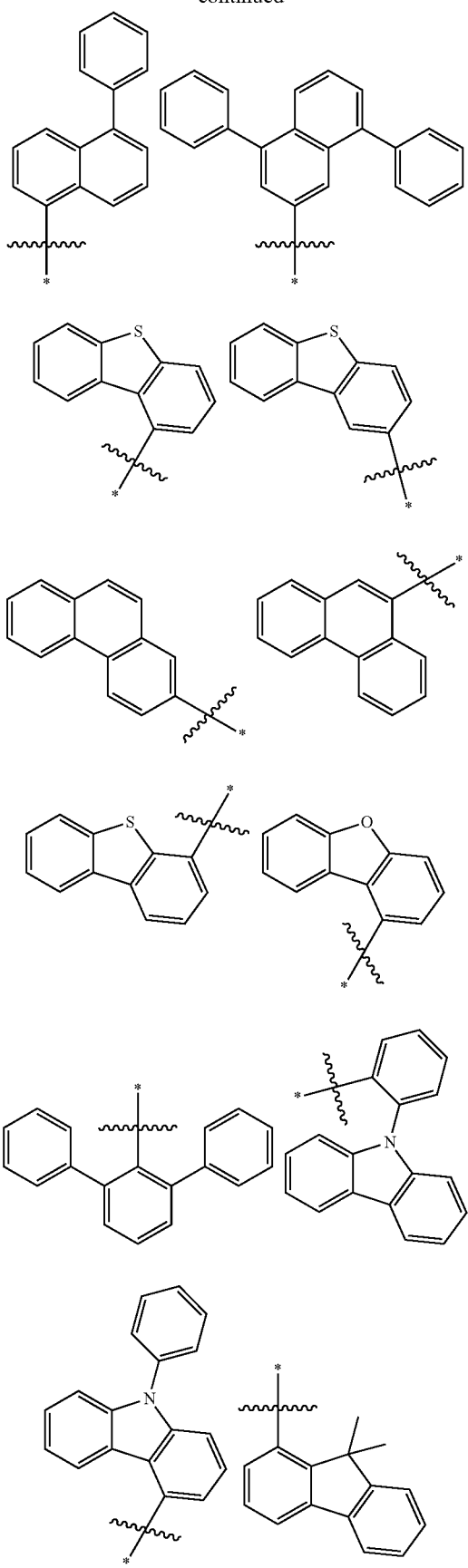

174
-continued

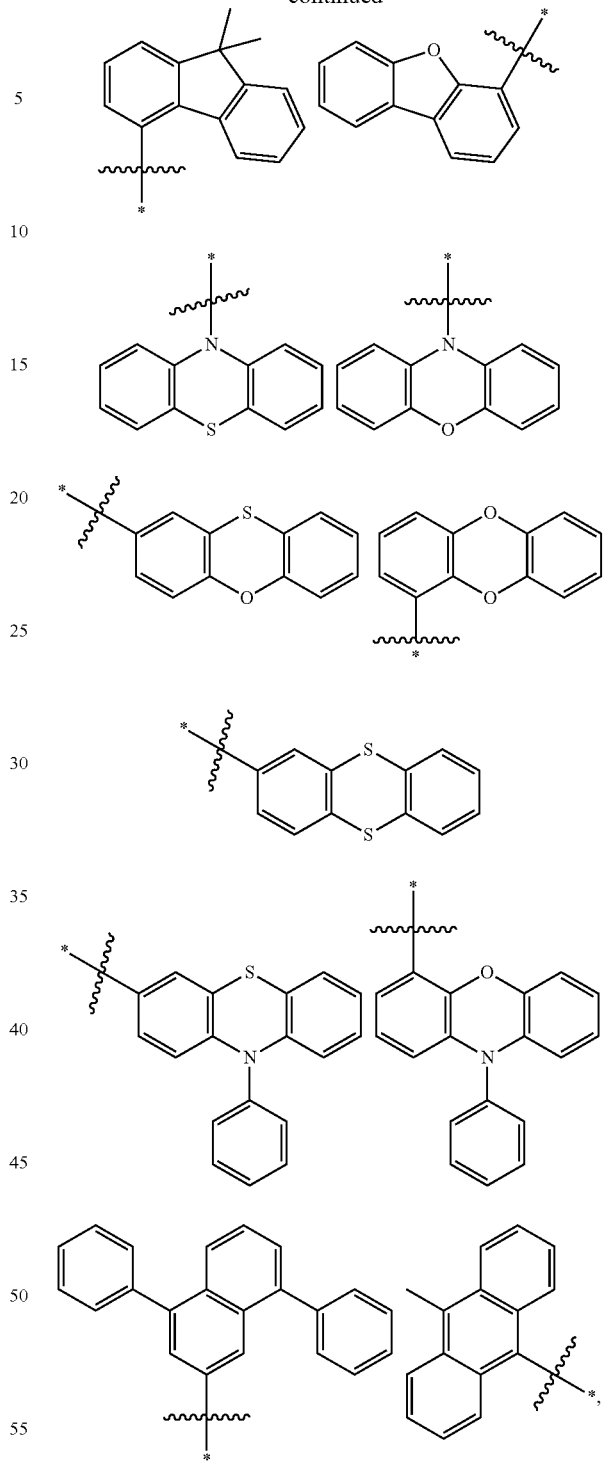

wherein the above groups are each optionally substituted by 0, 1, 2, 3, 4, or 5 substituents, and each of the substituents is independently selected from: deuterium, fluorine, chlorine, cyano, methyl, ethyl, isopropyl, tert-butyl, methoxy, ethoxy, isopropoxy, propoxy, cyclopentyl, cyclohexyl, trifluoromethyl, trimethylsilyl, phenyl, and naphthyl.

7. The organic compound according to claim 1, wherein $R_1$ and $R_2$ are the same or different, and are each independently selected from: hydrogen, deuterium,

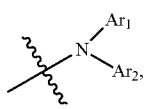

and substituted or unsubstituted following groups:

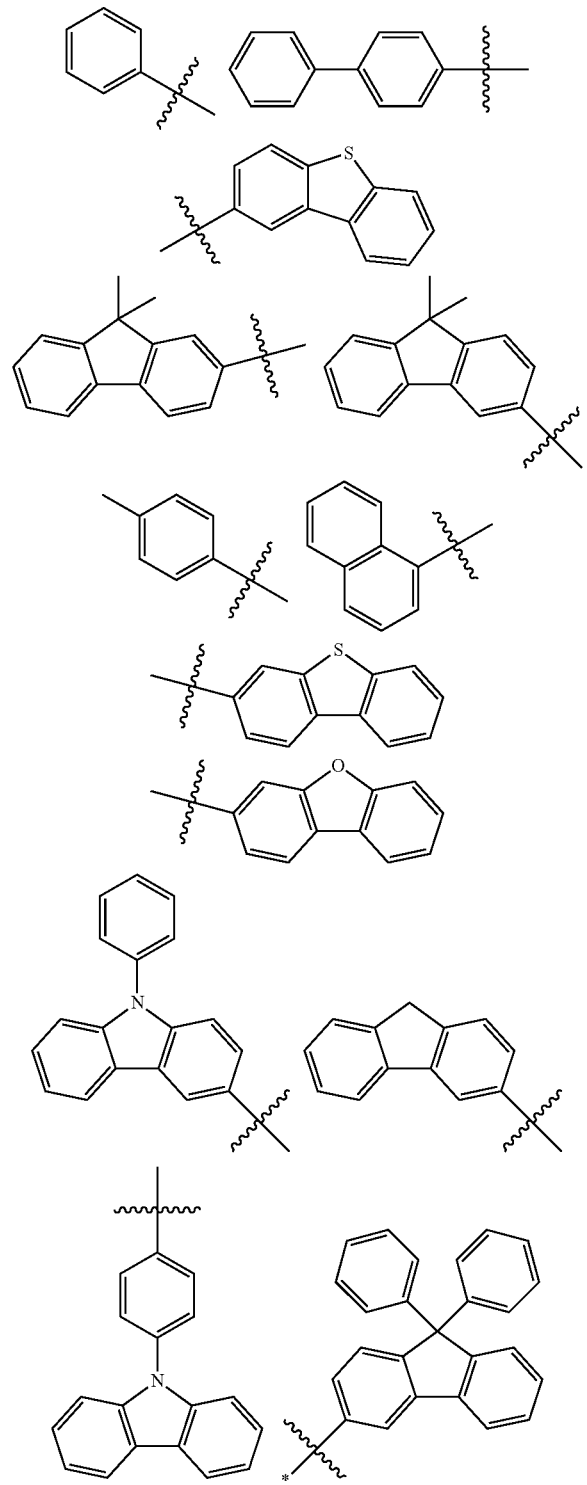

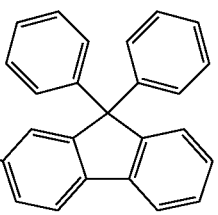

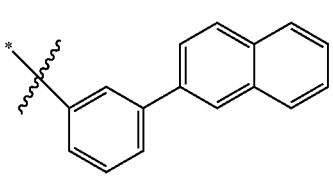

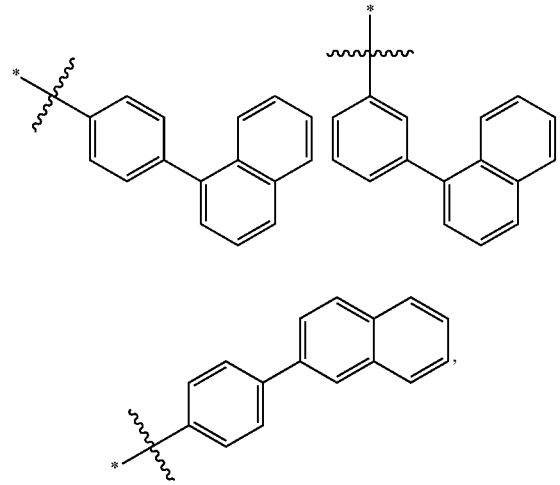

wherein the above groups are each optionally substituted by 0, 1, 2, 3, 4, or 5 substituents, and each of the substituents is independently selected from: deuterium, fluorine, chlorine, cyano, methyl, ethyl, isopropyl, tert-butyl, methoxy, ethoxy, isopropoxy, propoxy, cyclopentyl, cyclohexyl, trifluoromethyl, and alkylsilyl with 3 carbon atoms;

and at least one of $R_1$ and $R_2$ is

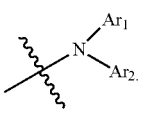

8. The organic compound according to claim 1, wherein $R_1$ and $R_2$ are the same or different, and are each independently selected from: hydrogen, deuterium,

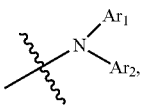

and substituted or unsubstituted following groups:
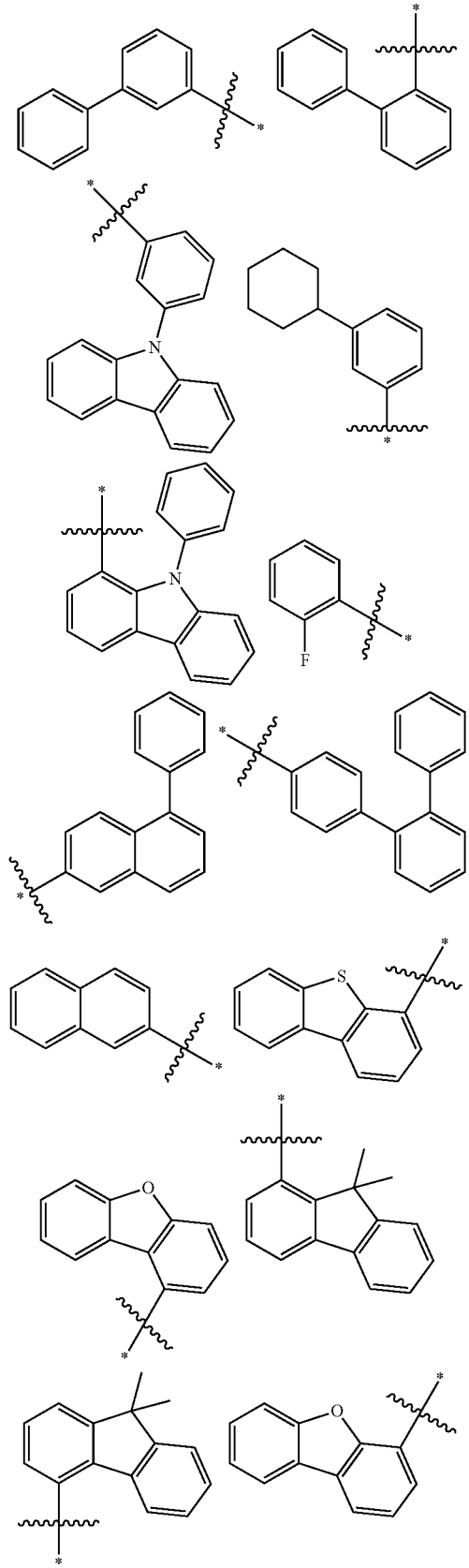
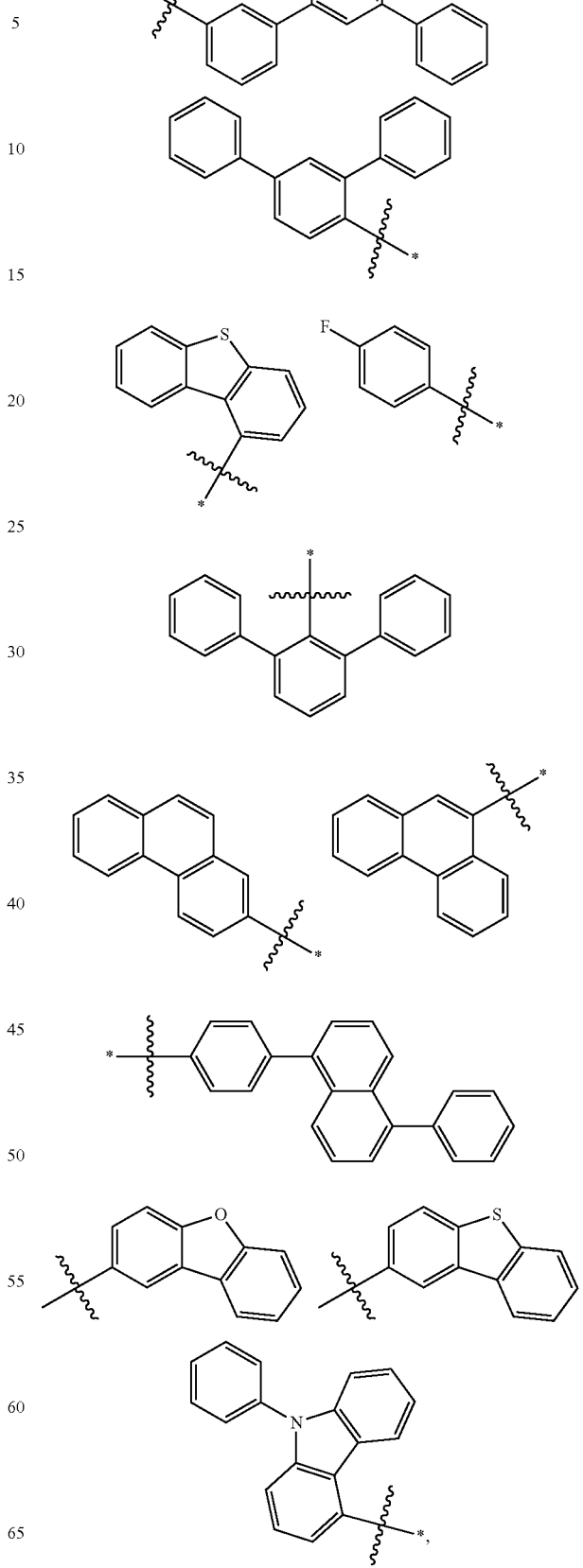

and at least one of $R_1$ and $R_2$ is

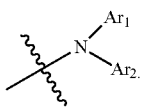

wherein the above groups are each optionally substituted by 0, 1, 2, 3, 4, or 5 substituents, and each of the substituents is independently selected from: deuterium, fluorine, chlorine, cyano, methyl, ethyl, isopropyl, tert-butyl, methoxy, ethoxy, isopropoxy, propoxy, cyclopentyl, cyclohexyl, trifluoromethyl, phenyl, naphthyl, and trimethylsilyl.

9. The organic compound according to claim 1, wherein the compound of formula I is selected from following compounds:

compound 1

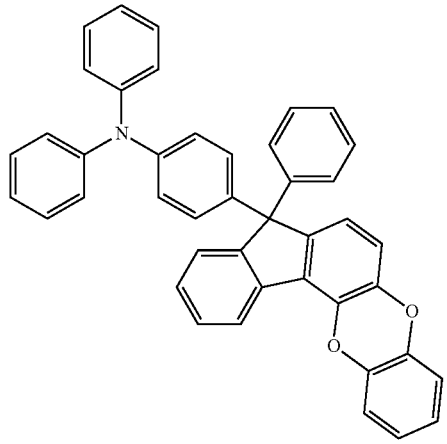

compound 2

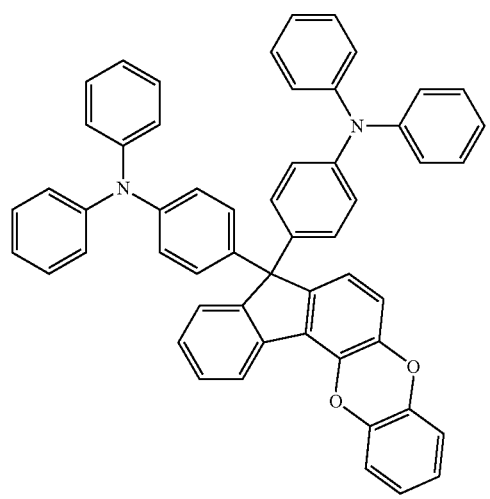

compound 3

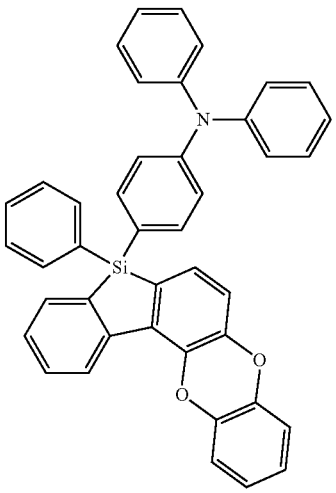

compound 4

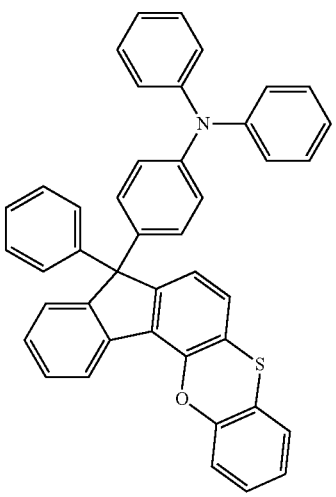

compound 5

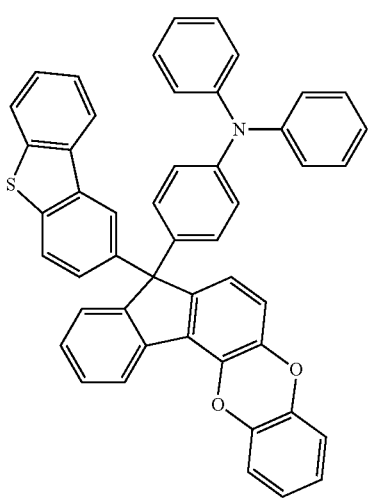

compound 6
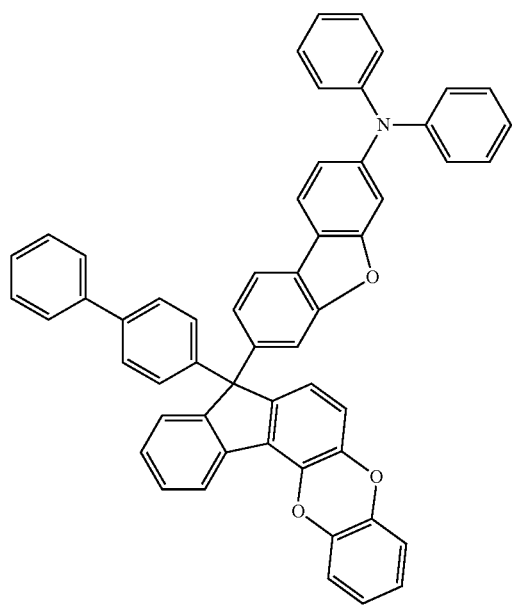
compound 7
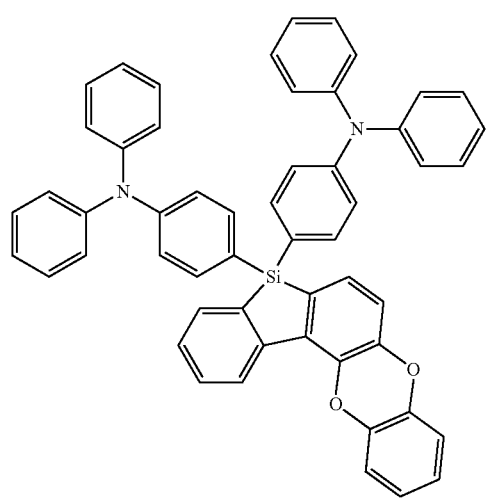
compound 8
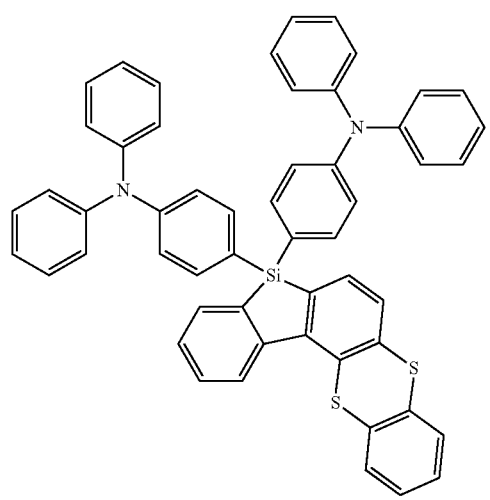
compound 10
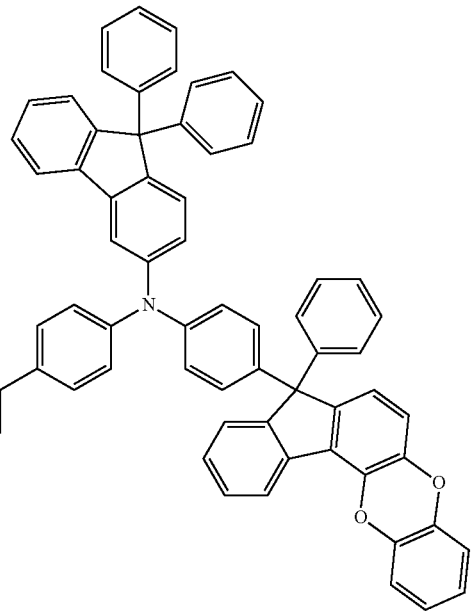
compound 12
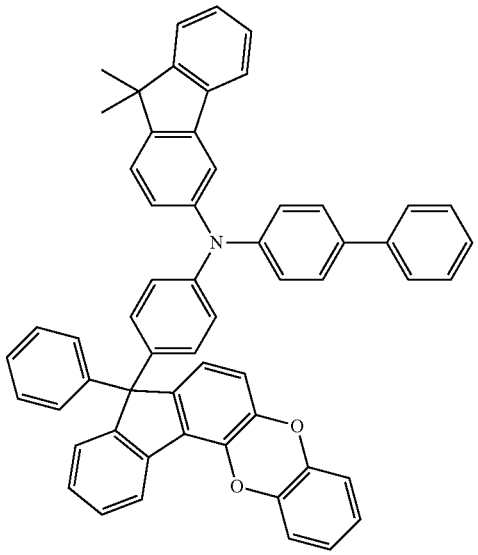

compound 13
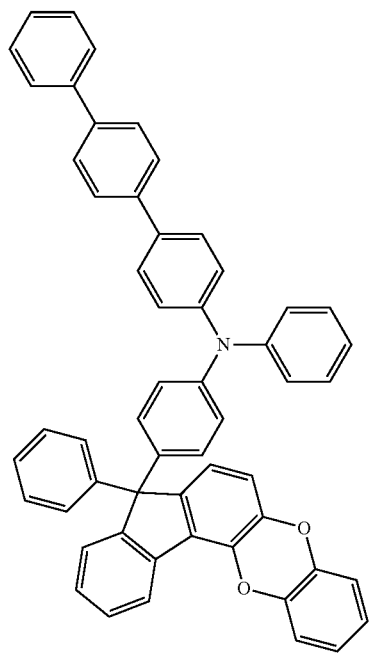
compound 14
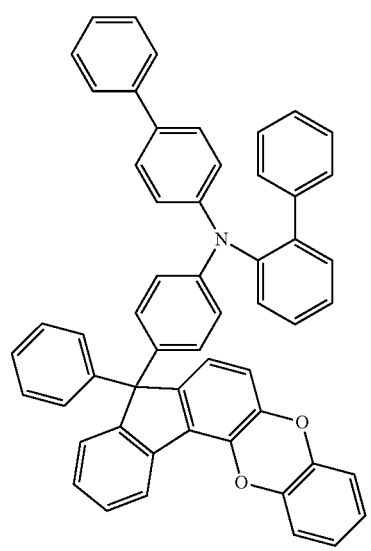
compound 16
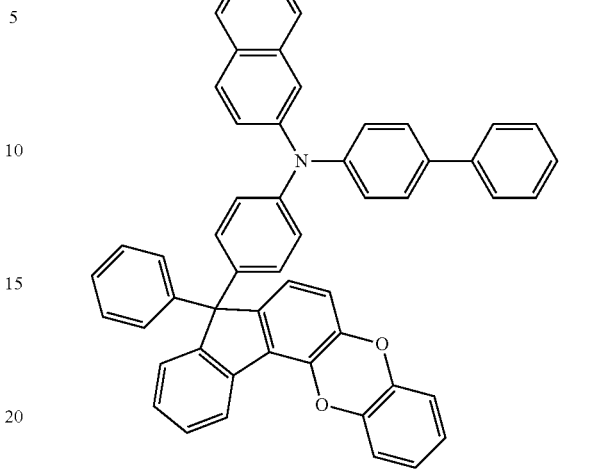
compound 17
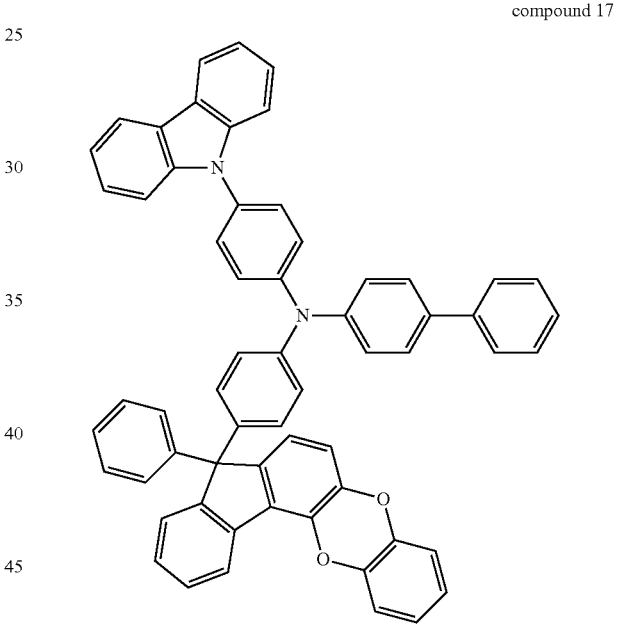
compound 18
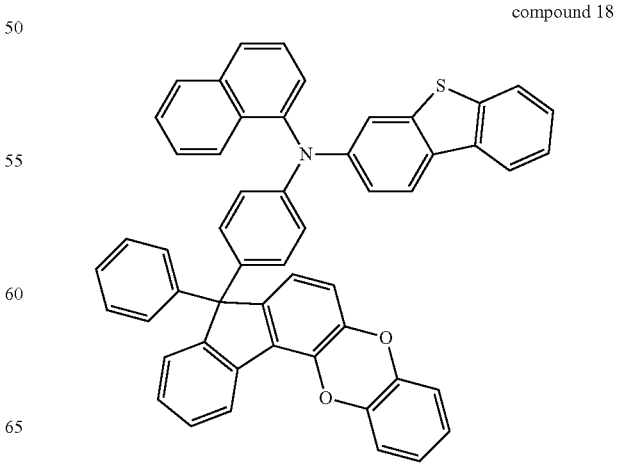

compound 19
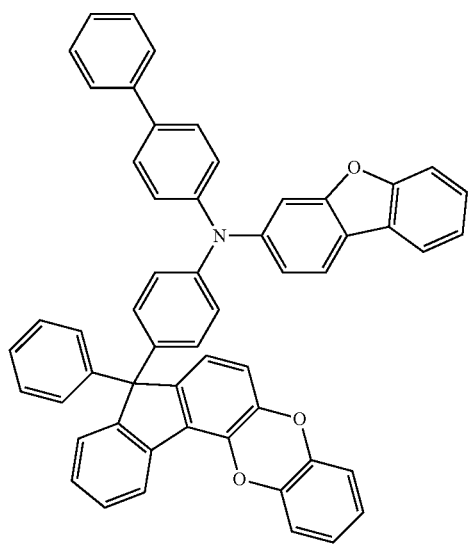
compound 23
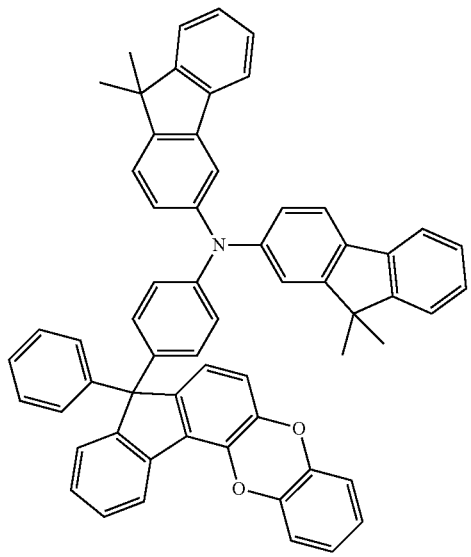
compound 21
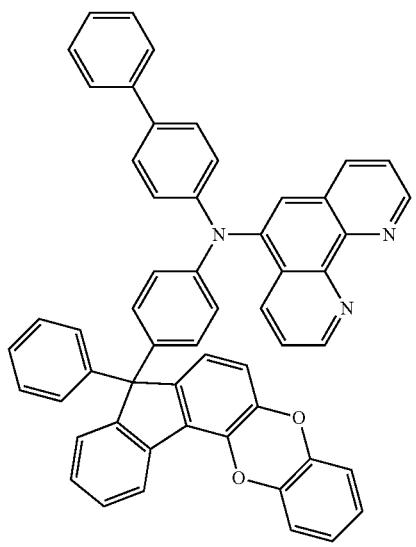
compound 25
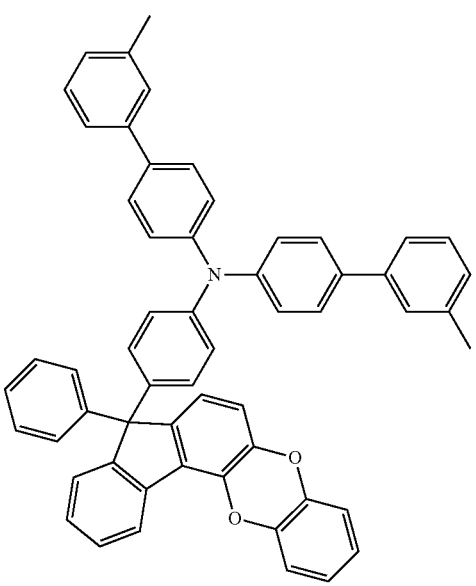

compound 29
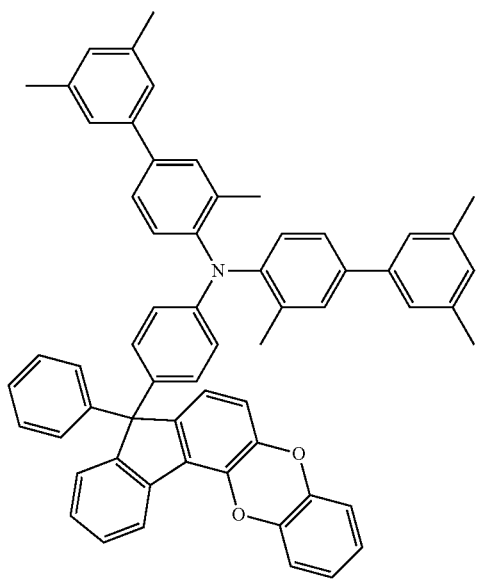
compound 33
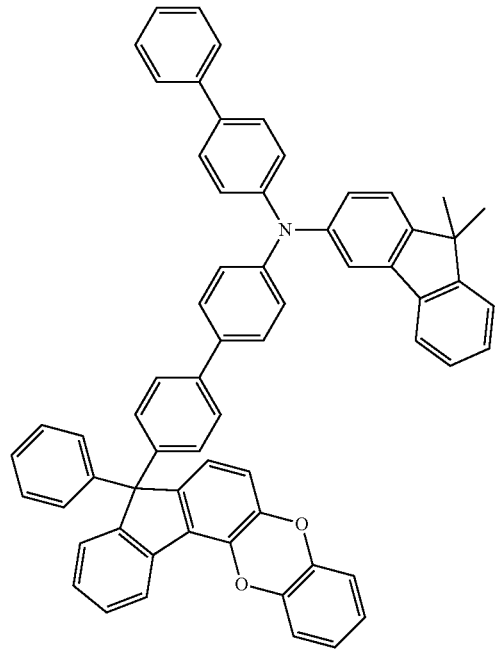
compound 31
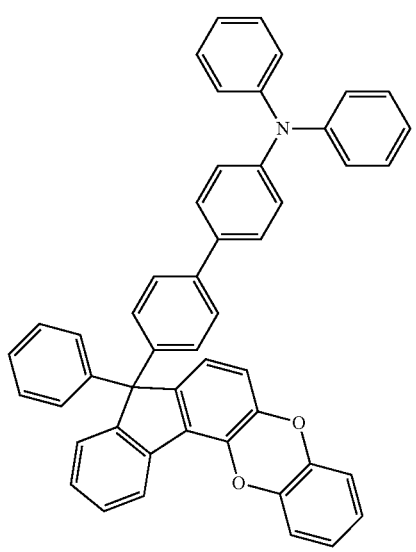
compound 34
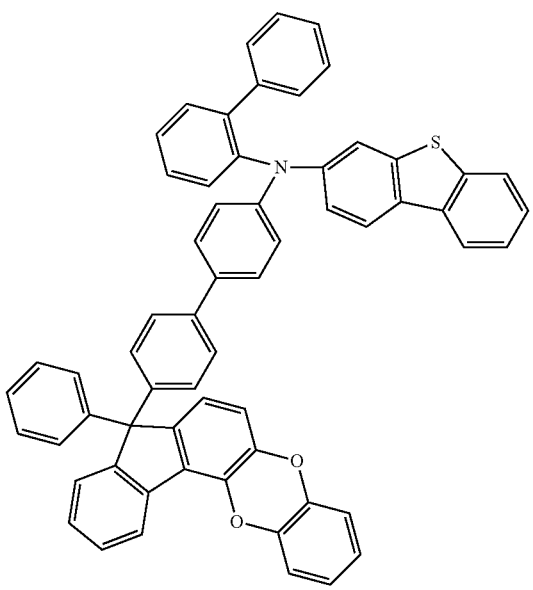

compound 35
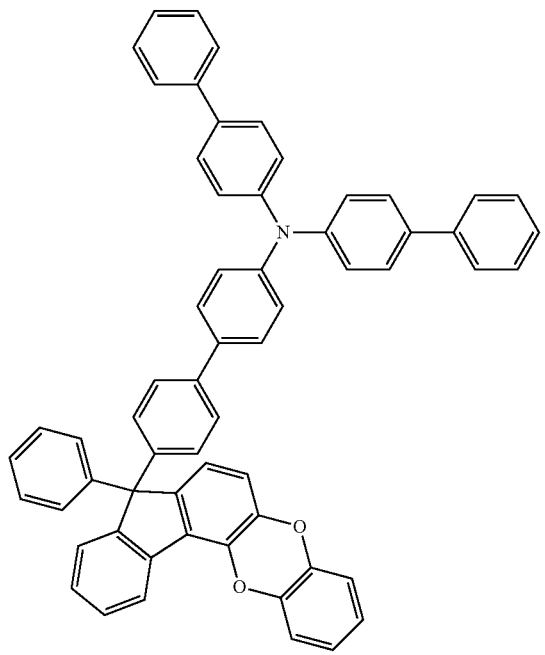
compound 39
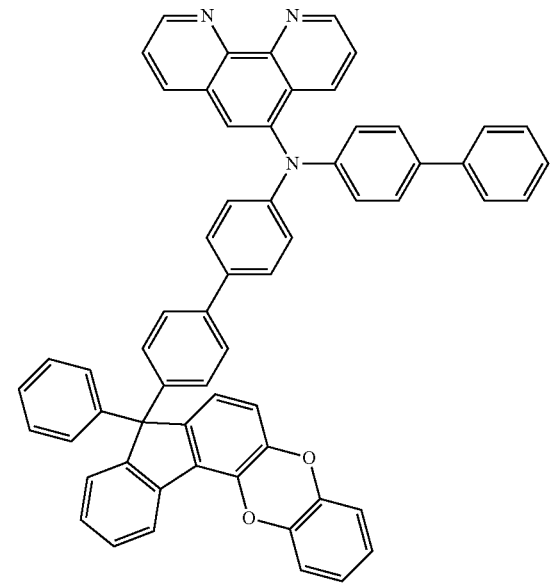
compound 36
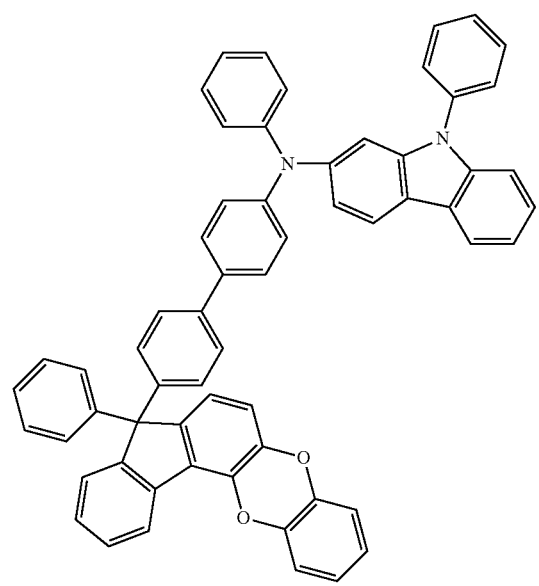
compound 41
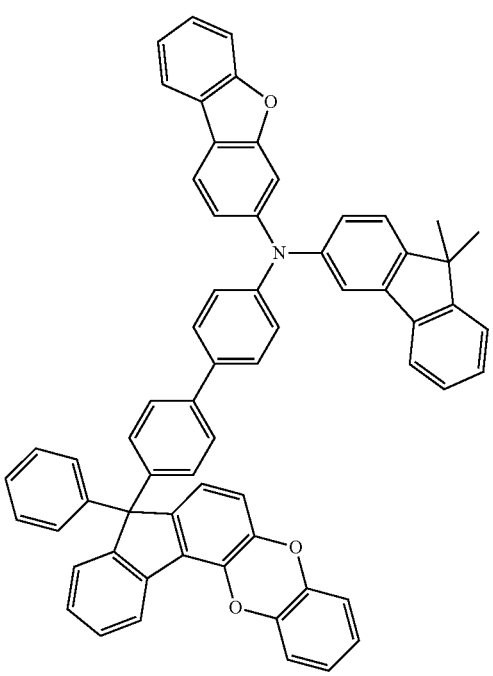

compound 42
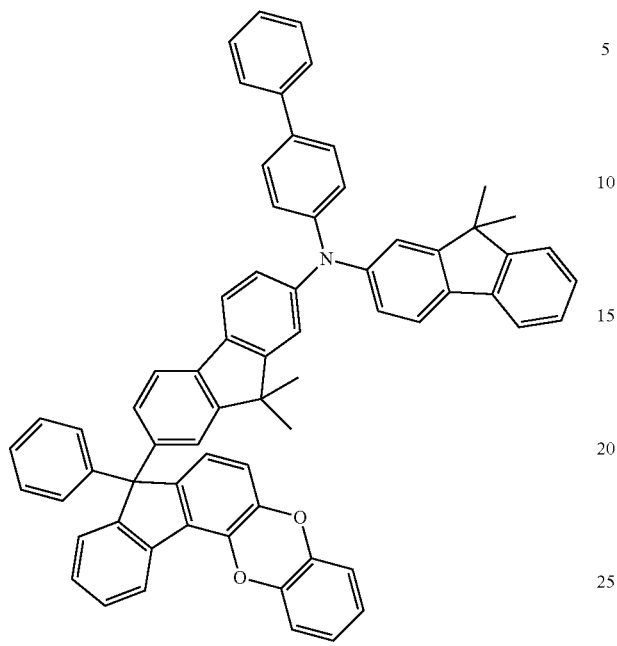
compound 44
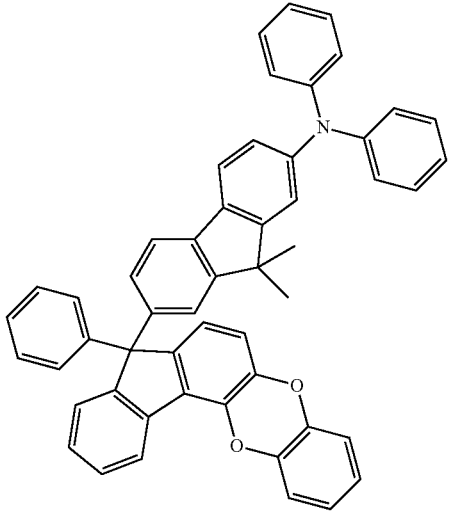
compound 43
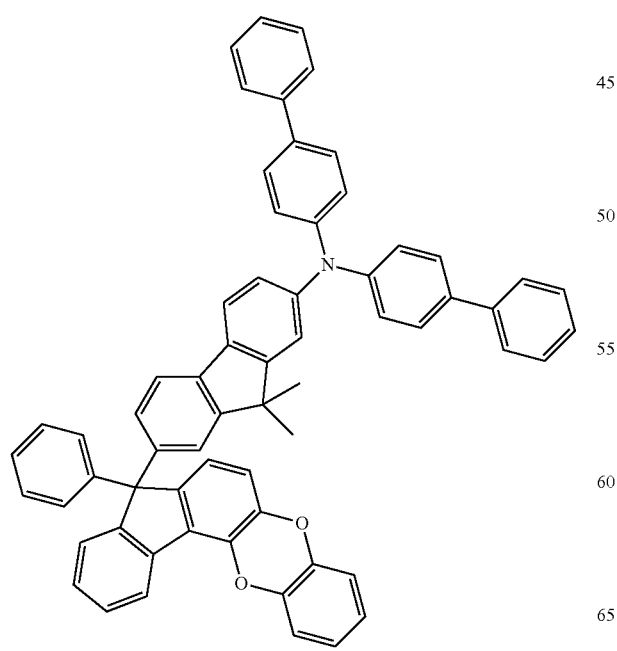
compound 46
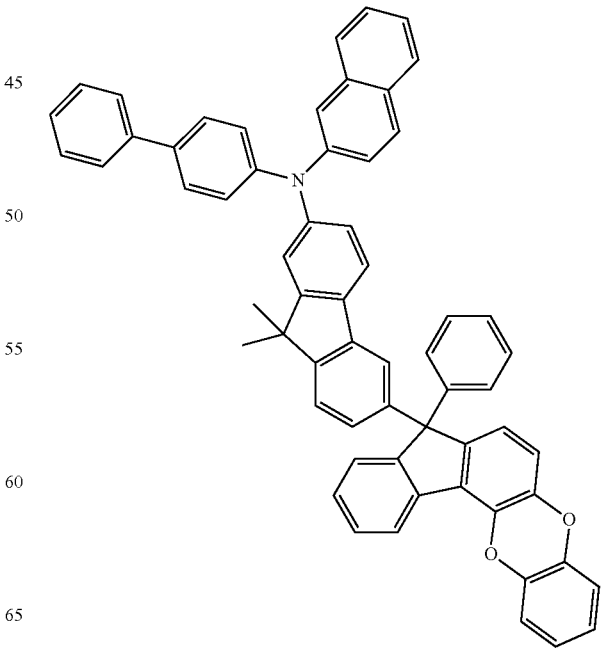

compound 47
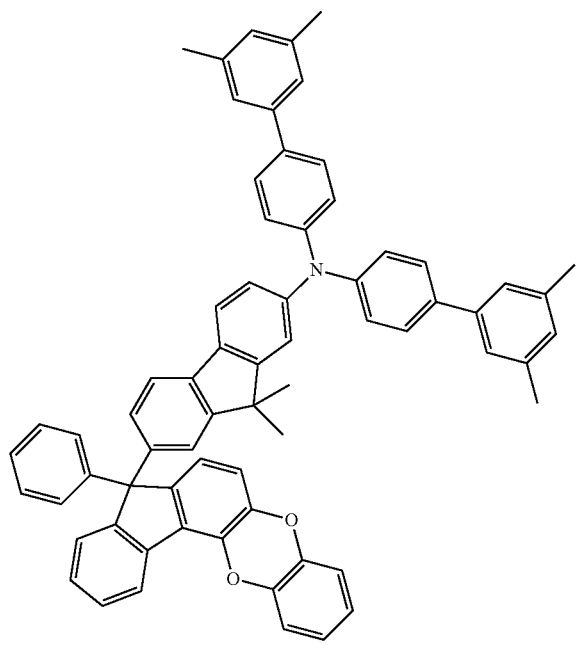
compound 49
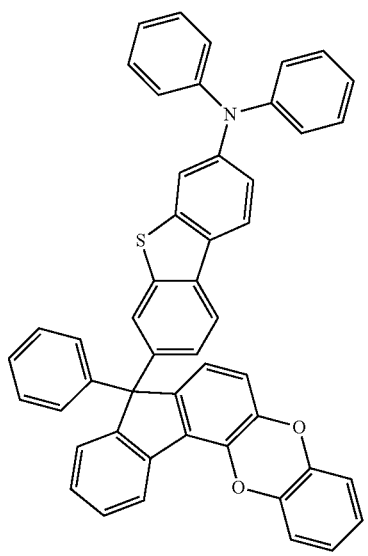
compound 50
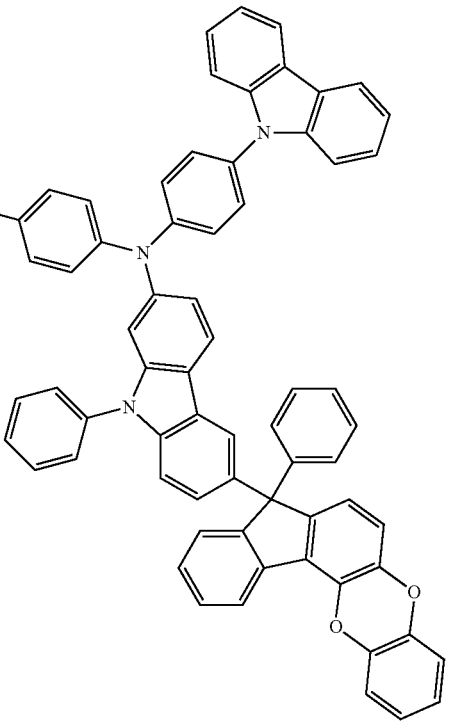
compound 52
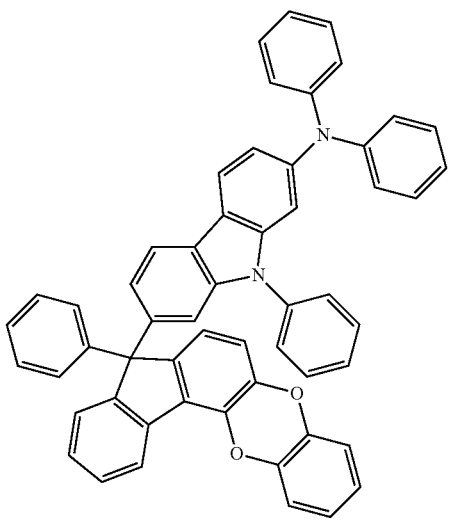

compound 57
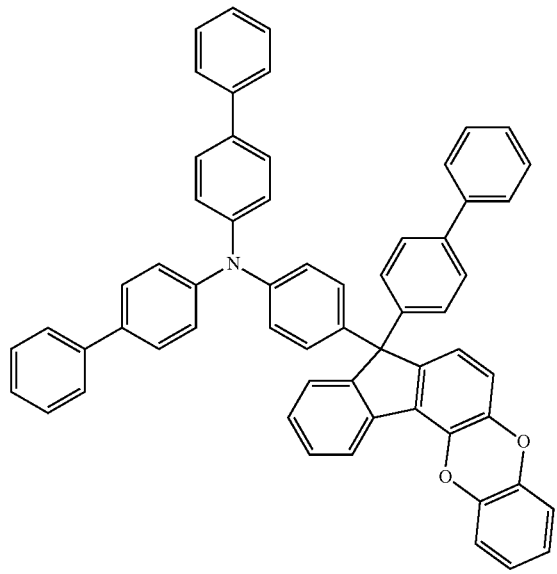
compound 58
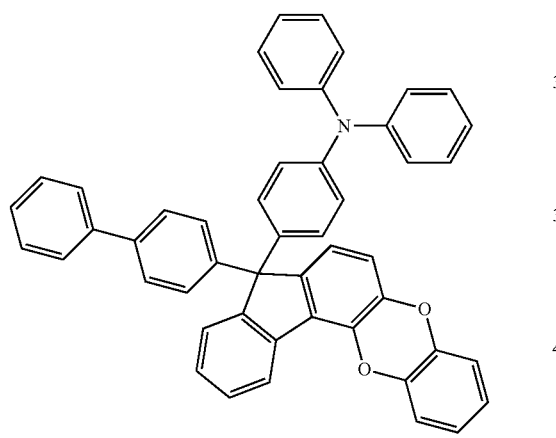
compound 60
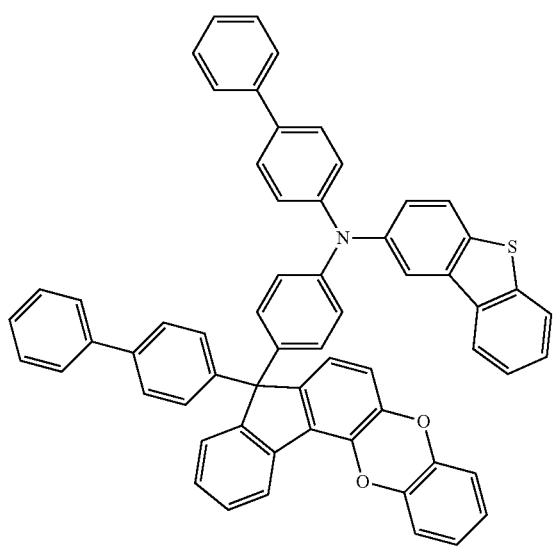
compound 61
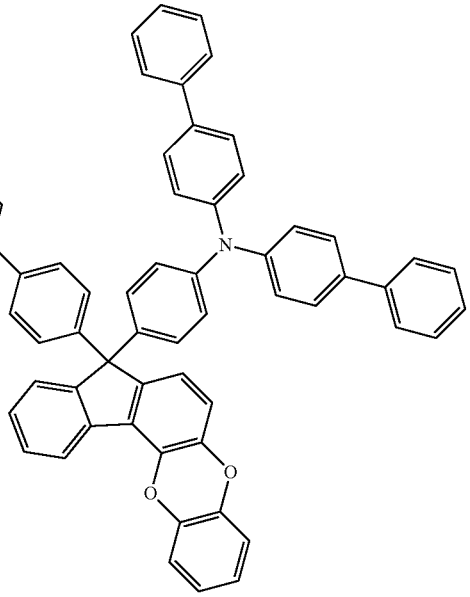
compound 62
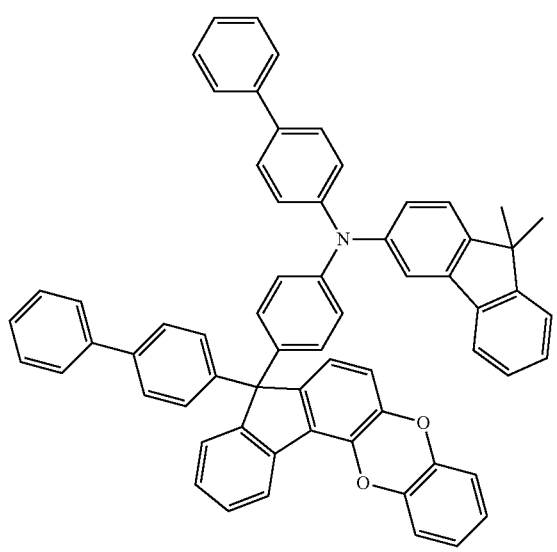

compound 63
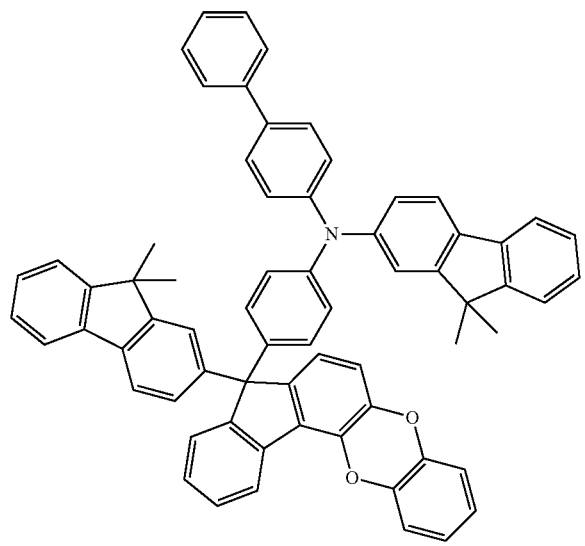
compound 64
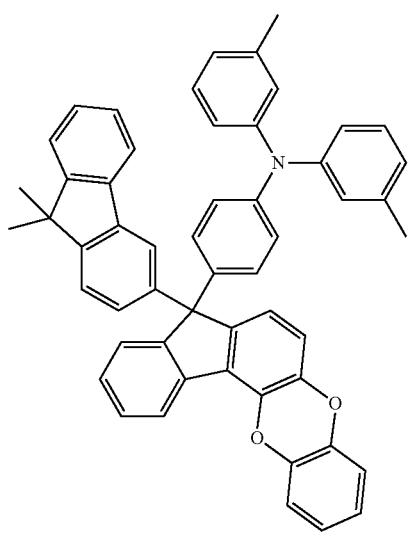
compound 66
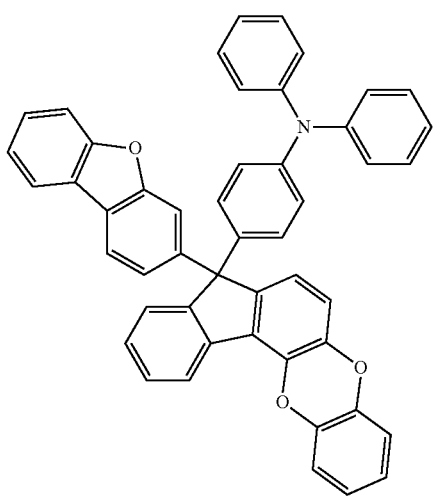
compound 67
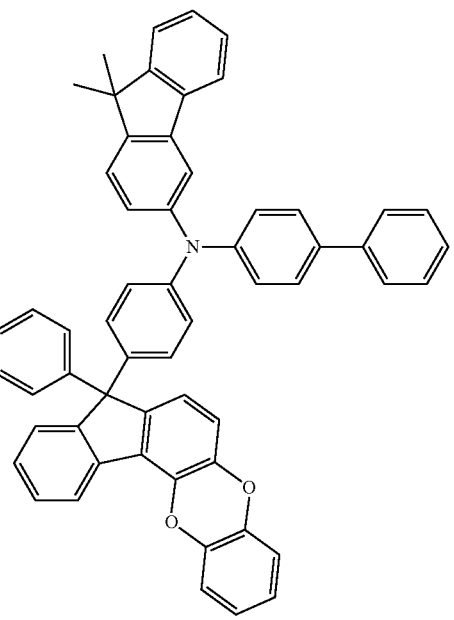
compound 68
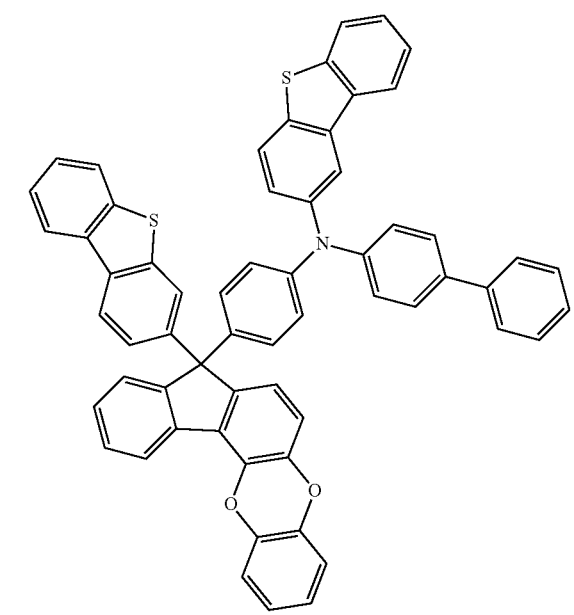

-continued
compound 69
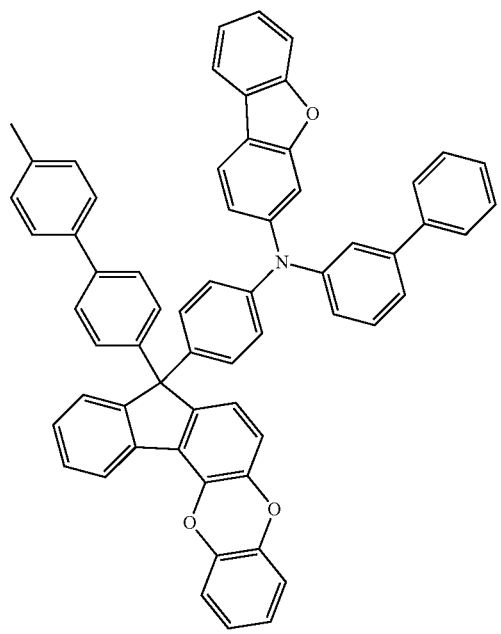
compound 70
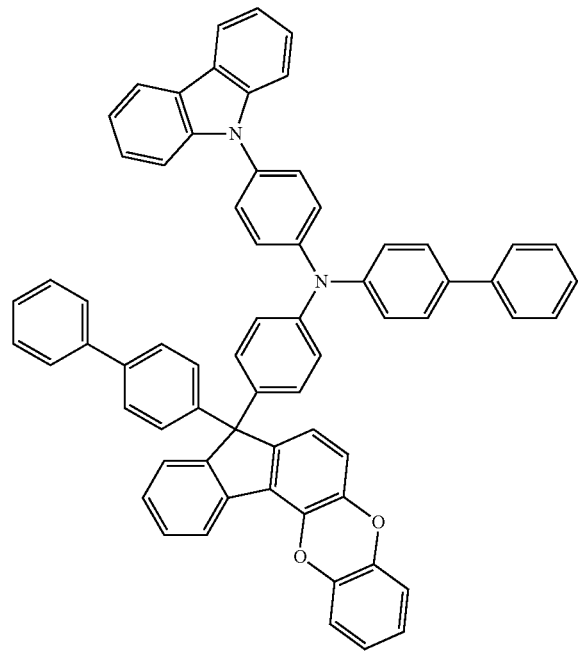
compound 72
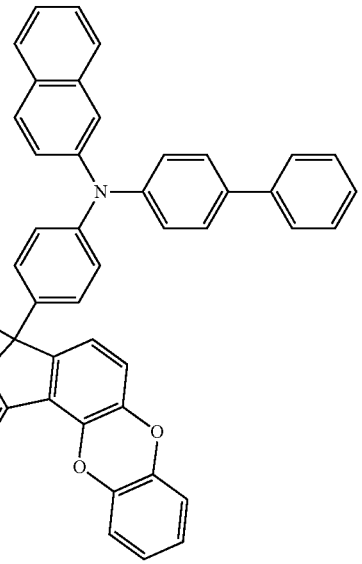
compound 73
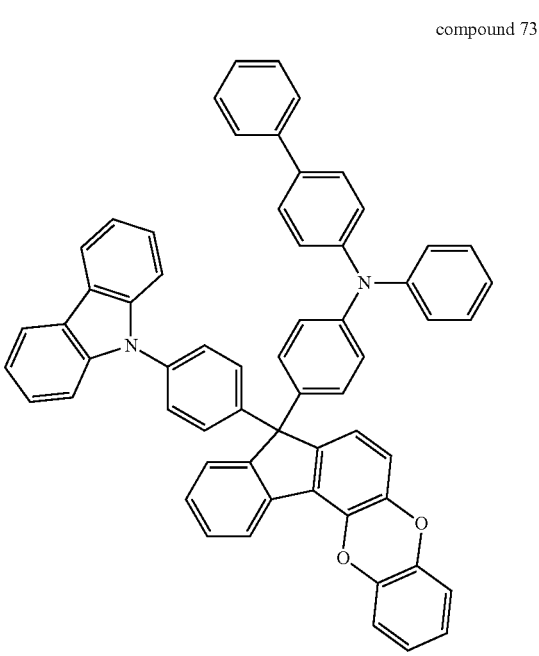

compound 76
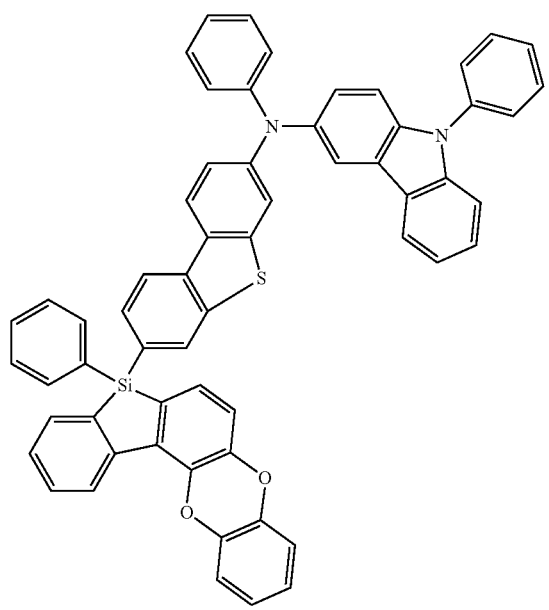
compound 78
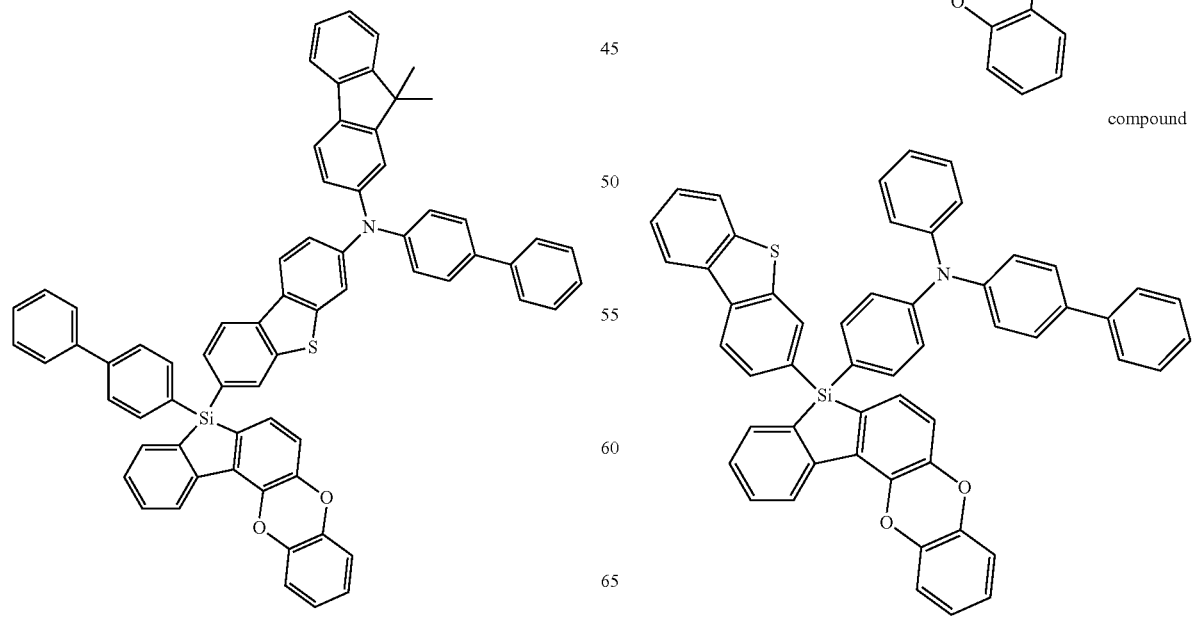
compound 79
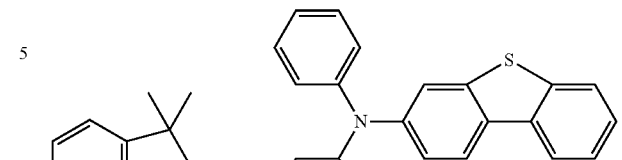
compound 80
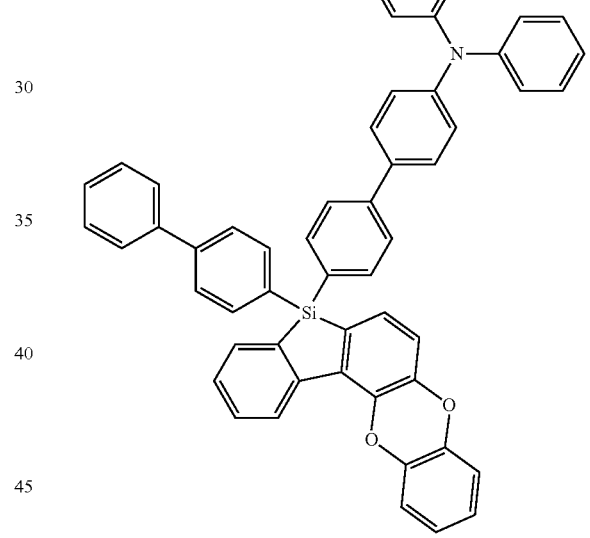
compound 81 compound 82
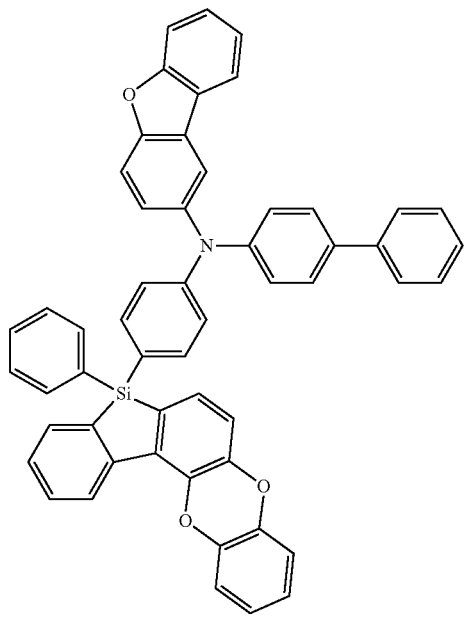
compound 84
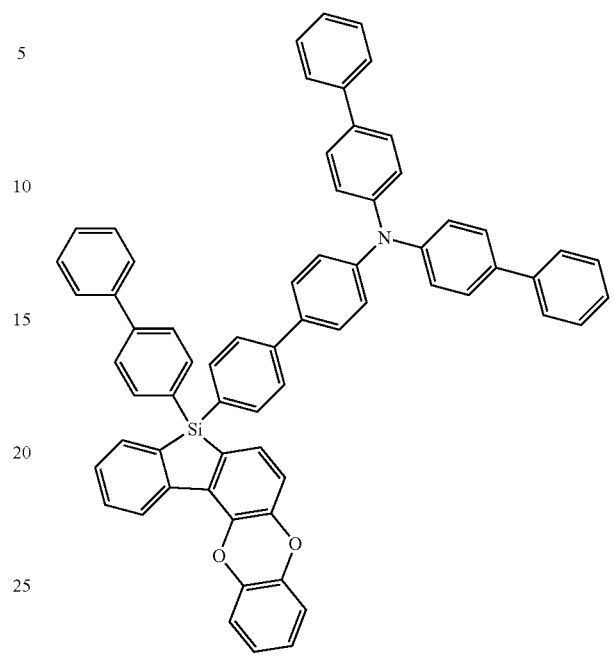
compound 83
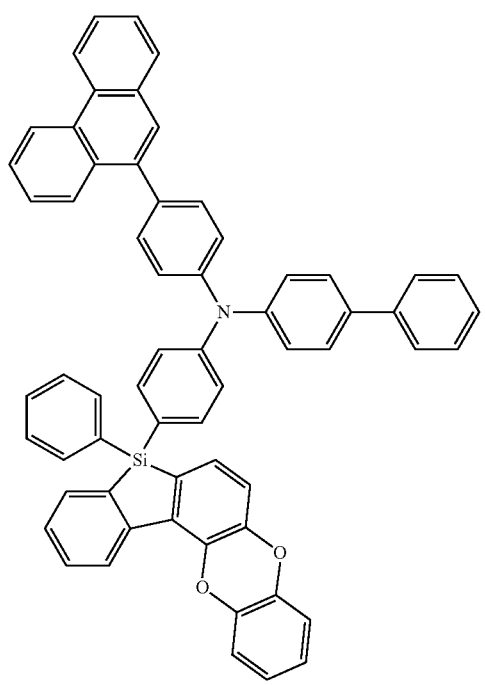
compound 85
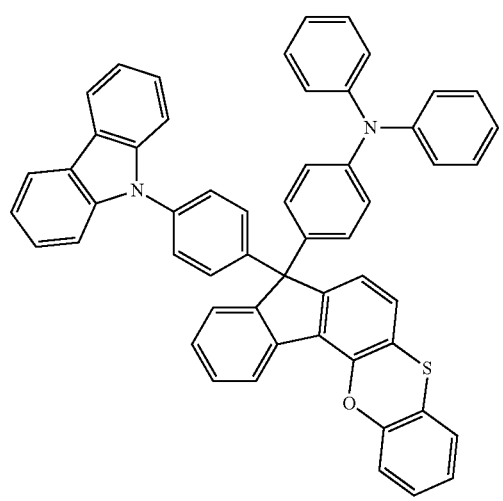

compound 86
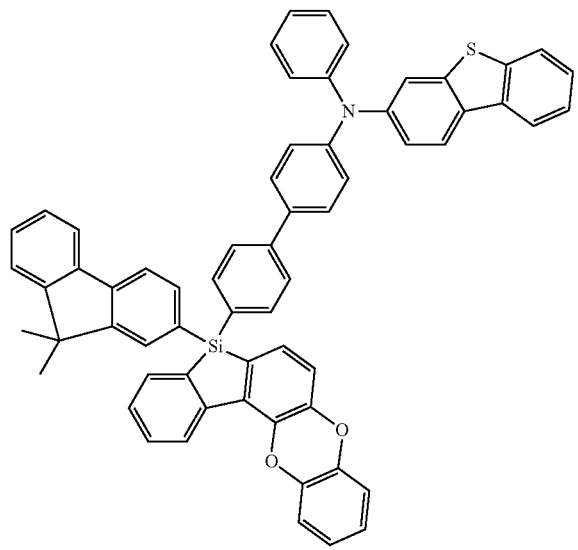
compound 88
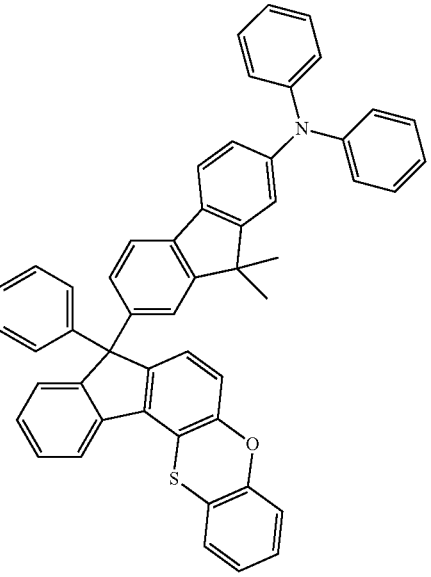
compound 87
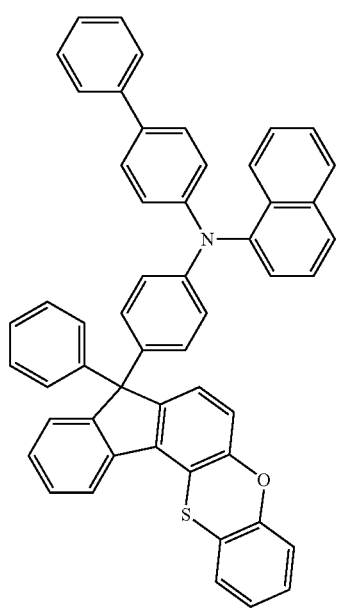
compound 89
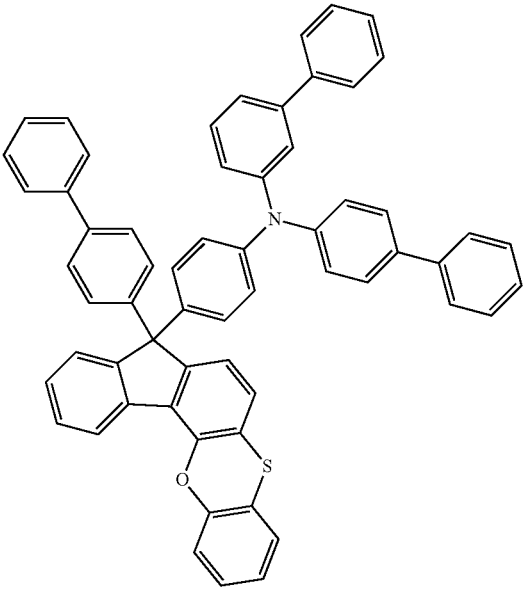

compound 90
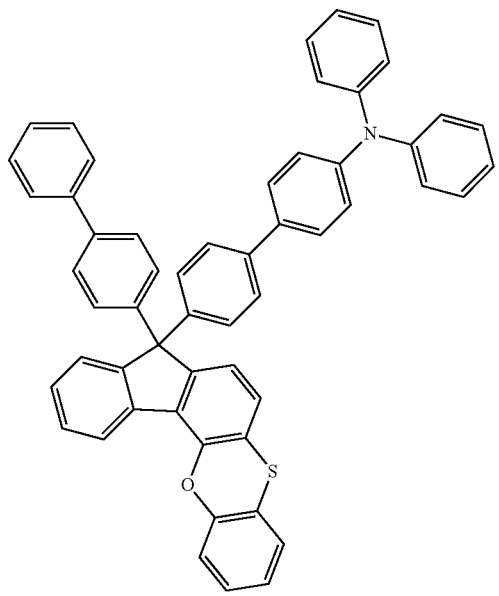
compound 93
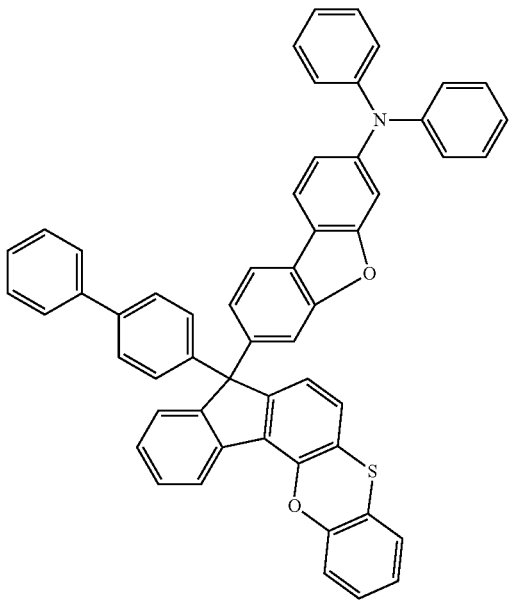
compound 92
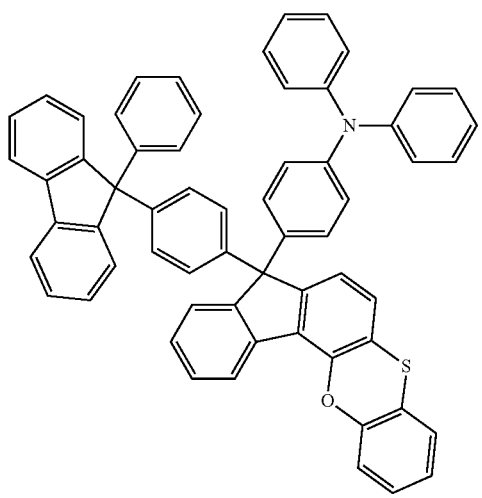
compound 94
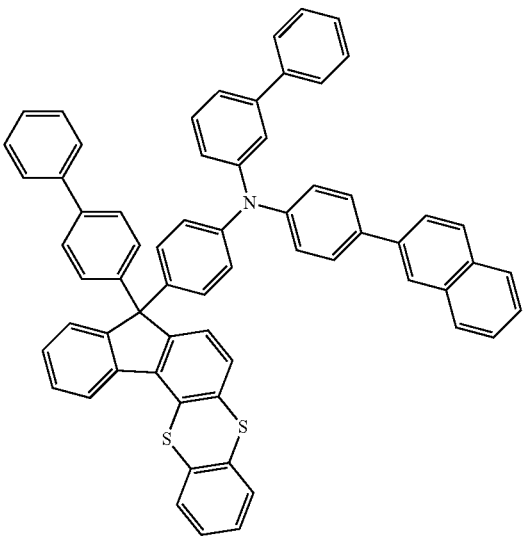

compound 95
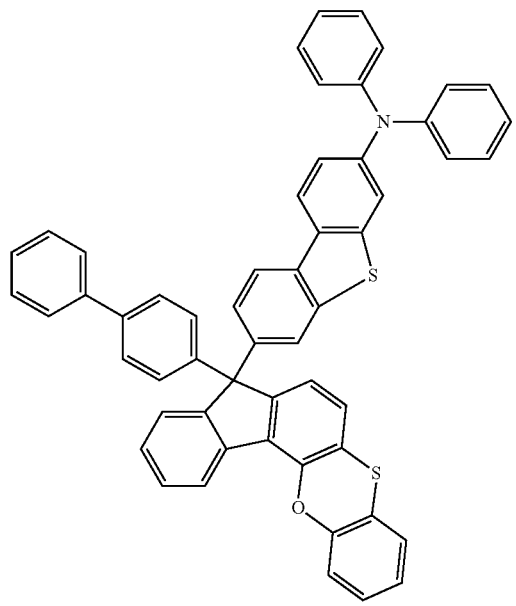
compound 96
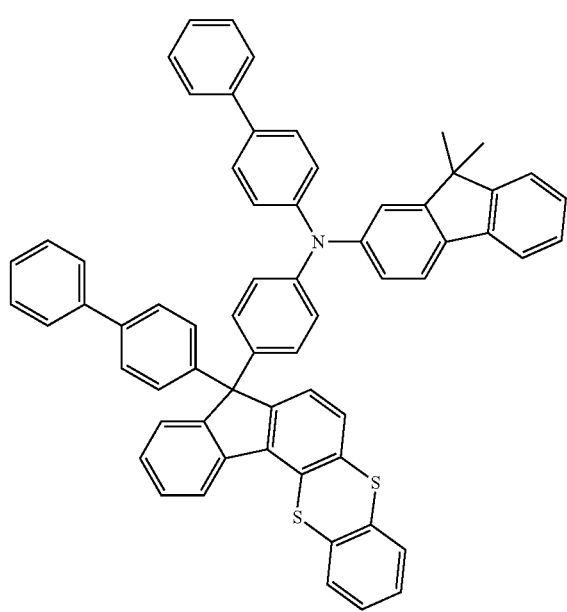
compound 97
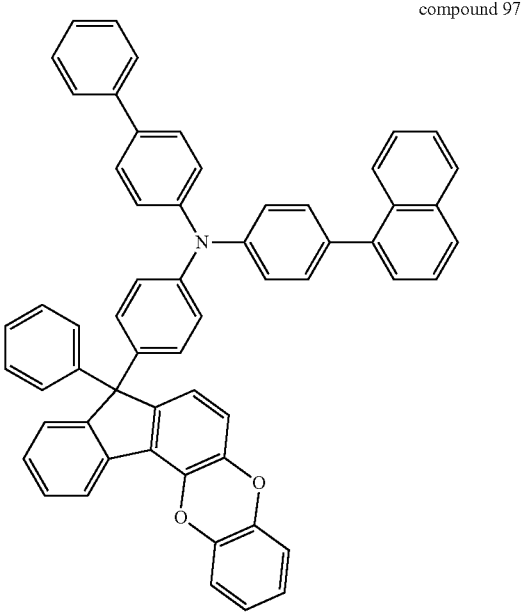
compound 98
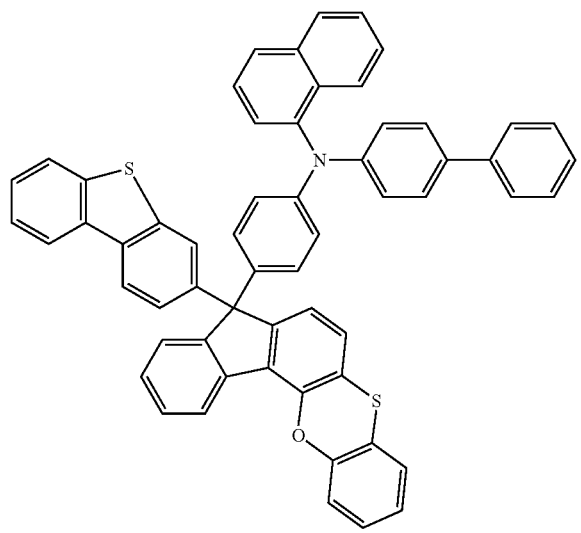

compound 99
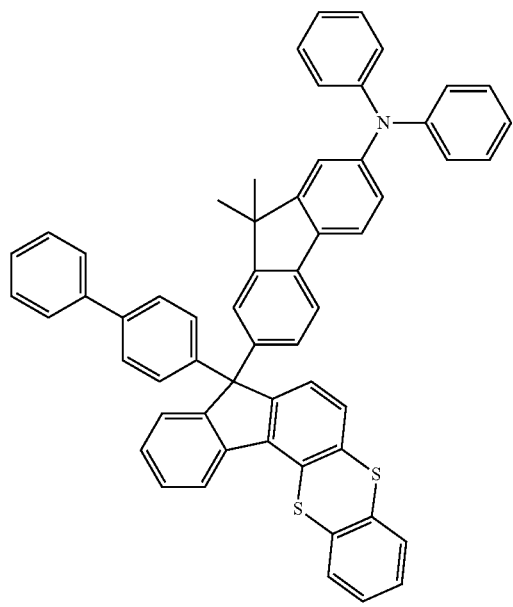
compound 100
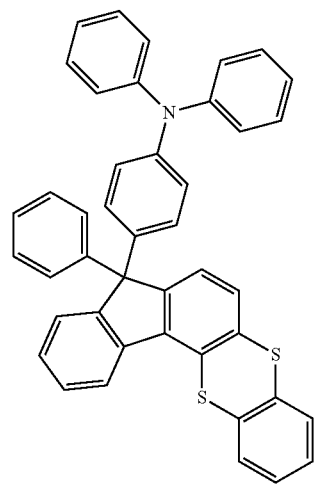
compound 101
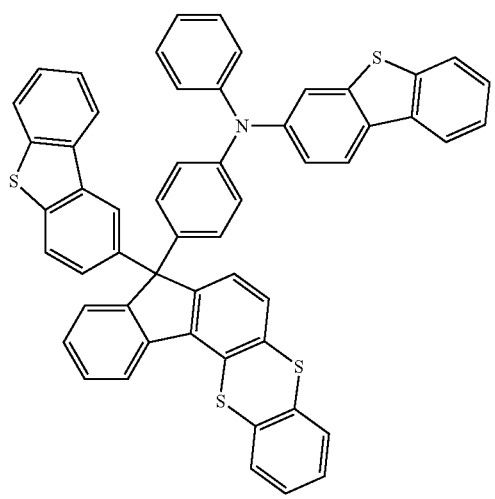
compound 102
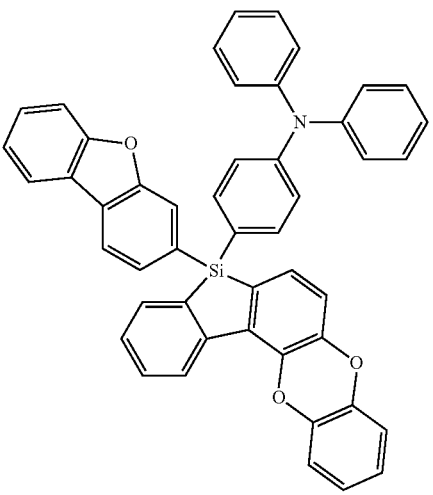
compound 103
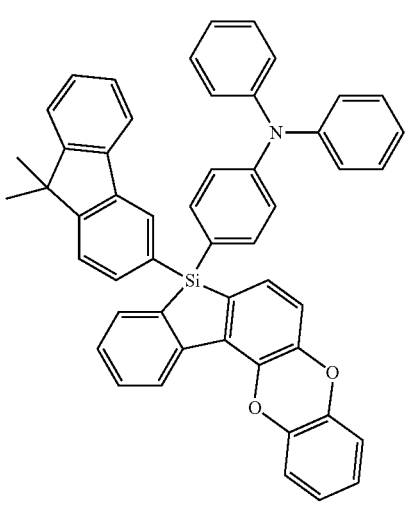
compound 104
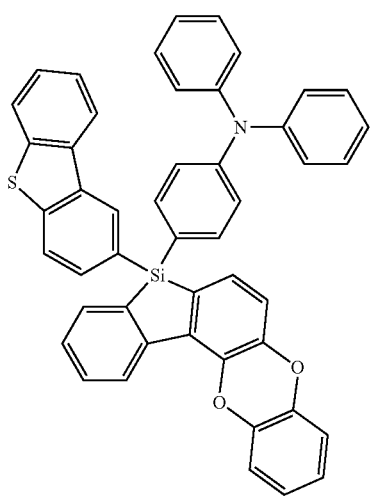

compound 106
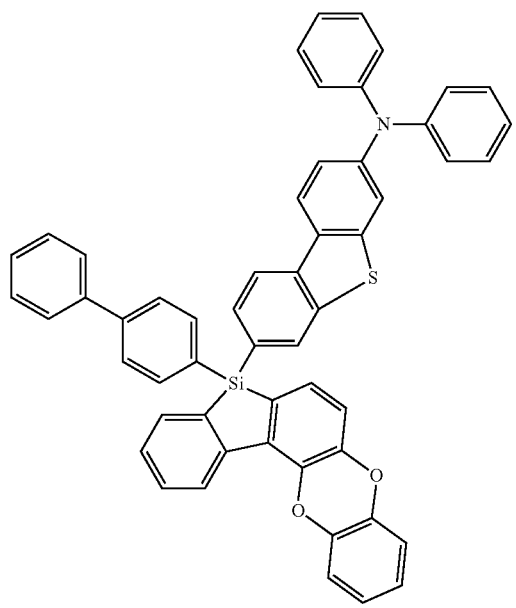
compound 108
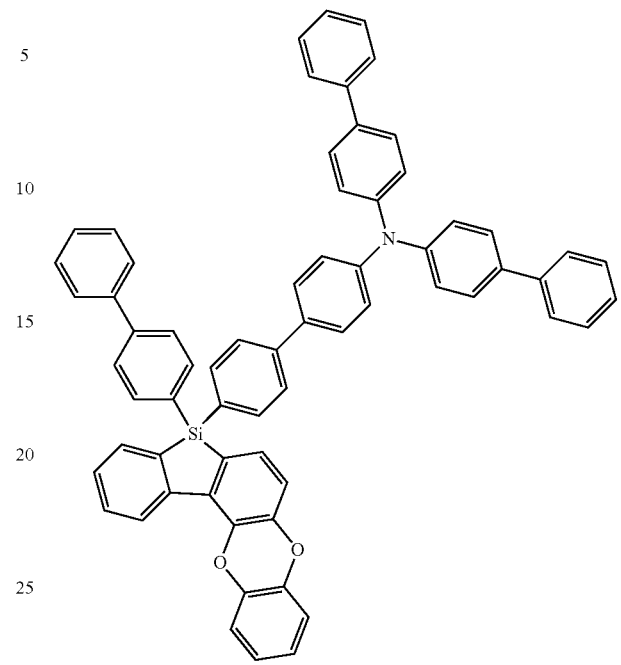
compound 107
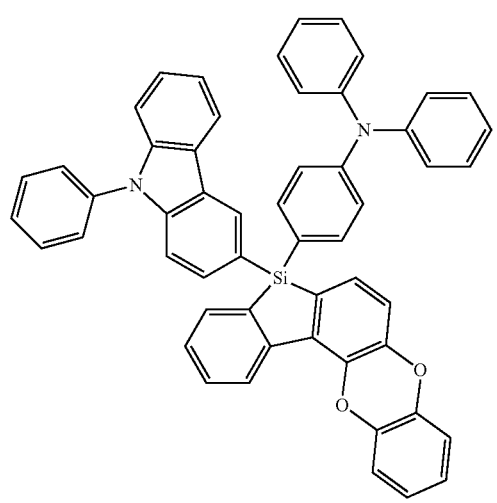
compound 109
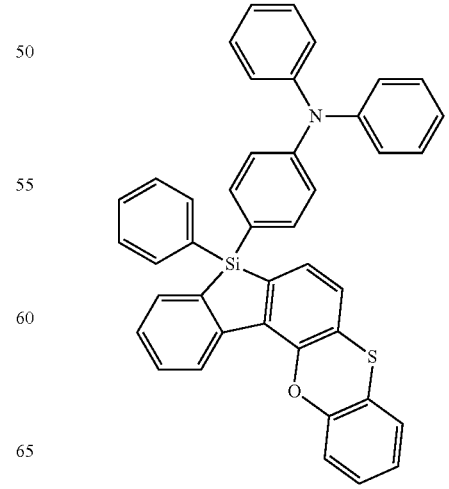

-continued
compound 110
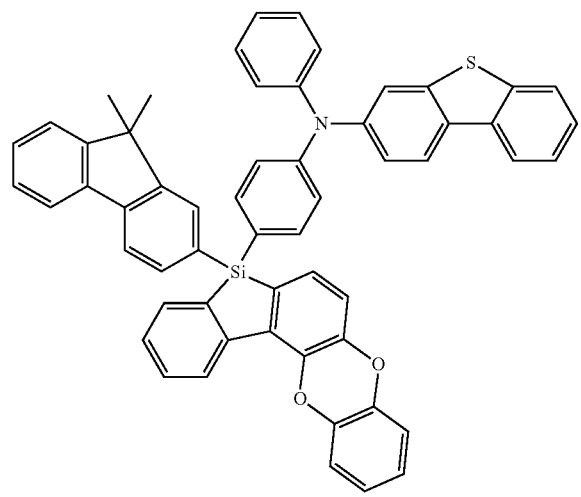
compound 111
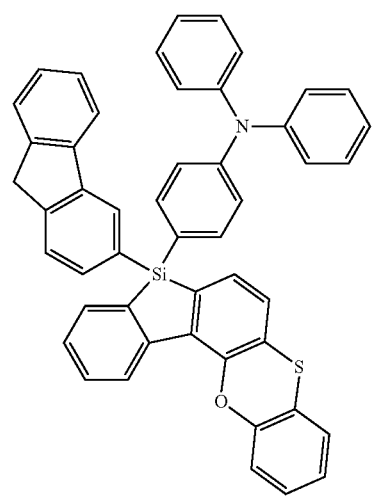
compound 112
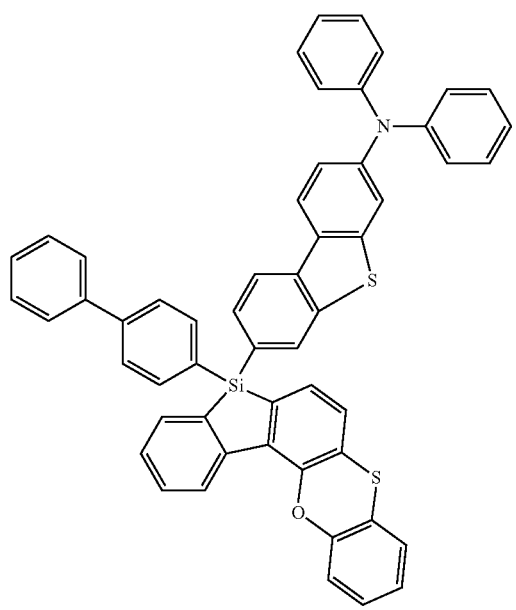
-continued
compound 113
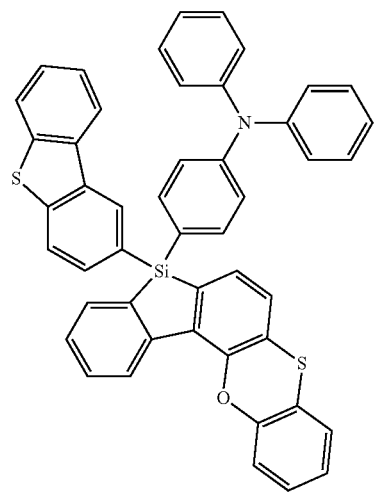
compound 114
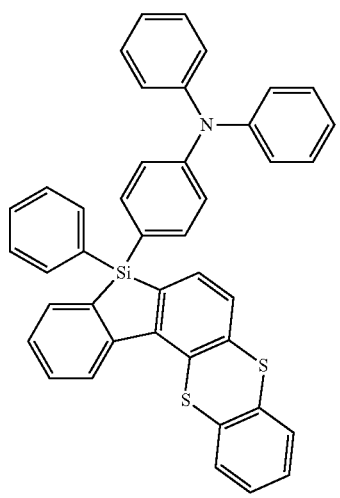
compound 115
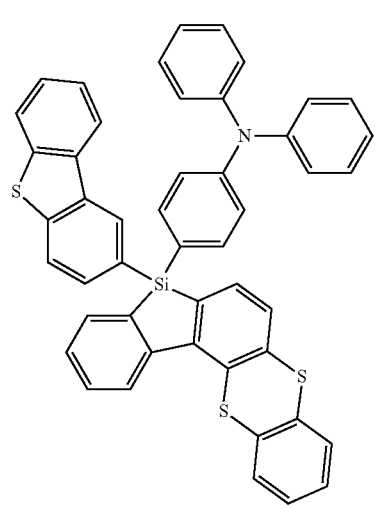

compound 116
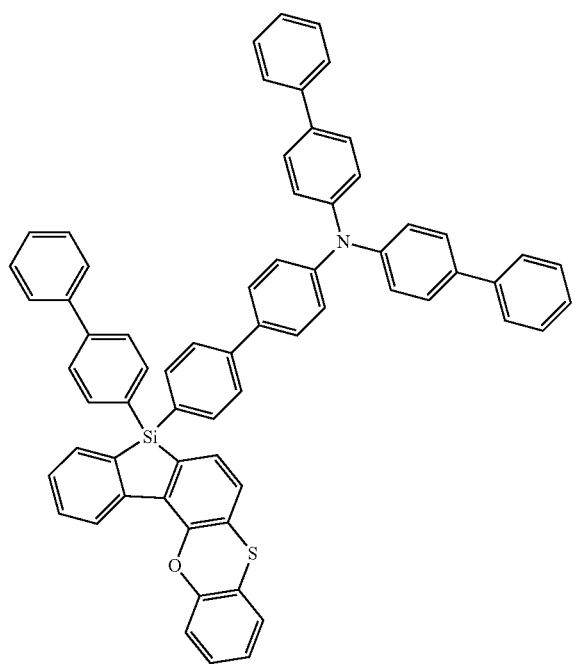
compound 117
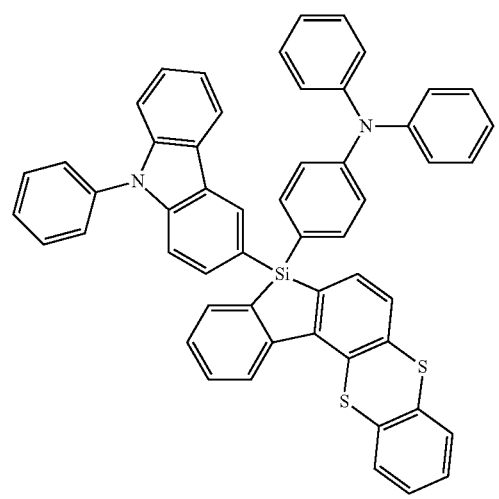
compound 118
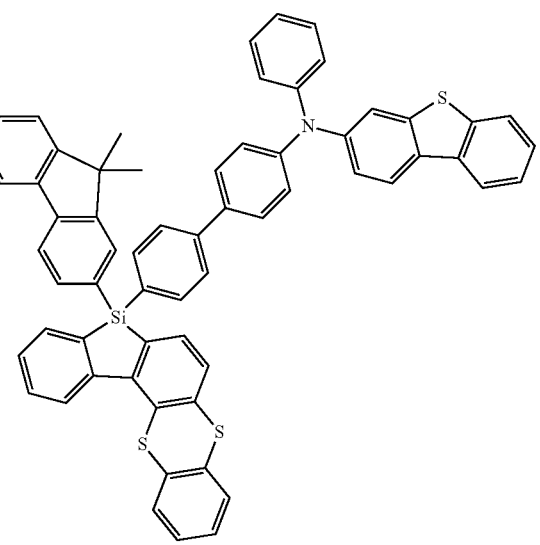
compound 119
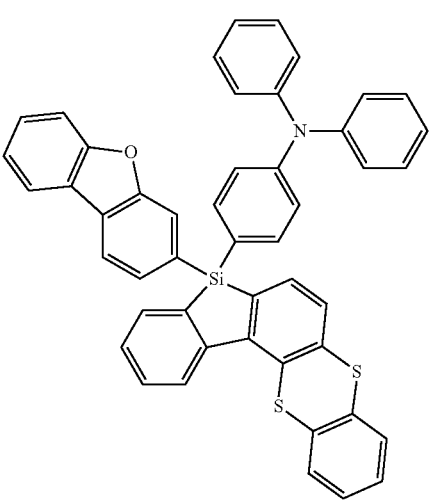
compound 120
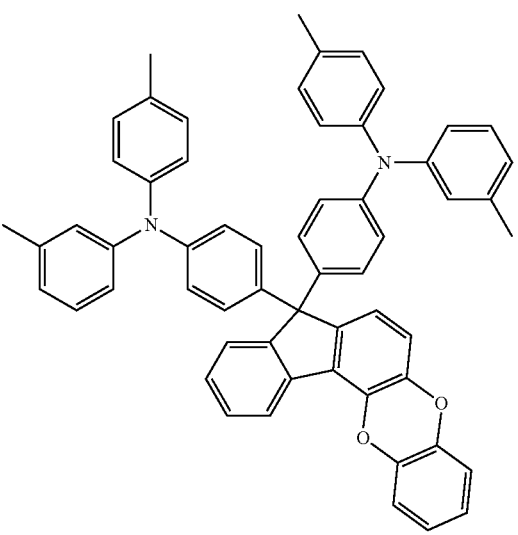

compound 122
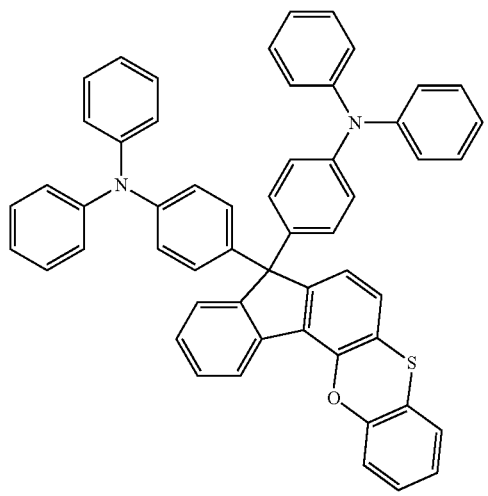
compound 123
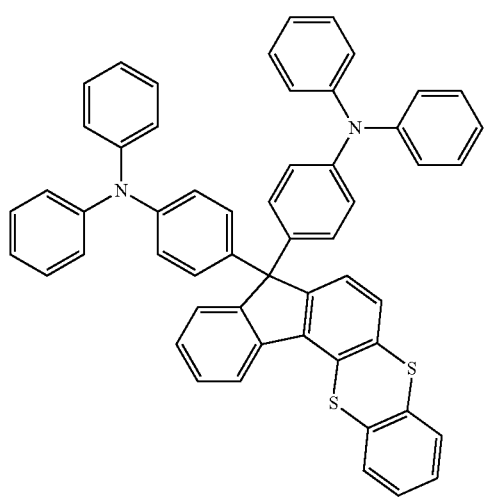
compound 125
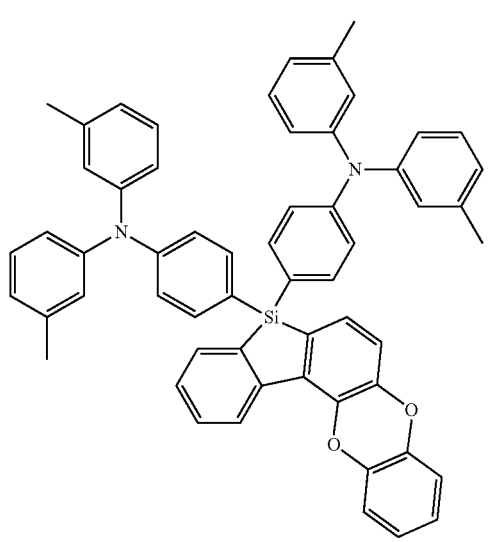
compound 127
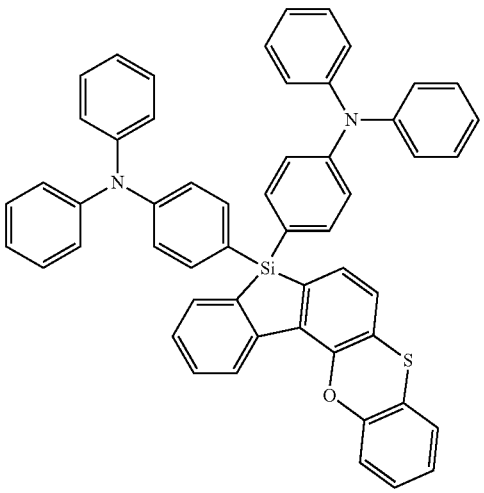
compound 129
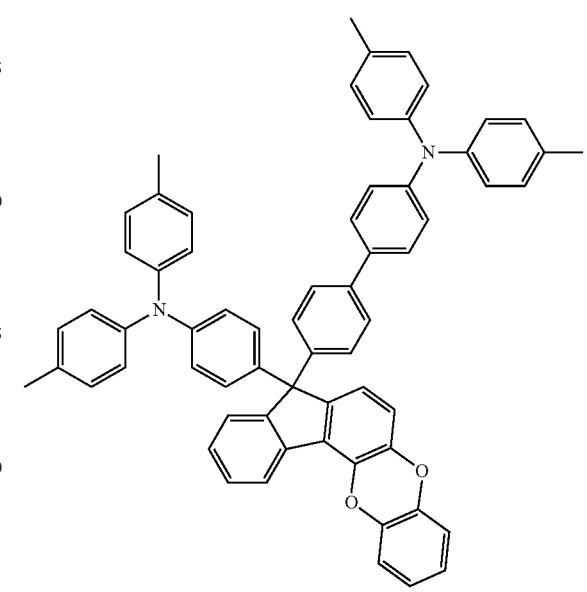
compound 130
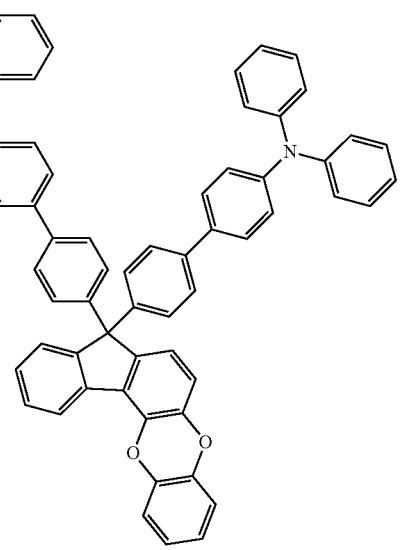

compound 131
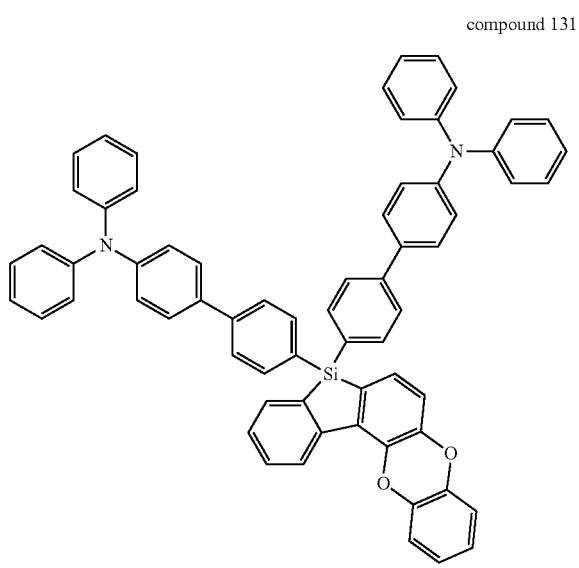
compound 132
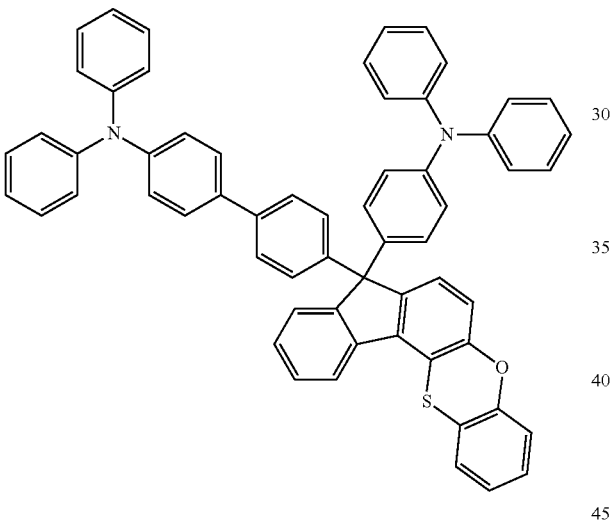
compound 133
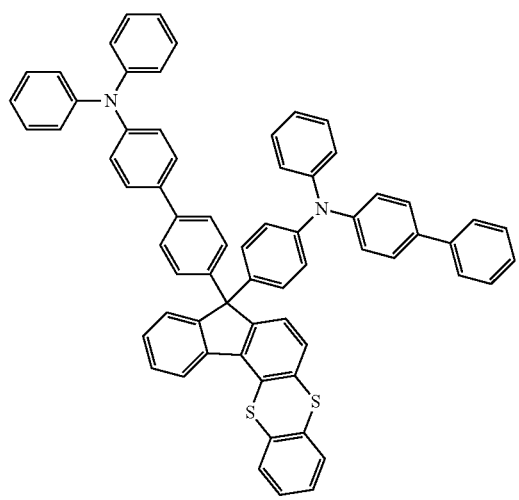
compound 135
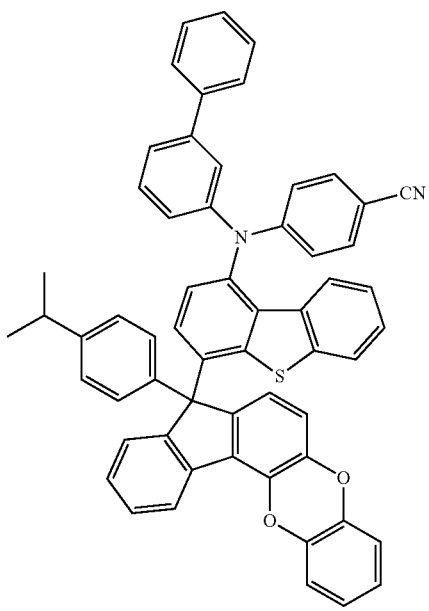
compound 138
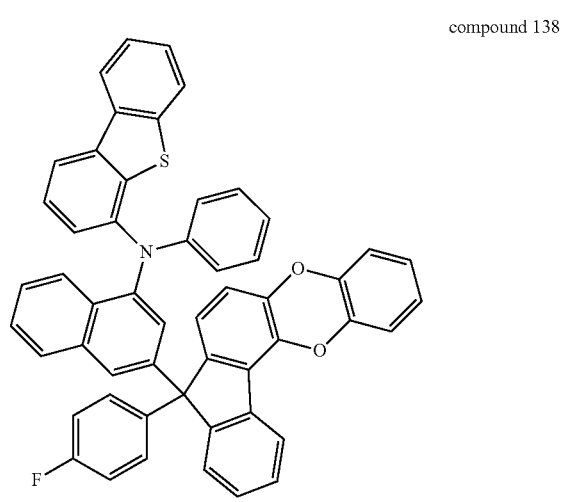
compound 139
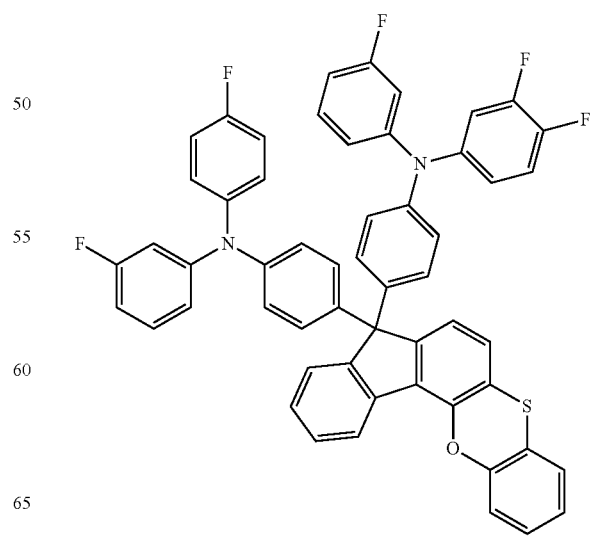

compound 140
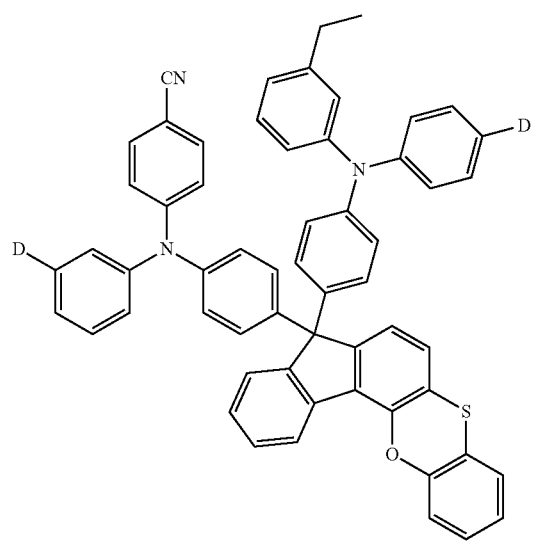
compound 141
compound 142
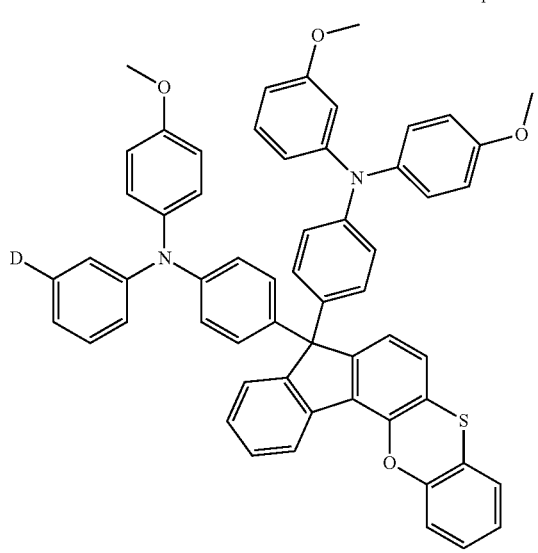
compound 143
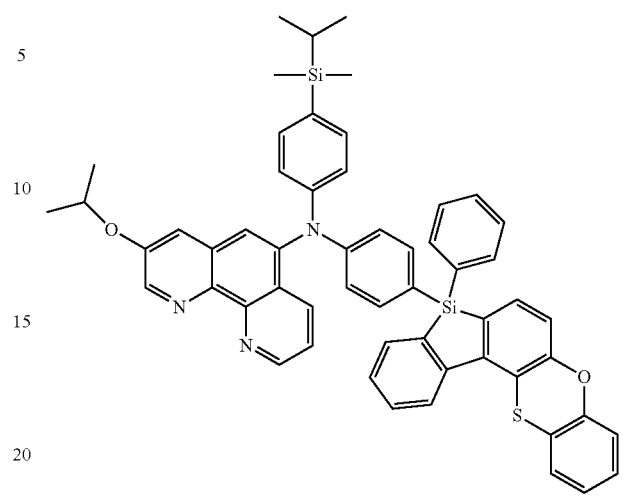
compound 146
compound 147
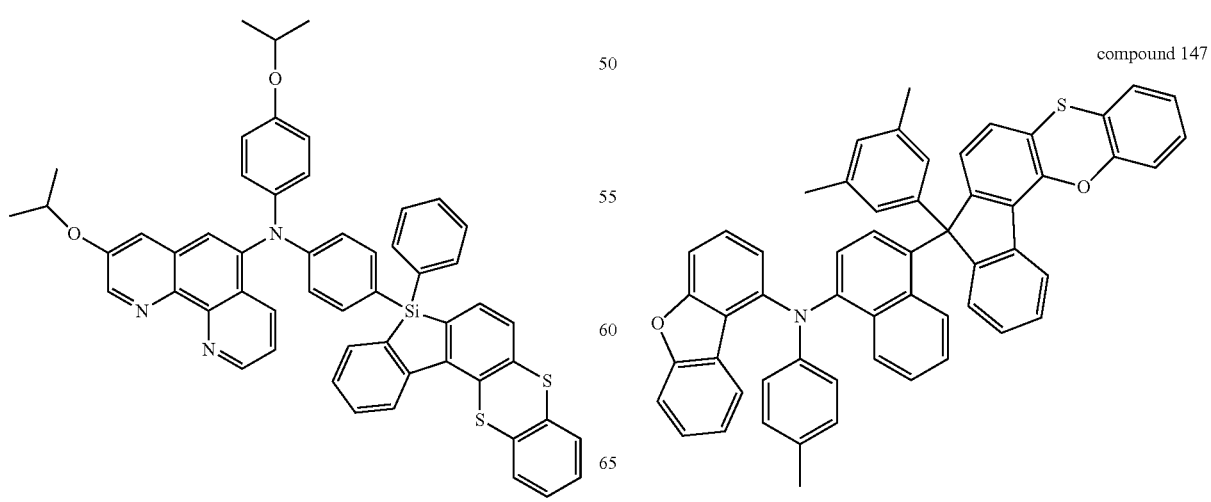

compound 150
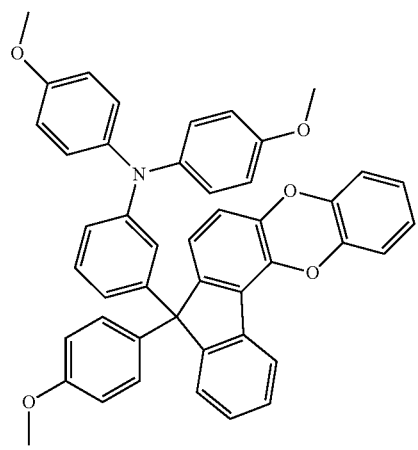
compound 151
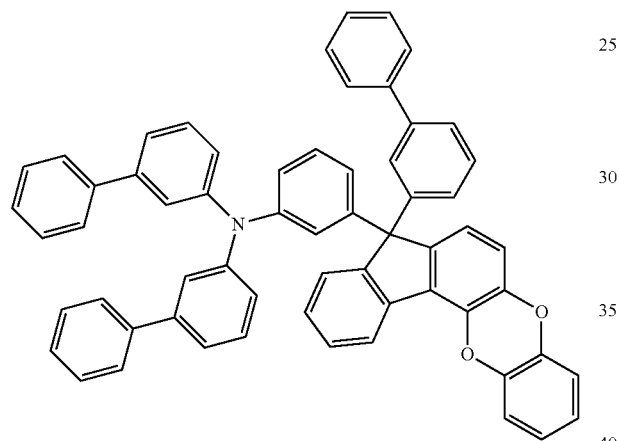
compound 152
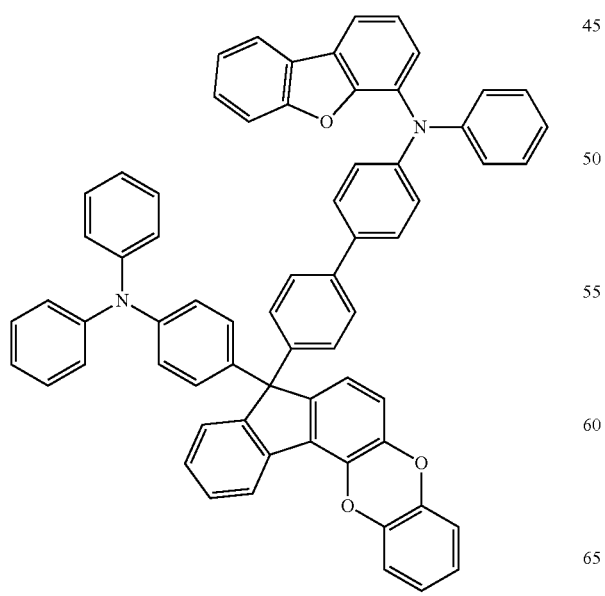
compound 153
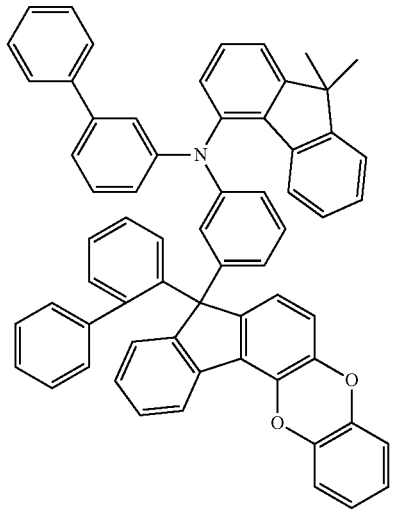
compound 154
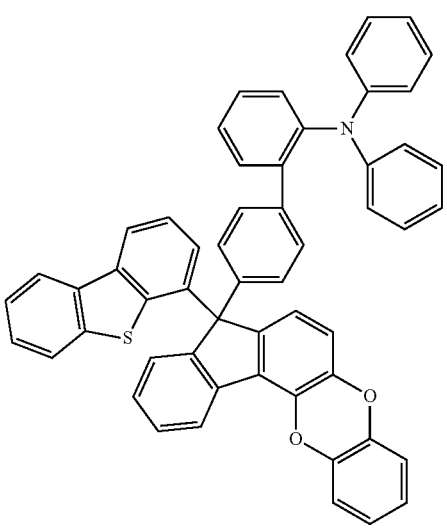
compound 155
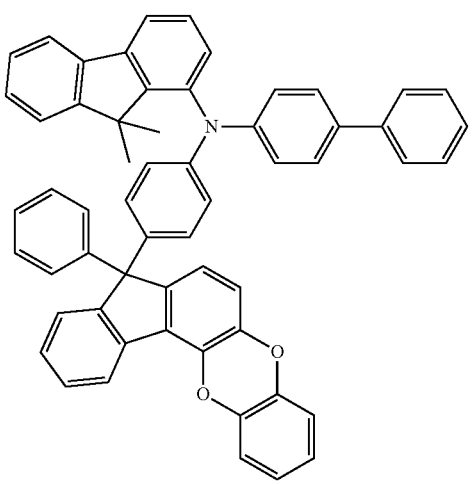

compound 157
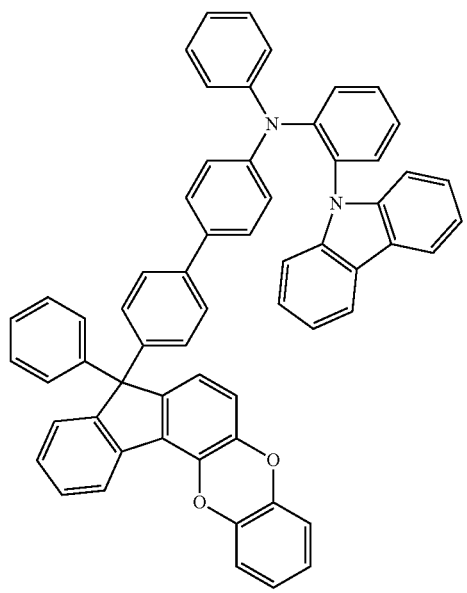
compound 159
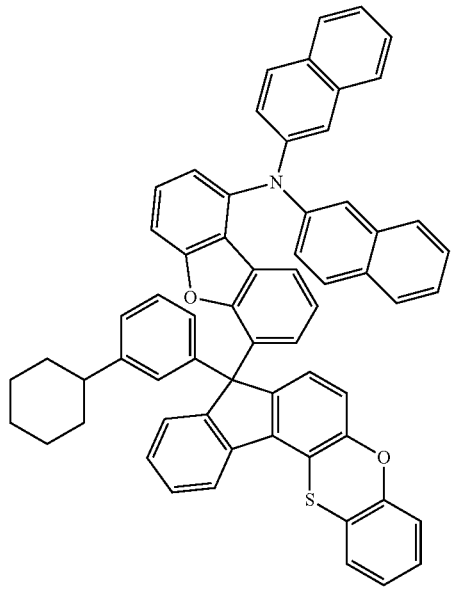
compound 160
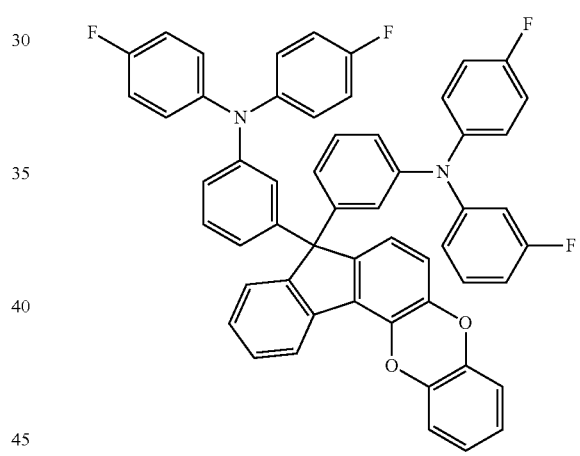
compouind 158
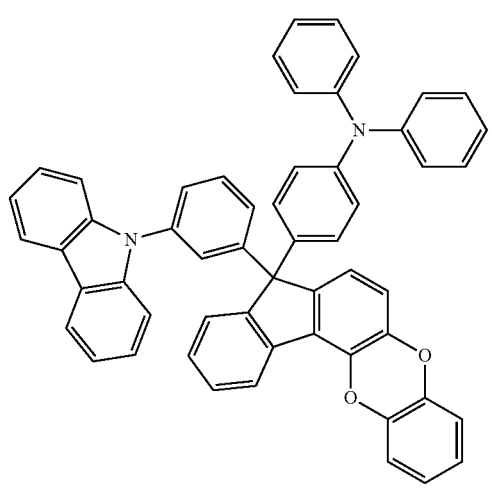
compound 161
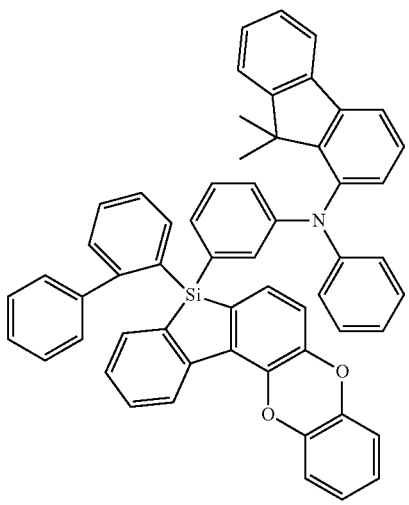

compound 162
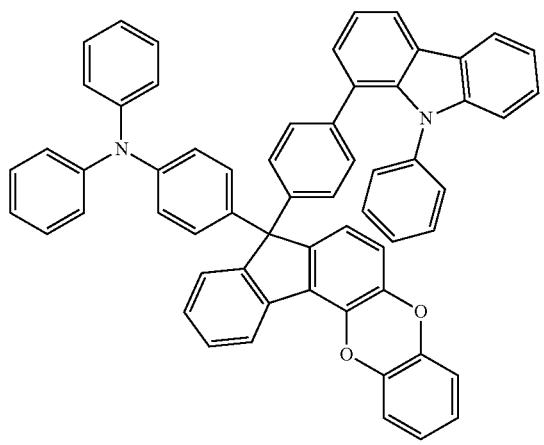
compound 166
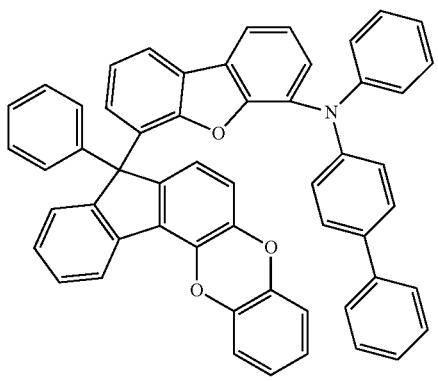
compound 164
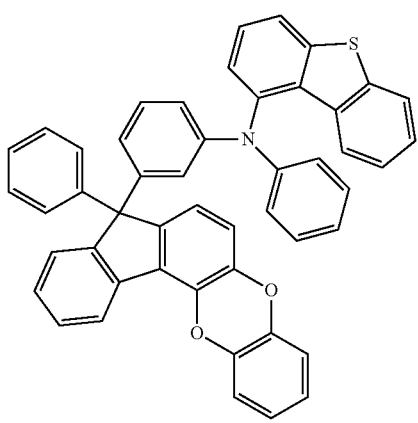
compound 167
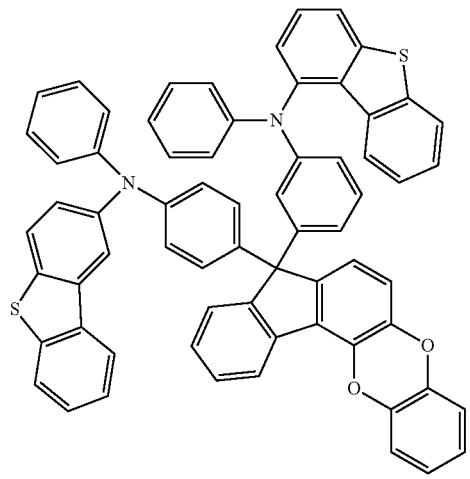
compound 165
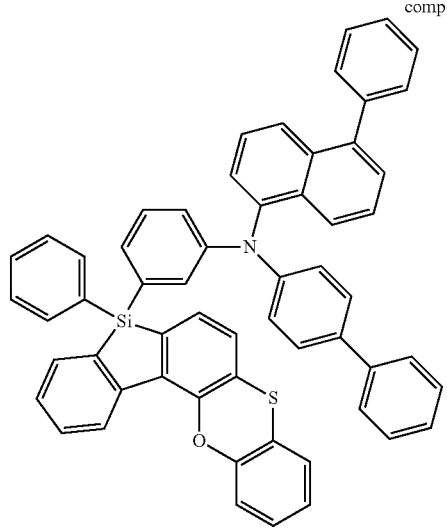
compound 168
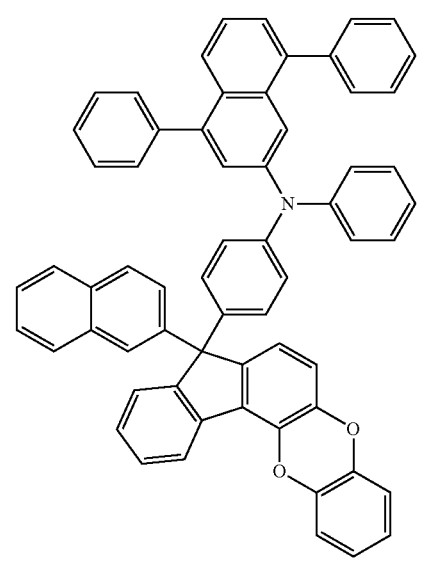

compound 169
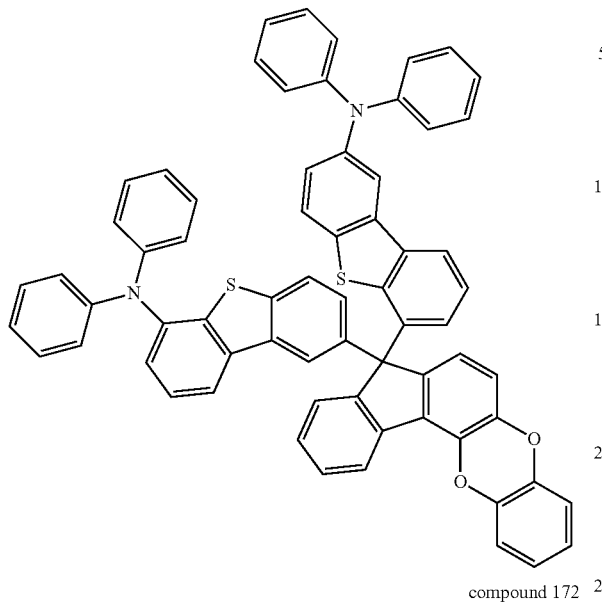
compound 178
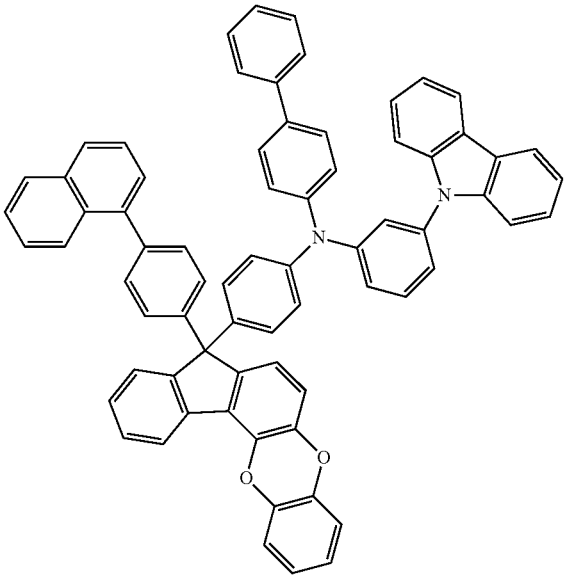
compound 172
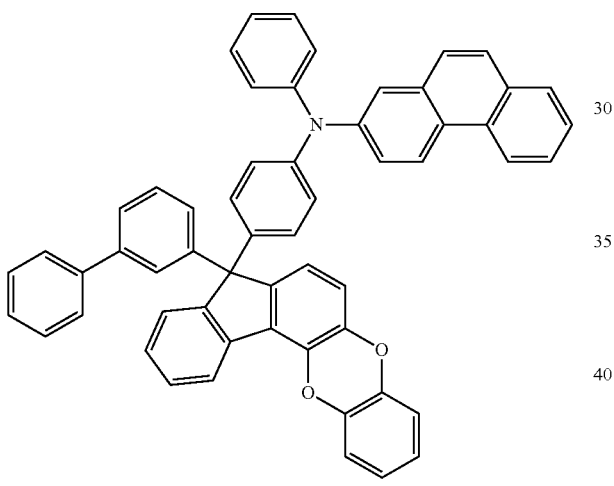
compound 179
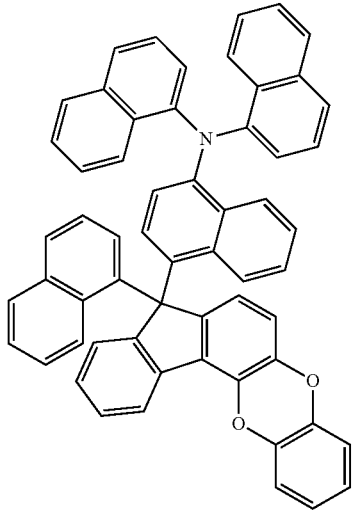
compound 177
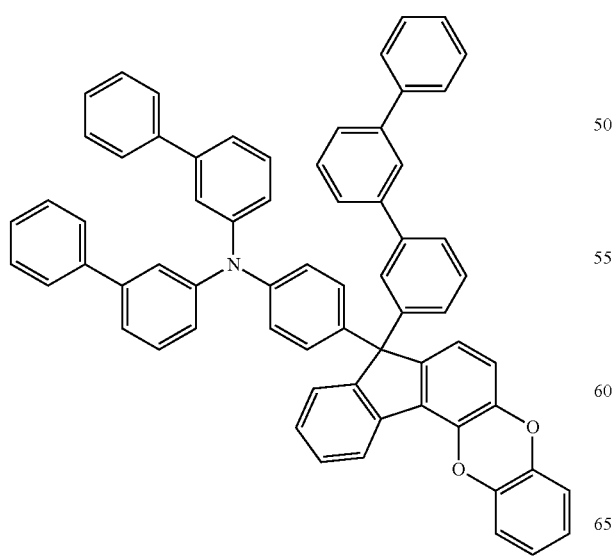
compound 180
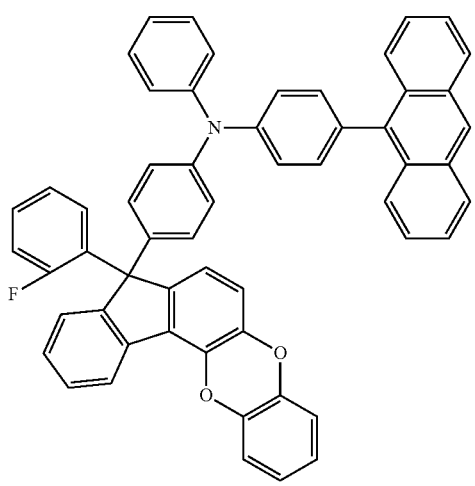

compound 181
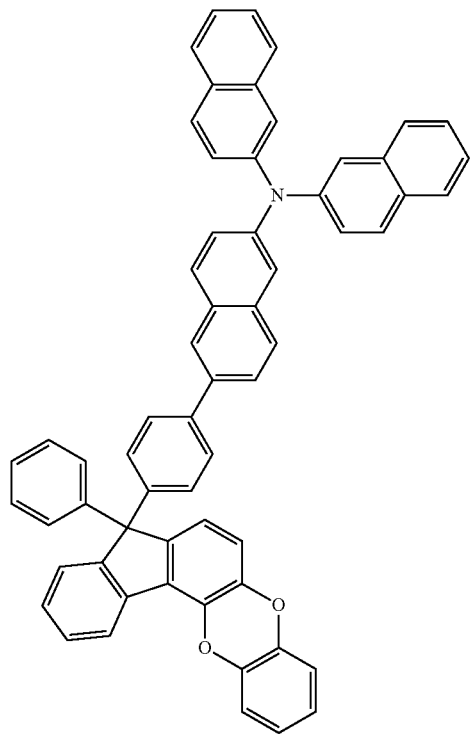
compound 182
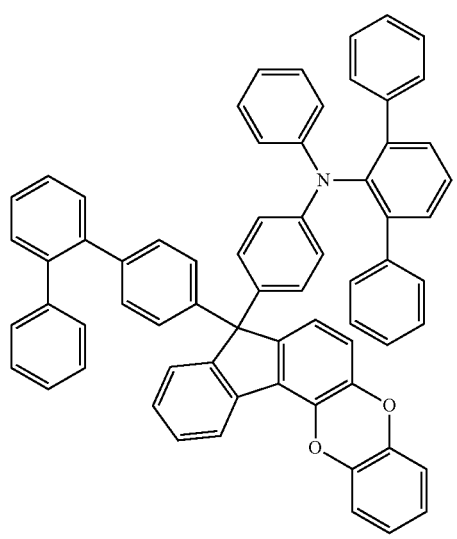
compound 184
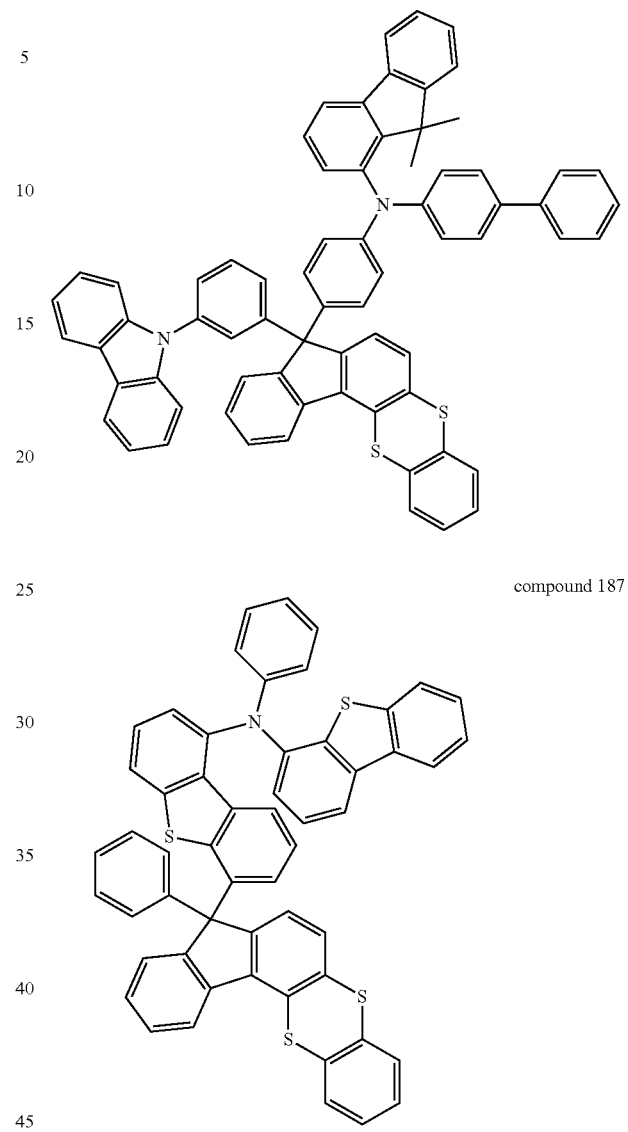
compound 187
compound 188
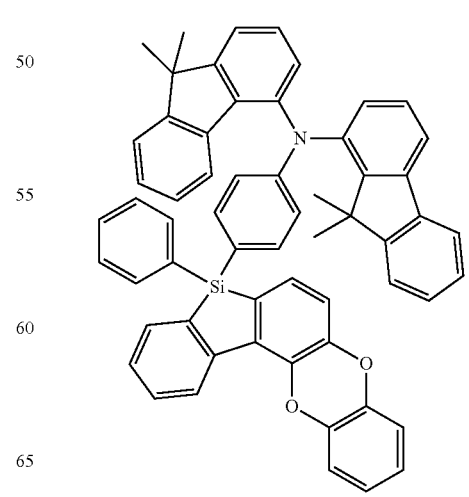

compound 189
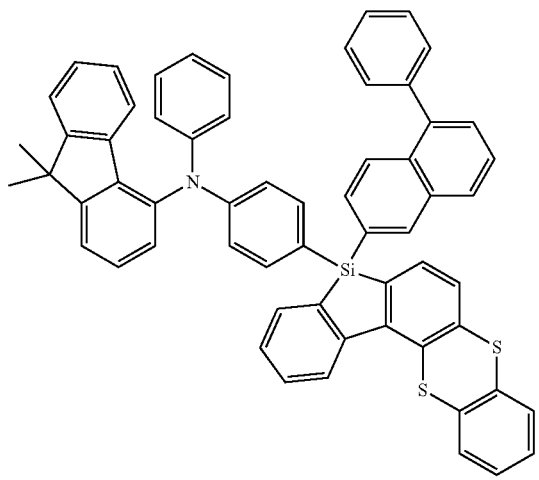
compound 190
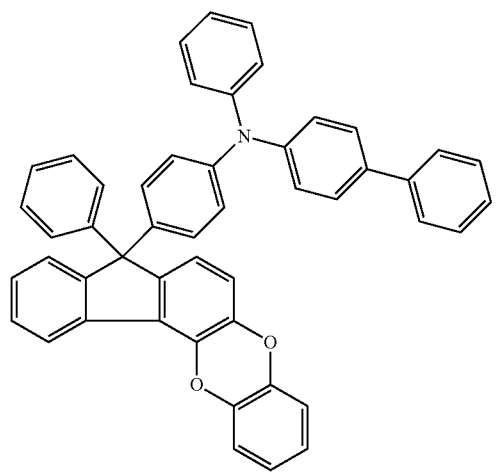
compound 191
compound 192
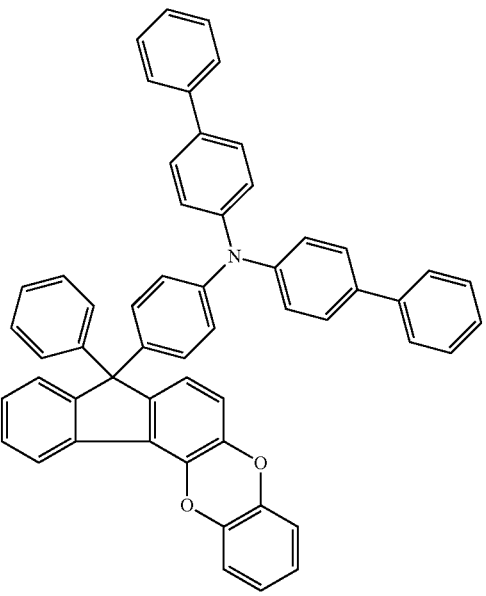
compound 193
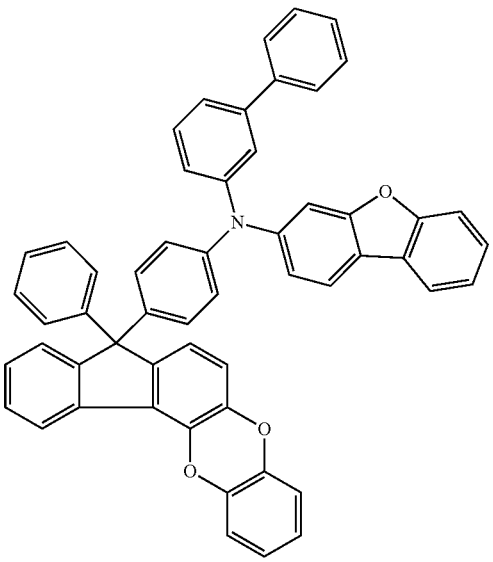

compound 194

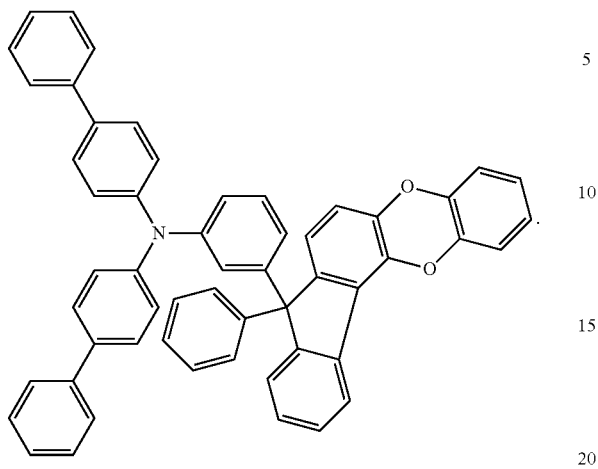

10. An electronic element, comprising an anode and a cathode that are arranged oppositely, and a functional layer arranged between the anode and the cathode,
   wherein the functional layer comprises a hole transport layer, and the hole transport layer comprises the organic compound according to claim 1.

11. The electronic element according to claim 10, wherein the electronic element is an organic light emitting device or a solar cell.

12. An electronic device, comprising the electronic element according to claim 10.

* * * * *